United States Patent
Kohn et al.

(10) Patent No.: US 9,326,972 B2
(45) Date of Patent: May 3, 2016

(54) USE OF PHENYLMETHIMAZOLES, METHIMAZOLE DERIVATIVES, AND TAUTOMERIC CYCLIC THIONES FOR THE TREATMENT OF AUTOIMMUNE/INFLAMMATORY DISEASES ASSOCIATED WITH TOLL-LIKE RECEPTOR OVEREXPRESSION

(75) Inventors: Leonard D. Kohn, Athens, OH (US); Norikazu Harii, Yaminashi (JP); Uruguaysito Benavides-Peralta, Montevideo (UY); Mariana Gonzalez-Murguiondo, Montevideo (UY); Christopher J. Lewis, Athens, OH (US); Douglas J. Goetz, Athens, OH (US); Giorgio Napolitano, Athens, OH (US); Cesidio Giuliani, Athens, OH (US); Ramiro Malgor, Athens, OH (US); Frank Schwartz, Vienna, WV (US); Kelly D. McCall, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 13/370,079

(22) Filed: Feb. 9, 2012

(65) Prior Publication Data
US 2012/0238610 A1  Sep. 20, 2012

Related U.S. Application Data

(63) Continuation of application No. 11/130,922, filed on May 17, 2005, now abandoned, which is a continuation-in-part of application No. 10/912,948, filed on Aug. 6, 2004, now Pat. No. 7,928,132, and a continuation-in-part of application No. 10/801,986, filed on Mar. 16, 2004, now abandoned.

(51) Int. Cl.
| | |
|---|---|
| *A61K 31/4164* | (2006.01) |
| *A61P 31/04* | (2006.01) |
| *A61P 31/00* | (2006.01) |
| *A61P 29/00* | (2006.01) |
| *A61K 31/4166* | (2006.01) |

(52) U.S. Cl.
CPC ......... *A61K 31/4164* (2013.01); *A61K 31/4166* (2013.01)

(58) Field of Classification Search
CPC ................ A61K 31/4164; A61K 31/4166
USPC ........................................................ 514/392
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,630,200 A | 12/1971 | Higuchi | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,734,421 A | 3/1988 | Hammond et al. | |
| 5,162,360 A | 11/1992 | Creswell et al. | |
| 5,556,574 A | 9/1996 | Rivas et al. | |
| 5,556,754 A | 9/1996 | Singer et al. | |
| 6,365,616 B1 | 4/2002 | Kohn et al. | |
| 6,465,472 B1 | 10/2002 | Upasani et al. | |
| 6,924,274 B2 | 8/2005 | Lardy et al. | |
| 7,928,132 B2 * | 4/2011 | Kohn et al. | ................... 514/386 |
| 2005/0209295 A1 | 9/2005 | Kohn et al. | |

FOREIGN PATENT DOCUMENTS

| | | |
|---|---|---|
| AU | 2005275023 B2 | 7/2005 |
| EP | 0692483 A1 | 1/1996 |
| WO | 97/23200 A1 | 7/1997 |
| WO | 98-52558 | 11/1998 |
| WO | 99/32106 | 7/1999 |
| WO | 99/32110 | 7/1999 |
| WO | 99/32111 | 7/1999 |
| WO | 99/32455 | 7/1999 |
| WO | 0012175 | 3/2000 |
| WO | 0025756 | 5/2000 |

(Continued)

OTHER PUBLICATIONS

Cybulsky et aL 1991. Endothelial expression of a mononuclear leukocyte adhesion molecule during atherogenesis. Science 251:788-791.

(Continued)

*Primary Examiner* — Barbara P Badio
*Assistant Examiner* — Sara E Townsley
(74) *Attorney, Agent, or Firm* — Dinsmore & Shohl LLP

(57) ABSTRACT

Treatment of autoimmune and/or inflammatory diseases associated with overexpression of Toll-like receptor 3 (TLR3) as well as Toll-like receptor 4 (TLR4) and/or TLR3/TLR4 signaling in nonimmune cells, monocytes, macrophages, and/or dendritic cells in association with related pathologies. The use of phenylmethimazoles, methimazole derivatives, and tautomeric cyclic thiones for the treatment of autoimmune and inflammatory diseases associated with TLR3 as well as TLR4 and/or TLR3/TLR4 cellular signaling in association with related pathologies is disclosed. Methods of treating a subject having a disease or condition associated with abnormal TLR-3 as well as TLR-4 and/or TLR3/TLR4 cellular signaling in association with related pathologies are also disclosed. The present disclosure also relates to the treatment of autoimmune-inflammatory pathologies and chemokine and cytokine-mediated diseases associated with TLR overexpression and signaling. The disclosure also relates to pharmaceutical formulations capable of inhibiting the IRF-3/Type 1 IFN/STAT/ISRE/IRF-1 pathway associated with Toll-like receptor overexpression or signaling.

22 Claims, 18 Drawing Sheets

(56) References Cited

FOREIGN PATENT DOCUMENTS

| WO | 2004/017962 A2 | 3/2004 |
| WO | 2005/094819 A1 | 10/2005 |
| WO | 2006/019962 A1 | 2/2006 |

OTHER PUBLICATIONS

Schurmann et al. 1995. Increased expression of cell adhesion molecule P-selectin in active inflammatory bowel disease. Gut 36:411-418.
Luscinskas et al. 1996. Endothelial-dependent mechanisms in chronic inflammatory leukocyte recruitment. Annu. Rev. Med. 47:413-421.
Soriano et al. 2000. VCAM-1, but not ICAM-1 or MAdCAM-1, immunoblockade ameliorates DSSinduced colitis in mice. Lab. Invest. 80: 1541-1551.
Panes et al. 1999. Leukocyte-endothelial cell adhesion: avenues for therapeutic intervention. Br J Pharmacol126:537-550.
Bevilacqua, M. P. 1993. Endothelial-leukocyte adhesion molecules. Annu. Rev. Immunol. 11 :767-804.
Schindler et al. 1994. Three NF-kappa B binding sites in the human E-selectin gene required for maximal tumor necrosis factor alpha-induced expression. Mol Cell Bioi 14:5820-5831.
Neish et al. 1992. Functional analysis of the human vascular cell adhesion molecule 1 promoter. J Exp Med 176: 1583-1593.
Neish et al. 1995. Sp1 is a component of the cytokine-inducible enhancer in the promoter of vascular cell adhesion molecule-1. J Bioi Chem 270:28903-28909.
Neish et al. 1995. Endothelial interferon regulatory factor 1 cooperates with NF-kappa B as a transcriptional activator of vascular cell adhesion molecule.
Iademarco et al. 1992. Characterization of the promoter for vascular cell adhesion molecule-1 (VCAM-1). J Bioi Chem 267:16323-16329.
Ledebur et al. 1995. Transcriptional regulation of the intercellular adhesion molecule-1 gene by inflammatory cytokines in human endothelial cells. Essential roles of a variant NF-kappa B site and p65 homodimers. J Bioi Chem 270:933-943.
Munoz et al. 1996. Transcriptional up-regulation of intracellular adhesion molecule-1 in human endothelial cells by the antioxidant pyrrolidine dithiocarbamate involves the activation of activating protein-1. J Immunol157:3587-3597.
May et al. 1998. Signal transduction through NF-kappa B. Immunol Today 19:80-88.
Conner et al. 1997. Proteasome inhibition attenuates nitric oxide synthase expression, VCAM-1 transcription and the development of chronic colitis. J Pharmacol Exp Ther 282:1615-1622.
Pierce et al. 1996. Salicylates inhibit I kappa B-alpha phosphorylation, endothelial-leukocyte adhesion molecule expression, and neutrophil transigation. J Immunol156:3961-3969.
Pierce et al. 1997. Novel inhibitors of cytokine-induced IkBa phosphorylation and endothelial cell adhesion molecule expression show anti-inflammatory effects in vivo. J. Biol. Chem. 272:21096-21103.
Weber et al. 1995. Aspirin inhibits nuclear factor-kappa B mobilization and monocyte adhesion in . stimulated human endothelial cells. Circulation 91 :1914-1917.
Umetani et al. 2000. A novel cell adhesion inhibitor, K-7174, reduces the endothelial VCAM-1 induction by inflammatory cytokines, acting through the regulation of GAT A. Biochem Biophys Res Commun 272:370-374.
Dagia et al. 2003. A proteasome inhibitor reduces concurrent, sequential and long term IL-1.beta. and TNF-.alpha. induced endothelial cell adhesion molecule expression and adhesion. Am. J. Phys. 285:C813-C822.
Cooper, D. S. 1984. Antithyroid drugs. N Engl J Med 311:1353-1362.
Elias et al. 1995. Effect of orally administered antithyroid thioureylenes on PCNA and P53 expression in psoriatic lesions. Int J Dermatol 34:280-283.

Chan et al. 1995. Periocular inflammation in mice with experimental systemic lupus erythematosus. A new experimental blepharitis and its modulation. J Immuno1154:4830-4835.
Davies et al. 1984. Influence of methimazole on murine thyroiditis. Evidence for immunosuppression in vivo. J Clin Invest 73:397-404.
Wang et al. 2003. Methimazole protects from experimental autoimmune uveitis by inhibiting antigen presenting cell function and reducing antigen priming. J Leukoc Bioi 73:57-64.
Saji et al. 1992. Major histocompatibility complex class I gene expression in rat thyroid cells is regulated by hormones, methimazole, and iodide as well as interferon. J Clin Endocrinol Metab 75:871-878.
Montani et al. 1998. Regulation of major histocompatibility class gene expression in FRTL-5 thyrocytes: opposite effects of interferon and methimazole. Endocrinology 139:290-302.
Mozes et al. 1993. Resistance of MHC class I-deficient mice to experimental systemic lupus erythematosus. Science 261 :91-93.
Wenisch et al. 1995. Circulating selecting, intercellular adhesion molecule-1, and vascular cell adhesion molecule-1 in hyperthyroidism. J Clin Endocrinol Metab 80:2122-2126.
Oren et al. 1997. Anti-thyroid drugs decrease mucosal damage in a rat model of experimental colitis. Aliment Pharmacol Ther 11: 341-345.
Suzuki et al. 1999. Activation of target-tissue immune-recognition molecules by double-stranded polynucleotides. Proc Natl Acad Sci USA 96:2285-2290.
Gopalan et al. 1996. Cell adhesion under hydrodynamic flow conditions. In Current Protocols in Immunology. J. E. Coligan, A. M. Kruisbeek, D. H. Margulies, E. M. Shevach, and W. Strober, eds. J. Wiley, New York, p. 7.29.1-7.29.23.
Carlos et al. 1991. Human monocytes bind to two cytokine-induced adhesive ligands on cultured human endothelial cells: endothelial-leukocyte adhesion molecule-1 and vascular cell adhesion molecule-1. Blood 77:2266-2271.
Zapolska-Downar et al. 2001. Selective inhibition by probucol of vascular cell adhesion molecule-1 (VCAM-1) expression in human vascular endothelial cells. Atherosclerosis 155: 123-130.
Alon et al. 1994. Distinct cell surface ligands mediate T lymphocyte attachment and rolling on Pand E-selectin under physiological flow. J. Cell Biol. 127:1485-1495.
Alon et al. 1995. The integrin VLA-4 supports tethering and rolling in flow on VCAM-1. J Cell Bioi. 128: 1243-1253.
Ochi et al. 2002. Hyperosmotic stimuli inhibit VCAM-1 expression in cultured endothelial cells via effects on interferon regulatory factor-1 expression and activity: Eur J Immunol32:1821-1831.
Koo et al. 2003. Iron chelators inhibit VCAM-1 expression in human dermal microvascular endothelial cells. J Invest Dermatol120:871-879.
Ahmad et al. 1998. Role of activating protein-1 in the regulation of the vascular cell adhesion molecule-1 gene expression by tumor necrosis factor-alpha. J Bioi Chem 273:4616-4621.
Umetani et al. 2001. Function of GAT A transcription factors in induction of endothelial vascular cell adhesion molecule-1 by tumor necrosis factor-alpha. Arterioscler Thromb Vasc Bioi 21: 917-922.
Kjellin et al. 1969. Tautom~ric Cyclic Thiones. Part III. Preparation of N- and S-Methyl Derivatives of Some Azoline-2-thiones. Acta Chemica Scandanavica 23: 2879-2887.
The Merck Manual, 17th edition (1999), p. 1769.
Calvey et al., J. Invest. Surg. (Mar.-Apr. 2007),20(2), pp. 71-85.
Isman et al., Journal of Endocrinology (2003), 177(3), 471-476.
The Merck Manual, 1ih edition (1999), pp. 310-311.
Grisham, M. B., and D. N. Granger. 1999. Leukocyte-endothelial cell interactions in inflammatory bowel disease. In Inflammatory bowel disease. J. B. Kirsner, ed. Saunders, Philadelphia, p. 55-64.
Cario, E .• and D. K. Podolsky. 2000. Differential alteration in intestinal epithelial cell expression of toll-like receptor 3 (TLR3) and TLR4 in inflammatory bowel disease. Infect Immun 68:7010-7017.
Singh, U. P., S. Singh, D. D. Taub. and J. W. Lillard, Jr. 2003. Inhibition of IFN-gamma-inducible protein-IO abrogates colitis in IL-IO-/- mice. J Immuno1171: 1401-1406.
Kobayashi M, Kweon MN, Kuwata H et al. Toll-like receptor-dependent. production ofIL-12p40 causes chronic enterocolitis in myeloid cell-specific Stat3~deficient mice. J Clin Invest 2003; 111(9): 1297-308.

(56) References Cited

OTHER PUBLICATIONS

Carlos, T. M., and J. M. Harlan. 1994. Leukocyte-endothelial adhesion molecules. Blood 84:2068-2/0/.

Springer, T. A. 1994. Traffic signals for lymphocyte recirculation and leukocyte emigration: the multistep paradigm Cell 76:301-314.

Targan. S. R., S. B. Hanauer. S. J. van Deventer, L. Mayer, D. H. Present, T. Braakman, K. L. DeWoody, T. F. Schaible, and P. J. Rutgeerts. 1997. A short-term study of chimeric monoclonal antibody cA2 to tumor necrosis factor alpha for Crohn's disease. Crohn's Disease cA2 Study Group. N Engl J Med 337: 1029-1035.

Wallace, J. L., A. Higa, G.W. McKnight, and D. E. MacIntyre. 1992. Prevention and reversal of experimental colitis by a monoclonal antibody which inhibits leukocyte adherence. Inflammation 16:343-354.

Singer, D. S., L. D. Kohn, H. Zinger, and E. Mozes. 1994. Methimazole prevents induction of experimental systemic lupus erythematosus in mice. J Immunol 153:873-880.

Dagia, N. M., N. Harii, A. E. Meli, X. Sun, C. J. Lewis, L. D. Kohn, and D. J. Goetz. 2004. Phenyl methimazole inhibits TNFa-induced VCAM-I expression in an IFN Regulatory Factor-I-dependent manner and reduces monocytic cell adhesion to endothelial cells—J Immunol 173:2041-2049.

Lange, S., D. S. Delbro, E. Jennische, and I. Mattsby-Baltzer. 1996. The role of the Lps gene in experimental ulcerative colitis in mice. Apmis 104:823-833.

Takeda, K., and S. Akira. 2003. Toll receptors and pathogen resistance. Cell Microbiol 5: 143-153.

Takeda, K., T. Kaisho, and S. Akira. 2003. Toll-like receptors. Annu Rev Immunol 21:335-376.

Oshiumi, H., M. Matsumoto, K Funami; T. Akazawa, and T. Seya. 2003. TICAM-I, an adaptor molecule that participates in Toll-like receptor 3-mediated interferon-beta induction. Nat Immunol 4: 161-167.

Yamamoto, M., S. Sato, K. Mori, K. Hoshino, O. Takeuchi, K. Takeda, and S. Akira. 2002. Cutting edge: a novel TolVIL-1 receptor domain-containing adapter that preferentially activates the IFN-beta promoter in the Toll-like receptor signaling. J Immunol 169: 6668-6672.

Bendjelloul, F., P. Rossmann, P. Maly, V. Mandys, M. Jirkovska, L. Prokesova, L. Tuckova, and H. Tlaskalova-Hogenova. 2000. Detection of ICAM-1 in experimentally induced colitis of ICAM-I-deficient and wild-type mice: an inununohistochemical study. Histochem J 32:703-709.

Mabley, J. G., P. Pacher, L. Liaudet, F. G. Soriano, G. Hasko, A. Marton, C. Szabo, and A. L. Salzman. 2003. Inosine reduces inflammation and improves survival in a murine model of colitis. Am J Physiol Gastrointest Liver Physiol 284:G138-144.

Dieleman, L. A., M. J. Palmen, H. Akol, E. Bloemena, A. S. Pena, S. G. Meuwissen, and E. P. Van Rees. 1998. Chronic experimental colitis induced by dextran, sulphate sodium (DSS) is characterized by Thl and Th2 cytokines. Clin Exp Immunol 114:385-391.

Tuvlin, J. A., and S. V. Kane. 2003. Novel therapies in the treatment of ulcerative colitis. Expert Opin Investig Drugs 12:483-490.

Pallone, F., V. Blanco Gdel, P. Vavassori, I. Monteleohe, D. Fina, and G. Monteleone. 2003. Genetic and pathogenetic insights into inflammatory bowel disease. Curr Gastroenterol Rep 5:487-492.

Panes, J., and D. N. Granger. 1998. Leukocyte-endotbeJial cell interactions: molecular mechanisms and implications in gastrointestinal disease. Gastroenterology 114: 1066-1090.

Ortega-Cava, C. F., S. Ishihara, M. A. Rumi, K. Kawashima, N. Ishimura, H. Kazumori, J. Udagawa, Y. Kadowaki, and Y. Kinoshita. 2003. Strategic compartmentalization of Toll-like receptor 4 in the mouse gut. J Immunof 170:3977-3985.

Fiocchi, C. 1998. Inflammatory bowel disease: etiology and pathogenesis. Gastroenterology 115: 182-205.

Szabo S.I et al. Molecular Mechanisms Regulating Thl Immune Responses. Annu. Rev. Immunol. 2003. 21:113-58.

The Merck Manual, 17th edition (1999), p. 307.

UCSF Med Fact Sheet Thyroid Autoantibodies (Jul. 7, 2003). Accessed on Apr. 6, 2011 at http://medicine.ucsf.edu/education/resed/Chiefs_cover_sheets/thyroid_antibodies.pdf).

Harii et al., Thyrocytes Express a Functional Toll-Like Receptor 3: Overexpression Can Be Induced by Viral Infection and Reversed by Phenylmethimazole and is Associated with Hasimoto's Autoimmune Thyroiditis, Molecular Endocrinology 2005, 19(5):1231-1250.

International Preliminary Report on Patentability, date of issuance of report Sep. 20, 2006, for Appln. No. PCT/US2004/007888, filed Mar. 16, 2004.

Written Opinion of the International Searching Authority, mailed Sep. 24, 2004, for Appl. No. PCT/US2004/007888, filed Mar. 16, 2004.

International Search Report, mailed Sep. 24, 2004, for PCT/2004/007888, filed Mar. 16, 2004.

Communication Pursuant to Article 94(3) EPC, dated Sep. 30, 2010 for Appln. No. EP20040821836, filed Sep. 18, 2006.

Communication Pursuant to Article 94(3) EPC, dated Dec. 8, 2009, for Appln. No. EP20040821836, filed Sep. 18, 2006.

Supplementary European Search Report under Article 153(7), dated Jul. 20, 2009, for Appln. No. EP20040821836, filed Sep. 18, 2006.

International Preliminary Report on Patentability, dated Nov. 27, 2006, for Appln. No. PCT/US2005/025067, filed Jul. 14, 2005.

Written Opinion of the Searching Authority, dated Dec. 15, 2005, for Appl. No. PCT/US2005/025067, filed Jul. 14, 2005.

International Search Report, dated Dec. 16, 2006, for Appl. No. PCT/US2005/025067, filed Jul. 14, 2005.

Communication Pursuant to Article 94(3) EPC, dated Jul. 17, 2009, for EP2005790042.5, filed Feb. 5, 2007.

Communication Pursuant to Article 96(2) EPC, dated Oct. 2, 2007, for EP2005790042.5, filed Feb. 5, 2007.

Annex I, dated Jan. 27, 2010, for Appln. No. EP2005790042.5, filed Feb. 5, 2007.

Preparation for Oral Proceedings, dated Oct. 5, 2010, for Appln. No. EP2005790042.5, filed Feb. 5, 2007.

Examination on Application Documents, dated Oct. 8, 2010, for Appln. No. EP2005790042.5, filed Feb. 5, 2007.

Minutes of the Oral Proceedings, dated Feb. 7, 2011, for Appln. No. EP2005790042.5, filed Feb. 5, 2007.

Summary of Facts and Submissions, dated Mar. 22, 2011, for Appln. No. EP2005790042.5, filed Feb. 5, 2007.

International Preliminary Report on Patentability, dated Nov. 20, 2007, for Appln. No. PCT/US2006/018554, filed May 11, 2006.

Written Opinion of the Searching Authority, dated Nov. 20, 2007, for Appln. No. PCT/US2006/018554, filed May 11, 2006.

International Search Report, dated Sep. 15, 2006, for Appln. No. PCT/US2006/018554, filed May 11, 2006.

Examiner's First Report, dated May 18, 2010, for Appln. No. AU2006/247504, filed Oct. 22, 2007.

Communication Pursuant to Rules 161 and 162 EPC, dated Jan. 29, 2008, for Appln. No. EP2006/770302, filed Dec. 14, 2007.

Communication Pursuant to Article 94(3) EPC, dated Mar. 24, 2009, for Appln. No. EP2006/770302, filed Dec. 14, 2007.

Communication Pursuant to Article 94(3) EPC, dated Nov. 2, 2011, for Appln. No. EP2006/770302, filed Dec. 14, 2007.

Communication Pursuant to Article 94(3) EPC, dated Jan. 17, 2012, for Appln. No. EP2006/770302, filed Dec. 14, 2007.

Summary of Facts and Submissions, for Appln. No. EP2006/770302, filed Dec. 14, 2007.

Moutaery, Ahmed Al, Methimazole Prevents Stress and Chemical Induced Gastropathy in Rats, Exp Toxic Pathol 2003, 55: pp. 277-285; http://www.elsevier-deutschland.de.

Restriction Requirement dated Apr. 14, 2011 from USPTO, pertaining to U.S. Appl. No. 12/286,880, filed Oct. 1, 2008.

Non-Final Office Action dated Feb. 4, 2010 from USPTO, pertaining to U.S. Appl. No. 10/912,948, filed Aug. 6, 2004.

Final Rejection dated Aug. 7, 2009 from USPTO, pertaining to U.S. Appl. No. 10/912,948, filed Aug. 6, 2004.

Non-Final Office Action dated Jan. 26, 2009 from USPTO, pertaining to U.S. Appl. No. 10/912,948, filed Aug. 6, 2004.

Advisory Action dated Oct. 2, 2008 from USPTO, pertaining to U.S. Appl. No. 10/912,948, filed Aug. 6, 2004.

(56) References Cited

OTHER PUBLICATIONS

Final Rejection dated May 7, 2008 from USPTO, pertaining to U.S. Appl. No. 10/912,948, filed Aug. 6, 2004.
Non-Final Office Action dated Jul. 13, 2007 from USPTO, pertaining to U.S. Appl. No. 10/912,948, filed Aug. 6, 2004.
Restriction Requirement dated Mar. 1, 2007 from USPTO, pertaining to U.S. Appl. No. 10/912,948, filed Aug. 6, 2004.
Non-Final Office Action dated Apr. 12, 2011 from USPTO, pertaining to U.S. Appl. No. 11/130,922, filed May 17, 2005.
Non-Final Office Action dated Nov. 13, 2009 from USPTO, pertaining to U.S. Appl. No. 11/130,922, filed May 17, 2005.
Restriction Requirement dated Apr. 17, 2009 from USPTO, pertaining to U.S. Appl. No. 11/130,922, filed May 17, 2005.
Restriction Requirement dated Aug. 7, 2007 from USPTO, pertaining to U.S. Appl. No. 11/130,922, filed May 17, 2005.
Non-Final Office Action dated Nov. 12, 2010 from USPTO, pertaining to U.S. Appl. No. 10/801,986, filed Mar. 16, 2004.
Advisory Action dated Jul. 27, 2009 from USPTO, pertaining to U.S. Appl. No. 10/801,986, filed Mar. 16, 2004.
Final Rejection dated Nov. 18, 2008 from USPTO, pertaining to U.S. Appl. No. 10/801,986, filed Mar. 16, 2004.
Final Rejection dated Feb. 5, 2008 from USPTO, pertaining to U.S. Appl. No. 10/801,986, filed Mar. 16, 2004.
Non-Final Office Action dated May 15, 2007 from USPTO, pertaining to U.S. Appl. No. 10/801,986, filed Mar. 16, 2004.
Restriction Requirement dated Jul. 27, 2006 from USPTO, pertaining to U.S. Appl. No. 10/801,986, filed Mar. 16, 2004.
European Examination Report dated Mar. 31, 2015, for EPO Application No. 06 770 302.5 filed May 11, 2006 entitled "Use of Phenylmethimazoles, Methimazole Derivatives, and Tautomeric Cyclic Thiones for the Treatment of Autoimmune/Inflammatory Diseases Associated Wtih Toll-Like Receptor Overexpression".
Canadian Examination Report dated Nov. 4, 2014, for Canadian Application No. 2,606,769 filed May 11, 2006 entitled Methods and Compositions for the Treatment of Autoimmune and Inflammatory Diseases Associated With Toll-Like Receptors.
Examination Report dated May 5, 2015 pertaining to European Patent Application No. 11 161 080.4.
Bengtsson, et al., Activation of Type I Interferon System in Systemic Lupus Erythematosus Correlates With Disease Activity but Not With Antiretroviral Antibodies, www.arnoldpublishers.com/journals, 2000, Lupus (2000) 9, pp. 664-671, Lund, Sweden.
Petros, et al., Effects of a Nitric Oxide Synthase Inhibitor in Humans With Septic Shock, Cardiovascular Research, 1994, pp. 34-39, vol. 28, St. George's Hospital and Medical School, London, United Kingdom.
Poltorak, et al., Defective LPS Signaling in C3H/HeJ and C57BL/10ScCr Mice: Mutations in Tlr4 Gene, www.sciencemag.org, 1998, vol. 282, pp. 2085-2088, USA.
Beutler, Inferences, Questions and Possibilities in Toll-Like Receptor Signalling, Nature Publishing Group, www.nature.com/nature, 2004, vol. 430, pp. 257-263, California, USA.
Gantner, et al., Collaborative Induction of Inflammatory Responses by Dectin-1 and Toll-Like Receptor 2, The Journal of Experimental Medicine, 2003, vol. 197, No. 9, pp. 1107-1117, USA.
Jones, et al., Differential Roles of Toll-Like Receptors in the Elicitation of Proinflammatory Responses by Macrophages, Ann Rheum Dis 2001, vol. 60, pp. iii6-iii12, Boston, MA, USA.
Zingarelli, et al., The Potential Role of Peroxynitrite in the Vascular Contractile and Cellular Energetic Failure in Endotoxic Shock, British Journal of Pharmacology, 1997, vol. 120, pp. 259-267, United Kingdom.
Bodgan, Nitric Oxide and the Immune Response, Nature Publishing Group, 2001, vol. 2, No. 10, pp. 907-916, Erlangen, Germany.
Grant, et al., DNA Binding and Transcription Activation by Chicken Interferon Regulatory Factor-3 (chIRF-3), Nucleic Acids Research, 2000, vol. 28, No. 23, pp. 4790-4799, Kingston, Ontario, Canada.
Feng, et al., An Alternate Pathway for Type 1 T Cell Differentiation, International Immunology, The Japanese Society for Immunology, 1999, vol. 11, No. 8, pp. 1185-1194, Japan.

Fiocchi, Intestinal Inflammation: A Complex Interplay of Immune and Nonimmune Cell Interactions, The American Physiological Society, 1997, pp. G769-G675, Cleveland, Ohio, USA.
Gagnon, et al., Peroxynitrite Production by Human Neutrophils, Monocytes and Lymphocytes Challenged With Lipopolysaccharide, Federation of European Biochemical Societies, 1998, pp. 107-110, Quebec, Canada.
Giuliani, et al., Hormonal Modulation of Major Histocompatibility Complex Class I Gene Expression Involves an Enhancer A-binding Complex Consisting of Fra-2 and the p50 Subunit of NF-kB*, The Journal of Biological Chemistry, 1995, pp. 11453-11462, vol. 27, No. 19, Bethesda, Maryland, USA.
Gonzalez, et al., Nitric Oxide From Endothelium and Smooth Muscle Modulates Responses to Sympathetic Nerve Stimulation: Implications for Endotoxin Shock, Biochemical and Biophysical Research Communication, 1992, pp. 150-156, vol. 186, No. 1, 1992, Academic Press, Inc., Salt Lake City, Utah, USA.
Ramos, et al., Direct Demonstration of P-Selectin- and VCAM-1-Dependent Mononuclear Cell Rolling in Early Atherosclerotic Lesions of Apolipoprotein E-Deficient Mice, American Heart Association, Inc, 1999, pp. 1237-1244, http://www.circresaha.org, USA.
Miceli-Richard, et al., Card15 Mutations in Blau Syndrome, Nature Publishing Group, , www.nature.com/nature, 2001, pp. 19-20, vol. 29, California, USA.
Szabo, Role of Nitric Oxide in Endotoxic Shock, Ann NY Acad. Sci., 1998, pp. 422-425, vol. 851, Ohio, USA.
Szabo, et al., Inhibition of the Production of Nitric Oxide and Vasodilator Prostaglandins Attenuates the Cardiovascular Response to Bacterial Endotoxin in Adrenalectomized Rats, The Royal Society, 1993, pp. 233-238, Proc Biol. Sci., vol. 253, Great Britain.
Wieland, et al., Pulmonary Inflammation Induced by Pseudomonas Aeruginosa Lipopolysaccharide, Phospholipase C, and Exotoxin A: Role of Interferon Regulatory Fact 1, Infection and Immunity, American Society for Microbiology, 2002, pp. 1352-1358, vol. 70, No. 3, USA.
Chakravortty, et al., Modulation of Barrier Function of Small Intestinal Epithelial Cells by Lamina Propria Fibroblasts in Response to Lipopolysaccharide: Possible Role of TNFx in Inducing Barrier Dysfunction, Microbiol Immunol., 1999, pp. 527-533, vol. 43, No. 6, National Center for Cell Science, Pune, India.
Bannerman, et al., A Constitutive Cytoprotective Pathway Protects Endothelial Cells from Lipopolysaccharide-Induced Apoptosis, The Journal of Biological Chemistry, 2001, pp. 14924-14932, vol. 276, No. 18, JBC Papers in Press, North Carolina, USA.
Danino, et al., Dynamin Family of Mechanoenzymes, Current Opinion in Cell Biology, 2001, pp. 454-460, vol. 13, Elsevier Science Ltd., USA.
Devendra, et al., Interferon Alpha-A Potential Link in the Pathogenesis of Viral-Induced Type 1 Diabetes and Autoimmunity, Clinical Immunology, 2004, pp. 225-233, vol. 111, Elsevier, USA.
Hawkins, et al., Human Interleukin 10 Suppresses Production of Inflammatory Mediators by LPS-Stimulated Equine Peritoneal Macrophages, Veterinary Immunology and Immunopathology, 1998, pp. 1-10, vol. 66, Elsevier, USA.
Panne, et al., Crystal Structure of ATF-2/c-Jun and IRF-3 Bound to the Interferon-B Enhancer, The EMBO Journal, 2004, pp. 4384-4393, vol. 23, No. 22, European Molecular Biology Organization, United Kingdom.
Schilling, et al., Toll-Like Receptor 4 and Toll-IL-1 Receptor Domain-Containing Adapter Protein (TIRAP)/Myeloid Differentiation Protein 88 Adapter-Like (Mal) Contribute to Maximal IL-6 Expression in Macrophages, The Journal of Immunology, 2002, pp. 5874-5880, vol. 169, The American Association of Immunologists, Inc., USA.
Smith, et al., IRF3 and IRF7 Phosphorylation in Virus-Infected Cells Does Not Require Double-Stranded RNA-Dependent Protein Kinase R or IkB Kinase but is Blocked by Vaccinia Virus E3L Protein, The Journal of Biological Chemistry, 2001, pp. 8951-8957, vol. 276, No. 12, The American Society for Biochemistry and Molecular Biology, Inc, USA.
Meylan, et al., RIP1 is an Essential Mediator of Toll-Like Receptor 3-Induced NF-kB Activation, Nature Immunology, 2004, pp. 503-507, vol. 5, No. 5, USA.

(56) References Cited

OTHER PUBLICATIONS

Mozes, et al., Spontaneous Autoimmune Disease in (NZB X NZW)F1 Mice is Ameliorated by Treatment with Methimazole, Journal of Clinical Immunology, 1998, pp. 106-113, vol. 18, No. 2, Plenum Publishing Company, New York, USA.
Hayashi, et al., The Innate Immune Response to Bacterial Flagellin is Mediated by Toll-Like Receptor 5, Nature, 2001, pp. 1099-1103, vol. 410, Macmillan Magazines, United Kingdom.
Luscinskas, et al., Monocyte Rolling, Arrest and Spreading on IL-4-Activated Vascular Endothelium Under Flow is Mediated via Sequential Action of L-Selectin, B1-Integrins, and B2-Integrins, The Journal of Cell Biology, 1994, pp. 1417-1427, vol. 125, No. 6, The Rockefeller University Press, New York, USA.
Andonegui, et al., Endothelium-Derived Toll-Like Receptor-4 is the Key Molecule in LPS-Induced Neutrophil Sequestration Into Lungs, The Journal of Clinical Investigation, 2003, pp. 1011-1020, vol. 111, No. 7, Maryland, USA.
Napolitano, et al., High Glucose Levels Increase Major Histocompatibility Complex Class I Gene Expression in Thyroid Cells and Amplify Interferon-y Action, Endocrinology, 2002, pp. 1008-1017, vol. 143, No. 3, USA.
Pasterkamp, et al., Role of Toll-Like Receptor 4 in the Initiation and Progression of Atherosclerotic Disease, European Journal of Clinical Investigation, 2004, pp. 328-334, vol. 34, Blackwell Publishing Ltd., Oxford, United Kingdom.
Hacker, et al., Immune cell Activation by Bacterial CpG-DNA Through Myeloid Differentiation Marker 88 and Tumor Necrosis Factor Receptor-Associated Factor (TRAF)6, The Journal of Experimental Medicine, 2000, pp. 595-600, vol. 192, No. 4, The Rockefeller University Press, New York, USA.
Hemmi, et al., The Roles of Two IkB Kinase-Related Kinases in Lipoplysaccharide and Double Stranded RNA Signaling and Viral Infection, The Journal of Experimental Medicine, 2004, pp. 1641-1650, vol. 199, No. 12, The Rockefeller University Press, New York, USA.
Hemmi, et al., Small Anti-Viral Compounds Activate Immune Cells via the TLR7 MyD88-Dependent Signaling Pathway, Department of Host Defense Research Institute for Microbial, Osaka University, 2002, pp. 196-200, vol. 3, No. 2, Nature Publishing Group, California, USA.
Ochi, et al., Hyperosmotic Stimuli Inhibit VCAM-1 Expression in Cultured Endothelial Cells Via Effects on Interferon Regulatory Factor-1 Expression and Activity, Eur. J. Immunol, 2002, pp. 1821-1831, vol. 32, Wiley-VCH Verlag Journal, Germany.
Oshiumi, et al., TIR-Containing Adapter Molecule (TICAM)-2, A Bridging Adapter Recruiting to Toll-Like Receptor 4 TICAM-1 That Induces Interferon-B, The Journal of Biological Chemistry by the American Society for Biochemistry and Molecular Biology, Inc., 2003, pp. 49751-49762, vol. 278, No. 50, http://www.jbc.org, USA.
Wekerle, The Viral Triggering of Autoimmune Disease, Nature Medicine, 1998, pp. 770-771, vol. 4, No. 7, Nature Publishing Group, http://www.nature.com/naturemedicine, USA.
Avontuur, et al., Inhibition of Nitric Oxide Synthesis Causes Myocardial Ischemia in Endotoxemic Rats, Circulation Research, 1995, pp. 418-425, vol. 76, CrossMark, American Heart Association Journals, circres.ahajournals.org/content/76/3/418.full, USA.
Gohda, et al., Cutting Edge: TNFR-Associated Factor (TRAF) 6 is Essential for MyD88-Dependent Pathway but Not Toll/IL-1 Receptor Domain-Containing Adaptor-Inducing IFN-B (TRIF)-Dependent Pathway in TLR Signaling, The Journal of Immunology, 2004, pp. 2913-2917, vol. 173, The American Association of Immunologists, Inc., http://www.jimmunol.org, USA.
Hiscott, et al., Convergence of the NF-kB and Interferon Signaling Pathways in the Regulation of Antiviral Defense and Apoptosis, Lady David Institute for Medical Research, 2003, pp. 237-248, Annals of the New York Academy of Sciences, USA.
Moore, et al., Endotoxemia Following Experimental Intestinal Strangulation Obstruction in Ponies, Canadian Journal of Comparative Medicines, 1980, pp. 330-332, vol. 45, U.S. National Library of Medicine National Institutes of Health, USA.

Xu, et al., Enhanced Expression of Nicotinamide N-Methyltransferase in Human Papillary Thyroid Carcinoma Cells, The Journal of Clinical Endocrinology & Metabolism, 2003, pp. 4990-4996, vol. 88, No. 10, The Endocrine Society, USA.
Fitzgerald, et al., LPS-TLR4 Signaling to IRF-3/7 and NF-kB Involves the Toll Adapters TRAM and TRIF, The Journal of Experimental Medicine, 2003, pp. 1043-1055, vol. 198, No. 7, The Rockefeller University Press, New York, USA.
Fitzgerald, et al., IKKe and TBKI are Essential Components of the IRF3 Signaling Pathway, Nature Immunology, 2003, pp. 491-496, vol. 4, No. 5, Nature Publishing Group, USA.
Fitzgerald, et al., Mal (MyD88-Adapter-Like) is Required for Toll-Like Receptor-4 Signal Transduction, Nature Immunology, 2001, pp. 78-83, vol. 413, 2001 Macmillan Magazines Ltd., London, England.
Ryan, et al., Reactive Oxygen and Nitrogen Species Differentially Regulate Toll-Like Receptor 4-Mediated Activation of NF-kB and Interleukin-8 Expression, Infection and Immunity, 2004, pp. 2123-2130, American Society for Microbiology, USA.
Hoebe, et al., Identification of Lps2 as a Key Transducer of MyD88-Independent TIR Signalling, Nature Immunology, 2003, pp. 743-748, vol. 424, Nature Publishing Group, USA.
Canadian Examination Report, dated Jan. 16, 2014, for Canadian Application No. 2,606,769 filed May 11, 2006 entitled Methods and Compositions for the Treatment of Autoimmune and Inflammatory Diseases Associated With Toll-Like Receptors.
Dagia et al., "Phenyl Methimazole Inhibits TNF-ox-Induced VCAM-1 Expression in an IFN Regulatory Factor-1-Dependent Manner and Reduces Monocytic Cell Adhesion to Endothelial Cells".
Examiner's Report dated Aug. 6, 2015 pertaining to Canadian Patent Application No. 2,606,769.
Hoshino, et al., Differential Involvement of IFN-B in Toll-Like Receptor-Stimulated Dendritic Cell Activation, International Immunology, 2002, pp. 1225-1231, vol. 14, No. 10, The Japanese Society for Immunology, Japan.
Hoshino, et al., Cutting Edge: Toll-Like Receptor 4 (TLR4)-Deficient Mice are Hyporesponsive to Lipopolysaccharide: Evidenice for TLR4 as theLps Gene Product1, Nature Immunology, 1999, pp. 3749-3752, vol. 162, The American Associate of Immunologist, USA.
Ishii, et al., Genomic DNA Released by Dying Cells Induces the Maturation of APCs1,2, Nature Immunology, 2001, pp. 2602-2607, vol. 167, The American Association of Immunologists, USA.
Kopydlowski, et al., Regulation of Macrophage Chemokine Expression by Lipopolysaccharide In Vitro and In Vivo1, Nature Immunology, 1999, pp. 1537-1544, vol. 163, The American Association of Immunologists, USA.
Ruckdeschel, et al., Divergence of Apoptosis-Inducing and Preventing Signals in Bacteria-Faced Macrophages Through Myeloid Differentiation Factor 88 and IL-1 Receptor-Associated Kinase Members1, Nature Immunology, 2002, pp. 4601-4611, vol. 168, The American Association of Immunologists, USA.
Michelsen, et al., TLR Signaling: An Emerging Bridge from Innate Immunity to Atherogensis1, Nature Immunology, 2004, pp. 5901-5907, vol. 173, The American Association of Immunologists, USA.
Michelsen, et al., Lack of Toll-Like Receptor 4 or Myeloid Differentiation Factor 88 Reduced Atherosclerosis and Alters Plaque Phenotype in Mice Deficient in Apolipoprotein E, Proceedings of the National Academy of Sciences, 2004, pp. 10679-10684, vol. 101, No. 29, The National Academy of Sciences of the USA.
Suzuki, et al., Transfection of Single-Stranded Hepatitis A Virus RNA Activates MHC Class I Pathway, Clinical Exp. Immunology, 2002, pp. 234-242, vol. 127, Blackwell Science, Oxford, United Kindgom.
Takeda, et al., Enhanced Th1 Activity and Development of Chronic Enterocolitis in Mice Devoid of Stat3 in Macrophages and Neutrophils, Immunity, 1999, pp. 39-49, vol. 10, Cell Press, Cambridge, Massachusetts, USA.
Takeda, et al., Toll-Like Receptors in Innate Immunity, International Immunity, 2005, pp. 1-14, vol. 17, No. 1, The Japanese Society for Immunology, Japan.

(56) References Cited

OTHER PUBLICATIONS

Eader, et al., Induction of Multiple Cytokine Gene Expression and IRF-1 mRNA by Flavone Acetic Acid in a Murine Macrophage Cell Line1, Cellular Immunology, 1994, pp. 211-222, vol. 157, Academic Press, Inc., Waltham, Massachusetts, USA.

Alexopoulou, et al., Recognition of Double-Stranded RNA and Activation of NF-kB by Toll-Like Receptor 3, Nature, 2001, pp. 732-738, vol. 413, Macmillan Magazines, Ltd., United Kingdom Farkas, et al., Plasmacytoid Dendritic Cells (Natural Interferon-Producing Cells) Accumulate in Cutaneous Lupus.

Farkas, et al., Plasmacytoid Dendritic Cells (Natural Interferon-Producing Cells) Accumulate in Cutaneous Lupus Erythematosus Lesions, American Journal of Pathology, 2001, pp. 237-243, vol. 159, vol. 1, American Society for Investigative Pathology, USA.

Guillot, et al., Response of Human Pulmonary Epithelial Cells to Lipopolysaccharide Involves Toll-Like Receptor 4 (TLR4)-dependent Signaling Pathways, The Journal of Biological Chemistry, 2004, pp. 2712-2718, vol. 279, No. 4, The American Society for Biochemistry and Molecular Biology, Inc., USA.

Guillot, et al., Involvement of Toll-like Receptor 3 in the Immune Response of Lung Epithelial Cells to Double-stranded RNA and Influenza A Virus, The Journal of Biological Chemistry, 2005, pp. 5571-5580, vol. 280, No. 7, The American Society for Biochemistry and Molecular Biology, Inc., http://www.jbc.org, USA.

Wen, et al., The Effect of Innate Immunity on Autoimmune Diabetes and the Expression of Toll-Like Receptors on Pancreatic Islets, The Journal of Immunology, 2004, pp. 3173-3180, vol. 172, The American Association of Immunologists, Inc., USA.

Dobrovolskaia, et al., Toll Receptors, CD14, and Macrophage Activation and Deactivation by LPA, 2002, Microbes and Infection, pp. 903-914, vol. 4, www.elsevier.com/locate/micinf, USA.

Delgado, et al., Vasoactive Intestinal Peptide and Pituitary Adenylate Cyclase-Activating Polypeptide Prevent Inducible Nitric Oxide Synthase Transcription in Macrophages by Inhibiting NF-kB and IFN Regulatory Factor 1 Activation, The Journal of Immunology, 1999, pp. 4685-4696, vol. 162, The American Association of Immunologists, USA.

Prummel, et al., Interferon-a and Autoimmune Thyroid Disease, Thyroid, 2003, pp. 547-551, vol. 13, No. 6, Mary Ann Liebert, Inc., New York, USA.

Fujimoto, et al., A Role for iNOS in Fasting Hyperglycemia and Impaired Insulin Signaling in the Liver of Obese Diabetic Mice, Diabetes, 2005, pp. 1340-1348, vol. 54, The American Diabetes Association, USA.

Hashimoto, et al., Separation and Structural Analysis of Lipoprotein in a Lipopolysacchiraide Preparation from Porphyromonas Gingivalis, International Immunology, 2004, pp. 1431-1437, vol. 16, No. 10, The Japanese Society for Immunology, Japan.

Servant, et al., Identification of Distinct Signaling Pathways Leading to the Phosphorylation of Interferon Regulatory Factor 3, The Journal of Biological Chemistry, 2001, pp. 355-363, vol. 376, No. 1, The American Society of Biochemistry and Molecular Biology, Inc., USA.

Servant, et al., Identification of the Minimal Phosphoacceptor Site Required for in Vivo Activation of Interferon Regulatory Factor 3 in Response to Virus and Double-stranded RNA, The Journal of Biological Chemistry, 2003, pp. 9441-9447, vol. 278, No. 11, The American Society of Biochemistry and Molecular Biology, Inc., USA.

Servant, et al., Overlapping and Distinct Mechanisms Regulating IRF-3 and IRF-7 Function, Journal of Interferon and Cytokine Research, 2002, pp. 49-58, vol. 22, Mary Ann Liebert, Inc., New York, USA.

Karaghiosoff, et al., Central Role for Type I Interferons and Tyk2 in Lipopolysaccharide-Induced Endotoxin Shock, Natural Immunology, 2003, pp. 471-477, vol. 4, No. 5, www.nature.com/natureimmunology, Nature Publishing Group, California, USA.

Miettinen, et al., IFNs Activate Toll-Like Receptor Gene Expression in Viral Infections, Genes and Immunity, 2001, pp. 349-355, vol. 2, Nature Publishing Group, California, USA.

Muzio, et al., Differential Expression and Regulation of Toll-Like Receptors (TLR) in Human Leukocytes: Selective Expression of TLR3 in Dendritic Cells1, Journal of Immunology, 2000, pp. 5998-6004, vol. 164, The American Association of Immunologists, USA.

Baker, et al., Interferon Regulatory Factor-1 Down-Regulates Cytokine-Induced IP-10 Expression in Pancreatic Islets, Surgery, 2003, pp. 134-141, vol. 134, Mosby, Inc., Missouri, USA.

Horwitz, et al., Diabetes Induced by Coxsackie Virus: Initiation by Bystander Damage and Not Molecular Mimicry, Nature Medicine, 1998, pp. 781-785, vol. 4, No. 7, Nature Publishing Group, California, USA.

Schnare, et al., Recognition of CpG DNA is Mediated by Signaling Pathways Dependent on the Adaptor Protein MyD88, Current Biology, 2000, pp. 1139-1142, vol. 10, Elsevier Science Ltd., USA.

Yamamoto, et al., TRAM is Specifically Involved in the Toll-Like Receptor 4-Mediated MyD88-Independent Signaling Pathway, Nature Immunology, 2003, pp. 1144-1150, vol. 4, No. 11, Nature Publishing Group, California, USA.

Yamamoto, et al., Essential Role for TIRAP in Activation of the Signalling Cascade Shared by TLR2 and TLR4, Nature, 2002, www.nature.com/nature, pp. 324-329, vol. 420, Nature Publishing Group, California, USA.

Riedemann, et al., The Enigma of Sepsis, The Journal of Clinical Investigation, 2003, pp. 460-467, vol. 112, No. 4, www.jci.org/articles/view/19523.

Harii, et al., Thyrocytes Express a Functional Toll-Like Receptor 3: Overexpression Can Be Induced by Viral Infection and Reversed by Phenylmethimazole and is Associated with Hashimoto's Autoimmune Thyroiditis, Molecular Endorinology, 2005, pp. 1231-1250, vol. 18, No. 5, The Encocrine Society, USA.

McCartney-Francis, et al ., Dysregulation of IFN-y Signaling Pathways in the Absence of TGF-b1, The Journal of Immunology, 2002, pp. 5941-5947, vol. 169, http://jimmunol.org, The American Association of Immunologists, Inc., USA.

Kobayashi, et al., Cyclooxygenase-2 Downregulates Inducible Nitric Oxide Synthase in Rat Intestinal Epithelial Cells, American Journal Physiol Gastrointest Liver Physiol, 2001, pp. 688-696, vol. 281, http://www.ajpgi.org, The American Physiological Society, USA.

Takeuchi, et al., Cellular Responses to Bacterial Cell Wall Components are Mediated Through MyD88-Dependent Signaling Cascades, International Immunology, 2000, pp. 113-117, vol. 12, No. 1., The Japanese Society for Immunology, Japan.

Tliba, et al., Tumor Necrosis Factor x Modulates Airway Smooth Muscle Function via the Autocrine Action of Interferon 13*, The Journal of Biological Chemistry, 2003, pp. 50615-50623, vol. 278, No. 50, The American Society for Biochemistry and Molecular Biology, Inc., USA.

Wolkow, Involvement and Dual Effects of Nitric Oxide in Septic Shock, Inflammation Research, 1998, pp. 152-166, vol. 47, Birkhaeuser Verlag, Basel, Switzerland.

Schmid, et al., The Type I Interferon System is Locally Activated in Psoriatic Lesions, Journal of Interferon Research, 1994, pp. 229-234, vol. 14, Mary Ann Liebert, Inc., Publishers, New York, USA.

Gianani, et al., Viruses, Cytokines, Antigens, and Autoimmunity, Proceedings of the National Academy of Sciences, 1996, pp. 2257-2259, vol. 93, USA.

Kamijo, et al., Requirement for Transcription Factor IRF-1 in NO Synthase Induction in Macrophages, Science, 1994, pp. 1612-1615, vol. 263, Journal Storage, USA.

Pine, et al., Tyrosine Phosphorylated p91 Binds to a Single Element in the ISGF2/IRF-1 Promoter to Mediate Induction by IFNx and IFNy, and is Likely to Autoregulate the p91, The EMBO Journal, 1994, pp. 158-167, vol. 13, No. 1, Oxford University Press, New York, USA.

Doyle, et al., IRF3 Mediates a TLR3/TLR4-Specific Antiviral Gene Program, Immunity, 2002, pp. 251-263, vo. 17, Cell Press, Maryland Heights, Missouri, USA.

Doyle, et al., Toll-Like Receptor 3 Mediates a More Potent Antiviral Response Than Toll-Like Receptor 4', The Journal of Immunology, 2003, pp. 3565-3571, The American Association of Immunologists, Inc., Bethesda, Maryland, USA.

(56) References Cited

OTHER PUBLICATIONS

Heinz, et al., Species-Specific Regulation of Toll-Like Receptor 3 Genes in Men and Mice, The Journal of Biological Chemistry, 2003, pp. 21502-21509, vol. 278, No. 24, http://www.jbc.org, The American Society for Biochemistry and Molecular Biology, Inc., Rockville, Maryland, USA.

Taniguchi, et al., Iodide Suppression of Major Histocompatibility Class I Gene Expression in Thyroid Cells Involves Enhancer A and the Transcription Factor NF-kB, Molecular Endocrinology, 1998, pp. 19-33, The Endocrine Society, Chase, Maryland, USA.

Sarkar, et al., Novel Roles of TLR3 Tyrosine Phosphorylation and PI3 Kinase in Double-Stranded RNA Signaling, Nature Structural & Molecular Biology, 2004, pp. 1060-1070, vol. 11, No. 11, Nature Publishing Group, Boston, Massachusetts, USA.

Diebold, et al., Viral Infection Switches Non-Plasmacytoid Dendritic Cells Into High Interferon Producers, Nature, 2003, pp. 324-328, vol. 424, Nature Publishing Group, Boston, Massachusetts, USA.

Sato, et al. A Variety of Microbial Components Induce Tolerance to Lipopolysaccharide by Differentially Affecting MyD88-Dependent and -Independent Pathways, International Immunology, 2002, pp. 783-791, vol. 14, No. 7, The Japanese Society of Immunology, Japan.

Sato, et al., Toll/IL-1 Receptor Domain-Containing Adaptor Inducing IFN-B (TRIF) Associates with TNF Receptor-Associated Factor 6 and Tank-Binding Kinase 1, and Activates Two Distinct Transcription Factors, NF-kB and IFN-Regulatory Factor-3, in the Toll-Like Receptor Signaling1, The Journal of Immunology, 2003, pp. 4304-4310, The American Association of Immunologists, Inc., Bethesda, Maryland, USA.

Sharma, et al., Triggering the Interferon Antiviral Response Through an IKK-Related Pathway, Science, 2003, pp. 1148-1151, vol. 300, www.sciencemag.org, Washington D.C., USA.

Uematsu, et al., Lipopolysaccharide-Dependent Prostaglandin E2 Production is Regulated by the Glutathione-Dependent Prostaglandin E2 Synthase Gene Induced by the Toll-Like Receptor 4/MyD88/NF-IL6 Pathway, The Journal of Immunology, 2002, pp. 5811-5816, The American Association of Immunologists, Inc., Bethesda, Maryland, USA.

Horng, et al., TIRAP: An Adapter Molecule in the Toll Signaling Pathway, Nature Immunology, 2001, pp. 835-841, vol. 2, No. 9, Nature Publishing Group, California, USA.

Horng, et al., The Adaptor Molecule TIRAP Provides Signalling Specificity for Toll-Like Receptors, Nature, 2002, pp. 329-333, vol. 420, Nature Publishing Group, California, USA.

Ito, et al., Interferon-x and Interleukin-12 are Induced Differentially by Toll-Like Receptor 7 Ligands in Human Blood Dendritic Cell Subsets, Journal of Experimental Medicine, 2002, pp. 1507-1512, vol. 1945, No. 11, The Rockefeller University Press, New York, USA.

Kawai, et al., Unresponsiveness of MyD88-Deficient Mice to Endotoxin, Immunity, 1999, pp. 115-122, vol. 11, Cell Press, Cambridge, Massachusetts, USA.

Kawai, et al., Lipopolysaccharide Stimulates the MyD88-Independent Pathway and Results in Activation of IFN-Regulatory Factor 3 and the Expression of a Subset of Lipopolysaccharide-Inducible Genes1, The Journal of Immunology, 2001, pp. 5887-5894, vol. 167, The American Association of Immunologists, Bethesda, Maryland, USA.

Liu, et al., Reactive Oxygen Species Mediate Virus-Induced STAT Activation, The Journal of Biological Chemistry, 2004, pp. 2461-2469, vol. 279, No. 4, The American Society for Biochemistry and Molecular Biology, Inc., Rockville, Maryland, USA.

Nakazawa, et al., Complete Suppression of Insulitis and Diabetes in NOD Mice Lacking Interferon Regulatory Factor-1, Journal of Autoimmunity, 2001, pp. 119-125, vol. 17, Academic Press, Inc., Waltham, Massachusetts, USA.

Ogawa, et al., Cell Activation by Porphyromonas Gingivalis Lipid A Molecule Through Toll-Like Receptor 4- and Myeloid Differentiation Factor 88-Dependent Signaling Pathway, International Immunology, 2002, pp. 1325-1332, vol. 14, No. 11, The Japanese Society for Immunology, Japan.

Watanabe, et al., NOD2 is a Negative Regulator of Toll-Like Receptor 2-Mediated T Helper Type 1 Responses, Nature Immunology, 2004, pp. 800-808, vol. 5, No. 8, Nature Publishing Group, California, USA.

Toshchakov, et al., TLR2 and TLR4 Agnoists Stimulate Unique Repertoires of Host Resistance Genes in Murine Macrophages: Interferon-B-Dependent Signaling in TLR4-Mediated Responses, Journal of Endotoxin Research, 2003, pp. 169-175, vol. 9, No. 3, W.S. Maney & Son Ltd., Philadelphia, PA, USA.

Raschke, et al., Functional Macrophage Cell Lines Transformed by Abelson Leukemia Virus, Cell, 1978, pp. 261-267, vol. 15, Massachusetts Institute of Technology, Massachusetts, USA.

Teng, et al., Molecular Mechanisms of iNOS Induction by IL-1B and IFN-y in Rat Aortic Smooth Muscle Cells, American Journal of Physiol Cell, 2002, pp. C144-C152, vol. 282, The American Physiological Society, Bethesda, Maryland, USA.

Li, et al., Role of p38x Map Kinase in Type I Interferon Signaling, The Journal of Biological Chemistry, 2004, pp. 970-979, vol. 279, No. 2, The American Society of Biochemistry and Molecular Biology, Inc., Rockville, Maryland, USA.

Nakashima, et al., Upregulation of VCAM-1 and ICAM-1 at Atherosclerosis-Prone Sites on the Endothelium in the ApoE-Deficient Mouse, Arterioscler Thrombosis Vascular Biology, 1998, pp. 845-851, vol. 18, American Heart Association, Inc., Dallas, Texas, USA.

Ohmori, et al., Synergy Between Interferon-y and Tumor Necrosis Factor-x in Transcriptional Activation is Mediated By Cooperation Between Signal Transducer and Activator of Transcription 1 and Nuclear Factor kB, The Journal of Biological Chemistry, 1997, pp. 14899-14907, vol. 23, The American Society of Biochemistry and Molecular Biology, Inc., Rockville, Maryland, USA.

Ohmori, et al., Requirement for STAT1 in LPS-Induced Gene Expression in Macrophages, Journal of Leukocyte Biology, 2001, pp. 598-604, vol. 69, http://www.jleukbio.org.

Pang, et al., Analysis of Genes Differentially Expressed in Astrocytes Stimulated with Lipopolysaccharide Using cDNA Arrays, Brain Research, 2001, pp. 15-22, vol. 914, www.elsevier.com/locate/bres, Elsevier Science B.V., Ithaca, New York, USA.

Jiang, et al., Toll-Like Receptor 3-Mediated Activation of Nf-kB and IRF3 Diverges at Toll-IL-1 Receptor Domain-Containing Adapter Inducing IFN-b, Proceedings of the National Academy of Sciences, 2004, pp. 3533-3538, vol. 101, No. 10, The National Academy of Sciences of the USA.

Fan, et al., Molecular Mechanisms of Endotoxin Tolerance, Journal of Endotoxin Research, 2004, vol. 10, No. 2, W.S. Maney & Son Ltd., Philadelphia, PA, USA.

Moore, et al., Prevention of Endotoxin-Induced Arterial Hypoxaemia and Lactic Acidosis With Flunixin Meglumine in the Conscious Pony, Equine Veterinary Journal, 1981, pp. 95-98, vol. 13, No. 2, Journal of Equine Veterinary Science, Philadelphia, PA, USA.

Kohn, et al., Toll-Like Receptors in Nonimmune Cells and Environmental Induction of the Pathologic Expression of Innate Immunity and Autoimmune Inflammatory Diseases: A New Therapeutic Opportunity, Research Ohio, 2005, pp. 1-23, vol. 15, A joint publication of Ohio University College of Osteopathic Medicine and the Ohio Osteopathic Foundation, Ohio, USA.

Mundschau, et al., Platelet-Derived Growth Factor Signal Transduction Through the Interferon-Inducible Kinase PKR, The Journal of Biological Chemistry, 1995, pp. 3100-3106, vol. 270, No. 7, The American Society for Biochemistry and Molecular Biology, Inc., Rockville, Maryland, USA.

Ivanovic, et al., Acute-Phase Protein Expression in DMSO-Intoxicated Rats, Toxicology Letters, 2004, pp. 153-159, Elsevier Ireland Ltd., Ireland.

Yamamoto, et al., Role of Adaptor TRIF in the MyD88-Independent Toll-Like Receptor Signaling Pathway, Science, New Series, 2003, pp. 640-643, vol. 301, No. 5633, American Association for the Advancement of Science, USA.

Wang, et al., Nitric Oxide—To Block or Enhance Its Production During Sepsis?, Archives of Surgery, 1994, pp. 1137-1143, vol. 129, American Medical Association Publishing Group, Chicago, IL, USA.

(56) References Cited

OTHER PUBLICATIONS

Kirchhoff, et al., NFkB Activation is Required for Interferon Regulatory Factor-1-Mediated Interferon B Induction, European Biochemical Societies, 1999, pp. 546-554, vol. 26, Blackwell Publishing Ltd., Oxford, United Kingdom.

Raghavendra, et al., Gene Expression Analysis of Spontaneously Hypertensive Rat Cerebral Cortex Following Transient Focal Cerebral Ischemia, Journal of Neurochemistry, 2002, pp. 1072-1086, vol. 83, International Society for Neurochemistry, Wiley Blackwell, Hoboken, New Jersey, USA.

Morris, Endotoxemia Horses, A Review of Cellular and Humoral Mediators Involved in its Pathogenesis, 1991, pp. 167-181, vol. 5, Blackwell Publishing, Oxford, United Kingdom.

Guardiola, et al., Control of MHC Class II Gene Expression in Autoimmune Infectious, and Neoplastic Diseases, Critical Reviews in Immunology, 1993, pp. 247-268, vol. 13, Nos. 3 and 4, CRC Press, Inc., Boca Raton, Florida, USA.

Imagawa, et al., Autoimmune Endocrine Disease Induced by Recombinant Interferon-x Therapy for Chronic Active Type C Hepatitis, Journal of Clinical Endocrine Society, 1995, pp. 922-926, vol. 80, No. 3, The Endrocine Society, Chevy Chase, Maryland, USA.

Burrows, Equine *Escherichia coli* Endotoxemia: Comparison of Intravenous and Intraperitoneal Endotoxin Administration, American Journal of Veterinary Research, 1979, pp. 991-998, vol. 40, American Veterinary Medical Association, Schaumburg, Illinois, USA.

Kohn, et al., Graves' Disease: A Host Defense Mechanism Gone Awry, International Reviews of Immunology, 2000, pp. 633-664, vol. 19, Overseas Publishers Association, The Harwood Academic Publishers, Malaysia.

Tomer, et al., Infection, Thyroid Disease, and Autoimmunity, Endocrine Reviews, 1993, pp. 107-120, vol. 14, No. 1, The Endocrine Society, Chevy Chase, Maryland, USA.

Mozes, et al., Modulation of Experimental Systemic Lupus Erythematosus, Israel Journal of Medical Sciences, 1996, pp. 19-21, vol. 32, Israel Medical Association, Israel.

Roitt, Essential Immunology, 7th Edition, 1991, Introduction (2 pages), pp. 312-346, Blackwell Scientific Publications, London, England.

Drabkova, Emergency Care and Resuscitation in Patients at Risk for Endotoxic Shock, Cesk Epidemiol Mikrobiol Imunol, 1992, English Abstract (1 page), pp. 102-105, vol. 42, Gr. T. Popa Publishing House, Iasi, Romania.

\* cited by examiner

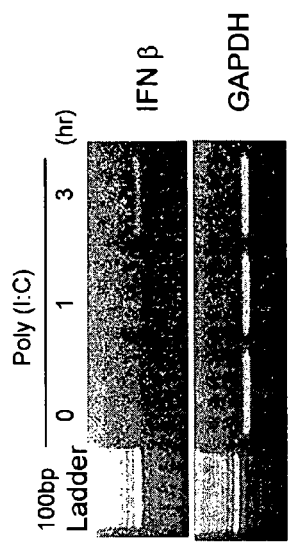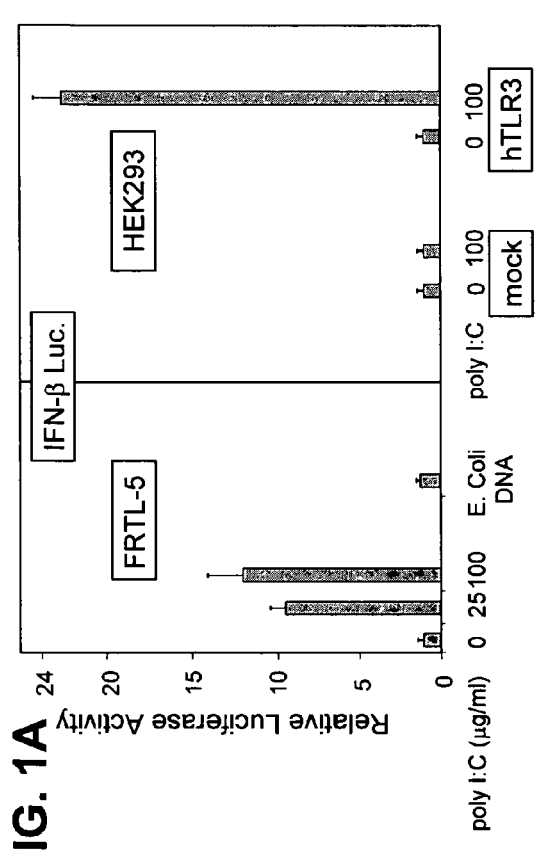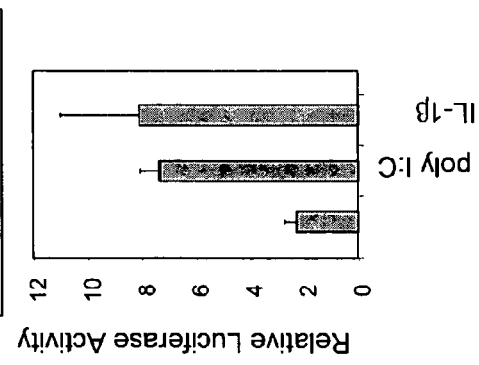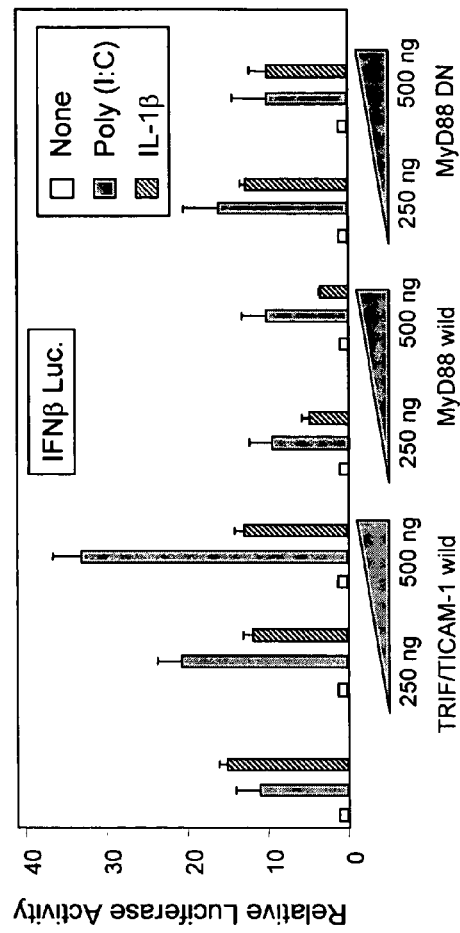

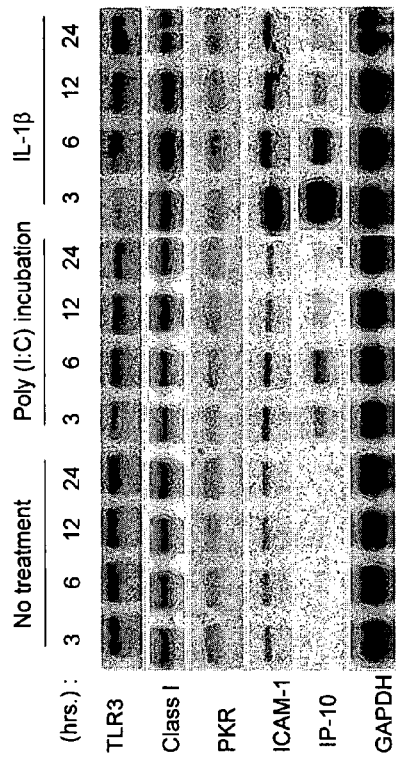
FIG. 2A
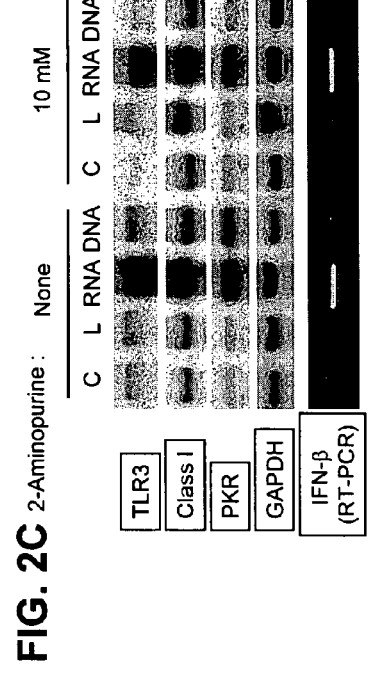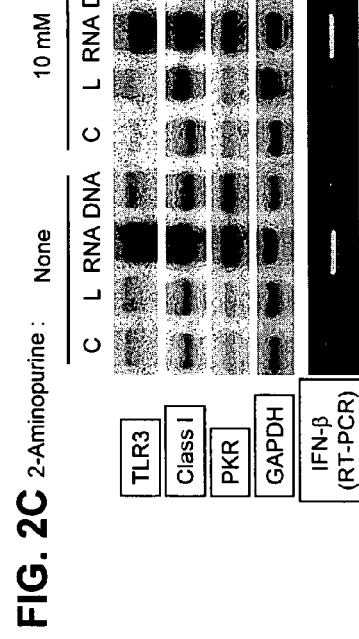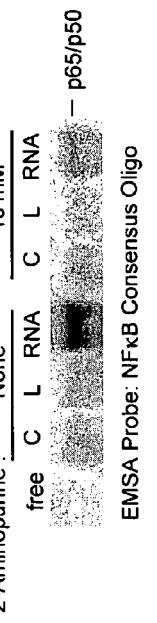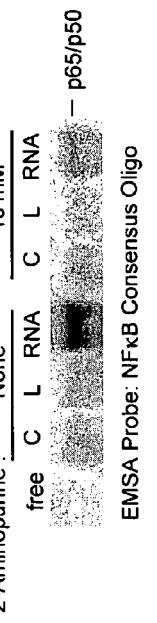
FIG. 2C
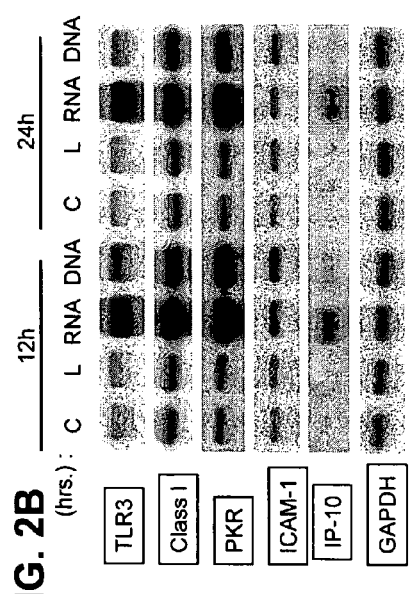
FIG. 2B

C10 reduces Stat1 activation in mice which are protected from LPS induced endotoxic shock

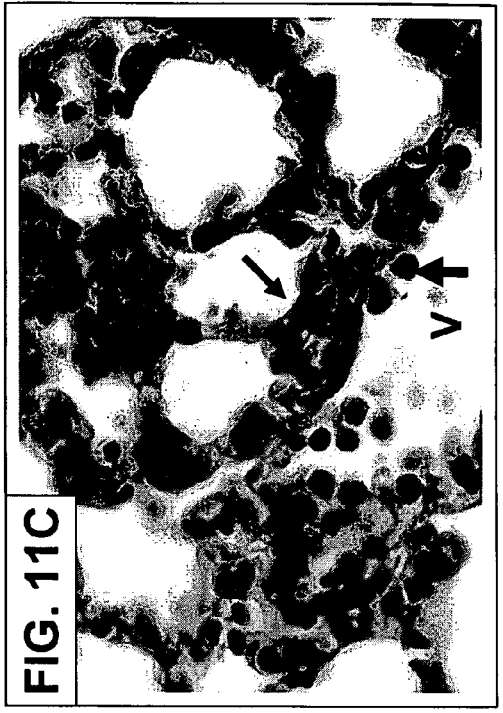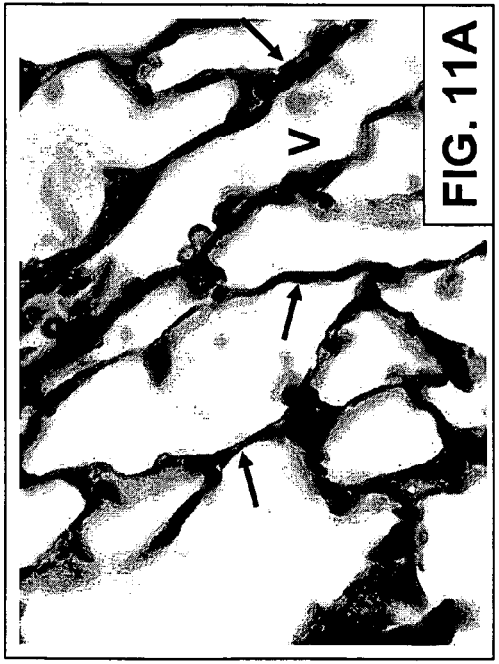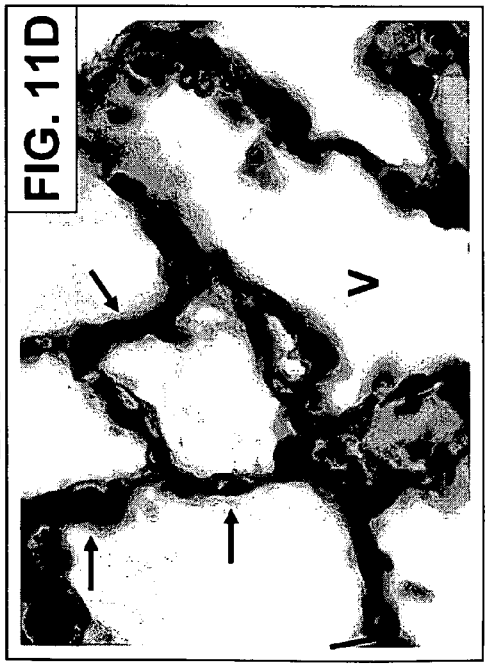

```
SEQUENCE LISTING

<160> NUMBER OF SEQ ID NOS: 34

<210> SEQ ID NO 1
<211> LENGTH: 15
<212> TYPE: DNA
<213> ORGANISM: Artificial sequence
<220> FEATURE:
<223> OTHER INFORMATION: ISRE-Luc NF- kB-Luc reporter element

<400> SEQUENCE: 1
tagtttcact ttccc                                                   15

<210> SEQ ID NO 2
<211> LENGTH: 14
<212> TYPE: DNA
<213> ORGANISM: Artificial sequence
<220> FEATURE:
<223> OTHER INFORMATION: ISRE-Luc NF- kB-Luc reporter element

<400> SEQUENCE: 2 tggggactttt ccgc                                                   14

<210> SEQ ID NO 3
<211> LENGTH: 15
<212> TYPE: DNA
<213> ORGANISM: Artificial sequence
<220> FEATURE:
<223> OTHER INFORMATION: NF- kB reporter element

<400> SEQUENCE: 3
tagtttcact ttccc                                                   15

<210> SEQ ID NO 4
<211> LENGTH: 14
<212> TYPE: DNA
<213> ORGANISM: Artificial sequence
<220> FEATURE:
<223> OTHER INFORMATION: NF- kB reporter element

<400> SEQUENCE: 4 tggggactttt ccgc                                                   14

<210> SEQ ID NO 5
<211> LENGTH: 30
<212> TYPE: DNA
<213> ORGANISM: Artificial sequence
<220> FEATURE:
<223> OTHER INFORMATION: TLR3 primer

<400> SEQUENCE: 5
ccatcagcac catgaaccca agtcctgccg                                   30

<210> SEQ ID NO 6
<211> LENGTH: 30
```

```
<212> TYPE: DNA
<213> ORGANISM: Artificial sequence
<220> FEATURE:
<223> OTHER INFORMATION: TLR3 primer

<400> SEQUENCE: 6
ggacgtcctc ctcatcgtcg actacactgg                                    30

<210> SEQ ID NO 7
<211> LENGTH: 22
<212> TYPE: DNA
<213> ORGANISM: Artificial sequence
<220> FEATURE:
<223> OTHER INFORMATION: Human IFN-beta primer

<400> SEQUENCE: 7
tggcaattga atgggaggct tg                                            22

<210> SEQ ID NO 8
<211> LENGTH: 24
<212> TYPE: DNA
<213> ORGANISM: Artificial sequence
<220> FEATURE:
<223> OTHER INFORMATION: Human IFN-beta primer

<400> SEQUENCE: 8
tccttggcct tcaggtaatg caga                                          24

<210> SEQ ID NO 9
<211> LENGTH: 32
<212> TYPE: DNA
<213> ORGANISM: Artificial sequence
<220> FEATURE:
<223> OTHER INFORMATION: Human IFN-beta promoter sequence primer

<400> SEQUENCE: 9
cagggtaccg agttttagaa actactaaaa tg                                 32

<210> SEQ ID NO 10
<211> LENGTH: 25
<212> TYPE: DNA
<213> ORGANISM: Artificial sequence
<220> FEATURE:
<223> OTHER INFORMATION: Human IFN-beta promoter sequence primer

<400> SEQUENCE: 10
gtactcgagc aaaggcttcg aaagg                                         25

<210> SEQ ID NO 11
<211> LENGTH: 22
<212> TYPE: DNA
<213> ORGANISM: Artificial sequence
<220> FEATURE:
<223> OTHER INFORMATION: NF- kB probe

<400> SEQUENCE: 11
agttgagggg actttcccag gc                                            22

<210> SEQ ID NO 12
<211> LENGTH: 21
<212> TYPE: DNA
<213> ORGANISM: Artificial sequence
<220> FEATURE:
<223> OTHER INFORMATION: NF- kB probe

<400> SEQUENCE: 12
```

```
gcctgggaaa gtcccctcaa c                                              21
```

```
<210> SEQ ID NO 13
<211> LENGTH: 30
<212> TYPE: DNA
<213> ORGANISM: Artificial sequence
<220> FEATURE:
<223> OTHER INFORMATION: TNF-alpha primer

<400> SEQUENCE: 13
ccatcagcac catgaaccca agtcctgccg                                     30

<210> SEQ ID NO 14
<211> LENGTH: 30
<212> TYPE: DNA
<213> ORGANISM: Artificial sequence
<220> FEATURE:
<223> OTHER INFORMATION: TNF-alpha primer

<400> SEQUENCE: 14
ggacgtcctc ctcatcgtcg actacactgg                                     30

<210> SEQ ID NO 15
<211> LENGTH: 30
<212> TYPE: DNA
<213> ORGANISM: Artificial sequence
<220> FEATURE:
<223> OTHER INFORMATION: primer

<400> SEQUENCE: 15
ctcatctggg atcctctcca gccaagcttc                                     30

<210> SEQ ID NO 16
<211> LENGTH: 30
<212> TYPE: DNA
<213> ORGANISM: Artificial sequence
<220> FEATURE:
<223> OTHER INFORMATION: Primer

<400> SEQUENCE: 16
ccatggtttc ttgtgaccct gagcgacctg                                     30

<210> SEQ ID NO 17
<211> LENGTH: 23
<212> TYPE: DNA
<213> ORGANISM: Artificial sequence
<220> FEATURE:
<223> OTHER INFORMATION: COX-1 primer

<400> SEQUENCE: 17
cccagagtca tgagtcgaag gag                                            23

<210> SEQ ID NO 18
<211> LENGTH: 22
<212> TYPE: DNA
<213> ORGANISM: Artificial sequence
<220> FEATURE:
<223> OTHER INFORMATION: COX-1 primer

<400> SEQUENCE: 18
caggcgcatg agtacttctc gg                                             22

<210> SEQ ID NO 19
<211> LENGTH: 22
<212> TYPE: DNA
<213> ORGANISM: Artificial sequence
```

<220> FEATURE:
<223> OTHER INFORMATION: COX-2 primer

<400> SEQUENCE: 19
gcaaatcctt gctgttccaa tc                    22

<210> SEQ ID NO 20
<211> LENGTH: 22
<212> TYPE: DNA
<213> ORGANISM: Artificial sequence
<220> FEATURE:
<223> OTHER INFORMATION: COX-2 primer

<400> SEQUENCE: 20
gcagaaggct tcccagcttt tg                    22

<210> SEQ ID NO 21
<211> LENGTH: 28
<212> TYPE: DNA
<213> ORGANISM: Artificial sequence
<220> FEATURE:
<223> OTHER INFORMATION: iNOS primer

<400> SEQUENCE: 21
cccttccgaa gtttctggcg acagcggc              28

<210> SEQ ID NO 22
<211> LENGTH: 25
<212> TYPE: DNA
<213> ORGANISM: Artificial sequence
<220> FEATURE:
<223> OTHER INFORMATION: iNOS primer

<400> SEQUENCE: 22
ggctgtcaga gcctcgtggc tttgg                 25

<210> SEQ ID NO 23
<211> LENGTH: 30
<212> TYPE: DNA
<213> ORGANISM: Artificial sequence
<220> FEATURE:
<223> OTHER INFORMATION: pORF9-mTNF-alpha primer

<400> SEQUENCE: 23
ccatcagcac catgaaccca agtcctgccg            30

<210> SEQ ID NO 24
<211> LENGTH: 30
<212> TYPE: DNA
<213> ORGANISM: Artificial sequence
<220> FEATURE:
<223> OTHER INFORMATION: pORF9-mTNF-alpha primer

<400> SEQUENCE: 24
ggacgtcctc ctcatcgtcg actacactgg            30

<210> SEQ ID NO 25
<211> LENGTH: 30
<212> TYPE: DNA
<213> ORGANISM: Artificial sequence
<220> FEATURE:
<223> OTHER INFORMATION: mIL-1beta primer

<400> SEQUENCE: 25
ctcatctggg atcctctcca gccaagcttc            30

<210> SEQ ID NO 26
<211> LENGTH: 30
<212> TYPE: DNA
<213> ORGANISM: Artificial sequence
<220> FEATURE:
<223> OTHER INFORMATION: mIL-1beta primer

<400> SEQUENCE: 26
ccatggtttc ttgtgaccct gagcgacctg                                    30

<210> SEQ ID NO 27
<211> LENGTH: 30
<212> TYPE: DNA
<213> ORGANISM: Artificial sequence
<220> FEATURE:
<223> OTHER INFORMATION: mIL-6 primer

<400> SEQUENCE: 27
ccagttgcct tcttgggact gatgctggtg                                    30

<210> SEQ ID NO 28
<211> LENGTH: 30
<212> TYPE: DNA
<213> ORGANISM: Artificial sequence
<220> FEATURE:
<223> OTHER INFORMATION: mIL-6 primer

<400> SEQUENCE: 28
gtccttagcc actccttctg tgactccagc                                    30

<210> SEQ ID NO 29
<211> LENGTH: 21
<212> TYPE: DNA
<213> ORGANISM: Artificial sequence
<220> FEATURE:
<223> OTHER INFORMATION: mIFN-beta primer

<400> SEQUENCE: 29
aagatcattc tcactgcagc c                                             21

<210> SEQ ID NO 30
<211> LENGTH: 20
<212> TYPE: DNA
<213> ORGANISM: Artificial sequence
<220> FEATURE:
<223> OTHER INFORMATION: mIFN-beta primer

<400> SEQUENCE: 30
tgaagacttc tgctcggacc                                               20

<210> SEQ ID NO 31
<211> LENGTH: 19
<212> TYPE: DNA
<213> ORGANISM: Artificial sequence
<220> FEATURE:
<223> OTHER INFORMATION: IFN-beta primer

<400> SEQUENCE: 31
atgagtggtg gttgcaggc                                                19

<210> SEQ ID NO 32
<211> LENGTH: 25
<212> TYPE: DNA
<213> ORGANISM: Artificial sequence
<220> FEATURE:
<223> OTHER INFORMATION: IFN-beta primer

```
<400> SEQUENCE: 32
tgacctttca aatgcagtag attca                               25

<210> SEQ ID NO 33
<211> LENGTH: 21
<212> TYPE: DNA
<213> ORGANISM: Artificial sequence
<220> FEATURE:
<223> OTHER INFORMATION: MxISRE probe

<400> SEQUENCE: 33
cggagaaacg aaactaagat c                                   21

<210> SEQ ID NO 34
<211> LENGTH: 38
<212> TYPE: DNA
<213> ORGANISM: Artificial sequence
<220> FEATURE:
<223> OTHER INFORMATION: IFN-beta-IRF site probe

<400> SEQUENCE: 34
gacataggaa aactgaaagg gagaagtgaa agtgggaa                 38
```

USE OF PHENYLMETHIMAZOLES, METHIMAZOLE DERIVATIVES, AND TAUTOMERIC CYCLIC THIONES FOR THE TREATMENT OF AUTOIMMUNE/INFLAMMATORY DISEASES ASSOCIATED WITH TOLL-LIKE RECEPTOR OVEREXPRESSION

RELATED APPLICATIONS

This application is a continuation of U.S. patent application Ser. No. 11/130,922 filed May 17, 2005 which is a continuation in part of U.S. patent application Ser. No. 10/912,948 filed Aug. 6, 2004, now U.S. Pat. No. 7,928,132 issued Apr. 19, 2011, and a continuation in part of U.S. patent application Ser. No. 10/801,986 filed on Mar. 16, 2004, now abandoned, which are hereby incorporated by reference.

TECHNICAL FIELD

The present invention relates to the treatment of autoimmune and/or inflammatory diseases associated with overexpression of Toll-like receptor 3 (TLR3) as well as Toll-like receptor 4 (TLR4) and/or TLR3/TLR4 signaling in nonimmune cells, monocytes, macrophages, and/or dendritic cells in association with related pathologies. This invention also relates to the use of phenylmethimazoles, methimazole (MMI) derivatives, and tautomeric cyclic thiones for the treatment of autoimmune and inflammatory diseases associated with Toll-like receptor 3 (TLR3) as well as Toll-like receptor 4 (TLR4) and/or TLR3/TLR4 signaling in nonimmune cells, monocytes, macrophages, and/or dendritic cells in association with related pathologies. This invention also relates to treating a subject having a disease or condition associated with abnormal Toll-like receptor 3 (TLR3) as well as Toll-like receptor 4 (TLR4) and/or TLR3/TLR4 signaling in nonimmune cells, monocytes, macrophages, and/or dendritic cells in association with related pathologies. This invention also relates to treating a subject having a disease or condition associated with abnormal Toll-like receptor expression or signaling involving activation of Type I interferons in nonimmune cells, monocytes, macrophages, and/or dendritic cells in association with related pathologies.

BACKGROUND OF THE INVENTION

A. Innate and Adaptive Immunity

Autoimmune diseases, are currently clinically defined by (i) humoral or autoantibody response to a self antigen, e.g. Graves' primary hyperthyroidism with antibodies to the TSH receptor, or (ii) cellular response wherein immune cells destroy nonimmune cells from which the self-antigen is derived, e.g. the thyrocyte (Hashimoto's thyroiditis) or pancreatic β-islet cell (Type 1 diabetes) (I. Roitt, *Essential Immunology*, 7th ed., 312-346 (1991)). Many autoimmune diseases are in fact a combination of both phenomena (I. Roitt, *Essential Immunology*, 7th ed., 312-346 (1991)); thus, Hashimoto's and Type 1 diabetes also have auto-antibodies, anti-thyroid peroxidase (TPO) or anti-glutamic acid decarboxylase (GAD)/Islet Cell. Additionally, autoimmune diseases often have a significant inflammatory component including increases in adhesion molecules, e.g. vascular cell adhesion molecule-1 (VCAM-1), and altered leukocyte adhesion to the vasculature, e.g., colitis, systemic lupus, systemic sclerosis, and the vascular complications of diabetes (I. Roitt, *Essential Immunology*, 7th ed., 312-346 (1991); S. A. Jimenez, et al., *Ann Intern Med*, 140:37-50 (2004)).

Recent studies demonstrate a formidable link between the Toll-like receptor (TLR) signaling pathway of innate immunity and the slower, more deliberate adaptive immune system that characterizes humoral and cellular autoimmunity (K. S. Michelsen, et al., *Proc Natl Acad Sci USA*, 101:10679-84 (2004); G. Pasterkamp, et al., *Eur J Clin Invest*, 34:328-34 (2004); K. Takeda, et al., *Annu Rev Immunol*, 21:335-76 (2003); K. Takeda, et al., *Cell Microbiol*, 5:143-53 (2003); R. J. Ulevitch, *J Infect Dis*, 187 Suppl 2:S351-5 (2003); L. Steinman, *Science*, 305:212-6 (2004); L. D. Kohn, et al., *Research Ohio*, In press, (2005); N. Harii, et al., *Mol Endocrinol*, 19:1231-50 (2005); D. Devendra, et al., *Clin Immunol*, 111:225-33 (2004); L. Wen, et al., *J Immunol*, 172:3173-80 (2004); H. Oshiumi, et al., *Nat Immunol*, 4:161-7 (2003); M. Yamamoto, et al., *J Immunol*, 169:6668-72 (2002); M. Miettinen, et al., *Genes Immun*, 2:349-55 (2001); L. Alexopoulou, et al., *Nature*, 413:732-8 (2001); G. Andonegui, et al., *J Clin Invest*, 111:1011-1020 (2003); C. Fiocchi, *Gastroenterology*, 115:182-205 (1998); E. Cario, et al., *Infect Immun*, 68:7010-7 (2000)). Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types (I. Roitt, *Essential Immunology*, 7th ed., 312-346, (1991)). Th1 cells mainly promote cellular immunity, whereas Th2 cells mainly promote humoral immunity. Though primarily a host protective system, pathologic expression of the innate immunity signals emanating from the TLR pathway are now implicated in initiating autoimmune-inflammatory diseases.

Therapies for autoimmune-inflammatory endocrine or non-endocrine diseases are largely aimed at treating the symptoms of the disease. For the most part, the underlying genetic susceptibilities are poorly defined, are multiple, are often not disease specific, and are largely not readily amenable to therapy. Immunosuppressive agents that are used to treat autoimmune-inflammatory diseases largely target the immune cell response or the cytokines they produce. They are only partially effective in inducing remission (methimazole in Graves'), toxic (cyclosporin for Type 1 diabetes), or simply palliative (anti-inflammatory corticosteroids for colitis or systemic lupus). The involvement of TLR in autoimmune-inflammatory diseases raises the possibility that diagnosis and treatment must undergo a re-alignment (K. S. Michelsen, et al., *Proc Natl Acad Sci USA*, 101: 10679-84 (2004); G. Pasterkamp, et al., *Eur J Clin Invest*, 34:328-34 (2004); L. D. Kohn, et al., *Research Ohio*, In press, (2005); N. Harii, et al., *Mol Endocrinol*, 19:1231-50 (2005); D. Devendra, et al., *Clin Immunol*, 111:225-33 (2004); L. Wen, et al., *J Immunol*, 172:3173-80 (2004); H. Oshiumi, et al., *Nat Immunol*, 4:161-7 (2003); M. Yamamoto, et al., *J Immunol*, 169:6668-72 (2002); M. Miettinen, et al., *Genes Immun*, 2:349-55 (2001); L. Alexopoulou, et al., *Nature*, 413:732-8 (2001); G. Andonegui, et al., *J Clin Invest*, 111:1011-1020 (2003); C. Fiocchi, *Gastroenterology*, 115:182-205 (1998); E. Cario, et al., *Infect Immun*, 68:7010-7 (2000)).

Thus, despite our knowledge that many autoimmune-inflammatory diseases were induced or worsened by an environmental agent, e.g. smoking or viral infections, little was known of the details by which this induction-signal process worked, nor was there a therapy to block this induction-signal process (I. Roitt, *Essential Immunology*, 7th ed., 312-346, (1991); J. George, et al., *Scand J Immunol*, 45:1-6 (1997); C. Nagata, et al., *Int J Dermatol*, 34:333-7 (1995)).

Thus, the recent description of TLR and the TLR signal mechanism of innate immunity, upon which adaptive (humoral or cell-mediated) immunity depends has created an opportunity to develop of a new class of drugs as well as new diagnostic paradigms (L. D. Kohn, et al., *Research Ohio*, In press, (2005); N. Harii, et al., *Mol Endocrinol*, 19:1231-50 (2005); D. Devendra, et al., *Clin Immunol*, 111:225-33 (2004); L. D. Kohn, et al., U.S. patent application Ser. No. 10/801,986 (2004); L. D. Kohn, et al., U.S. patent application Ser. No. 10/912,948 (2004)).

By attacking the innate immune induction event of autoimmune/inflammatory disease, early identification of the induction signal event or environmental insult in a person at risk and initiation of therapy post induction or during the latency period of disease onset could allow therapy to be more effective, prevent or retard cell destruction, avoid long term inflammatory complications, enhance quality of life, and decrease associated medical costs. Since, there is increasing evidence that the atherosclerotic process and cardiovascular disease, i.e. the vascular complications of type 2 and type 1 diabetes, exhibit similar mechanisms involving TLR and a pathologic innate immune response, they too can benefit from the same treatment paradigm, despite being currently considered late stage phenomena (K. S. Michelsen, et al., *Proc Natl Acad Sci USA*, 101:10679-84 (2004); G. Pasterkamp, et al., *Eur J Clin Invest*, 34:328-34 (2004); H. M. Dansky, et al., *Arterioscler Thromb Vasc Biol*, 21:1662-7 (2001); P. E. Szmitko, et al., *Circulation*, 108:2041-8 (2003); P. E. Szmitko, et al., *Circulation*, 108:1917-23 (2003); M. I. Cybulsky, et al., *Can J Cardiol*, 20 Suppl B:24B-8B (2004); P. M. Ridker, et al., *Circulation*, 109:IV6-19, (2004)). No such method exists although it is considered important.

B. Toll-Like Receptors and Signaling

At the end of the 20th century, Toll-like receptors (TLRs) were shown to be essential to induce expression of genes involved in inflammatory responses. Since their description, there has been rapid progress in our understanding that TLRs and the innate immune system is a critical step in the development of antigen-specific acquired immunity. This is recently reviewed by several groups (K. Takeda, et al., *Int Immunol*, 17:1-14 (2005); B. Beutler, *Nature*, 430:257-63 (2004); K. S. Michelsen, et al., *J Immunol*, 173:5901-7 (2004)); the material following is largely derived from one (K. Takeda, et al., *Int Immunol*, 17:1-14 (2005)) but is common to all (B. Beutler, *Nature*, 430:257-63 (2004); K. S. Michelsen, et al., *J Immunol*, 173:5901-7 (2004)) and represents only the current thoughts in a rapidly developing area.

The TLR Family. Mammalian TLRs comprise a large family consisting of at least 10 functional members such as TLR1-9 which are conserved between the human and mouse. The cytoplasmic portion of TLRs shows high similarity to that of the IL-1 receptor family and is termed a Toll/IL-1 receptor (TIR) domain. Despite this similarity, the extracellular portions of TLR are structurally unrelated. The IL-1 receptors possess an immunoglobulin-like domain, whereas TLRs bear leucine-rich repeats (LRRs) in the extracellular domain. TLRs play important roles in recognizing specific signature molecules derived from pathogens including bacteria, fungi, protozoa and viruses, derived from their invasion of cells, or resultant from the effects of noxious environmental stimuli which cause cell damage.

Toll-like Receptors 1, 2, and 6 (TLR1, TLR2 and TLR6). TLR2 recognizes a variety of lipoproteins/lipopeptides from various pathogens, e.g. Gram-positive bacteria, mycobacteria, *Trypanosoma cruzi*, fungi and *Treponema* (K. Takeda, et al., *Annu Rev Immunol*, 21:335-76 (2003)). In addition, TLR2 reportedly recognizes LPS preparations from non-enterobacteria such as *Leptospira interrogans*, *Porphyromonas gingivalis* and *Helicobacter pylori*. These LPS structurally differ from the typical LPS of Gram-negative bacteria recognized by TLR4 in the number of acyl chains in the lipid A component, which presumably confers differential recognition; thus, LPS from *P. gingivalis* only poorly activates TLR4 (M. Hashimoto, et al., *Int Immunol*, 16:1431-7 (2004)).

There are two proposed explanations that could explain why TLR2 recognizes a wide spectrum of microbial components. The first is that TLR2 forms heterophilic dimers with other TLRs such as TLR1 and TLR6, both of which are structurally related to TLR2. The second involves interactions (B. N. Gantner, et al., *J Exp Med*, 197:1107-17 (2003)) with distinct types of receptors such as dectin-1, a lectin family receptor for the fungal cell wall component beta-glucan. Thus, TLR2 recognizes a wide range of microbial products through functional cooperation with several proteins that are either structurally related or unrelated to TLR.

Toll-like receptor 3 (TLR3). Expression of human TLR3 in non-responsive cells confers enhanced activation of NF-κB in response to dsRNA. In addition, TLR3-deficient mice are impaired in their response to dsRNA (L. Alexopoulou, et al., *Nature*, 413:732-8 (2001)) which is produced by most viruses during their replication and which induces the synthesis of type I interferons (IFN-α/β). Type I IFNs induce anti-viral and immunostimulatory activities in the cells. Thus, TLR3 is implicated in the recognition of dsRNA and viruses and the antiviral gene response thereto.

Toll-like Receptor 4 (TLR4). TLR4 is an essential receptor for LPS recognition (A. Poltorak, et al., *Science*, 282:2085-8 (1998); K. Hoshino, et al., *J Immunol*, 162:3749-52 (1999)). In addition, TLR4 is implicated in the recognition of endogenous ligands, such as heat shock proteins (HSP60 and HSP70), domain A of fibronectins, as well as oligosaccharides of hyaluronic acid, heparan sulfate and fibrinogen. However, since these endogenous ligands require very high concentrations to activate TLR4, contamination by LPS is suspected.

Toll-like Receptor 5 (TLR5). Expression of human TLR5 in CHO cells confers response to flagellin, a monomeric constituent of bacterial flagella (F. Hayashi, et al., *Nature*, 410:1099-103 (2001)). TLR5 is expressed on the basolateral side of intestinal epithelial cells and intestinal endothelial cells of the subepithelial compartment. Further, flagellin activates lung epithelial cells to induce inflammatory cytokine production and a stop codon polymorphism in TLR5 has been associated with susceptibility to pneumonia caused by the flagellated bacterium *Legionella pneumophila*. These findings indicate the important role of TLR5 in microbial recognition at the mucosal surface of mammalian cells.

Toll-like Receptors 7 and 8 (TLR7 and TLR8). TLR7 and TLR8 are structurally highly conserved proteins, which recognize guanosine- or uridine-rich, single-stranded RNA (ss-RNA) from viruses such as human immunodeficiency virus, vesicular stomatitis virus and influenza virus (F. Heil, et al., *Science*, 303:1526-9 (2004); S. S. Diebold, et al., *Science*, 303:1529-31 (2004); J. M. Lund, et al., *Proc Natl Acad Sci USA*, 101:5598-603 (2004)). ssRNA is abundant in the host, but usually the host-derived ssRNA is not detected by TLR7 or TLR8. This might be due to the fact that TLR7 and TLR8 are expressed in the endosome, and host-derived ssRNA is not delivered to the endosome (see below).

Toll-like Receptor 9 (TLR9). TLR9 is a receptor for CpG DNA (H. Hemmi, et al., *Nature*, 408:740-5 (2000)). Bacterial and viral DNA contains unmethylated CpG motifs, which confer its immunostimulatory activity. In vertebrates, the frequency of CpG motifs is severely reduced and the cytosine residues of CpG motifs are highly methylated, leading to abrogation of the immunostimulatory activity. Structurally, there are at least two types of CpG DNA: B/K-type CpG DNA is a potent inducer of inflammatory cytokines such as IL-12 and TNF-α; A/D-type CpG DNA has a greater ability to induce IFN-α production from plasmacytoid dendritic cells (PDC), In addition to recognizing bacterial and viral CpG DNA, TLR9 is involved in pathogenesis of autoimmune disorders. Thus it may be important in Graves' autoimmune hyperthyroidism and mediates production of rheumatoid factor by auto-reactive B cells (G. A. Viglianti, et al., *Immunity*, 19:837-47 (2003)). Similarly, internalization by the Fc receptor can cause TLR9 mediated PDC induction of IFN-α by immune complexes containing IgG and chromatin, which are implicated in the pathogenesis of systemic lupus erythematosus (SLE) (M. W. Boule, et al., *J Exp Med*, 199:1631-40 (2004)). Thus, TLR9 appears to be involved in the pathogenesis of several autoimmune diseases through recognition of the chromatin structure. Chloroquine, which is clinically used for treatment of rheumatoid arthritis and SLE, is currently presumed to block TLR9-dependent signaling through inhibition of the pH-dependent maturation of endosomes by neutralizing acidification in the vesicle (H. Hacker, et al., *Embo J*, 17:6230-40 (1998)).

Toll-like Receptor 11 (TLR11). The most recently identified TLR11 has been shown to be expressed in bladder epithelial cells and mediate resistance to infection by uropathogenic bacteria in mouse (D. Zhang, et al., *Science*, 303:1522-6 (2004)).

Subcellular Localization of Some TLRs. Individual TLRs are differentially distributed within the cell. TLR1, TLR2, TLR3 and TLR4 are expressed on the cell surface; in contrast, TLR3, TLR7, TLR8 and TLR9 have been shown to be expressed in intracellular compartments such as endosomes. TLR3-, TLR7- or TLR9-mediated recognition of their ligands has been shown to require endosomal maturation and processing. Thus, for example, TLR9 is recruited from the endoplasmic reticulum upon non-specific uptake of CpG DNA (H. Hacker, et al., *Embo J*, 17:6230-40 (1998); E. Latz, et al., *Nat Immunol*, 5:190-8 (2004); C. A. Leifer, et al., *J Immunol*, 173:1179-83 (2004)). When either nonimmune cells that become antigen presenting cells, macrophages, monocytes, or dendritic cells engulf bacteria by phagocytosis, they degrade the bacteria and release CpG DNA in phagosomes-lysosomes or in endosomes-lysosomes where they can interact TLR9.

Similarly, as another example, when viruses invade cells by receptor-mediated endocytosis, the viral contents are exposed to the cytoplasm by fusion of the viral membrane with the endosomal membrane. This results in exposure of TLR ligands such as dsRNA, ssRNA and CpG DNA to TLR9 in the phagosomal/lysosomal or endosomal/lysosomal compartments.

TLR-independent Recognition of Micro-organisms—dsRNA Transfection De Novo or RNA/DNA Introduction By viruses—Can Nevertheless Activate TLR Signaling Pathways. Although TLR3 is involved in the recognition of viral-derived dsRNA, the impairment observed in TLR3-deficient mice is only partial (L. Alexopoulou, et al., *Nature*, 413:732-8 (2001); M. Yamamoto, et al., *Science*, 301:640-3 (2003)). Thus, introduction of dsRNA into the cytoplasm of dendritic cells leads to the induction of type I IFNs independent of TLR3 (S. S. Diebold, et al., *Nature*, 424:324-8 (2003)). Although PKR is implicated in dsRNA recognition, it is still controversial if it plays a critical role in dsRNA-induced type I IFN expression (E. J. Smith, et al., *J Biol Chem*, 276:8951-7 (2001)).

Recently, one key molecule that mediates TLR3-independent dsRNA recognition was shown to be Retinoic acid-inducible gene I (RIG-I). RIG-1 encodes a DExD/H box RNA helicase containing a caspase recruitment domain that augments dsRNA-dependent activation of the IRF-3-dependent promoter.

The nucleotide-binding oligomerization domain (NOD) family of proteins also plays an important role in the TLR-independent recognition of intracellular bacteria.

NOD1 contains a caspase-recruitment domain (CARD), a NOD domain and a C-terminal LRR domain. Overexpression of NOD1 enables cells to respond to peptidoglycans (PGN) which are recognized by TLR2 (O. Takeuchi, et al., *Immunity*, 11:443-51, (1999)); c-D-glutamyl-meso diaminopimelic acid (iE-DAP) is the minimal PGN structure required. NOD2 shows structural similarity to NOD1, but possesses two CARD domains and the essential structure recognized by NOD2 is a muramyl dipeptide MurNAc-L-Ala-D-isoGln (MDP) derived from PGN. MDP is found in almost all bacteria, whereas iE-DAP is restricted to Gram-negative bacteria.

Mutations in the NOD2 gene have been shown to be associated with Crohn's disease (Y. Ogura, et al., *Nature*, 411: 603-6 (2001); J. P. Hugot, et al., *Nature*, 411:599-603 (2001)), result in enhanced NF-κB activation and may contribute to enhanced NF-κB activity and Th1 responses in Crohn's disease patients (T. Watanabe, et al., *Nat Immunol*, 5:800-8 (2004)). NOD2 mutations also lead to an increase in NF-κB activity and are associated with Blau syndrome, a disease characterized by granulomatous arthritis, uveitis and skin rash (C. Miceli-Richard, et al., *Nat Genet*, 29:19-20 (2001)).

Rip2/RICK, a serine/threonine kinase, has a CARD domain in its C-terminal portion and an N-terminal catalytic domain that shares sequence similarity with Rip, a factor essential for NF-κB activation through the TNF receptor. NODs and Rip2/RICK interact via their respective CARD domains, and induce recruitment of the IKK complex to the central region of Rip2/RICK. This in turn leads to activation of NF-κB.

TLR Signaling Pathways—MyD88 Pathway and NF-κB/MAP Kinase Signals. In the signaling pathways downstream of the TIR domain, a TIR domain-containing adaptor, MyD88, was the first shown to be essential for induction of inflammatory cytokines such as TNF-α and IL-12 through all TLRs (F. Hayashi, et al., *Nature*, 410:1099-103 (2001); H. Hemmi, et al., *Nat Immunol*, 3:196-200 (2002); O. Takeuchi, et al., *Int Immunol*, 12:113-7, (2000); T. Kawai, et al., *Immunity* 11:115-22, (1999); M. Schnare, et al., *Curr Biol*, 10:1139-42 (2000); H. Hacker, et al., *J Exp Med*, 192:595-600 (2000)). However, activation of specific TLRs led to slightly different patterns of gene expression profiles. For example, activation of TLR3 and TLR4 signaling pathways resulted in induction of type I interferons (IFNs), but activation of TLR2- and TLR5-mediated pathways did not (V. Toshchakov, et al., *J Endotoxin Res*, 9:169-75 (2003); K. Hoshino, et al., *Int Immunol*, 14:1225-31 (2002); S. Doyle, et al., *Immunity*, 17:251-63 (2002)). TLR7, TLR8 and TLR9 signaling pathways also lead to induction of Type I IFNs through mechanisms distinct from TLR3/4-mediated induction (H. Hemmi, et al., *J Immunol*, 170:3059-64 (2003); T. Ito, et al., *J Exp Med*, 195:1507-12 (2002)). Thus, individual TLR signaling pathways are divergent, although MyD88 is common to all TLRs. It has thus become clear that there are MyD88-dependent and MyD88-independent pathways.

The MyD88-dependent pathway is analogous to signaling by the IL-1 receptors. As currently perceived, MyD88, harboring a C-terminal TIR domain and an N-terminal death domain, associates with the TIR domain of TLRs. Upon stimulation, MyD88 recruits IRAK-4 to TLRs through interaction of the death domains of both molecules, and facilitates IRAK-4-mediated phosphorylation of IRAK-1. Activated IRAK-1 then associates with TRAF6, leading to the activation of two distinct signaling pathways. One pathway leads to activation of AP-1 transcription factors through activation of MAP kinases. Another pathway activates the TAK1/TAB complex, which enhances activity of the IκB kinase (IKK) complex. Once activated, the IKK complex induces phosphorylation and subsequent degradation of IκB, which leads to nuclear translocation of transcription factor NF-κB. The MyD88-dependent pathway plays a crucial role and is essential for inflammatory cytokine production through all TLRs. Thus, MyD88-deficient mice do not show production of inflammatory cytokines such as TNF-α and IL-12p40 in response to all TLR ligands (F. Hayashi, et al., Nature, 410: 1099-103, (2001); H. Hemmi, et al., Nat Immunol, 3:196-200 (2002); O. Takeuchi, et al., Int Immunol, 12:113-7 (2000); T. Kawai, et al., Immunity, 11:115-22 (1999); M. Schnare, et al., Curr Biol, 10:1139-42 (2000); H. Hacker, et al., J Exp Med, 192:595-600 (2000)).

A MyD88 related TIR domain-containing molecule: TIRAP (TIR domain-containing adaptor protein)/Mal (MyD88-adaptor-like) (T. Horng, et al., Nat Immunol, 2:835-41 (2001); K. A. Fitzgerald, et al., Nature, 413:78-83 (2001)) has been shown to be essential for the MyD88-dependent signaling pathway via TLR2 and TLR4. Thus, TIRAP/Mal-deficient macrophages show impaired inflammatory cytokine production in response to TLR4 and TLR2 ligands (T. Horng, et al., Nature, 420:329-33 (2002); M. Yamamoto, et al., Nature, 420:324-9 (2002)) but are not impaired in their response to TLR3, TLR5, TLR7 and TLR9 ligands.

MyD88-independent/TRIF-dependent Pathway and IRF-3/Type 1 IFN Signaling. TLR4 ligand-induced production of inflammatory cytokines is not observed in MyD88-deficient macrophages, however activation of NF-κB is observed with delayed kinetics (T. Kawai, et al., J Immunol, 167:5887-94 (2001)). Thus, a MyD88-independent component exists.

In TLR3- and TLR4-mediated signaling pathways, activation of IRF-3 and induction of IFN-β are observed in a MyD88-independent manner. The TIR domain-containing adaptor, TRIF, is essential for the MyD88-independent pathway; however, in the case of TLR4, but not TLR3, the TIR domain-containing adaptor, TRAM, is also involved in the TRIF-dependent activation of IRF-3 and induction of IFN-β- and IFN-inducible genes pathway as evidenced in TRAM-deficient mice or by RNAi-mediated knockdown (K. A. Fitzgerald, et al., J Exp Med, 198:1043-55 (2003); M. Yamamoto, et al., Nat Immunol, 4:1144-50 (2003); H. Oshiumi, et al., J Biol Chem, 278:49751-62 (2003)).

Non-typical IKKs, IKKi/IKKe and TBK1, mediate activation of IRF-3 downstream of TRIF as well as the late phase of NF-κB activation in a MyD88-independent manner (T. Kawai, et al., J Immunol, 167:5887-94 (2001)). Activation of IRF-3 leads to production of IFN-β. IFN-β in turn activates Stat1 and induces several IFN-inducible genes (V. Toshchakov, et al., J Endotoxin Res, 9:169-75 (2003); K. Hoshino, et al., Int Immunol, 14:1225-31 (2002); S. Doyle, et al., Immunit, 17:251-63, (2002)). The physiological role of TRIF was demonstrated by generation of TRIF-deficient or TRIF-mutant mice which showed no activation of IRF-3 and had impaired expression of IFN-β- and IFN-inducible genes in response to TLR3 and TLR4 ligands (S. S. Diebold, et al., Nature, 424:324-8 (2003)).

In TRIF- and TRAM-deficient mice, inflammatory cytokine production induced by TLR2, TLR7 and TLR9 ligands was observed, as well as TLR4 ligand-induced phosphorylation of IRAK-1 (S. S. Diebold, et al., Nature, 424:324-8 (2003); M. Yamamoto, et al., Nat Immunol, 4:1144-50 (2003)). These findings indicate that the MyD88-dependent pathway is not impaired in these mice. However, TLR4 ligand-induced inflammatory cytokine production was also not observed in TRIF- and TRAM-deficient mice. Therefore, activation of both the MyD88-dependent and MyD88-independent/TRIF-dependent components is believed to be required for the TLR3/4-induced inflammatory cytokine production.

Key molecules that mediate IRF-3 activation have been revealed to be non-canonical IKKs, TBK1 and IKKi/IKKe. Thus, introduction of TBK1 or IKKi/IKKe, but not IKKb, resulted in phosphorylation and nuclear translocation of IRF-3. Also, RNAi-mediated inhibition of TBK1 or IKKi/IKKe expression led to impaired induction of IFN-β in response to viruses and dsRNA (S. Sharma, et al., Science, 300:1148-51, (2003)).

The Mechanisms of MyD88-independent TLR Signaling of Both IRF-3 and NF-κB Pathways by TLR3: The TIR domain of TRIF is located in the middle portion of this molecule, flanked by the N-terminal and C-terminal portions. Both N-terminal and C-terminal portions of TRIF mediate activation of the NF-κB-dependent promoter, whereas only the N-terminal portion is involved in IFN-β promoter activation (M. Yamamoto, et al., J Immunol, 169:6668-72 (2002)). Accordingly, the N-terminal portion of TRIF was shown to associate with IKKi/IKKe and TBK1, which mediate IRF-3-dependent IFN-β induction (K. A. Fitzgerald, et al., Nat Immunol, 4:491-6 (2003); S. Sato, et al., J Immunol, 171: 4304-10 (2003)). The N-terminal portion of TRIF was also shown to associate with TRAF6 (S. Sato, et al., J Immunol, 171:4304-10 (2003); Z. Jiang, et al., Proc Natl Acad Sci USA, 101:3533-8 (2004)); TRAF6 is critically involved in TLR-mediated NF-κB activation (J. Gohda, et al., J Immunol, 173:2913-7 (2004)), The C-terminal portion of TRIF was shown to associate with RIPl (E. Meylan, et al., Nat Immunol, 5:503-7 (2004)); thus, RIPl was shown to be responsible for NF-κB activation that originates from the C-terminal portion of TRIF.

Negative Regulation of TLR Signaling. Stimulation of TLRs by microbial components triggers the induction of inflammatory cytokines such as TNF-α, IL-6 and IL-12. When all these cytokines are produced in excess, they induce serious systemic disorders with a high mortality rate in the host. It is therefore not surprising that organisms have evolved mechanisms for modulating their TLR-mediated responses. TLR signaling pathways are negatively regulated by several molecules. IRAK-M inhibits dissociation of IRAK-1/IRAK-4 complex from the receptor. MyD88s blocks association of IRAK-4 with MyD88. SOCS1 is likely to associate with IRAK-1 and inhibits its activity. TRIAD3A induces ubiquitination-mediated degradation of TLR4 and TLR9. TIR domain-containing receptors SIGIRR and T1/ST2 are also shown to negatively modulate TLR signaling. Thus, several molecules are postulated to negatively modulate TLR signaling pathways and in combination may normally finely coordinate the TLR signaling pathway to limit exaggerated innate responses causing harmful disorders.

Exposure to microbial components such as LPS results in a severely reduced response to a subsequent challenge by LPS, termed endotoxin or LPS tolerance. Several negative regulation mechanisms are also shown to be involved in LPS tolerance (H. Fan, et al., J Endotoxin Res, 10:71-84 (2004)).

C. IRF-1 Signaling Induced by Overexpressed TLR3 or TLR4 Signaling is Critical in Autoimmune Inflammatory Disease The regulatory effect of IRF-1 has been reported in several in vitro and in vivo models of autoimmune-inflammatory diseases: Arthritis (A. Shiraishi, et al., *J Immunol*, 159:3549-54 (1997); T. Inoue, et al., *J Rheumatol*, 28:1229-37 (2001); S. John, et al., *J Rheumatol*, 28:1752-5 (2001)), colitis (M. Clavell, et al., *J Pediatr Gastroenterol Nutr*, 30:43-7 (2000)); (M. Kennedy, et al., *Int J Mol Med*, 4:437-43 (1999)), neurological inflammation (M. Delgado, et al., *J Immunol*, 162:4685-96 (1999); U. Schlomann, et al., *J Neurosci*, 20:7964-71 (2000)), cerebral ischemia (C. Iadecola, et al., *J Exp Med*, 189:719-27 (1999); W. Paschen, et al., *Neuroreport*, 9:3147-51 (1998)); V. L. Raghavendra Rao, et al., *J Neurochem*, 83:1072-86 (2002)), lung injury (V. R. Sunil, et al., *Am J Physiol Lung Cell Mol Physiol*, 282:L872-80 (2002)), myositis (S. Matsubara, et al., *J Neuroimmunol*, 119:223-30 (2001)), myocarditis (K. Azzam-Smoak, et al., *Virology*, 298:20-9 (2002); S. Kawamoto, et al., *J Virol*, 77:9622-31 (2003); R. Kamijo, et al., *Science*, 263:1612-5 (1994); J. R. Allport, et al., *J Exp Med*, 186:517-527 (1997)), endotoxic shock (G. Andonegui, et al., *J Clin Invest*, 111:1011-1020 (2003); V. L. Raghavendra Rao, et al., *J Neurochem*, 83:1072-86 (2002); S. Heinz, et al., *J Biol Chem*, 278:21502-9 (2003); C. W. Wieland, et al., *Infect Immun*, 70:1352-8 (2002); Y. Pang, et al., *Brain Res*, 914:15-22 (2001); O. Kobayashi, et al., *Am J Physiol Gastrointest Liver Physiol*, 281:688-96, (2001)), diabetes (A. Akabane, et al., *Biochem Biophys Res Commun*, 215:524-30 (1995); M. S. Baker, et al., *Surgery*, 134:134-41 (2003); C. A. Gysemans, et al., *Diabetologia*, 44:567-74 (2001); A. E. Karlsen, et al., *J Clin Endocrinol Metab*, 85:830-6 (2000); T. Nakazawa, et al., *J Autoimmun* 17:119-25, (2001)), hepatitis (B. Jaruga, et al., *Am J Physiol Gastrointest Liver Physiol*, 287:G1044-52 (2004); P. M. Pitha, et al., *Biochimie*, 80:651-8 (1998)), systemic lupus erythematosus (SLE), (K. M. Pollard, et al., *Ann NY Acad Sci*, 987:236-9 (2003)), and a multifocal inflammatory model with autoimmune components (N. L. Mccartney-Francis, et al., *J Immunol*, 169:5941-7 (2002)). IRF-1 is implicated in patients with, autoimmune myocarditis associated with viral infection in human and in rodent models (K. Bachmaier, et al., *Circulation*, 96:585-91 (1997)).

IRF-1 can up-regulate the inflammatory immune response at the innate and adaptive level by increasing the inflammatory gene expression in macrophages, dendritic cells and CD-4 T cells. Thus, upregulation of IRF-1 gene expression can increase the expression of inflammatory mediators such as arachidonic acid signaling, COX-1 and, COX-2 enzymes (X. Teng, et al., *Am J Physiol Cell Physiol*, 282:C144-52, (2002)), chemokines (M. S. Baker, et al., *Surgery*, 134:134-41 (2003); Y. Ohmori, et al., *J Leukoc Biol*, 69:598-604 (2001)), iNOS (M. Delgado, et al., *J Immunol*, 162:4685-96 (1999); M. S. Baker, et al., *Surgery*, 134:134-41 (2003); X. Teng, et al., *Am J Physiol Cell Physiol*, 282:C144-52 (2002); Y. Ohmori, et al., *J Leukoc Biol*, 69:598-604 (2001)), IL-12 p40 (M. Clavell, et al., *J Pediatr Gastroenterol Nutr*, 30:43-7 (2000); C. Feng, et al., *Int Immunol*, 11:1185-94 (1999)) Type 1 IFN-α and -β (L. A. Eader, et al., *Cell Immunol*, 157:211-22 (1994); S. Kirchhoff, et al., *Eur J Biochem*, 261:546-54 (1999)), as well as the pro-inflammatory cytokines TNF-α, IL1-β, IL-6, IL-12 and INF-γ. IRF-1 gene overexpression may thus induce autoimmune-inflammatory diseases by its effects on macrophages, dendritic cells and CD4±Th1 cell lymphocytic cells.

Despite information implicating the importance of IRF-1 signaling in macrophages, dendritic cells and CD4±Th1 cell lymphocytic cells, comparable effects, after TLR3 or TLR4 mediated increases of IRF-1 in nonimmune cells, have been less clear. However, studies of the effects of methimazole, methimazole derivatives, and tautomeric cyclic thiones, particularly phenylmethimazole (C10) related to Hashimoto's thyroiditis, Colitis, toxic shock, and atherosclerosis summarized herein establish the importance of its overexpression in nonimmune cells associated with or caused by TLR3 or TLR4 signal overexpression.

D. IRF-1 Signalling Induced by Overexpressed TLR4Signaling is Critical in Atherosclerosis Leukocyte adhesion is central to atherosclerosis, an autoimmune-inflammatory disease. One of the earliest steps in the development of atherosclerotic lesions is the adhesion of leukocytes (monocytes and lymphocytes) to the apical surface of the endothelium and subsequent migration across the endothelium into the subendothelial space at select anatomical sites in the arterial tree. This process occurs through a cascade of adhesive events. This adhesion cascade is mediated, in part, by binding of molecules present on the surface of the leukocyte (e.g. $\beta_1$ integrins) to adhesion molecules on the surface of the endothelium (e.g VCAM-1). Subsequent to migrating into the extravascular space, the monocyte-derived macrophages ingest lipids and become foam cells. Activation of the recruited leukocytes is believed to induce release of important mediators of inflammation (e.g. pro-inflammatory cytokines) that serve to continue the process of lesion development. Smooth muscle cells are recruited to the fatty spot and, together with the foam cells and lymphocytes, form the fatty streak (intermediate lesion). This entire process can continue leading to a fibrofatty lesion and ultimately to a fibrous plaque. Throughout plaque development, the vascular endothelium remains intact. Since the mechanisms of atherogenesis are similar to those present in "general" pathological inflammation, atherosclerosis is often considered a disease of pathological inflammation. Indeed, it has recently been shown that inhibition of the potent pro-inflammatory cytokine TNF-α reduces atherosclerosis in a murine model (L. Branen, et al., *Arterioscler Thromb Vasc Biol*, 24:2137-42 (2004)).

Endothelial cell adhesion molecules (ECAMs), which are known to participate in leukocyte recruitment during pathological inflammation, (e.g VCAM-1, E-selectin and ICAM-1), have been shown to be up-regulated at sites of inflammation and to contribute to disease progression and/or tissue damage by virtue of their role in leukocyte adhesion (F. W. Luscinskas, et al., *Annu. Rev. Med.*, 47:413-421 (1996)). VCAM-1 has received the most interest in the context of atherosclerosis. VCAM-1 has been observed in a localized fashion on aortic endothelium that overlies early foam cell lesions (M. I. Cybulsky, et al., *Science*, 251:788-791 (1991)) and has been shown to play an important role in monocyte and lymphocyte adhesion to and migration across the endothelium (F. W. Luscinskas, et al., *J. Cell Biol.*, 125:1417-27 (1994); C. L. Ramos, et al., *Circ. Res.*, 84:1237-44 (1999)). Studies with the Apolipoprotein E-deficient (ApoE$^{-/-}$) mouse, a well-accepted model of human atherosclerosis, revealed that VCAM-1 is present on endothelium at lesion-prone sites (as early as 5 weeks) and developed lesions (Y. Nakashima, et al., *Arterioscler. Thromb. Vasc. Biol.*, 18:842-51 (1998)). Monocytes exhibit greatly increased adhesion to carotid arteries isolated from ApoE$^{-/-}$ mice compared to carotid arteries isolated from wild-type mice and this increased adhesion is mediated, in part, by VCAM-1 (C. L. Ramos, et al., *Circ. Res.*, 84:1237-44 (1999)).

The expression of ECAMs is regulated, in part, by pro-inflammatory cytokines (e.g. TNF-α) which increase the activity of certain transcription factors (e.g. NF-κB) (M. J. May, et al., *Immunol. Today,* 19:80-88 (1998)) and IRF-1 (A. S, Neish, et al., *Mol. Cell. Biol.,* 15:2558-2569 (1995)). The activated or increased transcription factors bind to promoter, elements on the ECAM genes. Several current or potential therapeutics for pathological inflammation work, at least in part, by modulating the activity of transcription factors to inhibit leukocyte adhesion to the endothelium and reduce inflammation in animal models (E. M. Conner, et al., *J Pharmacol. Exp. Ther.,* 282:1615-1622 (1997); J. W. Pierce, et al., *J. Immunol.,* 156:3961-3969 (1996); N. M. Dagia, et al., *Am. J Phys.,* 285:C813-C822 (2003); C. Weber, et al., *Circulation,* 91:1914-1917 (1995)).

One such group includes methimazole, methimazole derivatives, and tautomeric cyclic thiones (Kohn, L. D., et al., U.S. Pat. No. 6,365,616 Apr. 2, (2002).; Kohn, L. D., et al., U.S. patent application Ser. No. 10/801,986, (2004)). When tested phenylmethimazole (C10), reduced pro-inflammatory (e.g TNF-α)-induced ECAM expression and consequent leukocyte adhesion to endothelial cells (N. M. Dagia, et al., *J Immunol,* 173:2041-9 (2004)), C10 (i) inhibits monocytic cell adhesion to cytokine inflamed human aortic endothelial cells (HAEC) under in vitro flow conditions that mimic conditions present in vivo; (ii) strongly inhibits cytokine-induced HAEC expression of VCAM-1 at the protein and mRNA level; (iii) has a modest effect on E-selectin expression; and (iv) has very little effect on ICAM-1 expression.

The VCAM-1 promoter contains several cis elements known to play a role in TNF-α induced human VCAM-1 expression: NF-κB, AP-1, SP-1, IRF-1 and GATA. TNF-α stimulation of endothelial cells activates NF-κB (M. J. May, et al., *Immunol. Today,* 19:80-88 (1998)); however, C10 does not appear to have any effect on NF-κB translocation to the nucleus or binding to the VCAM-1 promoter (N. M. Dagia, et al., *J Immunol,* 173:2041-9 (2004)). IRF-1 is present at a very low level in resting endothelial cells; however, upon stimulation with TNF-α, IRF-1 is induced, binds to the VCAM-1 promoter, and is necessary for full cytokine-induced transcriptional activation (A. S, Neish, et al., *Mol. Cell. Biol.,* 15:2558-2569 (1995); N. M. Dagia, et al., *J Immunol,* 173: 2041-9 (2004)). C10 inhibits TNF-α induced IRF-1 expression at the protein and mRNA level. While several inhibitors of VCAM-1 are known, very few, if any, have been shown to selectively suppress VCAM-1, to act via IRF-1, and to inhibit monocytic cell adhesion to cytokine inflamed endothelium under fluid shear.

The mechanism of TNF-α induction of IRF-1 in endothelial cells involves Stat1. The IRF-1 promoter region contains two NF-κB binding sites and an activated Stat1-GAS binding sequence (Y. Ohmori, et al., *J Biol Chem,* 272:14899-907 (1997); H. Ochi, et al., *Eur J Immunol,* 32:1821-31 (2002)). Although TNF-α-activated NF-κB is directly involved in the activation of IRF-1 gene transcription, NF-κB is, insufficient for full expression and requires Stat1 occupation of the GAS site. Stat1 could be increased by indirect or direct means. Thus, TNF-α could induce IRF-1 promoter activity by its effect on NF-κB, an increase in type I IFN, and the autocrine/paracrine activation of Type I IFN on Stat1 (O. Tliba, et al., *J Biol Chem,* 278:50615-23 (2003)) Alternatively, TNF-α may directly activate Stat1 since (H. Ochi, et al., *Eur J Immunol,* 32:1821-31 (2002)), cycloheximide, a protein synthesis inhibitor, does not affect TNF-α induced IRF-1 expression in human umbilical vein endothelial cells (HUVEC), suggesting that TNF-α can induce increased IRF-1 expression without protein synthesis, i.e., without de novo synthesis of IFN.

E. Overexpression of Toll-Life Receptors and Signalling in Autoimmune Inflammatory Disease Several lines of evidence have emerged in the past several years, which implicate TLRs in inflammatory-autoimmune disorders. For example, constitutive activation of immune cells caused by defective IL-10 signaling results in development of chronic enterocolitis (K. Takeda, et al., *Immunity,* 10:39-49 (1999)). Introduction of TLR4 deficiency into these mutant mice results in improvement of intestinal inflammation (M. Kobayashi, et al., *J Clin Invest,* 111:1297-308 (2003)). Development of atherosclerosis observed in apolipoprotein E-deficient mice is rescued by introduction of MyD88 deficiency, implicating the TLR-mediated pathway in the development of atherosclerosis (K. S. Michelsen, et al., *Proc Natl Acad Sci USA,* 101:10679-84 (2004)). Involvement of the TLR9-MyD88-dependent pathway in the induction of auto-antibodies in SLE and rheumatoid arthritis is described above.

Overexpressed TLR3/TLR4 and TLR3/TLR4Signals in Nonimmune Cells as well as Monocytes, Macrophages, and Dendritic Cells Are Associated with Autoimmune-inflammatory Diseases. Multiple autoimmune inflammatory diseases are now associated with overexpressed TLR3 and TLR4 and or their signals in nonimmune cells, monocytes, macrophages, and dendritic cells. In the case of TLR3/TLR3 signaling, these include Hashimoto's thyroiditis and Type 1 diabetes; in the case of TLR4/TLR4 signaling these include ulcerative colitis, Crohn's, atherosclerosis, and toxic shock. Overexpressed TLR3/4 or TLR3/4 signaling is not limited to these disorders and includes any disease where TLR signaling is activated and increases type I IFNs or cytokine-increased ECAM expression and leukocyte adhesion, e.g., systemic lupus, rheumatoid arthritis, or any autoimmune-inflammatory disease.

Hashimoto's Thyroiditis. It is well recognized that TLR3 on dendritic cells recognize dsRNA, then signal increases in cytokines and recognition molecules important for immune cell interactions. TLR3 mRNA and protein are now recognized to be expressed on thyrocytes and associated with Hashimoto's thyroiditis (N. Harii, et al., *Mol Endocrinol,* 19:1231-50 (2005)). TLR3 are functional, since incubating thyroid cells with Poly (I:C) causes (i) transcriptional activation of both the NF-κB/Elk1 and IRF-3/IFN-β signal paths, (ii) post transcriptional activation of NF-κB and ERK1/2, and (iii) increased IFN-β mRNA. TLR3 can be overexpressed, along with PKR, major histocompatibility complex (MHC)—I or II, and IRF-1, by transfecting dsRNA into the cells, infection with Influenza A virus, or incubation with IFN-β, but not by incubation with dsRNA or IFN-gamma, or by dsDNA transfection. Methimazole (MMI) and derivatives e.g., phenylmethimazole (C10), significantly prevents overexpression by inhibiting increased transcriptional activation of IRF-3 and ISREs, STAT phosphorylation, but not NF-6β activation. TLR3 can be functionally overexpressed in cultured human thyrocytes by dsRNA transfection or IFN-β treatment. Immunohistochemical studies show TLR3 protein is overexpressed in human thyrocytes surrounded by immune cells in 100% of patients with Hashimoto's thyroiditis examined, but not in normal or Graves' thyrocytes. Without wishing to be bound by theory in any way, it can be concluded that functional TLR3 are present on thyrocytes; TLR3 downstream signals can be overexpressed by pathogen-related stimuli; overexpression can be reversed by C10>>MMI by inhibiting only the IRF-3/IFN-β/STAT arm of the TLR3 signal system; and TLR3 overexpression can induce an innate immune response in thyrocytes which may be important in the pathogenesis of Hashimoto's thyroiditis and in the immune cell infiltrates.

Hashimoto's thyroiditis, the most frequent tissue-specific autoimmune disease in humans, is characterized by infiltration of the thyroid gland by B and T lymphocytes, cellular and humoral autoimmunity, and autoimmune destruction of the thyroid (C. M. Dayan, et al., *N Engl J Med*, 335:99-107 (1996)). Thyrocytes of patients with Hashimoto's thyroiditis, express ICAM-1, B7-1, essential co-stimulatory molecules important for immune cell interactions, major histocompatibility complex (MHC) class I, interferon (IFN) inducible protein IP-10, a CXCL chemokine that exerts a chemotactic activity on lymphoid cells, and Fas gene, a member of the closely linked group of tumor necrosis factor genes (G. Pesce, et al., *J Endocrinol Invest*, 25:289-95 (2002); M. A. Garcia-Lopez, et al., *J Clin Endocrinol Metab*, 86:5008-16 (2001)).

Infectious agents have been implicated in the induction of autoimmune disease (J. Guardiola, et al., *Crit Rev Immunol*, 13:247-68 (1993); R. Gianani, et al., *Proc Natl Acad Sci USA*, 93:2257-9 (1996); M. S. Horwitz, et al., *Nat Med*, 4:781-5 (1998); H. Wekerle, *Nat Med*, 4:770-1 (1998); C. Benoist, et al., *Nature*, 394:227-8 (1998)) including thyroiditis (Y. Tomer, et al., *Endocr Rev*, 14:107-20 (1993)). In the 1990's it was suggested that viral triggering of autoimmunity might result from local infection of tissues, induction of abnormal or increased expression of MHC genes, presentation of self-antigens to immune cells, and bystander activation of T cells (M. S. Horwitz, et al., *Nat Med*, 4:781-5, (1998); H. Wekerle, Nat Med, 4:770-1, (1998); C. Benoist, et al., *Nature*, 394:227-8, (1998)).

Endotoxic Shock. A variety of studies have implicated TLR4 in endotoxic shock. For example, C3H/HeJ mice have a point mutation in the Tlr4 gene that results in defects in TLR4 signaling and hypo-responsiveness to challenge with LPS (K. Hoshino, et al., *J Immunol*, 162:3749-52 (1999)). Recent work (G. Andonegui, et al., *J Clin Invest*, 111:1011-1020 (2003)) found strong evidence that endothelial TLR4, as opposed to leukocyte TLR4, is a critical player in endotoxic shock. Thus, mice deficient in endothelial TLR4, but not leukocyte TLR4, had significantly attenuated leukocyte sequestration in the lungs subsequent to challenge with LPS.

Cultured murine macrophages, for example RAW 264.7 cells, when treated with LPS display a rapid induction of many genes, which are regulators of the inflammatory response and are considered an in vitro model of changes in endotoxic shock (M. A. Dobrovolskaia, et al., *Microbes Infect*, 4:903-14 (2002)). LPS stimulated genes in cultured murine macrophages include genes coding for proinflammatory cytokines (IFN-β IL-1β, TNF-α, IL-6, and IL-12), which act on either the macrophages/monocytes themselves or on other target cells to regulate the inflammatory process, which occurs in septic shock. Upon stimulation with LPS, macrophages can also produce CXC chemokines such as IP-10, which serve to further attract immune cells to a site of inflammation (K. M. Kopydlowski, et al., *J Immunol*, 163:1537-44 (1999)). Macrophages stimulated with LPS can also produce nitric oxide (NO) as a result of expression of the inducible nitric oxide synthase enzyme (iNOS) (C. Bogdan, *Nat Immunol*, 2:907-16 (2001)). Each of these factors considered to be important in the pathogenesis of septic shock are typically absent or found at extremely low levels in unstimulated macrophages.

Binding of IFN-β to the type I interferon receptor results in phosphorylation of Stat I as a key component for the transduction of a signal to the nucleus to induce expression of iNOS and IP-10 in the mouse macrophage (Y. Ohmori, et al., *J Leukoc Biol*, 69:598-604 (2001)). Stat1 null animals show an approximately 50% enhanced survival rate when challenged with a lethal dose of LPS (M. Karaghiosoff, et al., *Nat Immunol*, 4:471-7 (2003)) whereas IFN-β null mice challenged with a lethal LPS dose showed a 100% enhancement of survival (M. Karaghiosoff, et al., *Nat Immunol*, 4:471-7 (2003)) Therefore, blocking parts of the IFN-β signal pathway is not as effective as blocking the pathway completely.

LPS treatment of macrophage/monocytes increases levels of Interferon Response factor (IRF)-1 (M. A. Dobrovolskaia, et al., *Microbes Infect*, 4:903-14 (2002)). IRF-1 acts as a transcription factor to directly bind to DNA to enhance transcription of other genes such as iNOS(R. Kamijo, et al., *Science*, 263:1612-5 (1994)). In macrophages treated with LPS IRF-1 is required for the transcriptional control of the iNOS gene (R. Kamijo, et al., *Science*, 263:1612-5 (1994)). Several other IRF-1 target genes exist such as the interferon inducible MX gene which codes for the antiviral Mx protein (D. Damino, et al., *Curr Opin Cell Biol*, 13:454-60 (2001)). The MX promoter has been shown to contain strong IRF-1 binding elements (C. E. Grant, et al., *Nucleic Acids Res*, 28:4790-9 (2000)).

The proinflammatory cytokines IL-1β, TNF-α, IL-6, and IL-12 can be induced by LPS signaling through TLR4 (M. A. Dobrovolskaia, et al., *Microbes Infect*, 4:903-14 (2002)) and play a role in endotoxic shock (N. C. Riedemann, et al., *J Clin Invest*, 112:460-7 (2003)). However, a recent report identified IFN-β as a critical secondary effector, which is induced upon LPS activation of TLR4 signaling and contributes to mortality in a murine septic shock model (M. Karaghiosoff, et al., *Nat Immunol*, 4:471-7 (2003)).

Inflammatory Bowel Disease (IBD). TLR4 and components of normal gastrointestinal gram-negative bacteria appear to play a key role in the pathogenesis of colitis (C. Fiocchi, *Gastroenterology*, 115:182-205 (1998); E. Cario, et al., *Infect Immun*, 68:7010-7 (2000)). The disease is associated with severe inflammation, edema, and leukocyte infiltration in the colonic tissues (C. Fiocchi, *Gastroenterology*, 115: 182-205 (1998); E. Cario, et al., *Infect Immun*, 68:7010-7 (2000); U. P. Singh, et al., *J Immunol*, 171:1401-6 (2003); M. B. Grisham, et al., *Inflammatory Bowel Disease*, 55-64 (1999)). There is increased interferon (IFN) production and secretion and increased levels of cytokines, including TNF-α and IL-1, that up-regulate endothelial cell adhesion molecules (ECAMs), in particular VCAM-1, which are associated with leukocyte adhesion. There are increased chemokine levels such as IP-10 which is known to be colitis related (U. P. Singh, et al., *J Immunol*, 171:1401-6 (2003)).

Cario et al. (E. Cario, et al., *Infect Immun*, 68:7010-7 (2000)), reported that TLR4 was upregulated in intestinal epithelial cell lines isolated from patients with IBD. Using the dextran sodium sulfate (DSS)—induced murine model of colitis related to Crohn's and ulcerative colitis, Ortega-Cava et al. (C. F. Ortega-Cava, et al., *J Immunol*, 170:3977-85 (2003)) found that TLR4 is upregulated in the colon of colitic mice relative to normal mice. Enterocolitis was reported to be significantly improved in TLR4/Stat3-deficient mice, whereas TNF-α/Stat3 deficient mice still had severe enterocolitis, also indicating the importance of TLR4 in mouse models of enterocolitis (M. Kobayashi, et al., *J Clin Invest*, 111:1297-308 (2003)).

Atherosclerosis and the Vascular Complications of Types 1 and 2 Diabetes, Obesity, and Hypertension: Recent studies have demonstrated the importance of TLR4 in the initiation and progression of atherosclerosis (K. S. Michelsen, et al., *Proc Natl Acad Sci USA*, 101:10679-84 (2004); G. Pasterkamp, et al., *Eur J Clin Invest*, 34:328-34 (2004); G. Andonegui, et al., *J Clin Invest*, 111:1011-1020 (2003)). Thus, mouse knockout studies and studies of human TLR4 polymorphisms have demonstrated that TLR4 plays a role in the initiation and progression of atherosclerosis and vascular disease. Further, (K. S. Michelsen, et al., *Proc Natl Acad Sci USA*, 101:10679-84 (2004)) mice deficient in endothelial cell TLR4 had a significant reduction in aortic plaque development in atherosclerosis-prone apolipoprotein E-deficient (ApoE−/−) mice and the lack of TLR4 signaling can result in reduced monocyte adhesion to TLR4$^{-/-}$ endothelium.

The model that has emerged is that oxidized LDL, enteroviruses or enterobacteria act as noxious injurious events to increase TLR expression in areas of turbulent blood flow. The increase in the MyD88 pathway, NF-κB, and the cytokine, TNFα, increase VCAM-1 and attract leukocytes. Thus, it is already suggested that it is important to not only block high lipids and or high blood pressure that induce damage at the lesion foci, but also to block pathologic TLR4 induction and signaling causing immune cell attraction and leukocyte adhesion (G. Pasterkamp, et al., *Eur J Clin Invest*, 34:328-34 (2004)).

Type 1 Diabetes: A recent report has associated overexpressed TLR3 in pancreatic β cells and destructive changes in Type 1 diabetes (L. Wen, et al., *J Immunol*, 172:3173-80 (2004)). Moreover, the report showed dsRNA could induce insulinitis and type 1 diabetes in animals, consistent with the known animal model wherein coxsacki virus induces Type 1 diabetes in NOD mice. Devendra and Eisenbarth (D. Devendra, et al., *Clin Immunol*, 111:225-33 (2004)) point out that a wide variety of studies have implicated enteroviruses as a potential agent in the pathogenesis of type 1 diabetes suggesting that the mechanism of viral infection leading to β cell destruction involves the cytokine interferon alpha (IFN-α) [a Type 1 IFN like IFIβ], and hypothesize that activation of TLR by dsRNA and induction of IFN-α, may activate or accelerate immune-mediated beta cell destruction. They conclude (D. Devendra, et al., *Clin Immunol*, 111:225-33 (2004)) that, "therapeutic agents targeting IFN-α may potentially be beneficial in the prevention of type 1 diabetes and autoimmunity."

Type I diabetes appears to require a permissive genetic background and an external factor which may be viral. Islet cell antibodies are common in the first months of the disease. They probably arise in part due to β cell injury and represent a primary autoimmune disease. The preeminent metabolic abnormality in Type 1 diabetes is hyperglycemia and glucosuria. Late complications of diabetes are numerous and include increased atherosclerosis with attendant stroke and heart complications, kidney disease and failure, and neuropathy that can be totally debilitating. The link to HLA antigens has been known since 1970. Certain HLA alleles are associated with increased frequency of disease, others with decreased frequency. Increased MHC class I and aberrant MHC class II expression in islet cells has been described (G. F. Bottazzo, et al., *N Engl J Med*, 313:353-60 (1985); A. K. Foulis, et al., *Diabetes*, 35:1215-24 (1986)). A definitive link to MHC class I has been made in a genetic animal model of the disease. Thus MHC class I deficiency results in resistance to the development of diabetes in the NOD mouse (D. V. Serreze, et al., *Diabetes*, 43:505-9 (1994); L. S. Wicker, et al., *Diabetes*, 43:500-4 (1994)). Combined with recent TLR3 data, and data from Coxsackie virus mouse models, it is hypothesized that infection or environmental induction of Type 1 diabetes occurs in a genetically susceptible mammal, that GAD and anti-islet cell antibodies are abnormal for a prolonged latent phase before total islet cell destruction, and that TLR-induced changes in MHC genes are important in disease expression.

Environmental Inducers of Autoimmune-Inflammatory Disease: The TLR signaling pathway and its pathologic expression in nonimmune cells represents an intriguing link between viral agents and autoimmune-inflammatory disease. For example, multiple viruses have been linked to type 1 diabetes, (e.g., Coxsackie B4 virus) (J. Guardiola, et al., *Crit Rev Immunol*, 13:247-68 (1993); R. Gianani, et al., *Proc Natl Acad Sci USA*, 93:2257-9 (1996); M. S. Horwitz, et al., *Nat Med*, 4:781-5 (1998); H. Wekerle, *Nat Med*, 4:770-1 (1998); C. Benoist, et al., *Nature*, 394:227-8 (1998); Y. Tomer, et al., *Endocr Rev*, 14:107-20 (1993); M. F. Prummel, et al., *Thyroid*, 13:547-51 (2003); G. S. Cooper, et al., *J Rheumatol*, 28:2653-6 (2001); M. M. Ward, et al., *Arch Intern Med*, 152:2082-8 (1992)). The involvement of other "noxious" environmental events is also suspected.

One example of a noxious environmental induction process is tobacco and smoking. Many epidemiologic studies have found a positive association between smoking and autoimmune-inflammatory conditions including rheumatoid arthritis, autoantibodies, Raynaud phenomenon, Goodpasture syndrome, and Graves' disease (I. Roitt, *Essential Immunology*, 7th ed., 312-346 (1991); S. A. Jimenez, et al., *Ann Intern Med*, 140:37-50 (2004); C. Nagata, et al., *Int J Dermatol*, 34:333-7 (1995)). A significant increase in the risk of systemic lupus erythematosus (SLE) has been indicated, as well as rapid development of end-stage renal disease in these patients (G. S. Cooper, et al., *J Rheumatol*, 28:2653-6 (2001); M. M. Ward, et al., *Arch Intern Med*, 152:2082-8 (1992)) Smoking is an independent risk factor for diabetes and aggravates the risk of serious disease and premature death (E. B. Rimm, et al., *Am J Public Health*, 83:211-4 (1993); E. B. Rimm, et al., *BMJ*, 310:555-9 (1995); N. Kawakami, et al., *Am J Epidemiol*, 145:103-9 (1997); D. Haire-Joshu, et al., *Diabetes Care*, 22:1887-98 (1999); J. C. Will, et al., *Int J Epidemiol*, 30:540-6 (2001)). Results from both cross-sectional and prospective studies show enhanced risk for micro- and macrovascular disease, as well as premature mortality from the combination of smoking and diabetes. On the molecular and cellular levels, a potentially important pathogenic mechanism is the production of chemically altered DNA by reactive elements in cigarette smoke, resulting in the production of autoantibodies specifically against altered DNA (B. H. Hahn, *N Engl J Med*, 338:1359-68 (1998); J. B. Winfield, et al., *J Clin Invest*, 59:90-6 (1977)). Additionally, smoking enhances the ability of high glucose levels to affect the walls of the arteries, making them more likely to develop fatty deposits. Smoking enhances a diabetic's chance of having high blood pressure, high levels of lipids such as triglycerides, and lower levels of the protective HDL cholesterol. Cigarette smoking may thus act in concert with other environmental triggers, such as obesity or infectious agents, and can be construed as a major and related environmental factor in the development of diabetes and its complications.

Therefore, it is evident that Hashimoto's thyroiditis may be grouped with insulinitis and Type 1 diabetes, colitis, toxic shock, and atherosclerosis as an autoimmune/inflammatory disease associated with TLR3 or TLR4 overexpression and signaling in nonimmune cells, monocytes, macrophages, and dendritic cells by an induction process involving molecular signatures of environmental pathogens (K. S. Michelsen, et al., *Proc Natl Acad Sci USA*, 101:10679-84 (2004); G. Pasterkamp, et al., *Eur J Clin Invest*, 34:328-34 (2004); D. Devendra, et al., *Clin Immunol*, 111:225-33 (2004); L. Wen, et al., *J Immunol*, 172:3173-80 (2004); G. Andonegui, et al., *J Clin Invest*, 111:1011-1020 (2003); C. Fiocchi, *Gastroenterology*, 115:182-205 (1998); B. Beutler, *Nature*, 430:257-63 (2004); K. S. Michelsen, et al., *J Immunol*, 173:5901-7 (2004)). The present invention provides for the use of phenylmethimazoles, methimazole derivatives, and tautomeric cyclic thiones for the treatment of autoimmune/inflammatory diseases associated with TLR3 or TLR4 overexpression and signaling in nonimmune cells as well as monocytes, macrophages, and dendritic cells. It additionally provides for the use of phenylmethimazoles, methimazole derivatives, and tautomeric cyclic thiones for the treatment of autoimmune/inflammatory diseases associated with pathologic activation of TLR signaling involving activation of IRF-3, synthesis of Type 1 IFN, activation of STATs, increased IRF-1 gene expression, and activation of proteins with ISRE elements.

SUMMARY OF THE INVENTION

The present invention relates to the treatment of autoimmune and/or inflammatory diseases associated with overexpression of toll-like receptor 3 as well as toll-like receptor 4, and or their signals, in nonimmune cells, as well as monocytes, macrophages, or dendritic cells, and related pathologies. This invention also relates to the use of phenylmethimazoles, methimazole derivatives, and tautomeric cyclic thiones for the treatment of autoimmune and inflammatory diseases associated with overexpression of toll-like receptor 3 as well as toll-like receptor 4, and or their signals, in nonimmune cells, as well as monocytes, macrophages, or dendritic cells, and related pathologies. This invention also relates to treating a subject having a disease or condition associated with abnormal toll-like receptor 3 as well as toll-like receptor 4, and or their signals, in nonimmune cells, as well as in monocytes, macrophages, or dendritic cells.

In another embodiment, the present invention provides for methods of treating a TLR mediated disease involving activation of, or pathologic signaling of, IRF-3. In another embodiment, the present invention provides' for methods of treating a disease involving overexpression or pathologic signaling Type 1 interferons. In another embodiment, the present invention provides for methods of treating a TLR mediated disease involving overexpression or pathologic signaling of ISRE containing genes. In another embodiment, the present invention provides for methods of treating a TLR mediated disease involving overexpression or pathologic signaling of IRF-1. In another embodiment, the present invention provides for methods of treating a TLR mediated disease involving activation of, or pathologic signaling by Stat1 or Stat3.

In another embodiment, the present invention provides for methods of treating a disease involving activation of, or pathologic expression, of the TLR signal pathway resulting in activation of IRF-3. In another embodiment, the present invention provides for methods of treating a disease involving overexpression or pathologic expression of the TLR signal pathway resulting in the synthesis of Type 1 interferons. In another embodiment, the present invention provides for methods of treating a disease involving overexpression or pathologic signaling of the TLR signal pathway resulting in the activation of ISRE containing genes. In another embodiment, the present invention provides for methods of treating a disease involving pathologic expression of the TLR signal pathway resulting in overexpression of IRF-1. In another embodiment, the present invention provides for methods of treating a disease involving activation of, or pathologic expression of the TLR signal pathway resulting in activation of Stat1 or Stat3.

In another embodiment, the present invention provides for methods of treating a TLR-mediated disease or disorder in a patient in need thereof comprising administering a therapeutically effective amount of phenylmethimazoles, methimazole derivatives, and/or tautomeric cyclic thiones.

In another embodiment, the present invention provides for methods of treating a TLR-mediated disease or disorder involving a pathological condition resulting from abnormal cell proliferation; transplantation rejection, autoimmune, inflammatory, proliferative, hyperproliferative, or cardiovascular disease in a patient in need thereof comprising administering a therapeutically effective amount of phenylmethimazoles, methimazole derivatives, and/or tautomeric cyclic thiones.

In another embodiment, the present invention provides for methods of treating a subject having a TLR-mediated autoimmune-inflammatory disease, or a predisposition to a TLR-mediated autoimmune-inflammatory disease, comprising administering to the subject a therapeutically effective amount of a composition of the present invention.

In one embodiment, the TLR-mediated autoimmune-inflammatory disease is Alopecia, Areata, Ankylosing Spondylitis, Antiphospholipid Syndrome, Autoimmune Addison's Disease, Autoimmune Hemolytic Anemia, Autoimmune Hepatitis, autoimmune blepharitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barre, Hashimoto's Thyroiditis, Post partum thyroiditis, Idiopathic Pulmonary Fibrosis, Idiopathic Thrombocytopenia Purpura (ITP), IgA Nephropathy, Insulin dependent Diabetes, Type 2 Diabetes, Complications of Type 1 or 2 diabetes, Juvenile Arthritis, Lichen Planus, Systemic Lupus, Meniere's Disease, Mixed Connective Tissue Disease, Neural inflammation, Lung Injury, Myositis, Myocarditis, Hepatitis, Granulomatous Arthritis, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiffman Syndrome, Takayasu Arteritis, Temporal Arteritis/Giant Cell Arteritis, Ulcerative Colitis, Uveitis, Vasculitis, Vitiligo, Wegener's Granulomatosis, or myasthenia gravis.

In another embodiment, the TLR-3 mediated autoimmune-inflammatory disease is Insulin-dependent Diabetes.

In another embodiment, the present invention provides for methods of treating a TLR-mediated disease in nonimmune cells or disorder in a patient in need thereof.

In another embodiment, the present invention provides for methods of treating a TLR-mediated autoimmune-inflammatory disease or disorder in a patient in need thereof comprising administering a therapeutically effective amount of phenylmethimazoles, methimazole derivatives, and/or tautomeric cyclic thiones.

In another embodiment, the present invention provides for methods of treating a TLR-mediated autoimmune-inflammatory disease or disorder involving nonimmune cells in a patient in need thereof comprising administering a therapeutically effective amount of phenylmethimazoles, methimazole derivatives, and/or tautomeric cyclic thiones.

In another embodiment, the present invention provides for methods of treating a TLR-mediated autoimmune-inflammatory disease or disorder associated with immune cell infiltration and destruction of the nonimmune cells in a patient in need thereof comprising administering a therapeutically effective amount of phenylmethimazoles, methimazole derivatives, and/or tautomeric cyclic thiones.

In another embodiment, the present invention provides for methods of treating a TLR-mediated disease or disorder involving a pathologic innate immune response in a patient in need thereof comprising administering a therapeutically effective amount of phenylmethimazoles, methimazole derivatives, and/or tautomeric cyclic thiones.

In one embodiment, the TLR-mediated disease or disorder is a pathological condition resulting from abnormal cell proliferation; transplantation rejections, autoimmune, inflammatory, proliferative, hyperproliferative, or cardiovascular diseases.

In another embodiment, the cardiovascular disease or disorder is restenosis, coronary artery disease, atherosclerosis, atherogenesis, cerebrovascular diseases or events, coronary events, angina, ischemic disease, congestive heart failure, pulmonary edema associated with acute myocardial infarction, thrombosis, high or elevated blood pressure in hypertension, platelet aggregation, platelet adhesion, smooth muscle cell proliferation, a vascular or non-vascular complication associated with the use of a medical device, a wound associated with the use of a medical device, vascular or non-vascular wall damage, peripheral vascular disease or neoinitimal hyperplasia following percutaneous transluminal coronary angiograph.

In one embodiment, the cerebrovascular disease or event is a cerebral infarction or stroke (caused by vessel blockage or hemorrhage), or transient ischemia attack (TIA), syncope, or atherosclerosis of the intracranial and/or extracranial arteries, and the like. In one embodiment, the coronary event is a myocardial infarction, myocardial revascularization procedures, angina, cardiovascular death or acute coronary syndrome.

In another embodiment, the present invention provides for a method of ameliorating one or more symptoms of atherosclerosis in a mammal, said method comprising administering to said mammal a methimazole derivative and/or tautomeric cyclic thione in an amount sufficient to ameliorate one or more symptoms of atherosclerosis.

In another embodiment, the present invention provides for a method of ameliorating one or more symptoms of myocardial diseases in a mammal, said method comprising administering to said mammal a methimazole derivative and/or tautomeric cyclic thione in an amount sufficient to ameliorate one or more symptoms of myocardial diseases. In another embodiment, the myocardial diseases have inflammatory and immunological properties. In another embodiment, the myocardial disease is coronary heart disease, reversible or irreversible myocardial ischemia/reperfusion damage, acute or chronic heart failure and restenosis.

In another embodiment, the present invention provides for a method of mitigating or preventing a coronary complication associated with an acute phase response to an inflammation in a mammal, wherein said coronary complication is a symptom of atherosclerosis, said method comprising administering to a mammal having said acute phase response, or at risk for said acute phase response, a methimazole derivative and/or tautomeric cyclic thione in an amount sufficient to mitigate or prevent said coronary complication.

In another embodiment, the present invention provides for a method of mitigating or preventing an acute phase response. In another embodiment, the acute phase response is an inflammatory response associated with a recurrent inflammatory disease.

In another embodiment, the acute phase response is associated with a disease selected from the group consisting of leprosy, tuberculosis, systemic lupus erythematosus, polymyalgia rheumatica, polyarteritis nodosa, scleroderma, idiopathic pulmonary fibrosis, chronic obstructive pulmonary disease, Alzheimer's Disease AIDS, coronary calcification, calcific aortic stenosis, osteoporosis, and rheumatoid arthritis.

In another embodiment, the acute phase response is an inflammatory response associated with a condition selected from the group consisting of a bacterial infection, a viral infection, a fungal infection, an organ transplant, a wound, an implanted prosthesis, parasitic infection, sepsis, endotoxic shock syndrome, and biofilm formation.

In another embodiment, the present invention provides for methods of treating a TLR-mediated autoimmune-inflammatory disease or disorder associated with immune cell infiltration and destruction of the nonimmune cells in a patient in need thereof, the method comprising administering a therapeutically effective amount of phenylmethimazoles, methimazole derivatives, and/or tautomeric cyclic thiones to a mammal in an amount or mixture effective for treating one or more conditions selected from the group consisting of septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, inflammatory bowel disease, regional enteritis, multiple sclerosis, systemic lupus erythrematosis, ENL in leprosy, radiation damage, asthma, and hyperoxic alveolar injury.

In one embodiment, the TLR-mediated autoimmune/inflammatory disease or disorder is an acute inflammatory disease. In another embodiment, the TLR-mediated autoimmune/inflammatory disease or disorder is an acute inflammatory disease selected from the group consisting of: (a) endotoxemia or (b) toxic shock syndrome associated with (c) septicemia; and (d) infectious disease.

In another embodiment, the TLR-mediated autoimmune/inflammatory disease or disorder is selected from septic shock of whatever type, etiology, or pathogenesis; or septic shock that is a associated with renal failure; acute renal failure; cachexia; malarial cachexia; hypophysial cachexia; uremic cachexia; cardiac cachexia; cachexia suprarenalis or Addison's disease; cancerous cachexia; and cachexia as a consequence of infection by the human immunodeficiency virus (HIV). In another embodiment, the septic shock is endotoxic shock. In another embodiment, the endotoxic shock is induced by gram negative bacteria. In yet another embodiment, the endotoxic shock is induced by gram positive bacteria. In another embodiment, the septic shock is LPS-induced shock. In another embodiment, the toxic shock, septic shock, endotoxemia, endotoxic shock or LPS-induced toxic shock syndrome is associated with a disease wherein an antibiotic is being administered to the subject.

In another embodiment, the present invention provides for methods of treating a TLR3-mediated pathological condition resulting from or in abnormal cell proliferation, a transplant rejection, an autoimmune, inflammatory, proliferative, hyperproliferative or vascular disease, for reducing scar tissue or for inhibiting wound contraction in a patient in need thereof comprising administering a therapeutically effective amount of phenylmethimazoles, methimazole derivatives, and/or tautomeric cyclic thiones to a subject in need of such therapy.

In another embodiment, the pathological condition resulting from abnormal cell proliferation is a cancer, a Karposi's sarcoma, a cholangiocarcinoma, a choriocarcinoma, a neoblastoma, a Wilm's tumor, Hodgkin's disease, a melanoma, multiple myelomas, a chronic lymphocytic leukemia or an acute or chronic granulocytic lymphoma.

In another embodiment, the autoimmune, inflammatory, proliferative, hyperproliferative or vascular disease is rheumatoid arthritis, restenosis, lupus erythematosus, systemic lupus erythematosus, Hashimoto's thyroiditis, myasthenia gravis, diabetes mellitus, uveitis, nephritic syndrome, multiple sclerosis, an inflammatory skin disease, an inflammatory lung disease, an inflammatory bowel disease, an inflammatory disease that affects or causes obstruction of a body passageway, an inflammation of the eye, nose or throat, a fungal infection or a food related allergy.

In another embodiment, the present invention provides for methods of treating a TLR3-mediated pathological condition resulting from an allergen. In another embodiment, the present invention provides for methods of treating a TLR3-mediated pathological condition resulting in an allergy.

In another embodiment, the present invention provides for methods of treating a TLR3/4-mediated disease, disorder or condition caused by is asthma, chronic bronchoconstriction, acute bronchoconstriction, bronchitis, small airways obstruction, emphysema, obstructive airways disease, inflammatory airways disease, acute lung injury or bronchiectasis. In another embodiment, the asthma is atopic asthma; non-atopic asthma; allergic asthma; atopic bronchial IgE-mediated asthma; bronchial asthma; essential asthma; true asthma; intrinsic asthma caused by pathophysiologic disturbances; extrinsic asthma caused by environmental factors; essential asthma of unknown or unapparent cause; bronchitic asthma; emphysematous asthma; exercise-induced asthma; allergen induced asthma; cold air induced asthma; occupational asthma; infective asthma caused by bacterial, fungal, protozoal or viral infection; non-allergic asthma; incipient asthma; wheezy infant syndrome; or bronchiolytis.

In another embodiment, the present invention provides for methods of treating a TLR3-mediated pathological condition resulting from an obstructive airways disease or inflammatory airways disease. In one embodiment, the obstructive airways disease or inflammatory airways disease is chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy or airways disease that is associated with pulmonary hypertension. In another embodiment, the obstructive airways disease or inflammatory airways disease is bronchitis. In one embodiment, the bronchitis is chronic bronchitis, acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* bronchitis, streptococcal bronchitis or vesicular bronchitis. In one embodiment, the bronchiectasis is cylindric bronchiectasis, sacculated bronchiectasis, fusiform bronchiectasis, capillary bronchiectasis, cystic bronchiectasis, dry bronchiectasis or follicular bronchiectasis.

In one embodiment, the present invention provides for methods of treating an autoimmune or inflammatory disease associated with Toll-like receptor 3 overexpression resulting from other inflammation inducing conditions that may be treated to ameliorate symptoms associated with inflammation or to diminish the existing inflammation. In one embodiment, the other inflammation or irritation associated therewith may be from a variety of sources either physical or chemical and may include: insect bites or stings, contact with a particular type plant (e.g., poison oak, etc.), radiation (e.g., U.V.), non-infectious conjunctivitis, hemorrhoids (acute), abrasions, ingrown finger or toenail (granulation), skin graft donor sites, vaginitis, psoriasis, herpes simplex (cold sores, aphthous ulcers), pruritis ani/cruri, chemical inflammation, and the like.

In one embodiment, the present invention provides for methods of treating an autoimmune or inflammatory disease associated with Toll-like receptor 3/4 overexpression resulting from other inflammation inducing conditions that may be treated to ameliorate symptoms associated with inflammation or to diminish the existing inflammation wherein the inflammation is the result of extraneously induced damage to cells or tissue. Such damage may be induced by chemical and/or physical influences upon the skin or mucus membranes of humans and animals. Examples of physical influences are infarction, heat, cold, radiation and electrical shock, and examples of chemical influences are contact with acids, bases and allergens. Inflammation may be induced by microorganisms or their molecular signature molecules acting on the skin, as well as being the result of microorganisms invading the human or animal body.

In another embodiment, the inflammatory responses that may be ameliorated may be on the skin or a mucus membrane of a subject and includes, but is not limited to, conditions such as inflammation around erupting wisdom teeth, following extraction of teeth, periodontal abscesses, prosthesis induced pressure sores on the mucosa, fungal infections, for treating exposed bone surface in alveolitis sicca dolorosa, which is a painful condition which may arise following extraction of teeth, chronic and acute inflammatory diseases including, but not limited to, pancreatitis, rheumatoid arthritis, osteoarthritis, asthma, inflammatory bowel disease, psoriasis and in certain neurological disorders such as Alzheimer's disease. Among other conditions are environmental, e.g., sun or wind exposure, trauma or wounds, e.g., cuts, burns or abrasions, exposure to chemicals such as alkaline soaps, heavy metals, e.g. lead or mercury, detergents, liquid solvents, oils, preservatives, and disease, e.g., eczema, psoriasis, seborrheic dermatitis.

In one embodiment, the present invention provides for methods of treating an autoimmune or inflammatory disease associated with Toll-like receptor 3 overexpression, e.g., Hashimoto's thyroiditis, inflammatory lung disease, and Type 1 diabetes).

In another embodiment, the present invention provides for methods of treating TLR3- or TLR4-linked diseases involving pathogen or pathogen molecular signals by inhibiting the increased IRF-3 signal pathway, but not the NF-kappa B signal pathway. In one embodiment, the pathogen related agent or product is a virus, bacteria, dsRNA, Type 1 IFN, or environmental induction event, e.g tobacco. In another embodiment the bacteria is exemplified by, but not limited to, *Chlamydia* or an enterobacteria. In still another embodiment, the bacteria are gram negative bacteria. In still another embodiment, the virus is an RNA virus, enterovirus, *Chlamydia*, or Coxsackie virus. In another embodiment, the virus is a single strand RNA virus. In another embodiment, the virus is Influenza A.

In another embodiment, the present invention provides for methods of treating TLR3- or TLR4-linked diseases involving pathogen or pathogen molecular signal increased Type 1 interferon gene expression. In one embodiment, the pathogen related agent or product is a virus, bacteria, dsRNA, Type 1 IFN, or environmental induction event, e.g. tobacco. In another embodiment the bacteria are exemplified by, but not limited to, *Chlamydia* or enterobacteria. In still another embodiment, the bacteria are gram-negative bacteria. In still another embodiment, the virus is an RNA virus, enterovirus, or Coxsackie virus. In another embodiment, the virus is a single strand RNA virus. In another embodiment, the virus is Influenza A.

In another embodiment, the present invention provides for methods of inhibiting TLR3- or TLR4-linked, pathogen or pathogen molecular signal increased Stat1 or Stat3 activation. In one embodiment, the pathogen related agent or product is a virus, bacteria, dsRNA, Type 1 IFN, or environmental induction event, e.g. tobacco. In another embodiment the bacteria are exemplified by, but not limited to, *Chlamydia* or enterobacteria. In still another embodiment, the bacteria re a gram negative bacteria. In still another embodiment, the virus is an RNA virus, enterovirus, or Coxsackie virus. In another embodiment, the virus is a single strand RNA virus. In another embodiment, the virus is Influenza A.

In another embodiment, the present invention provides for methods of inhibiting TLR3- or TLR4-linked, pathogen increased activation of interferon sensitive response element (ISRE). In one embodiment, the pathogen related agent or product is a virus, bacteria, dsRNA, Type 1 IFN, or environmental induction event, e.g. tobacco. In another embodiment the bacteria are exemplified by, but not limited to, *Chlamydia* or enterobacteria. In still another embodiment, the bacteria re a gram negative bacteria. In still another embodiment, the virus is an RNA virus, enterovirus, or Coxsackie virus. In another embodiment, the virus is a single strand RNA virus. In another embodiment, the virus is Influenza A.

In another embodiment, the present invention provides for methods of inhibiting TLR3- or TLR4-linked, pathogen or pathogen molecular signal increased Stat1 or Stat3 activation. In one embodiment, the pathogen related agent or product is lypopolysaccharide, Type 1 IFN, or environmental induction event, e.g. tobacco, hyperlipidemia. In another embodiment, the pathogen is bacteria. In another embodiment the bacteria are exemplified by, but not limited to, *Chlamydia* or enterobacteria. In still another embodiment, the bacteria are gram-negative bacteria. In still another embodiment, the bacteria are gram-negative bacteria. In another embodiment, the pathogen is a virus. In another embodiment, the virus is an enterovirus.

In another embodiment, the present invention provides for methods of inhibiting TLR3 or TLR4-linked, pathogen or pathogen molecular signal increased activation of genes with interferon sensitive response elements (ISREs). In one embodiment, the pathogen related agent or product is lypopolysaccharide, Type 1 IFN, or environmental induction event, e.g. tobacco, hyperlipidemia. In another embodiment, the pathogen is bacteria. In another embodiment, the bacteria are gram-negative bacteria. In another embodiment, the pathogen is a virus. In another embodiment, the virus is an enterovirus.

In another embodiment, the present invention provides for methods of inhibiting cytokine increased activation of interferon sensitive response element (ISRE). In one embodiment, the cytokine is IL-1. In another embodiment, the cytokine is TNF-alpha. In another embodiment, the cytokine is gamma interferon. In another embodiment the cytokine is a proinflammatory cytokine including but not limited to IL-6, IL-12, IFN-α, or IFN-β.

In another embodiment, the present invention provides for methods which measure therapeutic efficacy of an agent that reduces pathologic TLR3 or TLR4 expression and TLR3 or TLR4 mediated signal molecules in nonimmune cells, monocytes, macrophages or serum as well of a pathology such as an autoimmune or inflammatory disease (e.g Type 1 diabetes, colitis, autoimmune thyroiditis, atherosclerosis, and vascular complications of diabetes). In one embodiment, the levels of expression of TLR3 or TLR4 and TLR3-sor TLR4 signaling molecules in nonimmune cells, monocytes, or macrophages, or serum is a diagnostic measure to predict therapeutic efficacy of an agent that reduces pathologic TLR3 or TLR4 expression and TLR3 or TLR4 mediated signal molecules in an autoimmune-inflammatory diseases.

In another embodiment, the level of expression of TLR3 in thyrocytes or pancreatic islet cells is measured as a method not only for diagnosis of Hashimoto's disease, insulinitis or Type 1 diabetes but as a measure of therapy by an agent that reduces pathologic TLR3 expression and TLR3 mediated signal molecules altered in these autoimmune-inflammatory diseases. In still another embodiment the levels of expression of TLR4 and TLR4 mediated signal molecules in monocytes, macrophages, vascular endothelial cells, intestinal epithelial cells, is measured as a method not only for diagnosis but also as a measure of therapy by an agent that reduces pathologic TLR4 expression and TLR4 mediated signal molecules in a pathologic state such as an autoimmune or inflammatory disease, e.g. vascular disease, colitis, or toxic shock.

In another embodiment, the present invention provides for methods which measure diagnosis as well as therapeutic efficacy of an agent that reduces pathologic expression of TLR and TLR-mediated signal molecules in an autoimmune or inflammatory disease (e.g. systemic lupus, uveitis, rheumatoid arthritis, Graves' disease). In one embodiment, the levels of expression of TLR or TLR-signaling molecules is measured in nonimmune cells, monocytes, macrophages or serum in order to measure therapeutic efficacy of an agent that reduces pathologic TLR expression and TLR mediated signal molecules in an autoimmune-inflammatory disease.

In another embodiment, the present invention provides for methods which measure diagnosis as well as therapeutic efficacy of an agent that reduces pathologic expression of IRF-3/Type 1 IFN, STAT, IRF-3, or ISRE regulated molecules in the nonMyD88-related pathway of TLR involved autoimmune or inflammatory disease. In one embodiment, the levels of expression of IRF-3/Type 1 IFN, STAT, IRF-3, or ISRE regulated molecules in the nonMyD88-related pathway is measured in nonimmune cells, monocytes, macrophages or serum in order to measure therapeutic efficacy of an agent that reduces pathologic expression of an autoimmune-inflammatory disease.

In another aspect, the invention is concerned with a method for treating an inflammatory or infectious condition or disease by administering a therapeutically effective amount of an agent that decreases the endogenous amount of intracellular or extracellular cytokine or proinflammatory cytokine to a patient suffering from the inflammatory condition or disease. One skilled in the art will recognize that the term "an inflammatory or infectious condition or disease" includes, but is not limited to: autoimmune or inflammatory diseases such as multiple sclerosis, inflammatory bowel disease, insulin dependent diabetes mellitus, and rheumatoid arthritis, trauma, chemotherapy reactions, transplant rejections the generalized Schwartzman reaction, system inflammatory response syndrome, sepsis, severe sepsis, or septic shock.

In a further aspect, the invention concerns a method for treating a disease such as graft versus host disease, acute respiratory distress syndrome, granulomatous disease, transplant rejection, cachexia, parasitic infections, fungal infections, trauma, and bacterial infections by administering a therapeutically effective amount of an agent that decreases the endogenous amount of intracellular or extracellular TNFα to a patient suffering from the disease.

The present invention also provides for methods of treating a TLR3 or TLR4-mediated disease or disorder wherein the treatment is curative therapy, prophylactic therapy, ameliorative therapy or preventative therapy for a subject.

The present compounds may also be used in co-therapies, partially or completely, in place of other conventional anti-inflammatory agents, such as together with steroids, cyclooxygenase-2 inhibitors, NSAIDs, DMARDS, antibiotics, immunosuppressive agents, 5-lipoxygenase inhibitors, $LTB_4$ antagonists and $LTA_4$ hydrolase inhibitors and anti-cell adhesion molecules, such as anti E-selectin.

In another embodiment, the present invention contemplates a method of relieving symptoms utilizing a combination comprising methimazole derivatives and tautomeric cyclic thiones in combination with salicylates (including sulfasalazine, olsalazine, and mesalamine), corticosteroids, immunosuppressants (including azathioprine and 6-mercaptopurine), antibiotics, anti adhesion molecules such as anti E-selectin, and a vitamin D compound (e.g., 1-alpha, 25-dihydroxyvitamin $D_3$).

In one embodiment, the present invention provides for the use of methimazole (1-methyl-2-mercaptoimidazole) and its derivatives. In another embodiment, the present invention provides for the use of a prodrug form of methimazole, known as carbimazole (neomercazole) and its derivatives.

In another embodiment, the present invention provides for the use of a composition containing one or more of the compounds selected from the group consisting of: methimazole, metronidazole, 2-mercaptoimidazole, 2-mercaptobenzimidazole, 2-mercapto-5-nitrobenzimidazole, 2-mercapto-5-methylbenzimidazole, s-methylmethimazole, n-methylmethimazole, 5-methylmethimazole, 5-phenylmethimazole, and 1-methyl-2-thiomethyl-5 (4)nitroimidazole. Preferably, 5-phenylmethimazole is used.

In another embodiment, the present invention provides for the use of phenyl methimazole (compound 10; C-10; C10) and its derivatives for the treatment of autoimmune or inflammatory disease associated with toll-like receptor 3 or TLR4 overexpression and/or overexpressed signals derived therefrom and related pathologies.

Compounds of this invention may be synthesized using any conventional technique. Preferably, these compounds are chemically synthesized from readily available starting materials.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Once synthesized, the activities and specificities of the compounds according to this invention may be determined using in vitro and in vivo assays.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

Some embodiments of the present invention include methods of prophylaxis or treatment of a disease, disorder, condition or complication thereof as described herein, comprising administering to an individual in need of such prophylaxis or treatment a therapeutically effective amount or dose of a compound of the present invention in combination with at least one pharmaceutical agent selected from the group consisting of: sulfonylureas, meglitinides, biguanides, alpha-glucosidase inhibitors, peroxisome proliferators-activated receptor-gamma (i.e., PPAR-gamma) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), anti-platelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, methods of the present invention include compounds of the present invention and the pharmaceutical agents are administered separately. In further embodiments, compounds of the present invention and the pharmaceutical agents are administered together.

The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), cerivastatin, particularly the sodium salt thereof (see U.S. Pat. No. 5,177,080), pitavastatin also referred to as NK-104 (see PCT international publication number WO 97/23200) and ZD4522; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPAR-alpha agonists outside the thiazolidinedione structural class; PPAR delta agonists such as clofibrate, fenofibrate including micronized fenofibrate, and gemfibrozil; PPAR dual alpha/gamma agonists, vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR ligands including both inhibitors and agonists; bisphosphonate compounds such as alendronate sodium; and cyclooxygenase-2 inhibitors such as rofecoxib and celecoxib. Additionally, the compounds of this invention, may be used in combination with anti-retroviral therapy in AIDS infected patients to treat lipid abnormalities associated with such treatment, for example but not limited to their use in combination with HIV protease inhibitors such as indinavir, nelfinavir, ritonavir and saquinavir.

Still another type of agent that can be used in combination with the compounds of this invention is cholesterol absorption inhibitors including plant sterols. Cholesterol absorption inhibitors block the movement of cholesterol from the intestinal lumen into enterocytes of the small intestinal wall. This blockade is their primary mode of action in reducing serum cholesterol levels. These compounds are distinct from compounds that reduce serum cholesterol levels primarily by mechanisms of action such as acyl coenzyme A—cholesterol acyl transferase (ACAT) inhibition, inhibition of triglyceride synthesis, MTP inhibition, bile acid sequestration, and transcription modulation such as agonists or antagonists of nuclear hormones. Cholesterol absorption inhibitors are described in U.S. Pat. No. 5,846,966, U.S. Pat. No. 5,631,365, U.S. Pat. No. 5,767,115, U.S. Pat. No. 6,133,001, U.S. Pat. No. 5,886,171, U.S. Pat. No. 5,856,473, U.S. Pat. No. 5,756, 470, U.S. Pat. No. 5,739,321, U.S. Pat. No. 5,919,672, WO 00/63703, WO/0060107, WO 00/38725, WO 00/34240, WO 00/20623, WO 97/45406, WO 97/16424, WO 97/16455, and WO 95/08532, the entire contents of all of which are hereby incorporated by reference.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the prophylaxis or treatment of diseases, conditions or disorders that are linked to metabolic related disorders.

In one embodiment, the present invention provides for a method of diagnosing and following therapeutic efficacy of an agent inhibiting a TLR3 or TLR4 mediated and related disease in a subject, the method comprising detecting the level of expression of TLR3/TLR4 or TLR3/TLR4 signaled molecules (a) in a test sample of nonimmune tissue cells or serum obtained from the subject, and (b) in a control sample of known normal nonimmune tissue cells of the same cell type or serum, wherein a higher or lower level of expression of TLR3 or TLR4 or their signature signal molecules in the test sample as compared to the control sample is indicative of the presence of an TLR3/4 related disease or efficacy of therapy in the subject from which the test tissue cells were obtained.

In another embodiment, the present invention provides for a method of diagnosing, in a subject, an autoimmune or inflammatory disease associated with toll-like receptor overexpression in nonimmune cells, monocytes, macrophages, or dendritic cells, the method comprising detecting the level of expression of TLR or TLR signaled molecules (a) in a test sample of nonimmune cells monocytes, macrophages, or dendritic cells, or serum obtained from the subject, and (b) in a control sample of known normal nonimmune cells monocytes, macrophages, or dendritic cells of the same cell type, or in serum wherein a higher or lower level of expression of TLR or TLR-signaled molecules in the test sample as compared to the control sample is indicative of the presence or the efficacy of therapy of an autoimmune or inflammatory disease associated with toll-like receptor overexpression or overexpressed signaling in the subject from which the test tissue cells were obtained.

In another embodiment, the present invention provides for a method of diagnosing, in a subject, an autoimmune or inflammatory disease associated with overexpression of genes or gene products induced by pathologic activation of the nonMyD88 induced IRF-3/Type 1 IFN/STAT, IRF-1/ISRE signal system of TLR in nonimmune cells, monocytes, macrophages, or dendritic cells, or serum the method comprising detecting the level of expression of molecules altered by overexpression of the nonMyD88 induced IRF-3/Type 1 IFN/STAT, IRF-1/ISRE signal system of TLR (a) in a test sample of nonimmune cells monocytes, macrophages, or dendritic cells, or serum obtained from the subject, and (b) in a control sample of known normal nonimmune cells monocytes, macrophages, or dendritic cells, of the same cell type, or in serum wherein a higher or lower level of expression of TLR or TLR-signaled molecules in the test sample as compared to the control sample is indicative of the presence or the efficacy of therapy of an autoimmune or inflammatory disease associated with overexpressed signaling in the subject from which the test tissue cells were obtained.

In another embodiment, the present invention provides for a method of identifying a compound that inhibits the expression of toll-like receptor 3 or TLR4 or their signals, the method comprising contacting cells which normally exhibit TLR3 or TLR4 expression or activity with an enhancer of this expression or activity, e.g. LPS, Type I IFN, dsRNA transfection, a virus, IL-1β, TNF-α, together with, preceded, or followed by a candidate compound, and determining the responsiveness or lack of responsiveness by the cell to the test compound.

In another embodiment, the present invention provides for a method of identifying a compound that inhibits toll-like receptor 3 or TLR4 overexpression or overexpressed signaling in a nonimmune cell, the method comprising contacting nonimmune cells which overexpress TLR3 or TLR4 or TLR3/4 activity with a candidate compound, and determining the activity or expression of TLR3 or TLR4 or their signal molecules.

In another embodiment, the present invention provides for methods for screening a test compound for the potential to prevent, ameliorate, stabilize, or treat an autoimmune or inflammatory disease associated with toll-like receptor 3 or TLR4 overexpression and/or signaling in the subject comprising the steps of first contacting a nonimmune cell sample, monocyte, macrophage, or dendritic cell from a subject that has, or is at risk for developing, an autoimmune or inflammatory disease associated with toll-like receptor 3 or TLR4 overexpression and/or signaling in the subject with the test compound; b) contacting a second nonimmune cell sample, monocyte, macrophage, or dendritic cell from the subject with a known standard compound, wherein the first and second nonimmune cell samples are contacted with the test compound in the same manner; and c) measuring TLR3 or TLR4 expression or activity in the first and second samples, wherein the compound is determined to have the potential if the TLR3 or TLR4 expression or activity in the first sample is decreased relative to the second sample.

In another embodiment, the present invention provides for methods for screening a test compound for the potential to prevent, ameliorate, stabilize, or treat an autoimmune or inflammatory disease associated with toll-like receptor overexpression or signaling in the subject comprising the steps of: a) first contacting a nonimmune cell sample, monocyte, macrophage, or dendritic cell from a first subject that has, or is at risk for developing, an autoimmune or inflammatory disease associated with toll-like receptor overexpression or signaling in the subject with the test compound; b) contacting a second nonimmune cell, monocyte, macrophage, or dendritic cell sample from a second subject that does not have, or is not predisposed to developing, an autoimmune or inflammatory disease associated with toll-like receptor 3 or TLR4 overexpression or signaling with the test compound, wherein the first and second nonimmune cell samples, monocyte, macrophage, or dendritic cell are contacted with the test compound in the same manner; and c) measuring TLR3 or TLR4 expression or activity in the first and second samples, wherein the compound is determined to have the potential if the TLR3 or TLR4 expression or activity in the first sample is decreased relative to the second sample.

In another embodiment, the present invention provides for methods for screening a test compound for the potential to prevent, ameliorate, stabilize, or treat an autoimmune or inflammatory disease associated with increased nonMyD88 induced IRF-3/Type 1 IFN/STAT, IRF-1/ISRE signaling in the subject comprising the steps of a) first contacting a nonimmune cell, monocyte, macrophage, or dendritic cell sample from a first subject that has, or is at risk for developing, an autoimmune or inflammatory disease associated with overexpressed nonMyD88 induced IRF-3/Type 1 IFN/STAT, IRF-1/ISRE signaling in the subject with the test compound; b) contacting a second nonimmune cell, monocyte, macrophage, or dendritic cell sample from a second subject that does not have, or is not predisposed to developing, an autoimmune or inflammatory disease associated with overexpressed non-MyD88 induced IRF-3/Type 1 IFN/STAT, IRF-1/ISRE signaling with the test compound, wherein the first and second nonimmune cell samples, monocyte, macrophage, or dendritic cells are contacted with the test compound in the same manner; and c) measuring nonMyD88 induced IRF-3/Type 1 IFN/STAT, IRF-1/ISRE signaled gene or gene product expression or activity in the first and second samples, wherein the compound is determined to have therapeutic potential if the expression or activity in the first sample is decreased relative to the second sample.

In another embodiment, the present invention provides for methods for screening a test compound for the potential to prevent, ameliorate, stabilize, or treat an autoimmune or inflammatory disease associated with increased TLR3, TLR4, or TLR expression in or increased nonMyD88 induced IRF-3/Type 1 IFN/STAT, IRF-1/ISRE signaling in the subject comprising the steps of a) first contacting a nonimmune cell, monocyte, macrophage, or dendritic cell sample with an inducer of expression of TLR3, TLR4, or TLR expression or increased nonMyD88 induced IRF-3/Type 1 IFN/STAT, IRF-1/ISRE signaling b) contacting a second nonimmune cell, monocyte, macrophage, or dendritic cell sample with an inducer of expression of TLR3, TLR4, or TLR expression or increased nonMyD88 induced IRF-3/Type 1 IFN/STAT, IRF-1/ISRE signaling in the same manner but before or after a test compound, c) contacting a third nonimmune cell, monocyte, macrophage, or dendritic cell sample in the same manner with an inducer of expression of TLR3, TLR4, or TLR expression or increased nonMyD88 induced IRF-3/Type 1 IFN/STAT, IRF-1/ISRE signaling before or after a vehicle used with the test compound, wherein the first, second, and third nonimmune cell samples, monocyte, macrophage, or dendritic cells are contacted with the test compounds in the same manner; and d) measuring TLR3, TLR4, or TLR expression in or increased nonMyD88 induced IRF-3/Type 1 IFN/STAT, IRF-1/ISRE signaled gene or gene product expression or activity in the first, second, and third samples, wherein the compound is determined to have therapeutic potential if the expression or activity in the second sample is decreased relative to the first and third.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Throughout this document, all temperatures are given in degrees Celsius, and all percentages are weight percentages unless otherwise stated. All publications mentioned herein are incorporated herein by reference for the purpose of describing and disclosing the compositions and methodologies, which are described in the publications, which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

BRIEF DESCRIPTION OF THE DRAWINGS

This invention, as defined in the claims, can be better understood with reference to the following drawings:

FIG. 1. TLR3 are present and functional on thyrocytes exhibiting both increased MyD88 related (NF-κB/MAP Kinase) and NonMyD88 (IRF-3/IFN-β) signaling. To understand the significance of FIG. 1 with respect to the present invention, it must be understood that TLR3RNA is found at basal levels in the FRTL-5 thyrocyte. The RNA was detected by Northern analysis in FRTL-5 thyrocytes and various mouse thyroids but not in other cell lines. In these experiments, 20 μg (cell lines) and 7.5 μg (mouse tissues) of total RNA were used. Both 293 and CHO cells were used as negative controls and mouse spleen were used as positive controls. Blots were hybridized with radiolabeled mouse TLR3 cDNA. TLR3 protein expression was also detected in FRTL-5 cells by first immunoprecipitating cell lysates with (IP+) or without (IP−) 10 μg/ml of anti-TLR3 monoclonal antibody. The immunoprecipitated fractions were then blotted together with whole cell lysates (20 μg) from CHO-K1 cells transiently transfected with 20 μg of indicated TLR expression vector and analyzed by western blot with anti-TLR3 antibody (4 μg/ml).

Poly (I:C) (the dsRNA ligand commonly used as a test compound) activates the TLR3 mediated NF-κ β/Map kinase signal pathway in FRTL-5 thyrocytes. FRTL-5 cells were transiently transfected with 100 ng of luciferase reporter pNF-κB Luc and 2 ng of internal control phRL-Tk. After 36 h, cells were incubated with 100 μg/ml poly (I:C) or endotoxin-free $E.$ $coli$ DNA for 6 h. Measurements were made with the Dual Luciferase Assay System (Promega). Poly (I:C) increased TLR3 mediated NF-κB mediated luciferase activity (gene expression) 6 fold; dsDNA had no effect. Further support came from electrophoretic mobility shift analyses (EMSA). When FRTL-5 thyrocytes were incubated with 100 μg/ml poly (I:C), IL-1β, TNF-α or TPA, cells lysed after 1 h, and nuclear translocation of NF-κB measured. The poly (I:C) induced p50/p65 complex formation as measured by the presence of a specific new protein/DNA complex and its inhibition by anti-p50 and p65 antibodies, but not by anti-p52, c-rel and Rel B antibodies; the complex was also supershifted by anti-p50. Poly (I:C) also increased TLR3-mediated ERK1/2 and MAKK activity. FRTL-5 cells were maintained in medium (4 hormone or 4H) that does not contain insulin and TSH, and then were stimulated with 100 μg/ml of poly (I:C) or 10 μM insulin. After whole cell lysates (20 μg) were subjected to SDS-PAGE, Western blot analysis using an antibody against phosphorylation-specific ERK1/2 MAPK showed that Poly (I:C) as well as insulin increased ERK1/2 MAPK protein levels 2 to 4 fold. Additionally, when FRTL-5 cells were co-transfected with pCMV-BD-Elk 1 and pFR-luc, then incubated with 100 μg/ml poly (I:C) or IL-1β for 6 hrs, ELK1 transactivation was increased 2-fold by both Poly (I:C) and IL-1β when measured with the Dual Luciferase Assay System (Promega). NF-κB/MAP Kinase signals evoked by TLR3 binding dsRNA are only one portion of TLR3 functional expression. FIG. 1 shows signaling by the more important path, which is relevant to therapy with methimazole, methimazole derivatives, and tautomeric cyclic thiones as evidenced in the additional Figures below.

In FIG. 1A, FRTL-5 cells were transiently transfected with 100 ng of luciferase reporter IFN-β-promoter-luc and 2 ng of internal control phRL-Tk-Int. HEK293 cells were transfected with IFN-β-promoter-luc and phRL-Tk in the presence (hTLR3) or absence (mock) of co-transfection of human TLR3 expression plasmid. After 36 h, cells were incubated with the indicated dose of poly (I:C) or with endotoxin-free *E. coli* DNA for 6 h. Data was obtained with the Dual Luciferase Assay System (Promega). TLR3 activation thus increased IFN-β gene expression. In FIG. 1B, FRTL-5 cells were incubated with 100 μg/ml of poly (I:C). After the indicated time points, total RNA was isolated and IFN-β and GAPDH were determined by RT-PCR using gene specific primers (S. Yokoyama, et al., Biochem Biophys Res Commun, 232:698-701, (1997)). In FIG. 1C, cells were co-transfected with pCMV-BD-hIRF-3 and pFR-luc, then incubated with poly (I:C) or IL-1β for 6 hours. TLR3 activation in thyrocytes increased the activity of IRF-3 whose binding to the IFN-β promoter results in the increased IFN-β gene expression. In FIG. 1D, cells were transiently transfected with 200 ng of IFN-β-promoter-luc, the indicated dose of TRIF/TICAM-1, wild type MyD88 or dominant negative MyD88 and 2 ng of internal control phRL-Tk. After 36 h, cells were incubated with indicated dose of poly (I:C) or IL-1β for 6 h. Data was obtained with the Dual Luciferase Assay System (Promega). TRIF/TICAM is thus functional in thyrocytes. In sum, the TLR3 receptor on thyrocytes, when activated, can increase the TRIF coupled signal to increase IRF-3/IFN-β as well apparently increase the NF-κB signal system.

FIG. 2. Poly (I:C) incubation does not upregulate TLR 3 mRNA in FRTL-5 thyrocytes; in contrast, Poly (I:C) transfection increases TLR 3 expression independently of PKR. In FIG. 2A, the effect on mRNA levels of TLR3 and several other genes was measured after incubating FRTL-5 thyrocytes with 100 μg/ml of Poly (I:C) or 10 ng/ml of IL-1β for the indicated hours. After total RNA purification, 20 μg of total RNA were analyzed with indicated radiolabeled cDNA probes. Poly IC incubation did not increase TLR3, Major histocompatibility Class I, or PKR which are implicated in autoimmune-inflammatory diseases despite the increase in IP-10. In (B), the effect of transfection, rather than incubation, of double strand nucleotide on mRNA levels of TLR3 and several other genes was evaluated. Cells were transfected Lipofectamine 2000 alone (L) or with the indicated amount of Poly (I:C) (RNA) or endotoxin-free *E. coli* DNA. After 12 and 24 hours, 20 μg of total RNA was analyzed with the indicated radiolabeled cDNA probes. Poly IC (RNA) transfection did increase TLR3, Major histocompatibility Class I, and PKR which are implicated in autoimmune-inflammatory diseases; DNA transfection was much less effective. In (C), the effect of 2-aminopurine (a PKR inhibitor) on transfected dsRNA-induced TLR3 mRNA levels was measured. Again cells were transfected with Lipofectamine 2000 alone or Lipofectamine with the indicated amount of Poly (I:C) or endotoxin-free *E. coli* DNA in the presence or absence of 10 mM 2-aminopurine. After the indicated incubation time, cells were harvested and 20 μg of total RNA was analyzed with the indicated radiolabeled cDNA probes. A PKR inhibitor significantly reduced the ability of dsDNA to slightly increase PKR, MHC class I, and TLR3 mRNA levels but had no effect on dsRNA transfection in this regard. In the bottom of Panel C, the effect of 2-AP on IFN-β gene expression was measured by RT-PCR using gene specific primers (S. Yokoyama, et al., *Biochem Biophys Res Commun,* 232:698-701, (1997)); and the effect of 2-AP on dsRNA induced NF-κ β activation was measured by EMSA. 2-AP strongly reduced the dsRNA induced NF-κ complex but had no effect on IFN-β mRNA levels. Data are representative of multiple experiments. In sum, dsRNA transfection is needed to increase gene expression of signals implicated in autoimmune-inflammatory diseases such as MHC genes and high levels of Type I interferons, not simply activation of TLR by incubating thyrocytes with dsRNA by dsRNA binding to TLR3 receptors. Moreover, despite increased PKR, the critical signal involved in TLR3/Type I IFN signaling by dsRNA transfection is not PKR mediated.

FIG. 11. C10 ameliorates the pathological inflammatory effects of LPS-induced endotoxic shock in the lungs of mice. Hematoxylin and eosin staining of lung showed inflammatory changes at the microvascular level and inflammatory cell infiltration induced by endotoxic shock at 20× magnification. LPS treated mice from Table 5 showed an increase of inflammatory cells in the as a function of time (Panels B and C by comparison to Panel A at same magnification). There was an increase in inflammatory cells in the lumen of the vessel (indicated by V in all Panels). This was particularly evidenced by the margination or stickiness of the cells to the vessel wall which suggesting rolling and adhesion of the inflammatory cells (Panel C bold arrow). In Panel B and C, the thickening of the septum was increased in the LPS-treated group because of the infiltration of inflammatory cells (indicated by small arrows in Panels B and C vs small arrows in A). The decreased number of inflammatory cells in the lumen of vessels in the lung of mice treated with C10 (phenylmethimazole) was evident (Panel D, V) as were decreases in the thickness of the septum resultant from the marked decrease in inflammatory cells and inflammatory changes (Panel D, small arrows). When the LPS, and LPS plus C10 tissue sections are compared with normal lung (Panel A), it is clearly evident that the inflammatory process was significantly ameliorated by the C10 treatment. All this suggests that C10 blocks the increase in the inflammatory cells and their increase in margination, stickiness to the wall, diapedesis and movement from the lumen to the septum. C10 thus ameliorates the microcirculatory damage and inflammatory cell infiltration to the lung of LPS treated mice. The same results of C10 treatment in LPS-induced toxic shock changes in the lung inflammatory response were noted at 40× magnification. These experiments utilized tissues from the mice whose survival curves are detailed in Table 5. Attraction of inflammatory cells to the vessels of the lung and the tissues should be associated with increases in adhesion molecule expression in the vascular cells. In addition to decreasing inflammation in the lungs, C10 decreased the expression of adhesion molecules ICAM-1 and VCAM-1 in lung as evidenced when comparing lung tissues from different groups of mice treated with LPS (Panels B and C) or LPS+C10 (Panel D) with normal mice as a control (Panel A). The expression of the adhesion molecules was marked by the intensity of the brown color within the tissue. ICAM-1 and VCAM-1 molecule expression was clearly increased and localized to the vascular endothelium. C10 clearly decreased VCAM-1 expression compared with the LPS treated group, reverting changes toward normal levels. These data establish the effect of C10 to decrease leukocyte infiltration, vascular changes, and increased adhesion molecules induced by over-expression of the LPS-TLR-4 pathway in the lung endothelial cells. The ability of C10 to decrease inflammatory changes and adhesion molecule increases were not restricted to lung. Thus, ICAM-1 and VCAM-1 were up-regulated on the endothelial cells of the (centrolobular) vein and in the liver sinusoids in the LPS treated group and C10 suppressed the ICAM-1 VCAM-1 increase. Expression of both was returned toward normal by C10 treatment. These data establish the ability of C10 to decreases adhesion molecule over-expression induced by activation of the LPS-TLR-4 pathway in hepatic as well as lung vascular endothelial cells. Both tissues are sites of organ failure in endotoxic shock.

Figure 3B:
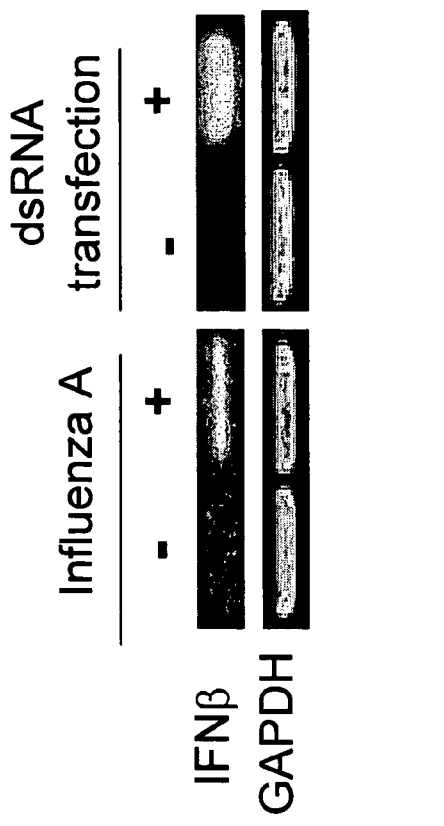
FIG. 3. Influenza A virus infection of FRTL-5 cells causes overexpression of TLR3, IRF-1, MHC class II, and IFN-β RNA levels similar to the action of dsRNA transfection. (A) Cells were infected for 24 hours with Influenza A (+) or were noninfected (−). Separately, cells were transfected with dsRNA (+) or exposed to a mock transfection (−). Total RNA, 20 ug, was isolated and Northern blotted to detect TLR3, IRF-1, and MHC II using radiolabeled cDNA probes. Ribosomal bands are shown as control for loading and integrity of samples. Influenza A infection mimicked the ability of dsRNA transfection to increase TLR3, IRF-1 and MHC Class II mRNA levels. In (B), cDNA was synthesized from total RNA and used as the template to amplify IFN-β or GAPDH by PCR. Influenza A and dsRNA transfection significantly increased IFN-β mRNA levels with no change in GAPDH, the housekeeping gene control. Thus, whether total RNA was used for Northern blot (A) or PCR (B), results were similar: Influenza A and dsRNA transfection had largely the same effects on TLR3 expression and signaling in thyrocytes. Data are representative of multiple experiments.

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

DETAILED DESCRIPTION OF THE INVENTION

Before the present compositions, devices and methods are described, it is to be understood that this invention is not limited to the specific methodology, devices, formulations, and compositions described as such may, of course, vary.

As used throughout the disclosure, the following terms, unless otherwise indicated, shall be understood to have the following meanings.

The term "administration" of the pharmaceutically active compounds and the pharmaceutical compositions defined herein includes systemic use, as by injection (especially parenterally), intravenous infusion, suppositories and oral administration thereof, as well as topical application of the compounds and compositions. Oral administration is particularly preferred in the present invention.

An "allergen" refers to a substance that can induce an allergic or asthmatic response in a susceptible subject. The list of allergens is enormous and can include pollens, insect venoms, animal dander, dust, fungal spores and drugs (e.g penicillin). Examples of natural, animal and plant allergens include proteins specific to the following genera: *Canine* (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g *Anthoxanthum odoratum*); *Arrhenatherum* (e.g. *Arrhenatherum elatius*); *Agrostis* (e.g. *Agrostis alba*); *Phleum* (e.g. *Phleum pratense*);

*Phalaris* (e.g. *Phalaris arundinacea*); *Paspalum* (e.g *Paspalum notatum*); *Sorghum* (e.g *Sorghum halepensis*); and *Bromus* (e.g *Bromus inermis*).

An "allergy" refers to acquired hypersensitivity to a substance (allergen). Allergic conditions include eczema, allergic rhinitis or coryza, hay fever, bronchial asthma, urticaria (hives) and food allergies, and other atopic conditions.

"Ameliorate" or "amelioration" means a lessening of the detrimental effect or severity of the disorder in the subject receiving therapy, the severity of the response being determined by means that are well known in the art.

"Asthma" refers to a disorder of the respiratory system characterized by inflammation, narrowing of the airways and increased reactivity of the airways to inhaled agents. Asthma is frequently, although not exclusively associated with atopic or allergic symptoms.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative and responsive to inflammatory growth factors, then secrete tissue-degradation enzymes and other proteins, which enable them to invade and spread into the inner vessel lining where they engulf fat and inflammatory debris, lyse, and repetitively cycle, thereby expanding the inner inflamed lining of the blood vessels. This process reduces vascular diameter, blocking blood flow, and making that vessel abnormally susceptible to being completely blocked by leukocytes and platelets, which adhere to adhesion molecules overexpressed on the vascular endothelium. Local blood clotting ensues, resulting in the death of the tissue served by that artery.

"Autoimmune, inflammatory, proliferative, hyperproliferative or vascular diseases" refers to any autoimmune, inflammatory, proliferative or hyperproliferative disease or disorder known in the art whether of a chronic or acute nature, including, but not limited to, rheumatoid arthritis, restenosis, lupus erythematosus, systemic lupus erythematosus, Hashimoto's thyroiditis, myasthenia gravis, diabetes mellitus, uveitis, nephritic syndrome, multiple sclerosis; inflammatory skin diseases, such as, for example, psoriasis, dermatitis, contact dermatitis, eczema and seborrhea; surgical adhesion; tuberculosis; inflammatory lung diseases, such as, asthma, pneumoconiosis, chronic obstructive pulmonary disease, emphysema, bronchitis, nasal polyps and pulmonary fibrosis; inflammatory bowel disease, such as, Crohn's disease and ulcerative colitis; graft rejections; inflammatory diseases that affect or cause obstruction of a body passageway, such as, vasculitis, Wegener's granulomatosis and Kawasaki disease; inflammation of the eye, nose or throat, such as, neovascular diseases of the eye including neovascular glaucoma, proliferative diabetic retinopathy, retrolental fibroblasia, macular degeneration, corneal neovascularization, such as, corneal infections; immunological processes, such as, graft rejection and Steven-Johnson's syndrome, alkali burns, trauma and inflammation (of any cause); fungal infections, such as, for example, infections caused by *Candida, Trichophyton, Microsporum, Eepidermophyton, Cryptococcus, Aspergillus, Coccidiodes, Paracocciciodes, Histoplasma* or *Blastomyces*; food related allergies, such as, for example, migraine, rhinitis and eczema; vascular diseases, such as, aortic aneurysm. A description of inflammatory diseases can also be found in WO 92/05179, WO 98/09972, WO 98/24427, WO 99/62510 and U.S. Pat. No. 5,886,026, the disclosures of each of which are incorporated herein in their entirety.

"Blood" includes blood products, blood components and the like.

"Cardiovascular disease or disorder" refers to any cardiovascular disease or disorder known in the art, including, but not limited to, restenosis, coronary artery disease, atherosclerosis, atherogenesis, cerebrovascular disease, angina, (particularly chronic, stable angina pectoris), ischemic disease, congestive heart failure or pulmonary edema associated with acute myocardial infarction, thrombosis, high or elevated blood pressure in hypertension (especially hypertension associated with cardiovascular surgical procedures), platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neoinitimal hyperplasia following percutaneous transluminal coronary angiograph, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, pulmonary thromboembolism, cerebral thromboembolism, thrombophlebitis, thrombocytopenia; bleeding disorders and/or any other complications which occur either directly or indirectly as a result of the foregoing disorders.

The term "cerebrovascular diseases or events" as employed herein refers to cerebral infarction or stroke (caused by vessel blockage or hemorrhage), or transient ischemia attack (TIA), syncope, atherosclerosis of the intracranial and/or extracranial arteries, and the like.

"Chemokines" are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GRO$\alpha$, GRO$\beta$, GRO$\gamma$, ENA-78, GCP-2, IP-10, MIG and PF4. CC chemokines include RANTES, MIP-1$\alpha$, MIP-2$\beta$, monocyte chemotactic protein-1 (MCP-1), MCP-2, MCP-3 and eotaxin.

By "compatible" herein is meant that the components of the compositions which comprise the present invention are capable of being commingled without interacting in a manner which would substantially decrease the efficacy of the pharmaceutically active compound under ordinary use conditions.

The term "coronary events" as employed herein refers to myocardial infarction, myocardial revascularization procedures, angina, cardiovascular death and acute coronary syndrome.

By "corticosteroid" is meant any naturally occurring or synthetic steroid hormone, which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at $\delta 4$, a C3 ketone, and a C20 ketone. Corticosteroids may have glucocorticoid and/or mineralocorticoid activity.

The term "endotoxic shock" or "septic shock" includes without limitation a physical or mental disturbance induced by the release of endotoxin from Gram-negative bacteria or by the release of super antigens from Gram-positive bacteria. The term "septic shock" or "sepsis" refers to a clinical disorder whose symptoms may include well defined abnormalities in body temperature, heart rate, breathing rate, white blood cell count, hypertension then hypotension, organ perfusion abnormalities, and multiple organ dysfunction. It may be caused by or associated with bacterial (either gram negative or gram positive), fungal, viral or other infection, as well as by non-infective stimuli such as multiple trauma, severe burns, organ transplantation and pancreatitis. Septic shock is commonly caused by "gram-negative" endotoxin—(LPS) producing aerobic rods—*Escherichia coli, Klebsiella pneumoniae, Proteus species, Pseudomonas aeruginosa* and *Salmonella*. Septic shock involved with gram negative bacteria is referred to as "endotoxic shock".

Exemplary corticosteroids include, for example, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, flumethasone, diflorasone, fluocinolone, clobetasol, cortisone, paramethasone, clocortolone, prednisolone 21-hemisuccinate free acid, prednisolone metasulphobenzoate, and triamcinolone acetonide 21-palmitate. By "low dose corticosteroid" is meant a dose that is less than a dose that would typically be given to a patient for treatment of inflammation. Exemplary low doses of corticosteroids are as follows: cortisol: 12 mg/day; cortisone: 15 mg/day; prednisone: 3 mg/day; methylprednisolone: 2.5 mg/day; triameinolone: 2.5 mg/day; betamethasone: 250 µg/day; dexamethasone: 450 µg/day; hydrocortisone: 9 mg/day.

"Cyclooxygenase-2 (COX-2) inhibitor" refers to a compound that selectively inhibits the cyclooxygenase-2 enzyme by comparison to the cyclooxygenase-1 enzyme. Preferably, the compound has a cyclooxygenase-2 $IC_{50}$ of less than about 0.5 µM, and also has a selectivity ratio of cyclooxygenase-2 inhibition over cyclooxygenase-1 inhibition of at least 50, and more preferably of at least 100. Even more preferably, the compound has a cyclooxygenase-1 $IC_{50}$ of greater than about 1 µM, and more preferably of greater than 20 µM. The compound can also inhibit the enzyme, lipoxygenase and/or phosphodiesterase. Such preferred selectivity may indicate an ability to reduce the incidence of common NSAID-induced side effects.

"HMG-CoA reductase inhibitor" where used in the specification and the appendant claims, is synonymous with the terms "3-hydroxy-3-methylglutary-1-Coenzyme A reductase inhibitor", "HMG-CoA inhibitor" and "statins." These three terms are used interchangeably throughout the specification and appendant claims. As the synonyms suggest, statins are inhibitors of 3-hydroxy-3-methylglutaryl-Coenzyme A reductase and, as such, are effective in lowering the level of blood plasma cholesterol. Statins and pharmaceutically acceptable salts thereof are particularly useful in lowering low-density lipoprotein cholesterol (LDL-C) levels in mammals and particularly in humans. The HMG-CoA reductase inhibitors suitable for use herein include, but are not limited to, simvastatin, pravastatin, rivastatin, mevastatin, fluindostatin, cerivastatin, velostatin, fluvastatin, dalvastatin, dihydrocompactin, compactin, or lovastatin; or a pharmaceutically acceptable salt of simvastatin, pravastatin, rivastatin, cerivastatin, mevastatin, fluindostatin, velostatin, fluvastatin, dalvastatin, dihydrocompactin, compactin, lovastatin, or pharmaceutically acceptable salts thereof. However, it is to be noted that atorvastatin calcium is a particularly preferred statin to be employed in the present combination. See U.S. Pat. No. 5,273,995 incorporated herein by reference. The statins disclosed herein are prepared by methods well-known to those skilled in the art. Specifically, simvastatin may be prepared according to the method disclosed in U.S. Pat. No. 4,444,784, which is incorporated herein by reference. Pravastatin may be prepared according to the method disclosed in U.S. Pat. No. 4,346,227, which is incorporated herein by reference. Cerivastatin may be prepared according to the method disclosed in U.S. Pat. No. 5,502,199, which is incorporated herein by reference. Cerivastatin may alternatively be prepared according to the method disclosed in European Patent Application Publication No. EP617019. Mevastatin may be prepared according to the method disclosed in U.S. Pat. No. 3,983,140, which is incorporated herein by reference. Velostatin may be prepared according to the methods disclosed in U.S. Pat. No. 4,448,784 and U.S. Pat. No. 4,450,171, both of which are incorporated herein by reference. Fluvastatin may be prepared according to the method disclosed in U.S. Pat. No. 4,739,073, which is incorporated herein by reference. Compactin may be prepared according to the method disclosed in U.S. Pat. No. 4,804,770, which is incorporated herein by reference. Lovastatin may be prepared according to the method disclosed in U.S. Pat. No. 4,231,938, which is incorporated herein by reference. Dalvastatin maybe prepared according to the method disclosed in European Patent Application Publication No. 738510 A2. Fluindostatin may be prepared according to the method disclosed in European Patent Application Publication No. 363934 A1. Dihydrocompactin may be prepared according to the method disclosed in U.S. Pat. No. 4,450,171, which is incorporated herein by reference. It will be recognized that certain of the above statins contain either a free carboxylic acid or a free amine group as part of the chemical structure. Further, certain statins within the scope of this invention contain lactone moieties, which exist in equilibrium with the free carboxylic acid form. These lactones can be maintained as carboxylates by preparing pharmaceutically acceptable salts of the lactone. Thus, this invention includes pharmaceutically acceptable salts of those carboxylic acids or amine groups. The expression "pharmaceutically acceptable salts" includes both pharmaceutically acceptable acid addition salts and pharmaceutically acceptable cationic salts. The expression "pharmaceutically acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. The pharmaceutically acceptable cationic salts of statins containing free carboxylic acids may be readily prepared by reacting the free acid form of the statin with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine, and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The pharmaceutically acceptable acid addition salts of statins containing free amine groups may be readily prepared by reacting the free base form of the statin with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate), or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The term "infectious disease" as used herein, includes, but is not limited to any disease that is caused by an infectious agent or organism. Infectious organisms may comprise viruses, (e.g., single stranded RNA viruses, double strand DNA viruses, single stranded DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria*, in particular, *M. tuberculosis*, *Salmonella*, *Streptococci*, *E. coli*, *Staphylococci*), fungi (e.g., *Candida* species, *Aspergillus* species), *Pneumocystis carinii*, and prions.

Examples of infectious virus include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., Ebola viruses); Paramnyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplx virus (HSV) 1 and 2, varicella zoster virus, cytomegalovirus (CMV), herpes viruses'); Poxyiridae (variola viruses, vaccinia viruses, pox viruses); and Iridoviridae (e.g., African swine fever virus); and unclassified viruses (e.g, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Nor-walk and related viruses, and astroviruses).

Examples of infectious bacteria include: *Helicobacter pyloris*, *Borelia burgdorferi*, *Legionella pneumophilia*, *Mycobacteria* spp. (e.g., *M. tuberculosis*, *M. avium*, *M. intracellulare*, *M. kansasii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic spp.), *Streptococcus pneumoniae*, pathogenic *Campylobacter* sp., *Enterococcus* sp., *Haemophilus influenzae*, *Bacillus anthracis*, *Corynebacterium diphtheriae*, *Corynebacterium* sp., *Erysipelothrix rhusiopathiae*, *Clostridium perfringens*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidum*, *Treponema pertenue*, *Leptospira*, and *Actinomyces israelli*.

Examples of infectious fungi include: *Cryptococcus neoformans*, *Histoplasma capsulatum*, *Coccidioides immitis*, *Blastomyces dermatitidis*, *Chlamydia trachomatis*, *Candida albicans*. Other infectious organisms (i.e., protists) include: *Plasmodium falciparum* and *Toxoplasma gondii*.

"Inflammatory disease or disorder" refers to reperfusion injury to an ischemic organ, myocardial infarction, inflammatory bowel disease, rheumatoid arthritis, osteoarthritis, hypertension, psoriasis, organ transplant rejection, organ preservation, a female or male sexual dysfunction, radiation-induced injury, asthma, atherosclerosis, thrombosis, platelet aggregation, restenosis, metastasis, influenza, incontinence, stroke, burn, trauma, acute pancreatitis, pyelonephritis, hepatitis, an autoimmune disease, an immunological disorder, senile dementia, insulin-dependent diabetes mellitus, disseminated intravascular coagulation, fatty embolism, Alzheimer's disease, adult or infantile respiratory disease, carcinogenesis or a hemorrhage in a neonate.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

"Niacin" includes such drugs as derivatives of niacinamide, niacin, and niacin esters. Such examples include but not limited to niacinamide salicylate, niacinamide lipoate, niacinamide mandelate, niacinamide lactate, niacinamide glycolate, niacinamide malate, niacinamide adenosine phosphate, niacinamide adenosine triphosphate, niacinamide ascorbate, niacinamide folate, niacinamide hydroxycitrate, niacinamide hydroxytetronate, niacinamide pantothenate, niacin salicylate, niacin lipoate, niacin mandelate, niacin lactate, niacin glycolate, niacin malate, niacin adenosine phosphate, niacin adenosine triphosphate, niacin ascorbate, niacin folate, niacin hydroxycitrate, niacin pantothenate, niacin hydroxytetronate, benzyl nicotinate lipoate (benzyl niacin lipoate), methyl nicotinate lipoate (methyl niacin lipoate), benzyl niacin ascorbate, methyl niacin ascorbate, benzyl niacin salicylate, methyl niacin salicylate, benzyl niacin pantothenate, methyl niacin pantothenate, benzyl niacin lactate, methyl niacin lactate, benzyl niacin malate, methyl niacin malate, lauryl niacin lipoate, lauryl niacin ascorbate, lauryl niacin salicylate, lauryl niacin lactate, methyl niacin glycyrrhetinate, niacinamide glycyrrhetinate, niacinamide glycyrrhizinate, niacinamide hyaluronate, niacinamide pyrrolidone carboxylate, benzyl niacin hyaluronate, benzyl niacin pyrrolidone carboxylate, niacinamide hydroquinone carboxylate, niacin hydroquinone carboxylate, methyl niacin hydroquinone carboxylate, benzyl niacin hydroquinone carboxylate, lauryl niacin hydroquinone carboxylate, methyl niacin ursolate, lauryl niacin ursolate, benzyl niacin ursolate, niacinamide ellagate, niacinamide rosmarinate, niacinamide chloroginate, methyl niacin ellagate, methyl niacin chloroginate, lauryl ellagate, lauryl chloginate, lauryl rosmarinate, and methyl niacin rosmarinate.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

The term "patient", as used herein, is intended to encompass any mammal, animal or human subject, which may benefit from treatment with the compounds, compositions and methods of the present invention, and includes children and adults.

"Pharmaceutically-acceptable" shall mean that the pharmaceutically active compound and other ingredients used in the pharmaceutical compositions and methods defined herein are suitable for use in contact with the tissues of humans and lower animals without undue toxicity, irritation, allergic response, and the like, commensurate with a reasonable benefit/risk ratio.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Alpha-adrenergic receptor antagonist" refers to any compound that reversibly or irreversibly blocks the activation of any alpha-adrenergic receptor.

"Phosphokinase inhibitor" refers to any compound that inhibits a phosphokinase, which includes but is not limited to kinases phosphorylating Stats, viral activated kinases, tamoxifen, dinitro-fluorobenzene (DNFB), and inhibitors of a serine kinase including isopentenyladenine, 6-dimethylaminopurine, olomoucine, roscovitine, CVT-313, purvanol, butyrolactone-I, flavopiridols, staurosporine, indirubins, hymenialdesine, and paullones.

The term "prodrug" indicates a therapeutic agent that is prepared in an inactive form that is converted to an active form (i.e., drug) within the body or cells thereof by the action of endogenous enzymes or other chemicals and/or conditions.

"Respiratory disease or disorder" refers to any pulmonary dysfunction including, for example, acute pulmonary vasoconstriction, pneumonia, traumatic injury, aspiration or inhalation injury, fat embolism in the lung, acidosis, inflammation of the lung, adult respiratory distress syndrome, acute pulmonary edema, acute mountain sickness, asthma, post cardiac surgery acute pulmonary hypertension, persistent pulmonary hypertension of the newborn, perinatal aspiration syndrome, hyaline membrane disease, acute pulmonary thromboembolism, heparin-protamine reactions, sepsis, asthma, status asthmaticus, or hypoxia (including that which may occur during one-lung anesthesia), chronic pulmonary vasoconstriction, chronic pulmonary hypertension, bronchopulmonary dysplasia, chronic pulmonary thromboembolism, idiopathic or primary pulmonary hypertension, or chronic hypoxia.

As used herein, a "safe and effective amount" means a sufficient amount of a pharmaceutically active compound to effect the inhibition of TLR-mediated disease expression and related pathologies. In one embodiment, a "safe and effective amount" means a sufficient amount of a pharmaceutically active compound to effect the inhibition of TLR3, TLR4, or TLR mediated disease expression and related pathologies involving abnormal MyD88-dependent and MyD88 independent signaling, most preferably TLR3, TLR4, or TLR mediated disease expression and related pathologies involving abnormal MyD88 independent signaling that increases IRF-3, Type 1 IFN, STAT, IRF-1, and ISRE increase or activation. Within the scope of sound medical judgment, therapeutically effective amounts of a pharmaceutically active agent or of the pharmaceutical composition containing that active agent will vary with the severity of the condition being treated, the duration of the treatment, the nature of adjunct treatment, the age and physical condition of the patient, the specific active compound employed, and like considerations discussed more fully hereinafter. In arriving at the "safe and effective amount" for a particular compound, these risks must be taken into consideration.

"Therapeutic agent" as used herein refers to those agents effective in the prevention or treatment of a disorder or pathologic physiological condition. Therapeutic agent includes the pro-drugs and pharmaceutical derivatives thereof including but not limited to the corresponding nitrosated and/or nitrosylated derivatives.

"Therapeutically effective amount" refers to the amount of the compound and/or composition that is effective to achieve its intended purpose.

"Toll-like receptors" or "TLRs" are type transmembrane proteins containing repeated leucine-rich motifs in their extracellular domains and a cytoplasmic tail that contains a conserved region called the Toll/IL1 receptor (TIR) domain. At least 10 mammalian TLR proteins have been identified, Toll-like receptors 1-10. TLRs play a critical role in early innate immunity to invading pathogens by sensing microorganisms or noxious environmental agents. These evolutionarily conserved receptors, homologues of the *Drosophila* Toll gene, recognize highly conserved structural motifs expressed by microbial pathogens, called pathogen-associated microbial patterns (PAMPs) and sense products of tissue damage by noxious agents or tissue injury, for example dsRNA. PAMPs include various bacterial cell wall components such as lipopolysaccharide (LPS), peptidoglycan (PGN) and lipopeptides, as well as flagellin, bacterial DNA and viral double-stranded RNA. TLR thus protect mammals from pathogenic organisms, such as viruses, bacteria, parasitic agents, or fungi, and from tissue injury, by generating an "innate immune" response to products of the pathogenic organism. They thus may additionally protect animals from noxious environmental agents that destroy cells and release dsRNA or other PAMPs that can interact with the TLR. The innate immune response results in increases in genes encoding several inflammatory cytokines, chemokines, as well as co-stimulatory molecules, and is critical for the development of antigen-specific adaptive immunity. Stimulation of TLRs by PAMPs initiates a signaling cascade that involves a number of proteins, such as MyD88 and IRAK1. This signaling cascade leads to the activation of the transcription factor NF-kB which induces the secretion of pro-inflammatory cytokines (such as TNF $\alpha$ and IL-1$\beta$) and effector cytokines that direct the adaptive immune response. The signaling cascade additionally involves adaptors such as TRIF/TICAM-1 which can signal the IRF-3 pathway to increase Type 1 IFN production, activate Stats, increase IRF-1 gene expression, and activate ISRE's, interferon response factor (IRF) elements. In the case of virus, injection of dsRNA or single strand RNA with its replication can activate viral kinases, bypass TLR, activate PKR and IRF-3, and initiate the NF-κB and Type 1 IFN cascades, which, by the autocrine/paracrine action of type 1 IFNs, the cytokines and the chemokines can initiate the innate immune-adaptive immune response sequence.

"Transplantation rejection" refers to the transplant of any organ or body part resulting in organ or tissue graft rejection, allograft rejection, and graft-versus-host disease, including but not limited to, heart, kidney, liver, lung, bone marrow, cornea and skin transplants.

"Treat," "treating," "treatment," and "therapy" as used herein refer to any curative therapy, prophylactic therapy, ameliorative therapy and preventative therapy for a subject.

"Vasoactive agent" refers to any therapeutic agent capable of relaxing vascular and/or nonvascular smooth muscle. Suitable vasoactive agents include, but are not limited to, potassium channel activators, calcium channel blockers, beta-blockers, long and short acting alpha-adrenergic receptor antagonists, prostaglandins, phosphodiesterase inhibitors, adenosine, ergot alkaloids, vasoactive intestinal peptides, dopamine agonists, opioid antagonists, endothelin antagonists, thromboxane inhibitors and the like.

"Viral infection" refers to both RNA and DNA viral infections. The RNA viral infections include, but are not limited to, orthomyxoviridae, paramyxoviridae, picornaviridae, rhabdoviridae, coronavaridae, togaviridae, bunyaviridae, arenaviridae and reteroviridae. The DNA viral infections include, but are not limited to, adenoviridae, proxyiridae, papovaviridae, herpetoviridae and herpesviridae. In one specific embodiment, the viral infections include, but are not limited to, double or single strand RNA viruses such as flu viruses, hepatitis virus, enteroviruses, and Coxsackie viruses, viruses of the herpetoviridae family, such as, for example, herpes simplex viruses HSV-1 and HSV-2, cytomegalovirus (CMV), herpes varicella-zoster (VZV), Epstein-Barr (EBV), HHV6, HHV7, pseudorabies and rhinotracheitis, and the like.

It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

The present invention relates to the treatment of TLR3 as well as TLR4 mediated diseases and related pathologies. This invention relates to the treatment of TLR3-mediated diseases, including Hashimoto's thyroiditis, Type I diabetes, and insulinitis but is not limited to these. This invention relates to the treatment of TLR4-mediated diseases, including toxic shock, atherosclerosis, vascular diseases associated with hyperlipidemia, ulcerative colitis, and Crohn's disease, but is not limited to these. The present invention also relates to the treatment of TLR mediated diseases and related pathologies, e.g. TLR9, which involve pathologic expression of MyD88-independent signaling involving activation of the IRF-3/Type I IFN signal pathway as in diseases including but not limited to systemic lupus and rheumatoid arthritis.

The present invention relates to the treatment of TLR3 as well as TLR4 mediated diseases in nonimmune cells, monocytes, macrophages, or dendritic cells and related pathologies. This invention relates to the treatment of TLR3-mediated diseases in nonimmune cells, monocytes, macrophages, or dendritic cells, including Hashimoto's thyroiditis, Type I diabetes, and insulinitis but is not limited to these. This invention relates to the treatment of TLR4-mediated diseases in nonimmune cells, monocytes, macrophages, or dendritic cells including toxic shock, atherosclerosis, vascular diseases associated with hyperlipidemia, ulcerative colitis, and Crohn's disease, but is not limited to these.

The present invention relates to the treatment of TLR mediated diseases with abnormal IRF-3, Type-1 IFN, STAT, and IRF-1 signaling and related pathologies. This invention thus relates to the treatment of TLR-mediated diseases, including Graves' disease, systemic lupus, rheumatoid arthritis, autoimmune uveitis, autoimmune blepharitis, and psoriasis, wherein there is abnormal TLR signaling through this pathway, but is but is not limited to these.

The present invention relates to the treatment of TLR mediated diseases with abnormal IRF-3, Type-1 IFN, STAT, and IRF-1 signaling in nonimmune cells, monocytes, macrophages, or dendritic cells and related pathologies. This invention thus relates to the treatment of TLR-mediated diseases in nonimmune cells, monocytes, macrophages, or dendritic cells, including Graves' disease, systemic lupus, rheumatoid arthritis, autoimmune uveitis, autoimmune blepharitis, and psoriasis, wherein there is abnormal TLR signaling in non-immune cells, monocytes, macrophages, or dendritic cells through this pathway, but is not limited to these.

This invention also relates to treating a subject having a disease or condition associated with an autoimmune inflammatory disease induced by abnormal Toll-like receptor 3 or TLR4 expression or signaling induced by viruses are noxious agents that enter the cell and cause abnormal NF-κB and IRF-3, Type-1 IFN, STAT, and IRF-1 signaling and related pathologies as exemplified by diseases with increased Type 1 IFN levels in the serum.

This invention also relates to treating a subject having a disease or condition associated with an autoimmune inflammatory disease induced by abnormal Toll-like receptor expression or signaling caused by phagocytosis of infectious or noxious agents that enter the cell and cause abnormal TLR-mediated expression of IRF-3, Type-1 IFN, STAT, and IRF-1 signaling and related pathologies as exemplified by diseases with increased Type 1 IFN levels in the serum.

This invention also relates to treating a subject having a disease or condition associated with an autoimmune inflammatory disease induced by abnormal Toll-like receptor 3 or TLR4 expression or signaling in a nonimmune cell, monocyte, macrophage, or dendritic cell induced by viruses or noxious agents that enter the cell and cause abnormal NF-κB and IRF-3, Type-1 IFN, STAT, and IRF-1 signaling and related pathologies as exemplified by diseases with increased Type 1 IFN levels in the serum.

This invention also relates to treating a subject having a disease or condition associated with an autoimmune inflammatory disease induced by abnormal Toll-like receptor expression or signaling in a nonimmune cell, monocyte, macrophage, or dendritic cell caused by phagocytosis of infectious or noxious agents that enter the cell and cause abnormal NF-κB and IRF-3, Type-1 IFN, STAT, and IRF-1 signaling and related pathologies as exemplified by diseases with increased Type 1 IFN levels in the serum.

This invention also relates to treating a subject having a disease or condition associated with an autoimmune inflammatory disease induced by abnormal Toll-like receptor 3 or TLR4 expression or signaling induced by viruses or noxious agents that enter the cell and cause abnormal IRF-3, Type-1 IFN, STAT, and IRF-1 signaling and related pathologies as exemplified by diseases with increased Type 1 IFN levels in the serum.

The present invention also provides for methods of treating such disease comprising administering to a patient in need of such treatment a therapeutically effective amount of one or more compound selected from methimazole (MMI), phenylmethimazole, and tautomeric cyclic thione compounds and active derivatives thereof of the present invention capable of preventing, ameliorating or inhibiting pathologies that are mediated or associated with Toll-like receptor 3 or Toll-like receptor 4 overexpression, activation, and signaling or both together.

The invention provides methods of inhibiting a TLR3- or TLR4 mediated autoimmune-inflammatory response comprising administering an amount of a therapeutically effective amount of a phenylmethimazole, methimazole derivative, and/or tautomeric cyclic thione compound. The immune response may be an inflammatory response. The immune response may be a leukocyte response. More specifically, the immune response may include one or more of: directed leukocyte migration; leukocyte superoxide production; leukocyte degranulation including but not limited to neutrophil elastase exocytosis; and, leukocyte transmigration and/or leukocyte extravasation. Leukocytes can be selected from the group consisting of neutrophils, eosinophils, basophils, T-lymphocytes, B-lymphocytes, monocytes, macrophages, dendritic cells, Langerhans cells, and mast cells. As used herein, an "endogenous factor" is defined as a product which is synthesized by host cells, e.g., cells of the individual being treated. Representative endogenous factors include but are not limited to tumor necrosis factor-α (TNF-α), complement factor C3a, complement factor C5a, chemokine CXCL1, chemokine CXCL2, chemokine CXCL3, chemokine CXCL4, chemokine CXCL5, chemokine CXCL6, chemokine CXCL7, interleukin 1α (IL-1α), interleukin 1β (IL-1β), interleukin 3 (IL-3), interleukin 6 (IL-6), interleukin 7 (IL-7), interleukin 8 (IL-8), interleukin 10 (IL-10), interleukin 11 (IL-11), interleukin 12 (IL-12), interleukin (IL-15), interleukin 17 (IL-17), interleukin 18 (IL-18), prostaglandins, monocyte chemo-attractant protein-1 (MCP-1), chemokine CCL5 (RANTES), macrophage inflammatory protein-1-α (MIP-1-α), stromal cell-derived factor-1 (SDF-1), eotaxins, granulocyte-macrophage colony-stimulating factor (GM-CSF), transforming growth factor-β (TGF-β), γ-interferon (IFN-γ), leukotriene B4 (LTB4), leukotriene C4 (LTC4), leukotriene D4 (LTD4), leukotriene E4 (LTE4), lipoxins, platelet-activating factor (PAF), and lysophospholipids.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, growth factors, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, or nonimmune cells that become antigen presenting cells (including but not limited to smooth muscle cells, endothelial cells, or epithelial cells). It will be appreciated by persons skilled in the art that the activation of one or a combination of these phenotypes in these cells can contribute to the initiation, perpetuation, or exacerbation of an inflammatory condition.

Thus, in various embodiments, the invention provides methods of treating various inflammatory conditions including but not limited to arthritic diseases such as rheumatoid arthritis (RA), osteoarthritis, gouty arthritis, spondylitis, and reactive arthritis; Behcet's syndrome; sepsis; septic shock; endotoxic shock; gram negative sepsis; gram positive sepsis; toxic shock syndrome; multiple organ injury syndrome secondary to septicemia, trauma, or hemorrhage; ophthalmic disorders including but not limited to allergic conjunctivitis, vernal conjunctivitis, uveitis, blepharitis, and thyroid-associated ophthalmopathy; eosinophilic granuloma; pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity; ischemic-reperfusion injury, e.g., of the myocardium, brain, or extremities; inflammation leading to fibrosis including but not limited to cystic fibrosis; inflammation leading to keloid formation or scar tissue formation; inflammation leading to atherosclerosis; autoimmune-inflammatory diseases including but not limited to systemic lupus erythematosus (SLE), lupus nephritis, autoimmune thyroiditis, multiple sclerosis, some forms of diabetes, and Reynaud's syndrome; tissue or organ transplant rejection disorders including but not limited to graft versus host disease (GVHD) and allograft rejection; chronic or acute glomerulonephritis; inflammatory bowel diseases including but not limited to Crohn's disease, ulcerative colitis necrotizing enterocolitis, and regional enteritis; inflammatory dermatitis including but not limited to contact dermatitis, atopic dermatitis, psoriasis, and urticaria; fever and myalgias due to infection; central or peripheral nervous system inflammatory conditions including but not limited to meningitis (e.g., acute purulent meningitis), encephalitis, and brain or spinal cord injury due to minor trauma; Sjorgren's syndrome; diseases involving leukocyte diapedesis; alcoholic hepatitis; bacterial pneumonia; community acquired pneumonia (CAP); neumocystis carinii pneumonia (PCP); antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; spinal cord injury; cardiovascular complications of type 1 and 2 diabetes, hyperlipidemia, and hypertension; and macro- or microvascular complications of diabetes including, but not limited to, nephropathy, neuropathy, retinopathy.

The invention provides methods for the use of the methimazole derivatives and tautomeric cyclic thione compounds of the present invention for the preparation of a medicament for the treatment or prevention of one or more of the following diseases, pathological disorders or conditions from the group consisting of: asthma of whatever type, etiology or pathogenesis, or asthma selected from the group consisting of atopic asthma, non-atopic asthma, allergic asthma, atopic, bronchial, IgE-mediated asthma, bronchial asthma, essential asthma, true asthma, intrinsic asthma caused by patho-physiological disturbances, extrinsic asthma caused by environmental factors, essential asthma of unknown or unapparent cause, non-atopic asthma, bronchitic asthma, emphysematous asthma, exercise-induced asthma, occupational asthma, infective asthma caused by bacterial, fungal, protozoal, or viral infection, non-allergic asthma, incipient asthma and wheezy infant syndrome; chronic or acute bronchoconstriction, chronic bronchitis, small airway obstruction and emphysema; obstructive or inflammatory airway diseases of whatever type, etiology or pathogenesis, or an obstructive or inflammatory airway disease selected from the group consisting of asthma, pneumoconiosis, chronic eosinophilic pneumonia, chronic obstructive pulmonary disease (COPD), COPD including chronic bronchitis, pulmonary emphysema or dyspnea associated therewith, COPD that is characterized by irreversible, progressive airway obstruction, adult respiratory distress syndrome (ARDS), and exacerbation of airway hyper-reactivity consequent to other medicament therapy; pneumoconiosis of whatever type, etiology or pathogenesis, or pneumoconiosis selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis; bronchitis of whatever type, etiology or pathogenesis, or bronchitis selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis; bronchiectasis of whatever type, etiology or pathogenesis, or bronchiectasis selected from the group consisting of cylindric bronchiectasis, sacculated bronchiectasis, fusiform bronchiectasis, capillary bronchiectasis, cystic bronchiectasis, dry bronchiectasis and follicular bronchiectasis; seasonal allergic rhinitis, or perennial allergic rhinitis, or sinusitis of whatever type, etiology or pathogenesis, or sinusitis selected from the group consisting of purulent or nonpurulent sinusitis, acute or chronic sinusitis and ethmoid, frontal, maxillary, or sphenoid sinusitis; rheumatoid arthritis of whatever type, etiology or pathogenesis, or rheumatoid arthritis selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis; gout, and fever and pain associated with inflammation; an eosinophil-related pathological disorder of whatever type, etiology or pathogenesis, or an eosinophil-related pathological disorder selected from the group consisting of eosinophilia, pulmonary infiltration eosinophilia, Loffier's syndrome, chronic eosinophilic pneumonia, tropical pulmonary eosinophilia, bronchopneumonic aspergillosis, aspergilloma, granulomas containing eosinophils, allergic granulornatous angijtis or Churg-Strauss syndrome, polyarteritis nodosa (PAN) and systemic necrotising vasculitis; atopic dermatitis, allergic dermatitis or allergic or atopic eczema; urticaria of whatever type, etiology or pathogenesis, or urticaria selected from the group consisting of immune-mediated urticaria, complement-mediated urticaria, urticariogenic material-induced urticaria, physical stimulus-induced urticaria, stress induced urticaria, idiopathic urticaria, acute urticaria, chronic urticaria, angioedema, cholinergic urticaria, cold urticaria in the autosomal dominant form or in the acquired form, contact urticaria, giant urticaria and papular urticaria; conjunctivitis of whatever type, etiology or pathogenesis, or conjunctivitis selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis; uveitis of whatever type, etiology or pathogenesis, or uveitis selected from the group consisting of inflammation of all or part of the uvea, anterior uveitis, iritis, cyclitis, iridocyclitis, granulornatous uveitis, nongranulornatous uveitis, phacoantigenic uveitis, posterior uveitis, choroiditis and chorioretinitis; psoriasis; multiple sclerosis of whatever type, etiology or pathogenesis, or multiple sclerosis selected from the group consisting of primary progressive multiple sclerosis and relapsing remitting multiple sclerosis; autoimmune/inflammatory diseases of whatever type, etiology or pathogenesis, or an autoimmune/inflammatory disease selected from the group consisting of autoimmune hematological disorders, hemolytic anaemia, aplastic anaemia, pure red cell anaemia, idiopathic thrombocytopenic purpura, systemic lupus erythematosus, polychondritis, sclerorma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, Crohn's disease, endocrin opthamopathy, Grave's disease, sarcoidosis, alveolitis, chronic hypersensitivity pneumonitis, primary biliary cirrhosis, juvenile diabetes or diabetes mellitus type 1, anterior uveitis, granulornatous or posterior uveitis, keratoconjunctivitis sicca, epidemic kerato-conjunctivitis, diffuse interstitial pulmonary fibrosis or interstitial lung fibrosis, idiopathic pulmonary fibrosis, cystic fibrosis, psoriatic arthritis, glomerulonephritis with and without nephrotic syndrome, acute glomerulo-nephritis, idiopathic nephrotic syndrome, minimal change nephropathy, inflammatory/hyperproliferative skin diseases, psoriasis, atopic dermatitis, contact dermatitis, allergic contact dermatitis, benign familial pemphigus, pemphigus erythematosus, pemphigus foliaceus and pemphigus vulgaris; prevention of foreign transplant rejection following organ transplantation; inflammatory bowel disease (IBD) of whatever type, etiology or pathogenesis, or inflammatory bowel disease selected from the group consisting of ulcerative colitis (UC), collagenous colitis, colitis polyposa, transmural colitis and Crohn's disease (CD); septic shock of whatever type, etiology or pathogenesis, or septic shock selected from the group consisting of renal failure, acute renal failure, cachexia, malarial cachexia, hypophysial cachexia, uremic cachexia, cardiac cachexia, cachexia suprarenalis or Addison's disease, cancerous cachexia, and cachexia as a consequence of infection by the human immunodeficiency virus (HIV); liver damage; pulmonary hypertension and hypoxia-induced pulmonary hyper-tension; bone loss diseases, primary osteoporosis and secondary osteoporosis; pathological disorders of the central nervous system of whatever type, etiology or pathogenesis, or a pathological disorder of the central nervous system selected from the group consisting of depression, Parkinson's disease, learning and memory impairment, tardive dyskinesia, drug dependence, arteriosclerotic dementia, and dementias that accompany Huntington's chorea, Wilson's disease, paralysis agitans and thalamic atrophies; infections, especially viral infections, where these viruses increase the production of TNF-α in their host and where these viruses are sensitive to up-regulation of TNF-α in their host so that their replication or other vital activities are adversely affected, including viruses selected from the group consisting of HIV-1, HIV-2 and HIV-3, cytornegalovirus, CMV, influenza, adenoviruses and Herpes viruses, including Herpes zoster and Herpes simplex; yeast and fungus infections, where these yeasts and fungi are sensitive to up-regulation by TNF-α or elicit TNF-α production in their host, for example fungal meningitis, particularly when administered in conjunction with other medicaments of choice for the treatment of systemic yeast and fungus infections, including, but are not limited to, polymycins, for example polymycin B, imidazoles, for example clotrimazole, econazole, miconazole and ketoconazole, triazoles, for example fluconazole and itranazole and amphotericins, for example amphotericin B and liposomal amphotericin B; ischemia-reperfusion damage, autoimmune diabetes, retinal autoimmunity, chronic lymphocytic leukemia, HIV infections, lupus erythematosus, kidney and ureter disease, urogenital and gastrointestinal disorders and prostate diseases; and any disease induced by an infectious agent or noxious environmental agent which elicits Type I IFN production in their host.

In particular, methimazole derivatives and tautomeric cyclic thione compounds of the present invention are suitable for the treatment of (1) inflammatory diseases and conditions, including joint inflammation, rheumatoid arthritis, rheumatoid spondylitis, osteoarthritis, inflammatory bowel disease, ulcerative colitis, chronic glomerulonephritis, dermatitis, atherosclerosis, the vascular complications of Type 2 diabetes, and Crohn's disease, (2) respiratory diseases and conditions, including asthma, acute respiratory distress syndrome, chronic pulmonary inflammatory disease, bronchitis, chronic obstructive airway disease and silicosis, (3) infectious diseases and conditions, including sepsis, septic shock, endotoxic shock, Gram-negative sepsis, toxic shock syndrome, fever and myalgias due to bacterial, viral or fungal infection, and influenza, (4) immune diseases and conditions, including autoimmune diabetes, systemic lupus erythematosis, GvH reaction, rejection of foreign transplants, multiple sclerosis, psoriasis and allergic rhinitis, and (5) other diseases and conditions, including bone absorption diseases, reperfusion damage, cachexia secondary to infection or malignancy, cachexia secondary to human acquired immune deficiency syndrome (AIDS), human immunodeficiency virus (HIV) infection, or AIDS related complex (ARC), keloid formation, scar tissue formation, type 1 diabetes mellitus and leukemia.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese. For example, the present invention relates to, but is not limited to, pre- or postoperative intervention in animals such as horses to prevent or treat toxic shock syndromes.

The pharmaceutical compositions of the present invention comprise specifically defined methimazole derivatives and tautomeric cyclic thiones, used in a safe and effective amount, together with a pharmaceutically acceptable carrier.

The methimazole derivatives used in the compositions of the present invention are those having the following structural formulae:

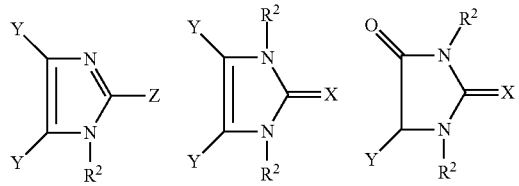

In these formulae, Y is selected from H, $C_1$-$C_4$ alkyl $C_1$-$C_4$ substituted alkyl, —$NO_2$, and the phenyl moiety:

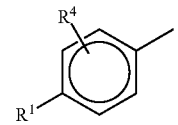

wherein no more than one Y group in said active compound may be the phenyl moiety; $R^1$ is selected from H, —OH, halogens (F, Cl, Br or I), $C_1$-$C_4$ alkyl, $C_1$-$C_4$ substituted alkyl, $C_1$-$C_4$ ester or $C_1$-$C_4$ substituted ester; $R^2$ is selected from H, $C_1$-$C_4$ alkyl or $C_1$-$C_4$ substituted alkyl; $R^3$ is selected from H, $C_1$-$C_4$ alkyl, $C_1$-$C_4$ substituted alkyl or —$CH_2$Ph (wherein Ph is phenyl); $R^4$ is selected from H, $C_1$-$C_4$ alkyl or $C_1$-$C_4$ substituted alkyl; X is selected from S or O; Z is selected from —$SR^3$, —$OR^3$, $S(O)R^3$ or $C_1$-$C_4$ alkyl; and wherein at least two of the $R^2$ and $R^3$ groups on said compound are $C_1$-$C_4$ alkyl when Y is not a phenyl moiety, and at least one Y is —$NO_2$ when Z is alkyl; together with a pharmaceutically-acceptable carrier.

Y is preferably H, the phenyl moiety or —$NO_2$, and is most preferably H or the phenyl moiety

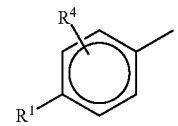

In the defined compounds, no more than one Y group may be the phenyl moiety. $R^1$ is selected from H, —OH, halogens (F, Cl, Br and I), $C_1$-$C_4$ alkyl, $C_1$-$C_4$ substituted alkyl, $C_1$-$C_4$ ester and $C_1$-$C_4$ substituted ester; preferably $R^1$ is H, —OH, halogen, —$OOCCH_2$M (where M is H or a halogen); and is most preferably H. $R^2$ is selected from H, $C_1$-$C_4$ alkyl and $C_1$-$C_4$ substituted alkyl; preferably one or both of the $R^2$ groups is methyl. As used herein, "substituted alkyl" or "substituted ester" is intended to include alkyl, aryl or ester groups which are substituted in one or more places with hydroxyl or alkoxyl groups, carboxyl groups, halogens, nitro groups, amino or acylamino groups, and mixtures of those moieties. Preferred "substituted alkyl" groups are $C_1$-$C_4$ hydroxyl or alkoxyl groups, as well as groups substituted with halogens. The $R^3$ groups in the above formulae are selected from H, $C_1$-$C_4$ alkyl, $C_1$-$C_4$ substituted alkyl and —$CH_2Ph$ (wherein Ph is phenyl); in preferred compounds, $R^3$ is H or $C_1$-$C_4$ alkyl; most preferably $R^3$ is $C_1$-$C_4$ alkyl, particularly methyl. $R^4$ is selected from H, $C_1$-$C_4$ alkyl and $C_1$-$C_4$ substituted alkyl, and preferably is H. X may be S or O, and is preferably S. Finally, Z is selected from $C_1$-$C_4$ alkyl, —$SR^3$, —$S(O)R^3$ and —$OR^3$, is preferably —$SR^3$, —$OR^3$, and —$S(O)R^3$; most preferably —$SR^3$ and —$OR^3$; and particularly —$SR^3$. In the above formulae, at least two of the $R^2$ and $R^3$ groups on the compound must be $C_1$-$C_4$ alkyl when Y is not a phenyl moiety. Further, at least one of the Y groups should be —$NO_2$, when Z is $C_1$-$C_4$ alkyl.

Compounds useful in the present invention include the tautomeric cyclic thiones, disclosed in Kjellin and Sandstrom, Acta Chemica Scandanavica 23: 2879-2887 (1969), incorporated herein by reference, having the formulae

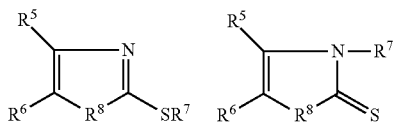

wherein $R^5$, $R^6$=$CH_3$, $CH_3$; Ph, H; H, Ph $R^7$=H, $CH_3$ $R^8\uparrow$O, S, NH, $NCH_3$ Preferred compounds for use in the compositions of the present invention include those having the formulae:

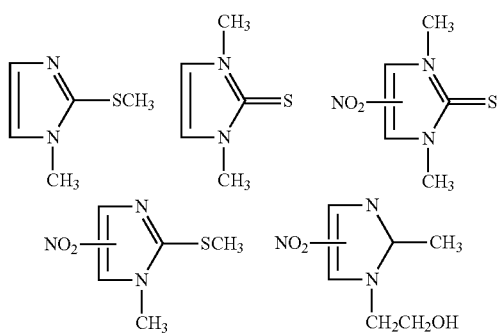

Another group of preferred compositions include those having the formulae:

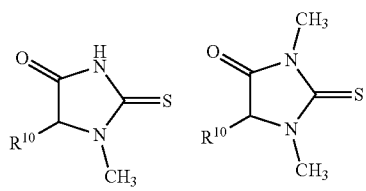

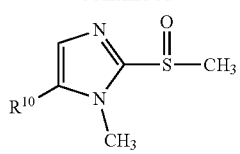

wherein $R^{10}$ is selected from H. $NO_2$, Ph, 4-HOPh and 4-m-Ph (wherein m is F, Cl, Br, or I).

A particularly preferred subset of the pharmaceutical compounds defined herein are those wherein one of the Y groups is the phenyl moiety defined above. These compounds have the following formulae:

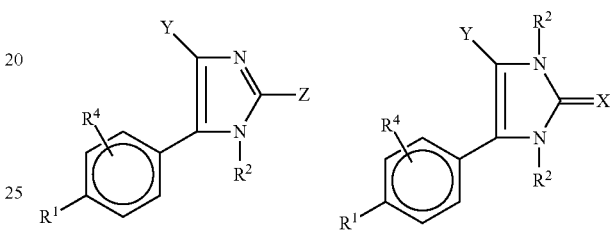

In these compounds, Y is selected from H, $C_1$-$C_4$ alkyl and $C_1$-$C_4$ substituted alkyl, and is preferably H. R' is selected from H, —OH, halogens (F, Cl, Br and I), $C_1$-$C_4$ alkyl, $C_1$-$C_4$ substituted alkyl, $C_1$-$C_4$ ester, and $C_1$-$C_4$ substituted ester, and is preferably H, —OH, halogen, —$OOCCH_2M$ (where) M is H or a halogen), and is not preferably H. $R^2$ is selected from H, $C_1$-$C_4$ alkyl and $C_1$-$C_4$ substituted alkyl, and it is preferred that at least one of the $R^2$ groups be methyl. $R^3$ is selected from H, $C_1$-$C_4$ alkyl, $C_1$-$C_4$ substituted alkyl, and —$CH_2Ph$; preferred $R^3$ moieties are H and methyl. $R^4$ is selected from H, $C_1$-$C_4$ alkyl and $C_1$-$C_4$ substituted alkyl, and is preferably H. X is selected from S and O, and is preferably S. Finally, the Z moiety is selected from —$SR^3$ and —$OR^3$, and is preferably —$SR^3$. Particularly preferred compounds are those having the structural formulae:

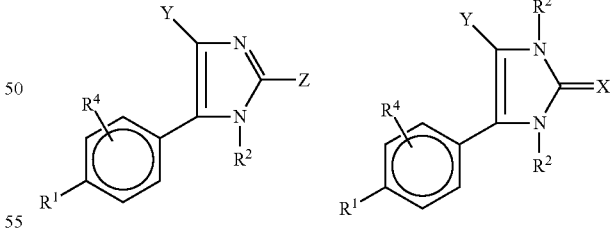

Other preferred compounds include:

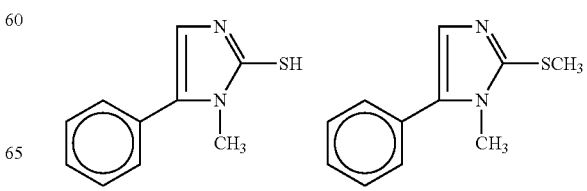

-continued

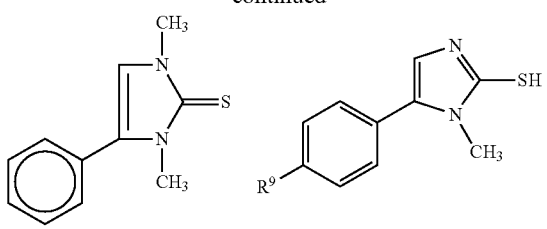

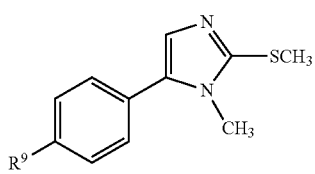

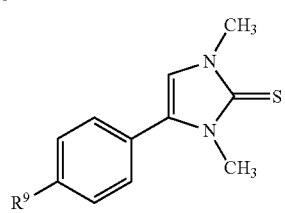

wherein $R^9$ is selected from —OH, —M and —OOCCH$_2$M; and M is selected from F, Cl, Br and I.

Most preferred is the compound having the structure given below.

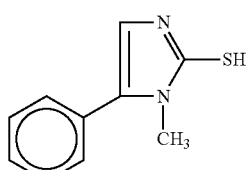

5-phenylmethimazole

Mixtures of the pharmaceutically active compounds defined herein may also be used. The methimazole derivatives and tautomeric cyclic thiones described above can be synthesized using techniques well known to those skilled in the art. For example, the synthesis of several tautomeric cyclic thiones is described in Kjellin and Sandstrom, (G. Kjellin, et al., *Acta Chem Scand*, 23:2879-2887 (1969)), incorporated herein by reference.

A representative methimazole derivative may be synthesized using the following procedure. Appropriately substituted analogs of acetaldehyde are brominated in the 2-position by treatment with bromine and UV light, followed by formation of the corresponding diethylacetal using absolute ethanol. The bromine is then displaced from this compound by treatment with anhydrous methylamine, or other suitable amine, in a sealed tube at about 120° for up to about 16 hours. Reaction of the resulting aminoacetal with potassium thiocyanate in the presence of hydrochloric acid, at steam bath temperatures overnight, provides the methimazole analogs.

Representative methimazole derivative compounds of the present invention are shown in Table 16.

TABLE 16

Structure of Compounds.

| Compounds | Imidazole | |
|---|---|---|
| #1 | 1-Methylimidazole-2-thiol (Methimazole) C$_4$H$_6$N$_2$S; 1-Methyl-2-mercaptoimidazole (MMI) | |
| #2 | 2-Methyl-5-nitro-1-imidazole ethanol (Metronidazole) C$_6$H$_9$N$_3$O$_3$; MW: 171.16 | |
| #3 | 2-Mercaptoimidazole MW: 100.14 | |
| #4 | 2-Mercaptobenzimidazole MW: 150.20 | |
| #5 | 2-Mercapto-5-nitrobenzimidazole MW: 195.20 | |
| #6 | 2-Mercapto-5-methylbenzimidazole MW: 164.23 | |
| #7 | S-Methylmethimazole C$_5$H$_8$N$_2$S; MW: 128.20 B. P. 48° @ 100 u (liq.) | |
| #8 | N-Methylmethimazole C$_5$H$_8$N$_2$S; MW: 128.20 B. P. 188°-194° | |
| #9 | 5-Methylmethimazole C$_5$H$_8$N$_2$S; MW: 128.20 B. P. 254°-255° | |

TABLE 16-continued

Structure of Compounds.

| Com-pounds | Imidazole | |
|---|---|---|
| #10 | 5-Phenylmethimazole<br>$C_{10}H_{10}N_2S$; MW: 190.27<br>B. P. 168°-173° | |
| #11 | 1-Methyl-2-Thiomethyl-5(4)nitroimidazole | |

The pharmaceutical compositions of the present invention comprise a safe and effective amount of one or more of the methimazole derivatives or tautomeric cyclic thione compounds (i.e., the active compounds). Preferred compositions contain from about 0.01% to about 25% of the active compounds, with most preferred compositions containing from about 0.1% to about 10% of the active compounds. The pharmaceutical compositions of the present invention may be administered in any way conventionally known, for example, intraperitoneally, intravenously, intramuscularly, or topically, although oral administration is preferred. Preferred compositions are in unit dosage form, i.e., pharmaceutical compositions, which are available in a pre-measured form suitable for single dosage administration without requiring that the individual dosage be measured out by the user, for example, pills, tablets or ampules.

The pharmaceutical compositions of the present invention additionally include a pharmaceutically-acceptable carrier compatible with the methimazole derivatives or tautomeric cyclic thiones described above. In addition to the pharmaceutically-acceptable carrier, the pharmaceutical compositions may contain, at their art accepted levels, additional compatible ingredients, such as additional pharmaceutical actives, excipients, formulational aids (e.g., tabletting aids), colorants, flavorants, preservatives, solubilizing or dispersing agents, and other materials well known to those skilled in the art.

As used herein, the term "pharmaceutical carrier" denotes a solid or liquid filler, diluent or encapsulating substance. These materials are well known to those skilled in the pharmaceutical arts. Some examples of the substances which can serve as pharmaceutical carriers are sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of *theobroma*; polyols, such as propylene glycol, glycerin, sorbitol, mannitol, and, polyethylene glycol; agar; alginic acid; pyrogen-free water; isotonic saline; and phosphate buffer solutions, as well as other non-toxic compatible substances used in pharmaceutical formulations. They may comprise liposomes or drug carriers made lipids or polymeric particles, including biodegradable polymers, or targeted delivery applications, e.g., coupling to antibodies. Wetting agents and lubricants, such as sodium lauryl sulfate, as well as coloring agents, flavoring agents, tableting agents, and preservatives, can also be present. They may include excipients such as cyclodextrins to improve aqueous solubilization. Formulation of the components into pharmaceutical compositions is done using conventional techniques.

The pharmaceutical carrier employed in conjunction with the pharmaceutical compositions of the present invention is used at a concentration sufficient to provide a practical size-to-dosage relationship. Preferably, the pharmaceutical carrier comprises from about 25% to about 99.99%, preferably from about 50% to about 99.9%, by weight of the total pharmaceutical composition.

The conditions treated with the pharmaceutical compositions of this invention generally include any autoimmune-inflammatory disease mediated by or associated with TLR3 or TLR4 overexpression or signaling, particularly in, but not limited to nonimmune cells, monocytes, macrophages, or dendritic cells, or both TLR3 or TLR4 overexpression or signaling, for example, but not limited to, Hashimoto's thyroiditis, insulinitis, Type 1 diabetes, atherosclerosis, vascular complications of type 1 or 2 diabetes, vascular complications associated with obesity or hyperlipidemias, toxic shock, colitis, or IBD and the various symptoms that fall within a definition of IBD. The formulations are administered to achieve a therapeutic effect. For those compounds that exhibit a long residency in the body, a once-a-day regimen is possible. Alternatively, multiple doses, such as up to three doses per day, typically, may offer more effective therapy. Thus, a single dose or a multidose regimen may be used.

The conditions treated with the pharmaceutical compositions of this invention generally include any autoimmune-inflammatory disease mediated by or associated with TLR overexpression or signaling, particularly in, but not limited to nonimmune cells, monocytes, macrophages, or dendritic cells which phagocytose infectious or noxious environmental agents inducing TLR overexpression or signaling, for example, but not limited to, systemic lupus erythematosis, Graves' disease, autoimmune blepharitis. The formulations are administered to achieve a therapeutic effect. For those compounds that exhibit a long residency in the body, a once-a-day regimen is possible. Alternatively, multiple doses, such as up to three doses per day, typically, may offer more effective therapy. Thus, a single dose or a multidose regimen may be used.

The present invention also provides for methods of diagnosing, treating, and following therapeutic intervention in any autoimmune-inflammatory disease mediated by or associated with TLR3 or TLR4 overexpression or signaling, particularly in, but not limited to nonimmune cells, monocytes, macrophages, or dendritic cells, or both TLR3 or TLR4 overexpression or signaling, for example, but not limited to, Hashimoto's thyroiditis, insulinitis, Type 1 diabetes, atherosclerosis, vascular complications of type 1 or 2 diabetes, vascular complications associated with obesity or hyperlipidemias, toxic shock, colitis, or IBD and the various symptoms that fall within a definition of IBD. For example, ulcerative colitis, which is a disease of the large intestine characterized by overexpressed TLR4 and TLR4 signaling in intestinal epithelial cells, monocytes, macrophages, and dendritic cells involves chronic diarrhea with cramping abdominal pain, rectal bleeding, and loose discharges of blood, pus and mucus. The manifestations of this disease vary widely. A pattern of exacerbations and remissions typifies the clinical course of most ulcerative colitis patients (70%), although continuous symptoms without remission are present in some patients with ulcerative colitis. Systemic complications of ulcerative colitis include arthritis, eye inflammation such as uveitis, skin ulcers and liver disease. In addition, ulcerative colitis and especially long-standing, extensive disease is associated with an increased risk of colon carcinoma. Similarly, Type I diabetes is an autoimmune inflammatory disease of the pancreas characterized by overexpressed TLR3 and TLR3 signaling in pancreatic P cells, monocytes, macrophages, and dendritic cells, characterized by a prolonged inflammatory state or insulinitis, a honeymoon period or lag phase with islet cell and GAD auto-antibodies, a destructive phase resulting in loss of insulin secretion, hyperglycemia, hyperlipidemia, and tissue complications such as macro- and microvascular diseases including atherosclerosis, strokes, myocardial infarcts, nephropathy, neuropathy, retinopathy, and higher incidences of autoimmune thyroid disease and cancer.

In any event, the pharmaceutical composition is administered in such a manner so that compound is delivered into the patient's bloodstream. One excellent mode for accomplishing this is intravenous administration. Intravenous dose levels range from about 0.01 mg/kg/hour of active amide compound to about 100 mg/kg/hour, all for from about 1 to about 120 hours and especially 1 to 96 hours. A preloading bolus of from about 0.001 to about 500 mg may also be administered to achieve adequate steady state levels. Other forms of parenteral administration, such as intramuscular or intraperitoneal injection can be used, as well. In this case, similar dose levels are employed.

With oral dosing, one to three oral doses per day, each from about 0.001 to about 150 mg/kg of active compound are employed, with preferred doses being from about 0.05 to about 100 mg/kg. With rectal dosing, one to three rectal doses per day, each from about 1 to about 150 mg/kg of active compound are employed, with preferred doses being from about 1 to about 100 mg/kg.

In any treatment regimen, the health care professional should assess the patient's condition and determine whether or not the patient would benefit from treatment. Some degree of routine dose optimization may be required to determine an optimal doing level and pattern. A positive dose-response relationship has been observed. As such and bearing in mind the severity of the side effects and the advantages of providing maximum possible amelioration of symptoms, it may be desired in some settings to administer large amounts of active compound, such as those described above.

The pharmaceutical compositions of the present invention are administered such that appropriate levels of pharmaceutical active are achieved in the bloodstream. The precise dosage level required in a given case will depend upon, for example, the particular methimazole derivative used, the nature of the disease being treated, and the size, weight, age and physical condition of the patient.

The term "pharmaceutically acceptable salts" refers to salts prepared from pharmaceutically acceptable non-toxic bases or acids including inorganic or organic bases and inorganic or organic acids. Salts derived from inorganic bases include: aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include: salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include: acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. It will be understood that, as used herein, the compounds referred to herein are meant to also include the pharmaceutically acceptable salts.

The magnitude of prophylactic or therapeutic dose of the therapeutic compound of the present invention will, of course, vary with the nature of the severity of the condition to be treated and with the particular therapeutic compound of the present invention and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous or intraperitoneal administration is employed, a suitable dosage range is from about 0.001 mg to about 25 mg (in another embodiment from 0.01 mg to about 1 mg) of a therapeutic compound of the present invention per kg of body weight per day and for cytoprotective use from about 0.01 mg to about 100 mg (in another embodiment from about 0.1 mg to about 100 mg and in another embodiment from about 1 mg to about 10 mg) of the therapeutic compound of the present invention per kg of body weight per day.

In the case where an oral composition is employed, a suitable dosage range is, e.g. from about 0.01 mg to about 100 mg of the therapeutic compound of the present invention per kg of body weight per day, in another embodiment from about 0.1 mg to about 10 mg per kg and for cytoprotective use from 0.1 mg to about 100 mg (in another embodiment from about 1 mg to about 100 mg and in another embodiment from about 10 mg to about 100 mg) of a therapeutic compound of the present invention per kg of body weight per day.

The present invention utilizes pharmaceutical formulation techniques to provide compositions of a methimazole derivatives and tautomeric cyclic thiones for treating the inflammatory and/or autoimmune diseases or autoimmune-inflammatory disease mediated by or associated with overexpression of TLR3 or TLR3 signaling, TLR4 or TLR4 signaling, or both in nonimmune cells, monocytes, macrophages, or dendritic cells including but not limited to Hashimoto's thyroiditis, insulinitis, Type 1 diabetes, atherosclerosis, vascular complications of diabetes, obesity, or hyperlipidemias, toxic shock, colitis, IBD, autoimmune uveitis, autoimmune blepharitis, psoriasis, as hereinbefore defined. It utilizes pharmaceutical formulation techniques to provide compositions of a methimazole derivatives and tautomeric cyclic thiones for treating the inflammatory and/or autoimmune diseases or autoimmune-inflammatory disease mediated by or associated with overexpression of TLR signaling involving over expressed IRF-3/Type 1 IFN/STAT/IRF-1/and genes with ISREs in non-immune cells, monocytes, macrophages, or dendritic cells including but not limited to systemic lupus and rheumatoid arthritis.

The dosage and dose rate of the compounds of this invention effective to prevent, suppress or inhibit diseases will depend on a variety of factors, such as the nature of the inhibitor, the size of the patient, the goal of the treatment, the nature of the pathology to be treated, the specific pharmaceutical composition used, and the judgment of the treating physician.

The transit time through the gastro-intestinal canal for different dosage forms are rather well known. When the dosage form has been emptied from the stomach the transit through the small intestine takes 3 to 5 hours. The residence time in the large intestine is considerably longer, 25 to 50 hours. Ideally, for local effects, as long as the dosage form remains in the stomach no release should occur. If colitis in the small intestine is going to be treated the release should continue during about 5 hours after the dosage form has left the stomach. If the large intestine is going to be treated, the local release should ideally start at caecum, and continue for up to 50 hours.

The term "composition", as in pharmaceutical composition, is intended to encompass a product comprising the active ingredient (s), and the inert ingredient (s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by mixing a compound of the present invention, additional active ingredient (s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders, which may be formulated and the powder composition may be inhaled with the aid of an insufflation powder inhaler device. The preferred delivery systems for inhalation are metered dose inhalation (MDI) aerosol, which may be formulated as a suspension or solution of a compound of the present invention in suitable propellants, such as fluorocarbons or hydrocarbons and dry powder inhalation (DPI) aerosol, which may be formulated as a dry powder of a compound of the present invention with or without additional excipients. Suitable topical formulations include transdermal devices, aerosols, creams, ointments, lotions, dusting powders, and the like.

In practical use, the compounds of the present invention can be combined as the active ingredient in intimate admixture with a pharmaceutical carrier according to conventional pharmaceutical compounding techniques. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, the therapeutic compound of the present invention may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combination Therapy—Prophylaxis and Treatment

In the context of the present invention, a compound as described herein or pharmaceutical composition thereof can be utilized for modulating the activity of TLR3/4 mediated diseases, conditions and/or disorders as described herein. Examples of modulating the activity of TLR3/4 mediated diseases include the prophylaxis or treatment of metabolic related disorders such as, but not limited to, type I diabetes, type II diabetes, inadequate glucose tolerance, insulin resistance, hyperglycemia, hyperlipidemia, hypertriglyceridemia, hypercholesterolemia, dyslipidemia and syndrome X. Other examples of modulating the activity of TLR3/4 mediated diseases include the prophylaxis or treatment of obesity and/or overweight by decreasing food intake, inducing satiation (i.e., the feeling of fullness), controlling weight gain, decreasing body weight and/or affecting metabolism such that the recipient loses weight and/or maintains weight. Also in the context of the present invention, a compound as described herein or pharmaceutical composition thereof can be utilized for modulating the activity of TLR mediated diseases, conditions and/or disorders as described herein with increased signaling involving IRF-3/Type 1 IFN/STAT/IRF-1/and ISRE containing genes. Examples of modulating the activity of these TLR mediated diseases include the prophylaxis or treatment of such disorders as, but not limited to, systemic lupus, rheumatoid arthritis, coliutis, Crohn's disease, or other inflammatory disorders.

While the compounds of the invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of prophylaxis and/or treatment of a metabolic related disorder or a weight related disorder, such as obesity, comprising administering to an individual in need of prophylaxis and/or treatment a therapeutically effective amount of a compound of the present invention, in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholecystokinin-A (CCK-A) agonists, serotonin and norepinephrine reuptake inhibitors (for example, sibutramine), sympathomimetic agents, beta-3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

In some embodiments, anti-obesity agents are used in conjunction with the present methods, selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

More specifically, and without limitation, the methods of the invention may comprise administering a therapeutically effective amount of phenylmethimazoles, methimazole derivatives, and/or tautomeric cyclic thiones with one or more of TNF, IL-1, IL-2, IL-3, IL4, IL-5, IL-6, IL-7, IL-8, IL-9, IL-1, IL-11, IL-12, IL-13, IL-14, IL-15, IL-16, IL-17, IL-18, IFN, G-CSF, Meg-CSF, GM-CSF, thrombopoietin, stem cell factor, and erythropoietin or antibodies thereto. Compositions in accordance with the invention may also include other known angiopoietins such as Ang-2, Ang-4, and Ang-Y, growth factors such as bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor a, cytokine-induced neutrophil chemotactic factor 1, cytokine-induced neutrophil chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor $\alpha$-1, glial cell line-derived neutrophic factor receptor a2, growth related protein, growth related protein a, growth related protein $\beta$, growth related protein $\gamma$, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor, nerve growth factor receptor, neurotrophin-3, neurotrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptors, pre-B cell growth stimulating factor, stem cell factor, stem cell factor receptor, transforming growth factor $\alpha$, transforming growth factor $\beta$, transforming growth factor $\beta$-1, transforming growth factor $\beta$-1, transforming growth factor $\beta$-2, transforming growth factor $\beta$-3, transforming growth factor $\beta$-5, latent transforming growth factor $\beta$-1, transforming growth factor $\beta$ binding protein I, transforming growth factor $\beta$ binding protein II, transforming growth factor $\beta$ binding protein III, tumor necrosis factor receptor type I, tumor necrosis factor receptor type II, urokinase-type plasminogen activator receptor, chimeric proteins and biologically or immunologically active fragments thereof, or antibodies thereto.

Compounds of the present invention may be used in combination with other drugs that are used in the treatment/prevention/suppression or amelioration of the diseases or conditions for which compounds of the present invention are useful. Such other drugs may be administered, by a route and in an amount commonly used therefore, contemporaneously or sequentially with a compound of the present invention, such as methimazole derivatives and tautomeric cyclic thiones. When a compound of the present invention is used contemporaneously with one or more drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VCAM-1, ICAM-1, or E-selectin antagonists; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (HI-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, CCR-3, and CXCR4; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (1) preparations of type 1 interferon (e.g., β-interferon and α-interferon); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents; (O) antibiotics; (p) antibodies which block cytokine or chemokine activity, e.g. anti-TNFα, or block leukocyte adhesion, e.g. anti-VCAM-1 or anti-E-selectin; antihypertensives agents, which inhibit platelet or leukocyte adhesion such as plaxel, etc.

Other suitable pharmaceutical agents that can be used in combination with the compounds of the present invention include agents useful in the treatment of metabolic related disorders and/or concomitant diseases thereof. For example, but not limited to, congestive heart failure, type I diabetes, type II diabetes, inadequate glucose tolerance, insulin resistance, hyperglycemia, hyperlipidemia, hypertriglyceridemia, hypercholesterolemia, dyslipidemia, syndrome X, retinopathy, nephropathy and neuropathy. Prophylaxis or treatment of one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists, adiponectin and the like. In accordance to one aspect of the present invention, a compound of the present can be used in combination with a pharmaceutical agent or agents belonging to one or more of the classes of drugs cited herein.

Moreover, the compounds of the present invention can be used alone or in combination with one or more additional agents depending on the indication and the desired therapeutic effect. For example, in the case of diabetes, insulin resistance and associated conditions or complications, including obesity and hyperlipidemia, such additional agent (s) may be selected from the group consisting of: insulin or an insulin mimetic, a sulfonylurea (such as acetohexamide, chlorpropamide, glimepiride, glipizide, glyburide, tolbutamide and the like) or other insulin secretagogue (such as nateglinide, repaglinide and the like), a thiazolidinedione (such as pioglitazone, rosiglitazone and the like) or other peroxisome proliferator-activated receptor (PPAR)-γ agonist, a fibrate (such as bezafibrate, clofibrate, fenofibrate, gemfibrozol and the like) or other PPAR-α agonist, a PPAR-δ agonist, a biguanide (such as metformin), a statin (such as fluvastatin, lovastatin, pravastatin, simvastatin and the like) or other hydroxymethylglutaryl (HMG) CoA reductase inhibitor, an α-glucosidase inhibitor (such as acarbose, miglitol, voglibose and the like), a bile acid-binding resin (such as cholestyramine, celestipol and the like), a high density lipoprotein (HDL)-lowering agent such as apolipoprotein A-I (apoA1), niacin and the like, probucol and nicotinic acid, Preferred additional agents include, for example, sulfonylurea, thiazolidinedione, fibrate or statin, preferably sulfonylurea.

In the case of inflammation, inflammatory diseases, autoimmune disease and other such cytokine mediated disorders, the additional agent (s) may be selected from the group consisting of: a nonsteroidal anti-inflammatory drug (NSAID) (such as diclofenac, diflunisal, ibuprofen, naproxen and the like), a cyclooxygenase-2 inhibitor (such as celecoxib, rofecoxib and the like), a corticosteroid (such as prednisone, methylprednisone and the like) or other immunosuppressive agent (such as methotrexate, leflunomide, cyclophosphamide, azathioprine and the like), a disease-modifying anti-rheumatic drug (DMARD) (such as injectable gold, penicilliamine, hydroxychloroquine, sulfasalazine and the like), a TNF-α inhibitor (such as etanercept, infliximab and the like), other cytokine inhibitor (such as soluble cytokine receptor, anti-cytokine antibody and the like), other immune modulating agent (such as cyclosporin, tacrolimus, rapamycin and the like, and immunostimulatory oligonucleotides and/or immunomers) and a narcotic agent (such as hydrocodone, morphine, codeine, tramadol and the like).

Preferred diseases that may be treated by the preferred methods include inflammatory or immunological disease, for example, rheumatoid arthritis, osteoarthritis, ankylosing spondylitis, psoriasis, psoriatic arthritis, asthma, acute respiratory distress syndrome, chronic obstructive pulmonary disease, or multiple sclerosis. Additional preferred diseases that may be treated by the preferred methods include diabetes, hyperlipidemia, includes coronary heart disease, cancer or proliferative disease.

Another aspect of the invention is a method of treating diabetes and related diseases comprising the step of administering to a subject suffering from a diabetic or related condition a therapeutically effective amount of a methimazole derivative and/or tautomeric cyclic thione compound described herein. Additionally, the invention provides a method of treating inflammation or inflammatory diseases or diseases mediated by cytokines, PDE4, PDE3, p44/42 MAP kinase, iNOS and/or COX-2 by administering to a subject in need of such treatment an effective amount of a methimazole derivative and/or tautomeric cyclic thione compound described herein. Further, pharmaceutical compositions containing a therapeutically effective amount of one or more methimazole derivative and/or tautomeric cyclic thione compounds described herein together with a pharmaceutically or physiologically acceptable carrier, for use in the treatments contemplated herein, are also provided.

The compounds of the invention are useful for the treatment of diabetes, characterized by the presence of elevated blood glucose levels, that is, hyperglycemic disorders such as diabetes mellitus, including both type 1 and 2 diabetes, as well as other hyperglycemic related disorders such as obesity, increased cholesterol, hyperlipidemia such as hypertriglyceridemia, kidney related disorders and the like. The compounds are also useful for the treatment of disorders linked to insulin resistance and/or hyperinsulinemia, which include, in addition to diabetes, hyperandrogenic conditions such as polycystic ovary syndrome (Ibanez et al., J. Clin Endocrinol Metab, 85:3526-30, (2000); Taylor A. E., Obstet Gynecol Clin North Am, 27:583-95, (2000)), coronary artery disease such as atherosclerosis and vascular restenosis, and peripheral vascular disease. Additionally, the compounds of the present invention are also useful for the treatment of inflammation and immunological diseases that include those mediated by signaling pathways linked to pro-inflammatory cytokines, such as rheumatoid arthritis, ankylosing spondylitis, multiple sclerosis, inflammatory bowel disease, psoriasis, and contact and atopic dermatitis.

In some embodiments, the immunostimulatory oligonucleotide and/or immunomer used in the method according to the invention comprises an immunostimulatory dinucleotide selected from the group consisting of CpG, C*pG, CpG*, and C*pG*, wherein C is cytidine or 2'-deoxycytidine, C* is 2'-deoxythymidine. arabinocytidine, 2'-deoxy-2'-substituted arabinocytidine, 2'-O-substitutedarabinocytidine, 2'-deoxy-5-hydroxycytidine, 2'-deoxy-N-4-alkyl-cytidine, 2'-deoxy-4-thiouridine, other non-natural pyrimidine nucleosides, or 1-(2'-deoxy-beta-D-ribofuranosyl-)-2-oxo-7-deaza-8-methyl-purine; G is guanosine or 2'-deoxyguanosine, G* is 2' deoxy-7-deazaguanosine, 2'-deoxy-6-thioguanosine, arabinoguanosine, 2'-deoxy-2'-substituted-arabinoguanosine, 2'-O-substituted-arabinoguanosin-e, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

β-adrenergic receptor antagonists block the action of the sympathetic nervous system and a portion of the involuntary nervous system. By blocking the action of these nerves, they reduce the heart rate and are useful in treating abnormally rapid heart rhythms. These drugs also reduce the force of heart muscle contractions and lower blood pressure. By reducing the heart rate and the force of muscle contraction, β-blockers reduce heart muscle oxygen demand. Useful β-adrenergic blocking agents are selected from a group including atenolol, betaxolol, acebutolol, bisoprolol, carteolol, labetalol, metoprolol, nadolol, oxprenolol, penbutolol, pindolol, propranolol, sotalol, and timolol. Atenolol is a presently preferred beta-adrenergic blocking agent.

This invention employs any effective cholesterol-lowering agent or combination of such agents in combination with the present methods. Useful cholesterol-lowering agents include HMG CoA reductase inhibitors, bile acid sequestrants, probucol, and fibric acid agents. Also useful is the selective inhibitor of intestinal cholesterol absorption having the adopted name "ezetimibe," and the chemical name 1-(4-fluorophenyl)-3(R)-[3-(4-fluorophenyl)-3(S)-hydroxypropyl]-4 (S)-(4-h-ydroxyphenyl)-2-azetidinone. Ezetimibe is particularly effective when administered together with a statin.

Preferred are the HMG CoA reductase inhibitors. These agents are competitive inhibitors of HMG CoA reductase, the rate-limiting step in cholesterol biosynthesis. They occupy a portion of the binding site of HMG CoA, blocking access of this substrate to the active site on the enzyme. HMG CoA reductase inhibitors comprise atorvastatin, cerivistatin, fluindostatin, fluvastatin, lovastatin, mevastatin, pravastatin, simvastatin, and velostatin; the most preferred agents are lovastatin and pravastatin, particularly lovastatin.

Suitable pharmaceutical agents that can be used in conjunction with compounds of the present invention include inhibitors of the renin-angiotensin system. The renin-angiotensin system plays a major role in regulating blood pressure. Renin, an enzyme, functions by acting on angiotensinogen to form the decapeptide angiotensin I. Angiotensin I is rapidly converted to the octapeptide angiotensin II by angiotensin converting enzyme (ACE). Angiotensin II acts by numerous mechanisms to raise blood pressure, including raising total peripheral resistance. Inhibitors of the renin-angiotensin system are classified as angiotensin converting enzyme (ACE) inhibitors and angiotensin II receptor antagonists (ARBs). Examples of angiotensin converting enzyme (ACE) inhibitors are captopril, cilazapril, delapril, enalapril, fentiapril, fosinopril, indolapril, lisinopril, perindopril, pivopril, quinapril, ramipril, spirapril, trandolapril, and zofenopril; preferred for use in this invention are captopril, enalapril, fosinopril, lisinopril, quinapril, ramipril, and trandolapril, and more preferred is enalapril. Useful angiotensin II receptor antagonists include losartan, irbesartan, eprosartan, candesartan, valsartan, telmisartan, zolasartin, and tasosartan. Preferred is losartan. In this invention, angiotensin converting enzyme (ACE) inhibitors are more preferred over angiotensin II receptor antagonists.

Cyclooxygenase inhibitors are useful in the present invention, due to their ability to affect platelets; the most widely used and studied cyclooxygenase inhibitor is aspirin, which has been shown to prevent myocardial infarction and strokes due to thrombosis, when administered in low daily doses over a long term to patients at risk for cardiovascular events. When sufficient aspirin is present in the circulatory system, platelets that are being formed have an impaired ability to aggregate over their entire 7-10 day lifetimes.

Diuretics increase the rate of urine flow and sodium excretion and are used to adjust the volume and/or composition of body fluids in a variety of clinical situations, including hypertension, congestive heart failure, renal failure, nephritic syndrome and cirrhosis. Diuretics can be selected from variety of classes such as inhibitors of carbonic anhydrase, loop diuretics, thiazides and thiazide-like diuretics, K+ sparing diuretics, and antagonists of mineralocorticoid receptors.

In an embodiment of this invention thiazides and thiazide-like derivatives are preferred diuretics, including bendroflumethazide, chlorothiazide, hydrochlorothiazide, hydroflumethazide, methyclothazide, polythiazide, trichlormethazide, chlorthalidone, indapamide, metolazone, and qiuriethazone. Presently, the most preferred diuretic is hydrochlorothiazide, which acts by blocking salt and fluid reabsorption in the kidneys, causing increased urine output (diuresis). It has also been widely used in treating mild hypertension.

Further, a combination product can include at least one antidiabetic agent, such as the oral hypoglycemic agents metformin, the sulfonylurea drugs glibenclamide, tolbutamide, tolazamide, glyburide, glipizide, and glimipiride, and the thiazolidinedione drugs troglitazone, rosiglitazone, and pioglitazone. These generally act to improve insulin utilization by the cells, and (in some instances) stimulate insulin production by the pancreas or decrease hepatic glucose production. An anti-diabetic agent can be included in a product that is intended for use by persons having non-insulin dependent diabetes mellitus.

Elevated serum levels of homocysteine are highly correlated with atherosclerosis, heart disease, stroke, and peripheral vascular disease. Vitamin B6, vitamin B12, and folic acid act to lower homocysteine levels and reduce the incidence of these disease states. Vitamin B6 may be included in amounts between about 2 mg and 2 grams. Vitamin B12 may be included in amounts between about 3 μg and 2 mg. Folic acid may generally be included in amounts up to about 5 mg, such as about 400 to 800 g, about 500 μg to 2 mg, or about 1 mg to 5 mg.

Suitable pharmaceutical agents that can be used in conjunction with compounds of the present invention include sulfonylureas. The sulfonylureas (SU) are drugs which promote secretion of insulin from pancreatic beta cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing HbAlc. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the alpha-glucosidase inhibitors. The alpha-glucosidase inhibitors competitively inhibit digestive enzymes such as alpha-amylase, maltase, alpha-dextrinase, sucrase, etc. in the pancreas and or small intestine. The reversible inhibition by alpha-glucosidase inhibitors retard, diminish or otherwise reduce blood glucose levels by delaying the digestion of starch and sugars. Examples of alpha-glucosidase inhibitors include acarbose, N-(1,3-dihydroxy-2-propyl)valiolamine (generic name; voglibose), miglitol, and alpha-glucosidase inhibitors known in the art.

Suitable pharmaceutical agents that can be used in conjunction with compounds of the present invention include the peroxisome proliferators-activated receptors (i.e., PPAR-Υ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the Fibrates. Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., ATI) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists; exendin-4; insulinotropin (NN22 11); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-alpha-[Bis[2,2-dimethyl-1-oxopropoxy)methoxy]phosphinyl]-3-phenoxyben-zenebutanesulfonic acid, mono potassium salt (BMS-188494) and squalene synthesis inhibitors known in the art.

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of disorder being treated, the age and condition of the patient, the stage and type of the patient's disease, and how the patient responds to the treatment. Additionally, a person having a greater risk of developing a disorder (e.g., a person who is genetically predisposed or previously had a disease or disorder) may receive prophylactic treatment to inhibit or delay a response. Similarly, the duration of the combination therapy depends on the type of autoimmune-inflammatory disorder associated with overexpressed TLR3, TLR4, TLR3 or TLR4 signaled events, overexpressed cytokines, chemokines, or interferons, the age and condition of the patient, the stage and type of the patient's disease, and how the patient responds to the treatment. Additionally, a person having a greater risk of developing a disease or a related autoimmune-inflammatory disease, i.e. thyroiditis in a diabetic, or a person who is genetically predisposed or previously had a disease or disorder may receive prophylactic treatment to inhibit or delay a response.

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of disease caused by or associated with TLR, TLR3, TLR4, or all overexpression and signaling in nonimmune cells, monocytes, macrophages or dendritic cells, including, but not limited to, Hashimoto's thyroiditis, type 1, insulinitis, Type 1 diabetes, atherosclerosis, vascular complications of diabetes, obesity, or hyperlipidemias, toxic shock, or autoimmune inflammatory disorder being treated, the age and condition of the patient, the stage and type of the patient's disease, and how the patient responds to the treatment. Additionally, a person having a greater risk of developing an autoimmune inflammatory disorder caused by or associated with TLR, TLR3, TLR4, or all overexpression and signaling in nonimmune cells, monocytes, macrophages or dendritic cells, including, but not limited to, Hashimoto's thyroiditis, type 1, insulinitis, Type 1 diabetes, atherosclerosis, vascular complications of diabetes, obesity, or hyperlipidemias, toxic shock, or autoimmune inflammatory disorder (e.g., a person who is genetically predisposed or previously had a disease or disorder) may receive prophylactic treatment to inhibit or delay a response.

The dosage, frequency and mode of administration of each component of the combination can be controlled independently. For example, one compound may be administered orally three times per day, while the second compound may be administered intramuscularly once per day. Combination therapy may be given in on-and-off cycles that include rest periods. The compounds may also be formulated together such that one administration delivers both compounds.

The relative efficacies of compounds can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of activity then are plotted against the inhibitor concentrations used. The concentration of the inhibitor that shows 50% activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc. A methimazole derivative and/or tautomeric cyclic thione compound is typically administered in an amount such that it selectively inhibits TLR3 or TLR4 expression or activity, as described above.

An optionally rate-limiting layer on the compositions comprises a water insoluble polymer or a mixture of water insoluble polymers or a mixture of water soluble and water insoluble polymers.

In one embodiment, the composition comprises the compounds of the present invention and a water-soluble or water-insoluble polymer that acts both as binder for the therapeutic compounds and as a rate-limiting layer for release of the compounds. Such polymers may be selected from cellulose derivatives, acrylic polymers and copolymers, vinyl polymers and other high molecular polymer derivatives or synthetic polymers such as methylcellulose, hydroxypropylcellulose, hydroxypropylmethylcellulose, ethylcellulose, cellulose acetate, polyvinyl pyrrolidone, polyvidone acetate, polyvinyl acetate, polymethacrylates and ethylene-vinyl acetate copolymer or a combination thereof. Preferred film-forming polymers are ethylcellulose or copolymers of acrylic and methacrylic acid esters in aqueous dispersion form.

In another embodiment, the composition comprises homogeneously distributed methimazole derivatives and tautomeric cyclic thiones contained in a water insoluble polymer or a mixture of water insoluble polymers or a mixture of water soluble and water insoluble polymers mentioned above.

In another embodiment, the composition comprises a second rate-limiting layer. The polymers in the second layer may be selected from the group of anionic carboxylic polymers suitable for pharmaceutical purposes and being soluble with difficulty at a low pH but being soluble at a higher pH, the pH limit for solubility being in the interval of pH 4 to pH 7.5, said group comprising cellulose acetate phthalate, cellulose acetate trimellitate, hydroxypropylmethylcellulose phthalate, polyvinyl acetate phthalate and acrylic acid polymers, e.g., partly asterified methacrylic acid-polymers. These polymers may be used alone or in combination with each other or in combination with water insoluble polymers mentioned before.

The coatings may optionally comprise other pharmaceutically acceptable materials that improve the properties of the film-forming polymers such as plasticizers, anti-adhesives, surfactants, and diffusion-accelerating or diffusion-retarding substances. Suitable plasticizers comprise phthalic acid esters, triacetin, dibutylsebacate, monoglycerides, citric acid esters and polyethyleneglycols. Preferred plasticizers are acetyltributyl citrate and triethyl citrate. Suitable anti-adhesives comprise talc and metal stearates.

The amount of the first coating applied on the units is normally in the range between 0.5% and 30% by weight, preferably between 1% and 15%. This amount includes in the relevant case the weight of the adjunct therapeutic, for example the steroid, or statin, as well. The amount of the second coating applied on the units is normally in the range between 1% and 50% by weight, preferably between 2% and 25%, calculated on the weight of the coated units. The remainder constitutes the weight of the dosage.

The weight ratio of the therapeutic compound of the present invention to the second or third active ingredient may be varied and will depend upon the effective dose of each ingredient. Generally, an effective dose of each will be used. Thus, for example, when a therapeutic is combined with an NSAID the weight ratio of the compound of the therapeutic compound of the present invention to the NSAID will generally range from about 1000:1 to about 1:100, preferably about 200:1 to about 1:200. Combinations of a therapeutic and other active ingredients will generally also be within the aforementioned range, but in each case, an effective dose of each active ingredient should be used.

Pharmaceutical Compositions of the Present Invention

For the treatment of autoimmune/inflammatory diseases associated with toll-like receptor 3 and 4 over-expression and pathologic signaling in nonimmune cells, macrophages, monocytes, or dendritic cells, pharmaceutical compositions in dosage unit form comprise an amount of composition that provides from about 0.05 to about 600 milligrams. In another embodiment, the composition provides from about 0.05 to about 200 milligrams of active compound per day. Useful pharmaceutical formulations for administration of the active compounds of this invention may be illustrated below. They are made using conventional techniques.

Capsules
Active ingredient 0.05 to 200 mg
Lactose 20-100 mg
Corn Starch U.S.P. 20-100 mg
Aerosolized silica gel 2-4 mg
Magnesium stearate 1-2 mg
  Tablets
Active ingredient 0.05 to 200 mg
Microcrystalline cellulose 50 mg
Corn Starch U.S.P. 80 mg
Lactose U.S.P. 50 mg
Magnesium stearate U.S.P. 1-2 mg
  This tablet can be sugar coated according to conventional art practices.
    Colors may be added to the coating.
    Chewable Tablets
Active ingredient 0.05 to 200 mg
Mannitol, N.F. 100 mg
Flavor 1 mg
Magnesium stearate U.S.P. 2 mg
    Suppositories
Active ingredient 0.05 to 200 mg
Suppository base 1900 mg
Dimethyl sulfoxide 0.1 to 3%
    Liquid
Active ingredient 2.0 percent
Polyethylene glycol 300, N.F. 10.0 percent
Glycerin 5.0 percent
Sodium bisulfite 0.02 percent
Sorbitol solution 70%, U.S.P. 50 percent
Methylparaben, U.S.P. 0.1 percent
Propylparaben, U.S.P. 0.2 percent
Distilled water, U.S.P. (q.s.) 100.0 cc
Dimethyl sulfoxide 0.1 to 3%
    Injectable
Active ingredient 0.02 to 200 mg
Polyethylene glycol 600 1.0 cc
Sodium bisulfite, U.S.P. 0.4 mg
Water for injection, U.S.P. (q.s.) 2.0 cc
Dimethyl sulfoxide 0.1 to 3%

In addition, information regarding procedural or other details supplementary to those set forth herein is described in cited references specifically incorporated herein by reference.

It would be obvious to those skilled in the art that modifications or variations may be made to the preferred embodiment described herein without departing from the novel teachings of the present invention. All such modifications and variations are intended to be incorporated herein and within the scope of the claims.

The following examples are intended to illustrate the pharmaceutically active compounds, pharmaceutical compositions and methods of treatment of the present invention, but are not intended to be limiting thereof.

EXAMPLES

Example 1

TLR3 is expressed in thyrocytes, is functional, can be pathologically overexpressed by viruses, is associated with Hashimoto's thyroiditis, and its pathological overexpressed state or signaling can be reversed by methimazole, methimazole derivatives, and tautomeric cyclic thiones.

TLR3 is present and functional in thyrocytes.

TLR3 is present in thyrocytes. Using Northern blotting, we showed that rat FRTL-5 thyrocytes contained detectable levels of a single 5.8 kb mRNA that hybridizes with a $^{32}$P-labeled mouse TLR3 cDNA probe and is present in mouse spleen (positive control). The presence of TLR3 on FRTL-5 thyrocytes grown in continuous culture was duplicated in intact mouse thyroids, which had a similarly sized RNA. Specificity was indicated since neither human embryonic kidney (HEK293), Chinese hamster ovary (CHO-K1) cell, or mouse liver exhibited significant levels of a similar sized hybridizing band. Further evidence of specificity was the observation that TLR9 mRNA, which is involved in the recognition of specific unmethylated CpG-ODN sequences that distinguish bacterial DNA from mammalian DNA, was not expressed basally in FRTL-5 cells despite its prominent appearance in spleen cells. The low level of TLR3 mRNA which we detected in mRNA from mouse heart is consistent with a previous report studying TLR3 expression in mouse heart, lung, brain and kidney (L. Alexopoulou, et al., *Nature*, 413:732-8, (2001)).

These data demonstrate for the first time that TLR3 mRNA is present basally in mouse thyroid tissue and rat thyroid cells. We could, however, also show TLR3 protein was expressed by Western blotting. Lysates of FRTL-5 cells were immuno-precipitated with a monoclonal TLR3 antibody and resolved by SDS-PAGE. An approximately 120 kDa protein was detected in FRTL-5 cell lysates immuno-precipitated by the TLR3 MAb. As a positive control, we showed that the TLR3 MAb detected a similarly sized TLR3 protein in CHO-K1 cells transiently transfected, with a human TLR3 expression vector or one from mouse. This was not the case when the CHO-K1 cells were transfected with a human TLR4 expression vector, demonstrating specificity of the protein identification and measurement procedure. These data established that TLR3 was expressed basally in thyrocytes; the following experiments established the TLR3 was functional.

TLR3 is Functional in thyrocytes. Poly (I:C), a chemically synthesized dsRNA that is a specific ligand for TLR3 (K. Takeda, et al., *Annu Rev Immunol*, 21:335-76 (2003); K. Takeda, et al., *Cell Microbiol*, 5:143-53 (2003); L. Alexopoulou, et al., *Nature,* 413:732-8 (2001)) was added to the culture medium to stimulate TLR3 signaling. Extracellular dsRNA is known to be specifically recognized by TLR3 as evidenced by the lack of response to extracellular dsRNA in TLR3−/− mouse-derived fibroblasts (L. Alexopoulou, et al., *Nature,* 413:732-8 (2001)) TLR3 activation of the NF-κB/p38MAPK and IRF-3/IFN-β signals bifurcate at TRIF (K. Takeda, et al., *Annu Rev Immunol,* 21:335-76 (2003); K. S. Michelsen, et al., *J Immunol,* 173:5901-7 (2004)) (K. Takeda, et al., *Cell Microbiol,* 5:143-53 (2003); H. Oshiumi, et al., *Nat Immunol,* 4:161-7 (2003); M. Yamamoto, et al., *J Immunol,* 169:6668-72 (2002); M. Miettinen, et al., *Genes Immun,* 2:349-55 (2001); Z. Jiang, et al., *Proc Natl Acad Sci USA,* 101:3533-8 (2004)) We asked if both of these pathways were activated in FRTL-5 thyroid cells.

The presence of the NF-6B pathway was evaluated by incubating extracellular dsRNA, [Poly (I:C)] with pNF-κB-luc-transfected FRTL-5 cells and measuring reporter gene activity and by EMSA in nontransfected cells, using an NF-κB consensus oligonucleotide probe. Poly (I:C) increased NF-κB Luc activity by comparison to non treated cells or cells incubated with *E. coli* dsDNA. Poly (I:C) incubation also increased formation of a p65/p50 NF-κB complex as evidenced by the appearance of a major complex whose formation was inhibited by incubations containing the nuclear extracts from treated cells with anti-p50 or anti-p65, but not by incubations with anti c-rel, anti-p52, or anti-relB, which served as negative antibody controls.

In the case of incubation with anti p50 and anti p65, the data were similar to results in studies of p50/p65 binding to the MHC class I (G. Pasterkamp, et al., *Eur J Clin Invest,* 34:328-34 (2004); C. Giuliani, et al., *J Biol Chem,* 270:11453-62 (1995); S. I. Taniguchi, et al., *Mol Endocrinol,* 12:19-3, (1998)) or VCAM-1 promoter (N. M. Dagia, et al., *J Immunol,* 173:2041-9 (2004)). Cells treated with IL-1β, TNF-α, or the phorbol ester, TPA, served as positive controls for formation of the p65/p50 complex in the FRTL-5 cells.

Poly (I:C) incubation was also able to activate ERK1/2 MAPK within 15 min as detected by measuring phosphorylated ERK1/2 in immunoblots. Lysates from insulin-treated FRTL-5 cells were used as a positive control. Elk1 was also transactivated by Poly (I:C) treatment of reporter gene-coupled ELK-1 in FRTL-5 cell transfectants, as measured by luciferase activity. IL-1β treatment, which can activate ELK-1 (K. Takeda, et al., *Annu Rev Immunol,* 21:335-76 (2003)) served as a positive control.

Most importantly and most relevant to the effect of methimazole, methimazole derivatives, and tautomeric cyclic thiones on TLR3 activity, we could show that the TLR3-IRF-3/IFN-β-coupled signal system was also expressed in FRTL-5 thyroid cells. Poly (I:C) incubations increased both IFN-β promoter activity (FIG. 1A) and IFN-β mRNA levels (FIG. 1B). IFN-β promoter activity was measured by incubating Poly (I:C) with FRTL-5 cells transfected with pIFN-β-luc constructs. Poly (I:C) incubation strongly increased IFN-β promoter activity, whereas *E. coli* dsDNA had no effect (FIG. 1A, left panel). As a control, it was demonstrated that pIFN-β-luc-transfected HEK293 cells, which do not have endogenous TLR3, failed to respond to Poly (I:C) incubation unless they were first transfected with a human TLR3 expression plasmid (FIG. 1A, right panel). Although Northern analysis did not detect significant levels of IFN-β mRNA, RT-PCR analysis using gene specific primers (S. Yokoyama, et al., *Biochem Biophys Res Commun,* 232:698-701 (1997)) demonstrated that IFN-β mRNA was increased in FRTL-5 cells by the addition of Poly (I:C) (FIG. 1B).

Since IRF-3 must be activated as an intermediate to increase IFN-β gene expression in the TRIF pathway coupled to TLR3 (K. Takeda, et al., *Cell Microbiol,* 5:143-53 (2003); H. Oshiumi, et al., *Nat Immunol,* 4:161-7 (2003); M. Yamamoto, et al., *J Immunol,* 169:6668-72 (2002); Z. Jiang, et al., *Proc Natl Acad Sci USA,* 101:3533-8 (2004)), we additionally showed that Poly (I:C) incubation increased IRF-3 transactivation activity in FRTL-5 thyrocytes (FIG. 1C). Incubation with IL-1β again served as a positive control.

To see if the TRIF adaptor protein could couple TLR3 and signal generation in FRTL-5 cells, we asked whether co-transfection of wild-type TIR domain-containing molecule adapter inducing IFN-β/TIR-containing adapter molecule (TRIF/TICAM)-1 would enhance Poly (I:C)-induced IFN-β gene activation. Exogenous expression of TRIF/TICAM-1 in FRTL-5 cells enhanced the Poly (I:C)-induced IFN-β promoter activity in a dose-dependent manner but did not enhance IL-1β-increased IFN-β promoter activity (FIG. 1D). IL-1β (negative control) does not activate IRF-3 and IFN-β by a TRIF coupling mechanism (D. Devendra, et al., *Clin Immunol,* 111:225-33 (2004); L. Wen, et al., *J Immunol,* 172:3173-80 (2004); E. Cario, et al., *Infect Immun,* 68:7010-7 (2000); K. S. Michelsen, et al., *J Immunol,* 173:5901-7 (2004); Z. Jiang, et al., *Proc Natl Acad Sci USA,* 101:3533-8 (2004); M. Muzio, et al., *J Immunol,* 164:5998-6004 (2000)). Overexpression of wild-type or dominant negative (DN) MyD88 (negative controls) did not result in any significant Poly (I:C)-induced IFN-β promoter activation or inhibition (FIG. 1D), nor did they significantly activate or inhibit Poly (I:C)-increased NF-6B luciferase activity (data not shown).

In sum, FRTL-5 cells not only express the TLR3 receptor, they seem to signal through both the NF-6B and IRF-3/IFN-β pathways when incubated with extracellular Poly (I:C), similar to immune cells. Their dual activation results in gene responses characteristic of an innate immune response (K. Takeda, et al., *Annu Rev Immunol,* 21:335-76 (2003); K. Takeda, et al., *Cell Microbiol,* 5:143-53 (2003); B. Beutler, *Nature,* 430:257-63 (2004); K. S. Michelsen, et al., *J Immunol,* 173:5901-7 (2004)).

Overexpression of TLR3 and TLR signaling in thyroid cells by dsRNA transfection or viral infection: Type I IFN is an important intermediate.

dsRNA transfection and IFN-β induce overexpression of TLR and TLR3 signaling: Incubating FRTL-5 thyroid cells with Poly (I:C) did not increase TLR3, PKR or MHC Class I mRNA levels over a 24 hour period, although Poly (I:C) incubation significantly increased IP-10 mRNA and slightly increased ICAM-1 mRNA levels, demonstrating the functional activity of the Poly (I:C) in this experiment (FIG. 2A). IL-1β (the positive control) also caused an increase in IP-10 and ICAM-1 mRNA levels but did not change TLR3, Class I, or PKR mRNA levels (FIG. 2A). This suggested that dsRNA incubation with TLR3 was not an effective means of increasing TLR3 expression in FRTL-5 cells nor induce changes in genes important in the expression of autoimmune-inflammatory diseases.

In sharp contrast to the Poly (I:C) incubation data, transfection of Poly (I:C) into the cytoplasm of FRTL-5 cells strongly increased TLR3 mRNA, as well as MHC Class I, PKR, ICAM-1, and IP-10 mRNA levels, both 12 and 24 hrs after transfection, by comparison to control cells (C) or a mock transfection (L) without dsRNA (FIG. 2B, lanes 3 and 7). Unlike dsRNA, dsDNA transfection was only weakly effective in increasing TLR3 mRNA and at 12 hrs only (FIG. 2B, lanes 4 and 8), but, as previously reported (K. Suzuki, et al., *Proc Natl Acad Sci USA,* 96:2285-90 (1999)), was effective in increasing PKR and MHC Class I, as well as ICAM-1, and IP-10 mRNA levels 12 hrs after transfection, by comparison to control cells (C) or a mock transfection (L) (FIG. 2B, lanes 1, 2, 5, and 6). These results suggest that the transfected dsRNA action to increase TLR 3 is different from the ability of dsRNA to bind to TLR3 during incubations and to induce signaling by a receptor-ligand interaction. They also showed dsRNA transfection appeared to be different from the action of dsDNA transfection. These results further indicated that overexpression of TLR3 in nonimmune cells requires a pathogenic stimulus not simply binding of dsRNA to the TLR3.

As reported (K. Suzuki, et al., *Proc Natl Acad Sci USA*, 96:2285-90 (1999)), dsRNA transfection and dsDNA transfection differ primarily in the induction of IFN-β but not PKR. Nevertheless, to evaluate a possible role of PKR activation in TLR3 overexpression by transfected dsRNA, we treated cells with 2-aminopurine (2-AP) (FIG. 2C), a PKR inhibitor (L. J. Mundschau, et al., *J Biol Chem*, 270:3100-6 (1995)). TLR3 mRNA was still increased by dsRNA transfection by comparison to control cells (C) or a mock transfection (L) in the presence of 2-AP (FIG. 2C, lane 7 vs 3). Like the case for TLR3 expression, 2-AP did not inhibit the dsRNA-transfection-induced increase in IFN-β mRNA levels (FIG. 2C, lane 7 vs 3), however, 2-AP strongly inhibited the ability of dsRNA-transfection to increase NF-κB p65/p50 complex formation in EMSA (FIG. 2C, bottom). Moreover, whereas the dsRNA transfection-induced increase in PKR and MHC Class I was only slightly decreased by 10 mM 2-AP (FIG. 2C, lane 7 vs 3), the dsDNA transfection-induced increase in PKR was eliminated and the increase in MHC I was reduced to near control levels (FIG. 2C, lane 8 vs 4). This suggested a different mechanism of upregulation of PKR and MHC class I by the two transfecting agents, the dsDNA effect possibly linked to NF-6B activation whereas the dsRNA transfection effect potentially more linked to IRF-3/IFN-β signaling. We have reported that dsDNA transfection together with the TSHR in fibroblasts can result in Graves' disease if the fibroblasts are killed with mitomycin and injected intraperitoneally over the course of six weeks ((L. D. Kohn, et al., *Research Ohio*, In press, (2005); K. Suzuki, et al., *Proc Natl Acad Sci USA*, 96:2285-90 (1999); L. D. Kohn, et al., *Int Rev Immunol*, 19:633-64 (2000); N. Shimojo, et al., *Int Rev Immunol*, 19:619-31 (2000); K. Suzuki, et al., *Clin Exp Immunol*, 127:234-42 (2002)). The dsDNA effect may be consistent with the activity of TLR9, which is not present basally, but could be expressed in the lysosomal-endosomal fractions of thyrocytes after transfection and phagocytosis.

The possibility that Type I interferon produced by dsRNA transfection might be an autocrine/paracrine activator of thyrocytes post dsRNA transfection was considered and confirmed. Like mouse macrophages (M. Miettinen, et al., *Genes Immun*, 2:349-55 (2001)), exogenously added Type I IFN, in our case IFN-β, increased TLR3 mRNA levels in FRTL-5 thyrocytes in a time- and dose-dependent manner (Table 1). The increases were not duplicated by a Type II IFN, IFN-γ, even if a high dose (1000 Units/ml) of IFN-γ was used (Table 1). IFN-β also increased MHC I, PKR, and IP-10 mRNA levels, concurrent with the increase in TLR3 mRNA levels.

TABLE 1

IFN-β not IFN-γ (100 U/ml each) can mimic dsRNA transfection effect on RNA levels of genes important in autoimmune-inflammatory diseases.

| mRNA | % of Control at 0 Time (±15%) | | |
|---|---|---|---|
| | 3 hr | 6 hr | 12 hr |
| IFN-β 1 hr | | | |
| TLR3 | 100 550 | 450 | 250 |
| MHC Class I | 100 300 | 400 | 425 |
| PKR | 100 500 | 450 | 450 |
| IP-10 | 100 580 | 300 | 200 |
| GAPDH | 100 100 | 100 | 100 |
| IFN-γ 1 hr | | | |
| TLR3 | 100 100 | 100 | 100 |
| MHC Class I | 100 100 | 100 | 100 |
| PKR | 100 100 | 100 | 100 |
| IP-10 | 100 100 | 100 | 100 |
| GAPDH | 100 100 | 100 | 100 |

Data are representative of multiple experiments.

In Table 1, the effect of IFN-β or IFN-γ on mRNA levels of TLR3 and several other genes was measured as a function of time. FRTL-5 cells were incubated with 100 U/ml of IFN-β or IFN-γ for between 1 and 12 hours. IFN-β duplicated the effect of dsRNA transfection by increasing TLR3, PKR, MHC Class I, and IP-10 RNA levels whereas IFN-γ had no effect. Similarly when cells were stimulated with between 10 and 1000 units of IFN-β or IFN-γ for 3 hours, total RNA purified, and 20 μg of total RNA analyzed by Northern analysis using the radiolabeled cDNA probes of FIG. 2, only IFN-β increased TLR3, PKR, MHC Class I, and IP-10 RNA levels.

In sum, these experiments support the data that the mechanism of action of transfected dsRNA is distinct from that of transfected dsDNA (K. Suzuki, et al., *Proc Natl Acad Sci USA*, 96:2285-90, (1999)). The data support the possibility that IFN-β may be a mediator or autocrine/paracrine intermediate in the ability of dsRNA transfection to increase TLR3. It additionally, appears that the action of dsDNA, but not dsRNA transfection, is entirely PKR dependent and coupled solely to the NF-6B signal pathway. In contrast, the dsRNA transfection-induced increases in IFN-β, PKR, and MHC I mRNA probably result from activation of a signal by the IRF-3-related signal path linked to a viral activated kinase, VAK, now known to involve 16B-related kinases (IKK)-IKKepsilon/TANK binding kinase 1 (TBK1) (S. Sharma, et al., *Science*, 300:1148-51 (2003); K. A. Fitzgerald, et al., *Nat Immunol*, 4:491-6 (2003); Z. Jiang, et al., *Proc Natl Acad Sci USA*, 101:3533-8 (2004); M. J. Servant, et al., *J Biol Chem*, 276:355-63 (2001); M. J. Servant, et al., *J Interferon Cytokine Res*, 22:49-58 (2002); M. J. Servant, et al., *J Biol Chem*, 278:9441-7 (2003); J. Hiscott, et al., *Ann NY Acad Sci*, 1010: 237-48 (2003); H. Hemmi, et al., *J Exp Med*, 199:1641-50 (2004)).

Influenza A virus mimics the action of dsRNA transfection and IFN-β to induce overexpression of TLR and TLR3 signaling: The ability of dsRNA transfection, but not dsRNA incubation, to increase TLR3 levels is presumed to mimic the action of a virus to inject RNA into the cell as previously suggested (M. Yamamoto, et al., *J Immunol*, 169:6668-72 (2002); M. Miettinen, et al., *Genes Immun*, 2:349-55 (2001); L. Alexopoulou, et al., *Nature*, 413:732-8 (2001); S. Sharma, et al., *Science*, 300:1148-51 (2003); K. A. Fitzgerald, et al., *Nat Immunol*, 4:491-6 (2003); Z. Jiang, et al., *Proc Natl Acad Sci USA*, 101:3533-8 (2004); J. Guardiola, et al., *Crit. Rev Immunol*, 13:247-68 (1993); R. Gianani, et al., *Proc Natl*

Acad Sci USA, 93:2257-9 (1996); M. S. Horwitz, et al., *Nat Med,* 4:781-5 (1998); H. Wekerle, *Nat Med,* 4:770-1 (1998); C. Benoist, et al., *Nature,* 394:227-8 (1998); Y. Tomer, et al., *Endocr Rev,* 14:107-20 (1993); K. Suzuki, et al., *Proc Natl Acad Sci USA,* 96:2285-90 (1999); J. Hiscott, et al., *Ann NY Acad Sci,* 1010:237-48 (2003); H. Hemmi, et al., *J Exp Med,* 199:1641-50 (2004)). To test this possibility we infected FRTL-5 cells with influenza A virus, a single strand RNA virus.

Figure 3A:
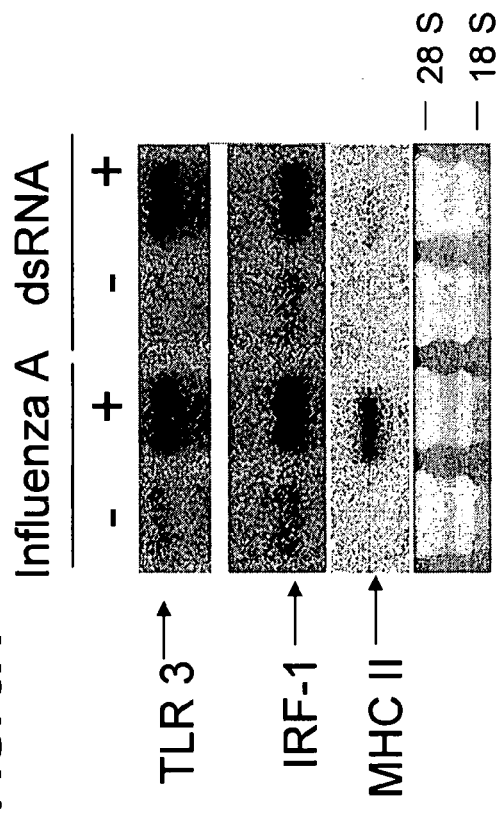

Treatment of FRTL-5 cells with influenza A for 24 hours mimicked the ability of dsRNA transfection to overexpress TLR3 mRNA as measured by Northern analysis (FIG. 3A) and increase IFN-β mRNA as measured by PCR (FIG. 3B). Of note, both dsRNA transfection and influenza A infection also caused increases in IRF-1 and MHC class II mRNA levels (FIG. 3A); the less impressive MHC II complex induced by dsRNA transfection is consistent with our previous results indicating a greater response of MHC I than II(K: Suzuki, et al., *Proc Natl Acad Sci USA,* 96:2285-90 (1999)). The data were obtained at an MOI of 1 and were not duplicated by Coxsackie or Herpes simplex infection at the same or 10-fold higher MOIs (data not shown). Viral specificity remains to be further investigated as will be discussed below.

The increase in MHC class II compliments the increase in class I by dsRNA transfection already demonstrated (FIG. 2; K. Suzuki, et al., *Proc Natl Acad Sci USA,* 96:2285-90 (1999)). The increase in IRF-1 is interesting since IRF-1 gene overexpression is required for optimal TNF-α-increased VCAM-1 gene expression and leukocyte adhesion as well as NF-βB (N. M. Dagia, et al., *J Immunol,* 173:2041-9 (2004)) The present data would suggest that IRF-1 gene overexpression results from the same pathogenic stimuli that cause TLR3 overexpression. In the following experiments, we demonstrate that phenylmethimazole (C10) and MMI, i.e. methimazole, methimazole derivatives, or tautomeric cyclic thiones, inhibit Stat1 phosphorylation which regulates IRF-1 gene expression (R. Pine, et al., *Embo J,* 13:158-67 (1994)) and that this effect reflects an action to inhibit the TRIF-couples IRF-3/IFN-β not the TRIF-coupled NF-6B signal pathway.

Phenylmethimazole (C-10), a tautomeric cyclic thione and methimazole derivative, inhibits TLR3 signaling through the IRF-3/ISRE/STAT pathway in thyrocytes.

C10 and MMI inhibit TLR3 expression and signaling. Methimazole (MMI) is used to treat autoimmune Graves' disease and is effective, in part, because it inhibits thyroid hormone formation (D. S. Cooper, *N. Engl. J. Med.,* 311: 1353-62 (1984)). However, MMI contributes to long-term remission of autoimmune/inflammatory diseases by functioning as a broadly active immunomodulator. Thus, MMI has been used as an immunosuppressive in treating psoriasis in humans (A. N. Elias, et al., *Int. J Dermatol.,* 34:280-3 (1995)) and in treating murine models of systemic lupus, autoimmune blepharitis, autoimmune uveitis, thyroiditis, and diabetes (L. D. Kohn, et al., U.S. Pat. No. 6,365,616, April: (2002); C. C. Chan, et al., *J Immunol,* 154:4830-5 (1995); T. F. Davies, et al., *J Clin Invest,* 73:397-404 (1984); P. Wang, et al., *J Leukoc Biol,* 73:57-64 (2003)). It is a transcriptional inhibitor of abnormally increased MHC Class I and II gene expression in FRTL-5 cells and has been suggested to mimic the effect of a Class I knockout in preventing autoimmune disease (M. Saji, et al., *J Clin Endocrinol Metab,* 75:871-8 (1992); V. Montani, et al., *Endocrinology,* 139:290-302 (1998); L. D. Kohn et al., U.S. Pat. No. 6,365,616 (2002); E. Mozes, et al., *Science,* 261:91-3 (1993); D. S. Singer, et al., *J Immunol,* 153:873-80 (1994)). Phenylmethimazole (C10) is a derivative that is 50-100-fold more potent in suppressing MHC gene expression (L. D. Kohn et al., U.S. Pat. No. 6,365, 616 (2002)).

Figure 4A:
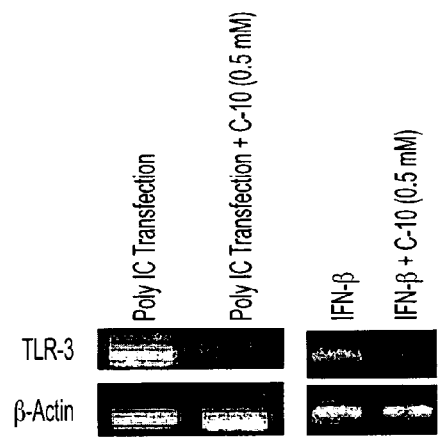
FIG. 4. Phenylmethimazole (C10) and Methimazole (MMI) inhibit the ability of IFN-β to increase TLR3, PKR, and MHC class I RNA levels in FRTL-5 thyrocytes. Cells were incubated with or without 100 U/ml of IFN-β for 3 hours in the presence of dimethyl sulfoxide (DMSO), C10, or MMI. DMSO is the vehicle control. Northern blots were performed with 20 ug of total RNA to detect TLR 3, PKR, MHC I, and GAPDH using radiolabeled cDNA probes. Data are representative of multiple experiments. As was the case for Poly (I:C) transfection in FIG. 2B, IFN-β increased TLR3. The increase in TLR3 induced by both poly(I:C) transfection (data not shown) and IFN-β was totally prevented by the action of C10 whether measured by PCR (A) or Northern analysis (B). The IFN-β increased MHC class I levels and PKR mRNA levels in (B) were also significantly decreased by C10 and C10 was more effective than methimazole (MMI).

We evaluated the ability of C10 and MMI to inhibit TLR3 expression and signaling. C10 prevented the ability of dsRNA transfection and incubation with IFN-β to increase TLR3 RNA levels in FRTL-5 cells, as measured by PCR (FIG. 4A). Additionally it prevented the ability of both IFN-β (FIG. 4B) and dsRNA transfection (data not shown) to increase TLR3 by Northern analysis and was significantly better than MMI in this respect, even at 10-fold lower concentrations (0.5 vs 5 mM). DMSO is the vehicle for C10 because of the hydrophobicity of C10; it had no significant effect on basal activity and was used as the control value in all experiments described herein.

Figure 4B:
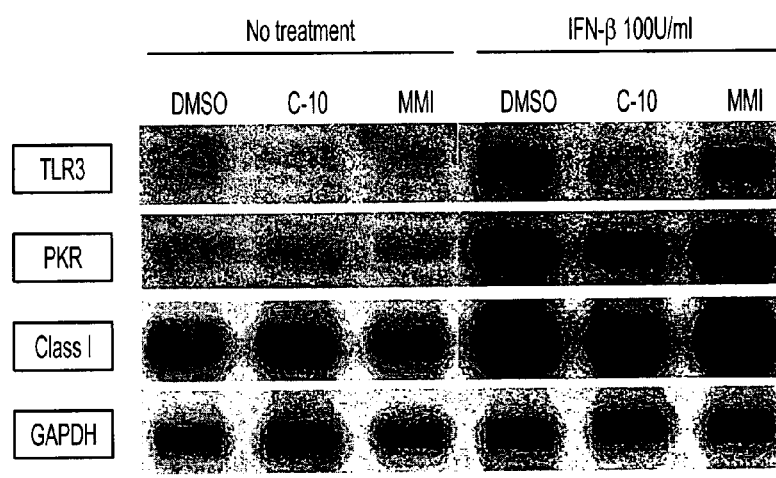

The C-10 and MMI reduced the ability of IFN-β to increase PKR and MHC class I RNA levels, albeit relatively less than TLR3 (FIG. 4B). C10 slightly reduced the basal level of TLR 3 mRNA, without affecting control PKR or class I RNA levels (FIG. 4B, lane 2 vs 1). The Northern data thus suggested C10, to a far greater extent than MMI, could block pathogenic expression of the TLR3 induced innate immune response in FRTL-5 thyrocytes. We questioned the C10 mechanism of action.

C10, at 0.5 mM, inhibited the ability of poly (I:C) to increase IFN-β promoter activity (luciferase luminescence; P<0.01) when incubated with FRTL-5 thyrocytes transfected with pIFN-β-luc constructs (FIG. 5 Top Left, Poly (I:C) vs untreated (−)). Even at the concentrations used, which are maximal for MMI (data not shown), the C-10 was significantly better than MMI (P<0.05 or better) (FIG. 5 Top Left, Poly (I:C) treated, MMI vs C10 and vs untreated (−)). Lipopolysaccharide (LPS) incubation, as well as treatment with IL-1β, also increased IFN-β luciferase activity in FRTL-5 cells (FIG. 5 Top Left) and in both cases 0.5 mM C-10 and 5 mM MMI significantly (P<0.05 or better) inhibited the increase [FIG. 5 Top Left, LPS or IL-1β plus C-10 or MMI vs untreated (−)]. Again, C-10 was significantly better than MMI (P<0.05 or better) (FIG. 5 Top Left), bringing values to basal levels.

Figure 5:
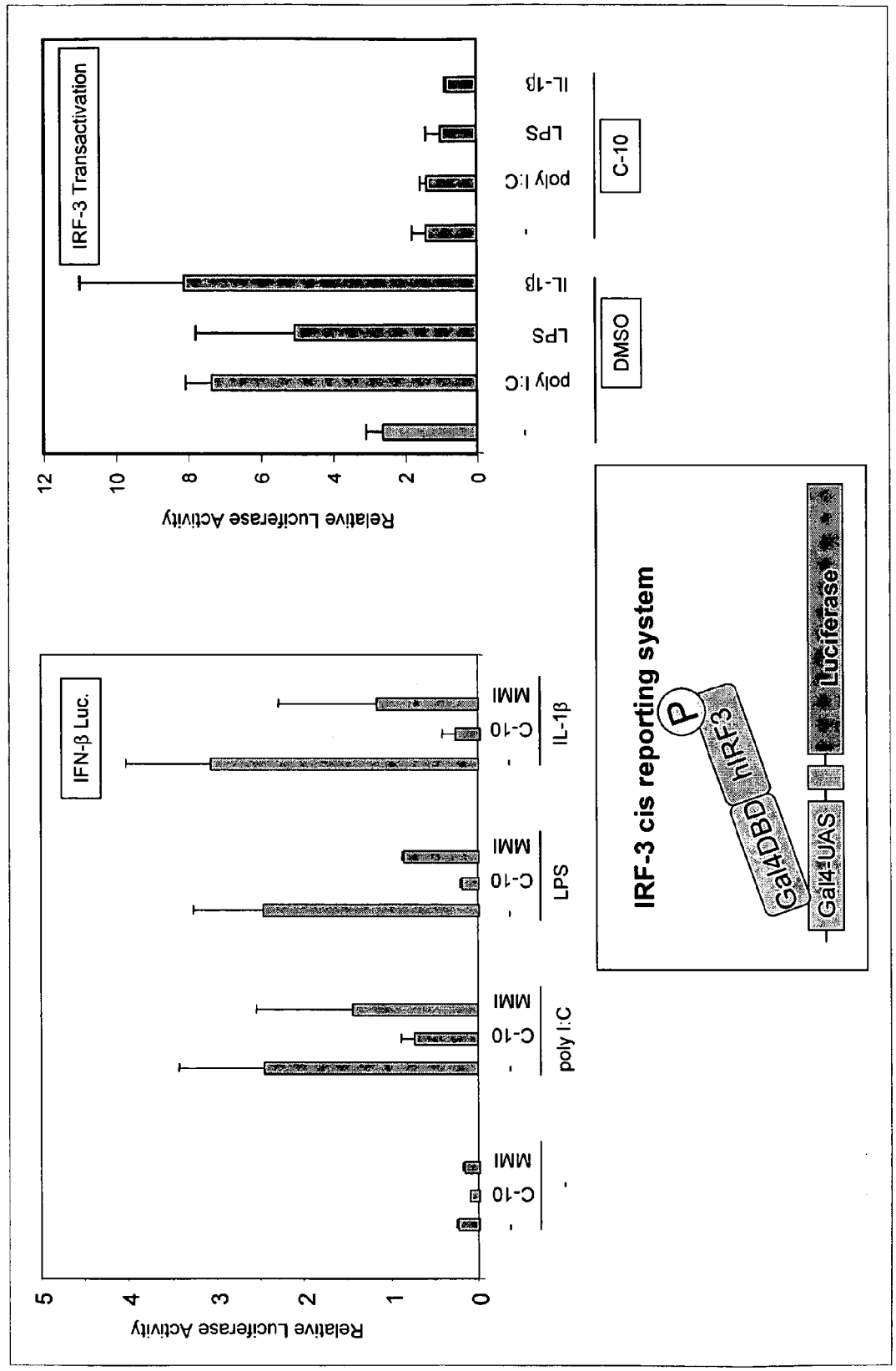
FIG. 5. Phenylmethimazole (CIO) and Methimazole (MMI) inhibit the ability of Poly (I:C), lipopolysaccharide (LPS) and IL-1β to increase IFN-β gene expression (Top Left) and IRF-3 transactivation (Top Right) in FRTL-5 thyrocytes. (Top Left) Cells were co-transfected with IFNβ-Luc and control vector (pRLTk-Int), then treated with or without (−) Poly (I:C) (100 μg/ml), LPS (100 ng/ml), or IL-1β (10 ng/ml) in the presence of the vehicle (DMSO) alone (−), C10, or MMI for 6 hours. Data was obtained with the Dual Luciferase Assay system. (Top Right) Cells were co-transfected with Gal4 DBD/IRF-3 and Gal4-Luc then treated with nothing (−), poly (I:C), LPS, or IL-1β as in (Top Left) in the presence of DMSO or C10 for 6 hours. Data was obtained by Luciferase assay. Also shown is a graphic depiction (Bottom) of how the cis reporting system is working. Data are representative of multiple experiments. C10 significantly attenuates the effects of Poly (I:C) (100 μg/ml), LPS (100 ng/ml), or IL-1β (10 ng/ml) on IRF-3 transactivation and IFN-β gene expression; its effect is much better than MMI.

These data confirm that FRTL-5 thyrocytes have functional IL-1 receptors (see also FIG. 1C). IL-1 receptors are reported to activate IRF-3 and IFN-β by a non TRIF coupling mechanism (D. Devendra, et al., *Clin Immunol,* 111:225-33 (2004); L. Wen, et al., *J Immunol,* 172:3173-80 (2004); E. Carlo, et al., *Infect Immun,* 68:7010-7 (2000); B. Beutler, *Nature,* 430: 257-63 (2004); K. S. Michelsen, et al., *J Immunol,* 173:5901-7 (2004); M. Muzio, et al., *J Immunol,* 164:5998-6004 (2000); S. E. Doyle, et al., *J Immunol,* 170:3565-71 (2003)). The predominant target of LPS is TLR4; we could demonstrate TLR4 mRNA on FRTL-5 cells, but no ability of LPS or poly (I:C) to increase TLR4 mRNA (data not shown). These data would suggest that C10, and to a significantly lesser degree MMI, can inhibit the increase IFN-β luciferase activity independent of the specific receptor activated (TLR3, TLR4, or IL-1) or the coupling protein utilized (TRIF or non TRIF) (FIG. 5, Top Left). These data suggested that a common denominator by which C10 might act was downstream, i.e. it might inhibit IRF-3 transactivation.

We measured the ability of C10 to inhibit IRF-3 transactivation activity in FRTL-5 thyrocytes, using the IRF-3 cis reporter system (FIG. 5, bottom). We, could show that incubation with 0.5 mM C-10 significantly (P<0.05 or better) inhibited IRF-3 transactivation by poly (I:C), LPS, or IL-1β (FIG. 5, Top Right). MMI was significantly less effective (data not sown).

Figure 6A:
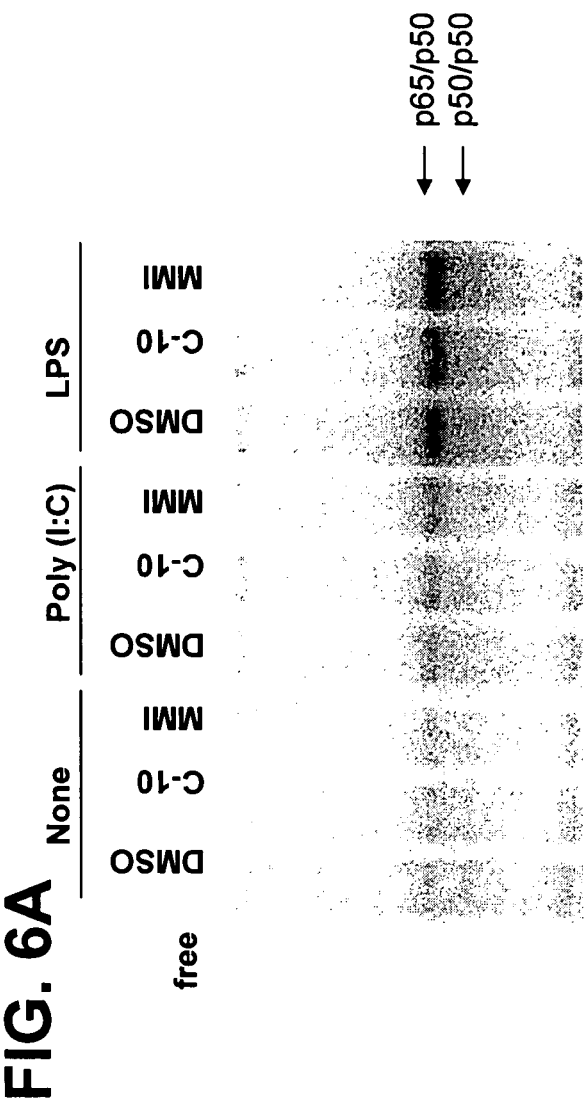
FIG. 6. Phenylmethimazole (C10) has no effect on the ability of Poly (I:C) or LPS to increase formation of the p50/p65 heterodimer complex of NF-6B (A), but can inhibit the Influenza A induced activation of Stat1 phosphorylation in FRTL-5 thyrocytes (B). In (A), EMSA were performed using nuclear extracts from cells which were treated with nothing (none), Poly (I:C) (100 μg/ml), LPS (100 ng/ml), in the presence of DMSO, C10, or MMI for 6 hours. Probe was the NF-κβ consensus oligonucleotide. The p65/p50 and p50/p50 complexes are indicated and were identified as in FIG. 2B by antibody inhibition or supershifts of the p50 or p65 components of the induced complexes. In (B), cells were infected with Influenza A for 24 hours and then DMSO or C10 were added to the medium for 6 hours. In each, 25 μg of nuclear extracts were used in Western blots performed to detect Stat1 PY701. Blots were then stripped and reprobed for unphosphorylated Stat1. The first lane is a non infected control (−). Duplicate effects were seen with serine phosphorylation of Stat1 and with phosphorylated Stat3 (see below).

A key to activation of other IFN-inducible genes by the autocrine/paracrine action of IFN-β is its action to regulate downstream genes with ISREs, in part by phosphorylation of STATS, which are important activators of interferon-stimulated response elements (ISRE) and interferon-γ-activated sites (GAS). Using an ISRE sequence coupled to luciferase as a reporter gene (ISRE-Luc) we could show that C-10 was an effective inhibitor of ISRE activation by poly (I:C), LPS, IL-1β, TNF-α, IFN-β and IFN-γ (Table 2). Despite the similarity in sequence between ISRE and NF-6B binding sites and despite the ability of Poly (I:C) to activate NF-6B-luc in FRTL-5 cells, both 0.5 mM C10 or 5 mM MMI had a minimal effect on Poly (I:C)-increased NF-6B-luciferase activity (Table 2). Additionally, they did not have any significant effect on Poly (I:C)— or LPS-increased p65/p50 complex formation (FIG. 6A).

TABLE 2

Phenylmethimazole (C10) inhibits the ability of Poly (I:C), LPS, IL-1 β, TNF-α, IFN-β, and IFN-γ to activate an ISRE [ISRE(TAGTTTCACTTTCCC)$_5$-Luc (SEQ ID NO: 1)] but not an NF-κB [NF-κB (TGGGGACTTTCCGC)$_5$-Luc (SEQ ID NO: 2)] reporter gene in FRTL-5 thyrocytes. Relative Luciferase Activity % of Control (±15%)

| Ligand | ISRE-Luc | | NF-κB Luc | |
|---|---|---|---|---|
| | +DMSO | +C10 | +DMSO | +C10 |
| Poly (I:C) | 300 | *80* | 300 | 300 |
| LPS | 250 | *100* | 250 | 250 |
| IL-1β | 350 | *110* | 350 | 350 |
| TNF-α | 225 | *115* | 225 | 225 |
| IFN-β, | 150 | *50* | 150 | 150 |
| IFN-γ | 180 | *60* | 180 | 180 |
| None | 100 | 100 | 100 | 100 |

*Values in bold and italics decreased significantly (P < 0.05 or better)

As shown in Table 2, phenylmethimazole (C10) inhibits the ability of Poly (I:C), LPS, IL-1β, TNF-α, IFN-β, and IFN-γ to activate an ISRE reporter gene in FRTL-5 thyrocytes. Cells were co-transfected with ISRE-Luc and pRLTk-Int and then treated without (none) or with Poly I:C (100 µg/ml), LPS (100 ng/ml), IL-1β (10 ng/ml) TNF-α (25 ng/ml), IFN-β (100 U/ml) or IFN-γ (1000 U/ml) in the presence of DMSO (−) or C10 for 6 hours. Data were obtained using the Dual Luciferase Assay system. The effect on the ISRE element is not duplicated by an NF-κB reporter plasmid despite the similarity of the two elements: (TAGTTTCACTTTCCC)$_5$ (SEQ ID NO:3) vs. (TGGGGACTTTCCGC)$_5$ (SEQ ID NO:4), respectively. Data are representative of multiple experiments. C10 significantly inhibits the action of Poly I:C, LPS, TNF-α, IFN-β or IFN-γ to increase expression of genes containing ISREs not NF-κB elements.

Figure 6B:
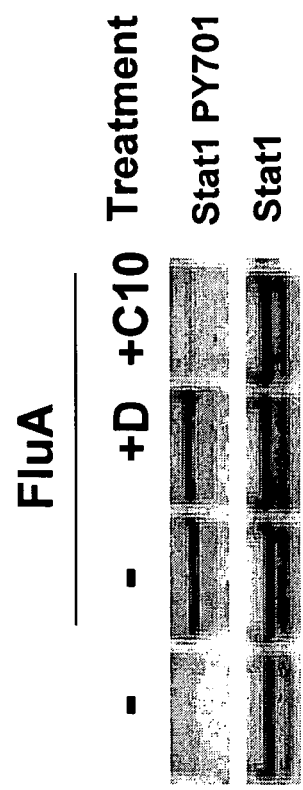

Additionally, C10 was a profound inhibitor of virus (FIG. 6B) or IFN-β-stimulated (data not shown) Stat1 phosphorylation without a change in Stat1 total protein (FIG. 6B). D in this experiment was the vehicle (DMSO) control.

TLR3 Expression in Hashimoto's Disease: A prototype of Type 1 Diabetes

TLR3 expression and regulation in humans can be very different from that in rats or mice. To address this, we first asked if TLR3 RNA was expressed in human thyroid tissue using commercial tissue blots from Clontech. We detected TLR3 RNA expression in thyroid tissue by comparison with the spleen positive control; results were thus similar to our observations in mouse tissues.

In order to confirm the presence and functionality of TLR3 in human thyrocytes, we evaluated TLR3 expression in cultured NPA human thyrocytes. NPA thyrocytes are from a papillary carcinoma but are known to retain functional properties of normal thyrocytes. Transfection with dsRNA [Poly (I:C)], but not transfection by dsDNA or incubation with Poly (I:C), was able to increase TLR3 mRNA levels in Northern blots. The dsRNA, but not the dsDNA transfection, could also increase IFN-β mRNA levels, measured as before with PCR. Additionally, as was the case for FRTL-5 cells and dsRNA transfection, IFN-β increased PKR mRNA levels as well as TLR3 RNA levels. Finally, as was again the case for FRTL-5 cells, we could show that 0.5 mM C10 decreased the ability of dsRNA transfection or IFN-β to increase TLR3 mRNA levels.

A fundamental question posed by the sum of data thus far, was whether TLR3 was overexpressed in autoimmune/inflammatory disease in vivo not only human thyrocytes in culture. We evaluated TLR3 protein levels in human thyroid tissues by immunohistochemistry. Immunohistochemistry of thyroid tissues was performed using TLR3 antibody (1:100). In normal thyroid and in tissues from Graves' disease, no immunoreactive TLR3 was detected. In chronic lymphocytic thyroiditis (Hashimoto's), TLR3 was detected in epithelial cells (as indicated by brown deposit in cytoplasm) in 100% of patients tested (Table 3). The intensity of staining was highest in metaplastic oxyphilic epithelium in the regions of lympho-plasmacytic infiltration.

TABLE 3

TLR3 protein is present in thyrocytes of 100% of patients examined with Hashimoto's thyroiditis but not in thyrocytes from normal thyroids or thyroids from patients with Graves' disease: there is coincident expression of Type 1 IFN not PKR signaling.

| Tissue Source | TLR3 Present/ Number patients Tested | IFN-β Present/Number patients Tested | PKR/Number patients Tested |
|---|---|---|---|
| Hashimoto's | 21 of 21 | 20 of 21 | 10 of 21 |
| Graves' | 0 of 20 | 16 of 20 | 8 of 20 |
| Normal | 0 of 20 | 0 of 20 | 0 of 20 |

Bold Values represent statistically significant correlation P < 0.01.

TLR3 and IFN-β are jointly upregulated in 95% of thyroids from patients with Hashimoto's thyroiditis (Table 3), whereas PKR is upregulated in less than 50% of Hashimoto's thyroiditis patients (Table 3). Positive thyrocytes in these experiments appear brown and the absence of brown staining in lymphocytes in the IFN-β analyses was striking relative to the thyrocytes. The increase in TLR-3 signaled IRF-3/IFN-β in the Hashimoto's thyrocytes correlated with TLR3 overexpression in a statistically significant manner by comparison to the TLR3 and PKR association in Hashimoto's and when compared with the presence of IRF-3/IFN-β signaling in Graves' vs TLR3 expression, which was zero.

The presence of increased IRF-3/IFN-β signaling in Graves' is consistent with the ability of dsDNA transfection and overexpressed TSHR to induce Graves' (L. D Kohn et al., US. Application Publication US2005/0036993 A1 Feb. 17, 2005). It is equally consistent with the expression of TLR9 activity in the case of Graves' since TLR9 recognizes dsDNA and also signals through IRF-3/IFN-β.

The sum of these data are consistent with, but not limited to, the interpretation that TLR3 can be overexpressed in non-immune cells and can produce an innate immune gene response that leads to an adaptive immune cell (TH1) response. A critical signal system involved is Type I IFN. Methimazole, methimazole derivatives, and tautomeric cyclic thiones, exemplified by C10, can prevent this by inhibiting predominantly the IRF-3/Type I IFN signal system activated when dsRNA or viruses overexpress TLR3 signals.

Materials and Methods

Materials. Poly (I:C) [a synthetic dsRNA], endotoxin free E. coli DNA, the mouse TRIF/TICAM-1, the mouse and human TLR3 expression vectors were purchased from (Invivogen, San Diego, Calif.). TNF-α, IFN-β, IFN-γ, and IL-162 were from (Biosource International, Camarillo, Calif.). Insulin and 2-Aminopurine were from Sigma (St. Louis, Mo.). The antibodies used in this study were anti-TLR3 (IM-GENEX, San Diego, Calif.), anti-IFN-β (Chemicon International, Temecula, Calif.), anti-Stat1PY701 (Cell Signaling Technologies, Beverley, Mass.), anti-Stat1p84/p91 E-23 (Santa Cruz Biotechnology Inc., Santa Cruz, Calif.), anti-PKR (Cell Signaling Technology, Beverly, Mass.), and anti-phosphospecific ERK 1/2 (Biosource International, Camarillo, Calif.). Vectastain Universal Quick kit (Vector Laboratories, Burlingame, Calif.) antigen unmasking solution and DAB substrate kit were used. C-10 was synthesized as described by Ricerca (Cleveland, Ohio) (L. D. Kohn et al., U.S. Pat. No. 6,365,616 (2002)). C-10 was prepared as 200 mM stock solution in DMSO. MMI was from Sigma. The source of all other materials was the same as previously reported (K. Suzuki, et al., *Proc Natl Acad Sci USA*, 96:2285-90 (1999)).

Cells. The F1 subclone of FRTL-5 thyrocytes (Interthyr Research Foundation, Baltimore, Md. [ATCC CRL 8305]) was grown in Coon's modified Ham's F-12 medium supplemented with 5% calf serum, 2 mM glutamine and 1 mM nonessential amino acids, plus a six-hormone mixture (6H medium), containing bovine TSH ($1 \times 10^{-10}$ M), insulin (10 μg/ml), cortisol (0.4 ng/ml), transferrin (5 μg/ml), glycyl-L-histidyl-L-lysine acetate (10 ng/ml), and somatostatin (10 ng/ml). HEK293H cells (Invitrogen, Carlsbad, Calif.) were maintained in DMEM with 10% fetal calf serum. CHO-K1 cells (ATCC CCL-61) were maintained in Ham's F-12 medium with 10% fetal calf serum.

NPA-87 cells are a continuous line of human thyrocytes derived from papillary carcinoma cells. They retain several functional responses including TSH-increased cAMP signaling (J. Xu, et al., *J Clin Endocrinol Metab*, 88:4990-6 (2003)). They were kindly provided by Dr. Guy Julliard (University of California, Los Angeles, Calif.) and grown in RPMI 1640 medium supplemented with 2 g/liter sodium bicarbonate, 0.14 mM nonessential amino acids, 1.4 mM sodium pyruvate, and 10% fetal bovine serum, pH 7.2.

RNA Isolation and Northern Analysis. RNA was prepared using the RNeasy Mini Kit (Qiagen Inc., Valencia, Calif.) and the method described by the manufacturer. For Northern, 15 to 20 μg total RNA were run on denatured agarose gels, capillary blotted on Nytran membranes (Schleicher & Schuell, Keene, N.H.), UV cross-linked, and subjected to hybridization. Probes were labeled with [α-$^{32}$P] dCTP using a Ladderman Labeling Kit (Takara, Madison, Wis.). The probes for MHC Class I, ICAM-1, IRF-1, PKR and GAPDH have been described (K. Suzuki, et al., *Proc Natl Acad Sci USA*, 96:2285-90 (1999)). The probes for IFN-β were obtained using gene specific primers that have also been described (S. Yokoyama, et al., *Biochem Biophys Res Commun*, 232:698-701 (1997)). The probes for TLR3 were mouse or human whole cDNAs obtained from the Invivogen expression vectors. The IP-1 0 probe was a partial mouse IP-10 cDNA (469 bp) prepared by RT-PCR from mouse macrophage total RNA with the following primers: mIP-10 (5'): 5'-CCATCAGCACCATGAACCCAAGTCCTGCCG-3' (SEQ ID NO:5) and mIP-10 (3'): 5'-GGACGTCCTCCT-CATCGTCGACTACACTGG-3'. (SEQ ID NO:6) Membranes were hybridized and washed as described previously (K. Suzuki, et al., *Proc Natl Acad Sci USA*, 96:2285-90 (1999)).

RT-PCR. DNA was removed from total RNA using the DNA-free Kit (Ambion) according to the manufacturer's instructions. One μg of RNA was used to synthesize cDNA using the Advantage RT-for-PCR Kit (BD Biosciences) according to the manufacturer's protocol. Fifty ng of cDNA was subsequently used for PCR of TLR-3, and β-Actin; 250 ng of cDNA was used for PCR of IFN-β. The primers used for amplification of human TLR-3 and β-Actin have been previously described (K. U. Saikh, et al., Clin Diagn Lab Immunol, 10:1065-73 (2003)). The gene-specific primers for rat IFN-β and GAPDH and PCR conditions have been described (S. Yokoyama, et al., *Biochem Biophys Res Commun*, 232:698-701 (1997); K. Suzuki, et al., *Proc Natl Acad Sci USA*, 96:2285-90 (1999)) Human IFN-β primers are as follows: (5' primer) 5'-TGGCAATTGAATGGGAGGCTTG-3' (SEQ ID NO:7) and (3' primer) 5'-TCCTTGGCCTTCAGGTAATG-CAGA-3'. (SEQ ID NO:8) PCR reaction conditions for human TLR-3 and β-Actin are as follows: 94° C. for 5 min. followed by 35 cycles of 94° C. for 30 sec., 55° C. for 30 sec., 72° C. for 1 min., and a final cycle of 72° C. for 7 min. Human IFN-β PCR reaction conditions are: 94° C. for 3 min., followed by 35 cycles of 94° C. for 10 sec., 58° C. for 30 sec., 72° C. for 1 min., and a final cycle of 72° C. for 10 min.

Plasmids for Reporter Gene Assays. Human IRF-3 was amplified from human cDNA and cloned into pCR 2.1 by the TOPO/TA (Invitrogen, Carlsbad, Calif.) cloning method, and then sequenced. IRF-3 was then excised by EcoRI digestion and subcloned into pCMV-BD (Stratagene, La Jolla, Calif.) for use in transactivation assays. To construct IFN-β-luc the human IFN-β promoter sequence was amplified from human genomic DNA (Clontech, Palo Alto, Calif.)) using Ex Taq™ Polymerase (Takara, Madison, Wis.). The PCR fragment contained human IFN-β promoter sequence from −125 to +34 relative to the transcription start site (+1) and incorporated KpnI and XhoI restriction sites at the 5' and 3' ends, respectively. The primers were as follows: hIFN-β (−125) KpnI (5'-CAGGGTACCGAGTTTTAGAAACTACTAAAATG-3') (SEQ ID NO:9) and hIFN-β (+34) XhoI (5'-GTACTCGAG-CAAAGGCTTCGAAAGG-3'). (SEQ ID NO: 10) The fragment was digested with KpnI and XhoI then ligated into a similarly digested pGL3 Basic (Promega, Madison, Wis.) vector. The human MyD88 wild and dominant negative expression vectors were kindly donated by Dr. P. E. Auron. pFR-luc (5×Gal4 DNA binding domains and minimal TATA box), ISRE-Luc, NF-κB-luc and the Elk1 trans-Reporting System were purchased from Stratagene. pRL TK-Int was purchased from Promega.

Transient Expression Analysis. A DEAE procedure was used to transfect promoter-luciferase gene constructs and expression plasmids into FRTL-5 cells. Briefly, FRTL-5 cells were grown in 24-well plates to about 70% confluence, washed with 0.5 ml of serum-free culture medium (6H0 medium), then exposed to 125 μl of premade plasmid-DEAE mixture per well for 15 min at room temperature. The plasmid-DEAE mixture was prepared by incubating 100 ng of plasmid DNA, unless otherwise noted in individual experiments, with 3.125 µl of DEAE-Dextran (10 mg/ml) (Promega, Madison Wis.). FRTL-5 cells were incubated with this mixture for 2 hr at 37° C. in a $CO_2$ incubator, before 2 ml of 6H5 medium was added. CHO-K1 and FRTL-5 cells for transfecting expression vectors were subjected to the lipofection method. Cells were grown in 10 cm dishes to about 80% confluence and then exposed to the plasmid-Lipofectamine-2000 mixture as described by the manufacturer (Invitrogen, Calif.).

Immunoprecipitation and Western Blot Analysis. Whole cell lysates were prepared in lysis buffer (10 mM Tris-HCl (pH 7.5), 150 mM NaCl, 1% NP-40) containing protease inhibitors. Nuclear extracts were prepared using the NE-PER extraction reagents with protease inhibitors stated below (Pierce Chemical Co., Rockford, Ill.). Twenty-five (25) µg of either whole cell lysate or nuclear extract was resolved on denaturing gels using the Nu-PAGE System (Invitrogen, Carlsbad, Calif.). All proteins were transferred to nitrocellulose membranes and subsequent antibody binding was revealed using ECL Plus reagents (Amersham Pharmacia Biotech, Piscataway, N.J.). For immunoprecipitation, lysates were incubated with anti-TLR3 antibody (Imgenex, San Diego, Calif.) (10 µg/ml) at 4° C. for 6 hours, followed by adsorption to protein G-Sepharose beads (Amersham Pharmacia Biotech). Precipitates were washed and resolved as stated above. CHO-K1 cells were transiently transfected with 20 µg of expression vector.

Nuclear Extracts and DNA Mobility Shift Assays (EMSA). FRTL-5 cells were harvested by scraping into PBS (pH 7.4) and washing twice with PBS. Nuclear extracts were then prepared using NE-PER extraction reagents (Pierce Chemical Co., Rockford, Ill.). The protocol was as per manufacturer instructions and involved the presence of protease inhibitor cocktail III (AEBSF hydrochloride, aprotinin, bestatin, E-64 protease inhibitor, leupeptin, pepstatin) (Calbiochem). Oligonucleotides (NF-κB sense 5'-AGT TGA GGG GAC TTT CCC AGG C-3' (SEQ ID NO:11); NF-κK anti sense 5'-GCC TGG GAA AGT CCC CTC AAC T-3' (SEQ ID NO: 12)) were annealed and labeled with [$\gamma^{32}P$]-ATP using T4 polynucleotide kinase. EMSA was performed using 3 µg of nuclear extracts. In competition studies 50-fold molar excess of unlabeled oligonucleotide or 2 µg of antibody was added to the mixtures. A $^{32}$P-labeled oligonucleotide probe (100,000 cpm) was added and the incubation was continued for 20 min at room temperature. Mixtures were analyzed on 5% native polyacrylamide gels and autoradiographed.

Virus Infections. Influenza A A/Victoria/3/75 was obtained from Diagnostic Hybrids Inc. (Athens, Ohio). FRTL-5 cells were grown in 6H growth media until 60% confluence and then maintained in 5H (-TSH) media for 7 days before infections. Ten (10) cm dishes were 95-100% % confluent at the time of infection. Seven (7) million viral particles were added to each 10 cm dish of cells in 5H media. Fresh 5H media was added 24 hours prior to infection. Cells were incubated with virus for 24 hours at which point C10 was added directly to the media and incubated for 6 hours before cells were harvested.

Patients and Tissue Samples. Tissue specimens were obtained from 30 individuals treated at the Ukrainian Center of Endocrine Surgery in Kiev. Thyroid lesions were classified as Hashimoto's thyroiditis in 21 cases, hyperplasia associated with Graves' disease in 20 cases. Normal thyroid tissue was from the contralateral glands of 20 patients undergoing thyroid surgery for adenomas or tumors. After fixation in 10% formalin and embedding in paraffin, 5-µm-thick serial sections were made for each specimen. The 5-µm sections were stained with hematoxylin and eosin.

Immunohistochemical Staining. Sections were dewaxed, soaked in alcohol and after microwave treatment in antigen unmasking solution for 10 min incubated in 3% hydrogen peroxide for 15 min to inactivate endogenous peroxidase activity. Then sections were incubated at 4° C. overnight with anti-TLR3 antibody (1:100 dilution). Immunostaining was performed by use of the Vectastain Universal Quick kit according to the manufactured instruction. Peroxidase staining was revealed in 3,3-diaminobenzidine. Negative control was applied by omission of antiserum.

Example 2

Phenylmethimazole (C10) protects mice from TLR3 mediated Type 1 diabetes and improves survival.

In Example 1 we show that TLR3 and IFN-β protein are expressed in situ in thyrocytes from patients with Hashimoto's thyroiditis which are surrounded by immune cells but not in thyrocytes from normal individuals or Graves' autoimmune hyperthyroidism, a novel finding never previously demonstrated. The results from human thyrocytes in culture indicate that TLR3 activation and functional increases in signaling can occur in human as well as rat thyrocytes in culture and this can occur in the absence of lymphocytes or a lymphocyte-produced IFN, since lymphocytes primarily produce type II interferon (T. Taniguchi, et al., *Annu Rev Immunol*, 19:623-55 (2001)). Consistent with this, the immunocytochemistry study shows that the intense brown stain for IFN-β is localized in the thyrocytes and is not significant in the immune cells. The results thus raise the possibility that thyrocytes are affected by a primary insult, which activates the TLR3 system to produce an innate immune response mimicking that of a dendritic cell. The resultant cytokine and co-stimulatory molecule changes in the thyrocyte may then contribute to attracting lymphocytes to the gland, since unlike dendritic cells, the thyrocytes cannot migrate to the lymphoid organ.

The results herein are startlingly similar to studies of another disease with TLR3 involvement and overexpression, a role for pathogen induction and dsRNA, involvement of a Type 1 IFN as an apparent autocrine/paracrine factor, immune cell infiltrates, and cell specific destruction causing hypofunction, i.e., insulinitis and type 1 diabetes (D. Devendra, et al., *Clin Immunol*, 111:225-33 (2004); L. Wen, et al., *J Immunol*, 172:3173-80 (2004)). Wen, et al. (L. Wen, et al., *J Immunol*, 172:3173-80 (2004)) show that dsRNA could induce insulinitis and type 1 diabetes in animals, consistent with the known animal model wherein Coxsackie's virus induces Type 1 diabetes in NOD mice. Devendra and Eisenbarth (D. Devendra, et al., *Clin Immunol*, 111:225-33 (2004)) emphasize human relevance and note that enteroviruses have been the focus of many research studies as a potential agent in the pathogenesis of type-1 diabetes. They note that the mechanism of viral infection leading to β cell destruction involves IFN-α [a Type I IFN like IFNβ]. They hypothesize that activation of TLR by double stranded RNA or Poly-IC (a viral mimic), through induction of IFN-α, may activate or accelerate immune-mediated β cell destruction. They note that numerous clinical case reports have implicated IFN-α therapy with autoimmune diseases [thyroiditis, in particular (see below)] and that elevated serum IFN-α levels have been associated with Type 1 diabetes as well as thyroid autoimmune/inflammatory disease (M. F. Prummel, et al., *Thyroid*, 13:547-51 (2003)). Taken together with data in the present report, we considered the possibility of an important mechanistic association relevant to disease pathogenesis. Hashimoto's and Type 1 diabetes may have immune cell infiltrates and destructive thyrocyte or β-cell changes because of a primary insult to the specific tissue cell that activates TLR3 and an innate immune response in the tissue cells; this may be an early event in the pathogenic mechanism (D. Devendra, et al., *Clin Immunol*, 111:225-33 (2004); L. Wen, et al., *J Immunol*, 172:3173-80 (2004); B. Beutler, *Nature*, 430:257-63 (2004); K. S. Michelsen, et al., *J Immunol*, 173:5901-7 (2004)).

Devendra and Eisenbarth suggest (D. Devendra, et al., *Clin Immunol*, 111:225-33 (2004)) that therapeutic agents targeting IFN-α [over production or activity] may potentially be beneficial in the prevention of type 1 diabetes and autoimmunity. Example 1 looked at whether TLR3 overexpression/signaling leading to increased Type I IFN levels might be sensitive to the immunomodulatory actions of methimazole (MMI) or its more potent derivative, phenylmethimazole (C10) (M. Saji, et al., *J Clin Endocrinol Metab*, 75:871-8 (1992); V. Montani, et al., *Endocrinology*, 139:290-302 (1998); L. D. Kohn et al., U.S. Pat. No. 6,365,616 (2002); E. Mozes, et al., *Science*, 261:91-3 (1993); D. S. Singer, et al., *J Immunol*, 153:873-80 (1994)) and how the data indicate that C10, to a significantly greater extent than MMI, blocks overexpression of TLR/TLR signaling by inhibition of the TLR3 regulated IRF-3/IFN-β/ISRE/STAT signal path not the NF-6B signal path. It acts more broadly than just inhibition of IRF-3 transactivation and, therefore, may inhibit activation of a broad range of ISRE sequences on other genes. In this respect, it is notable that, in addition to an NF-6B site, IRF-1 has a GAS, which binds Stat1. It is reasonable to suggest that the ability of C10 to block IRF-1 gene expression, both herein and in our studies of C10 inhibition of TNF-α-induced VCAM-1 and leukocyte adhesion, is related to its action on components of the TLR3 regulated IRF-3/IFN-β/ISRE/STAT signal path. In short, C10 may be an example of an agent that meets the new therapeutic paradigm requested by Davendra and Eisenbath in their review (D. Devendra, et al., *Clin Immunol*, 111:225-33 (2004)).

The NOD mouse is a prototypical example of type 1 diabetes. In experiments in a "nonclean" animal facility, C10 was effective in retarding the development of glucosuria in the NOD mice (Table 4). When this was repeated in a "clean" laboratory, no effect of C10 was noted. What was noted, however, was the onset of glucosuria in the mice was much earlier in the animals maintained in "nonclean" as opposed to "clean" mouse facilities (Table 4). Enteroviruses are associated with expression of Type 1 diabetes and there is a well-described Coxsackie's virus mouse model of type 1 diabetes. We thus hypothesized that our results might be explained by viral induction of disease in the nonclean facility; and we tested whether C10 was effective in the Coxsackie's virus induced NOD mouse model of diabetes. In experiments to test this hypothesis (Table 4), C10 was effective in retarding glucosuria and death in this model. We thus can conclude that C10, as a representative lead compound of the MMI derivative, tautomeric cyclic thione family, can reverse a TLR3/TLR3 signaling disease in vivo and very likely can prevent it if disease expression is induced by environmental pathogens as in the Coxsackie model of diabetes in NOD mice. The MMI, MMI derivative, tautomeric cyclic thione family of drugs are likely to prevent both the initial insult and repeated insults during the lag phase. Further intermittent therapy may be useful to extend the life of the lag phase, if not to totally prevent disease. This would be applicable to Hashimoto's autoimmune thyroiditis, as well as Type 1 diabetes in humans, since the NOD model is broadly used for evaluating mechanisms and therapies applicable to inducing an autoimmune-inflammatory human disease and has been shown to be associated with iodide induced thyroiditis as well as Type I diabetes.

TABLE 4

C10 protects NOD mice from infection-induced Type 1 Diabetes

| Rx | Week 1 Glucosuria % of Total | Week 4 Glucosuria % of Total | Week 8 Glucosuria % of Total | Week 12 Glucosuria % of Total | Week 16 Glucosuria % of Total | Week 20 Glucosuria % of Total | Facility |
|---|---|---|---|---|---|---|---|
| None | 0 | 0 | 15 | 100 | NA | NA | Dirty |
| C10 | 0 | 0 | 0 | 0 | NA | NA | Dirty |
| None | 0 | 0 | 0 | 10 | 50 | 100 | Clean |
| C10 | 0 | 0 | 0 | 20 | 40 | 100 | Clean |
| None + virus | 10 | 70 | 100 | NA | NA | NA | Dirty |
| C10 + virus | 0 | 0 | 20 | 30 | NA | NA | Dirty |

NA: Not Assayed.

Table 4 shows the ability of C10 to attenuate Coxsackie virus-induced Glucosuria in NOD mice. Mice were housed in germ free facilities, termed clean, or normal facilities where viral infections can occur, termed dirty. Animals showing urine Tes-Tape positivity greater than 1+ are considered positive and to have diabetes (L. S. Wicker, et al., *Diabetes*, 35:855-60 (1986)). In experiments in a "dirty" animal facility, C10 was effective in retarding the development of glucosuria in the NOD mice. When this was repeated in a "clean" or germ free laboratory, no effect of C10 was noted. What was noted, however, was the onset of glucosuria in the mice was much earlier in the animals maintained in "dirty" as opposed to "clean" mouse facilities. Further, in experiments with 8 mice in each group, even in a dirty facility, the injection of CVB4 Edwards Coxsackie virus advanced the expression of glucosuria (last two rows). These results suggest C10 inhibits environmental or virus induced expression of Type 1 diabetes in genetically susceptible NOD mice.

In animals with diabetes, glucosuria was confirmed by measuring blood levels, viral titers in the pancreas were determined to be positive, and insulinitis 2+ to 4+ was observed microscopically in diabetic but not C10 treated animals.

Materials and Methods

Induction of Diabetes and treatment with drugs. NOD/Lt female mice were from the Jackson Laboratory (Bar Harbor, Me.). All experiments were carried out in accordance with "Guide for Care and Use of Laboratory Animals" (NIH Publication No. 85-23, revised 1985). Mice were injected with 200 µl PBS or $5\times10^5$ PFU of the CVB4 Edwards Coxsackie virus strain ip (D. V. Serreze, et al., J Virol, 79:1045-52 (2005)). Mice were treated daily with i/p injections of C-10, MMI, 2.5% DMSO(C10 carrier control), or PBS (MMI carrier control). After injections, blood and urinary glucose levels were monitored weekly using Chemstrips (Boehringer Mannheim). Consecutive values of >240 mg/dl on two occasions >24 h apart were considered diagnostic of diabetes. Experiments used 8 mice/group in up to 3 experiments.

Assessment of viral titer. Pancreases from euthanized mice were weighed, placed in PBS, minced, sonicated, and subjected to 3 freeze-thaw cycles followed by a low-speed centrifugation (D. V. Serreze, et al., J Virol, 79:1045-52 (2005)) to isolate islets for analyses as above. Serial dilutions of the cleared lysates were made in PBS and 200 µl aliquots added to 35 mm wells of confluent BSC40 cells (American Type Culture Collection). After overlaying with 1% methylcellulose medium and incubation for 72 h at 37° C., the overlay was removed and monolayers fixed with methanol-oxaloacetate, then stained with crystal violet. Plaques were counted and titers calculated as follows: number of plaques/volume of inoculate)/dilution factor.

Assessment of insulinitis. Pancreases were fixed in Bouin's solution and sectioned at three nonoverlapping levels (D. V. Serreze, et al., J Virol, 79:1045-52 (2005)). Granulated 13 cells were stained with aldehyde fuchsin and leukocytes stained with a hematoxylin-and-eosin counterstain. Islets (at least 20 per mouse) were scored as: 0, no lesions; 1, peninsular leukocytic aggregates and periductal infiltrates; 2, <25% islet destruction; 3, >25% islet destruction; and 4, complete islet destruction. An insulitis score for each mouse was obtained by dividing the total score for each pancreas by the number of islets examined. Data were determined as mean insulitis scores i standard errors of the mean for the experimental groups.

Example 3 phenyl methimazole protects mice from LPS-induced endotoxic shock mediated by TLR4 signals and improves survival The LPS that causes endotoxic shock binds to TLR-4 receptors on nonimmune cells, monocytes, macrophages, and dendritic cells, then activates two signal pathways, (S. Sato, et al., Int Immunol, 14:783-91 (2002)), MyD88-dependent (M. Yamamoto, et al., J Immunol, 169:6668-72 (2002); T. Ogawa, et al., Int Immunol, 14:1325-32 (2002); K. Ruckdeschel, et al., J Immunol, 168:4601-11 (2002)) and MyD88-independent (M. Yamamoto, et al., Nature, 430:218-22 (2004)) Both pathways contribute to the fatal consequences of the syndrome. The MyD88-dependent pathway activate the NF-κB signal and MAP Kinase signal systems. After phosphorylation and degradation of IκB and after the release of the p50 and p65 subunits from IκB, p50 and p60 enter the nucleus to interact with a multiplicity of gene promoters, causing the synthesis and secretion of proinflammatory cytokines TNF-α, IL-1, IL-6, and IL12, as well as the synthesis of the adhesion molecules ICAM-1 and VCAM-1, cytokines such as IFN-γ, and chemokines such as MCP-1 (S. Uematsu, et al., J Immunol, 168:5811-6 (2002); K. A. Ryan, et al., Infect Immun, 72:2123-30 (2004)). These gene products are only some of the mediators that contribute to the inflammatory syndrome in all organs, to the acute systemic failure of all organs, and to the hypotension, hypothermia, and shock. Additionally, the MyD88 independent pathway activates the interferon regulatory factor (IRF) gene promoter, IRF-3, which causes the up-regulation, synthesis and secretion of INF-β, the activation of Stat1, the activation of a multiplicity of genes with ISREs (Interferon sensitive response elements), and increases in the expression of IRF-1 and the chemokine IP-10 (V. Toshchakov, et al., J Endotoxin Res, 9:169-75 (2003); K. Hoshino, et al., Int Immunol, 14:1225-31 (2002); T. Kawai, et al., J Immunol, 167:5887-94 (2001); K. A. Fitzgerald, et al., Nat Immunol, 4:491-6 (2003); K. Hoebe, et al., Nature, 424:743-8 (2003); D. D. Bannerman, et al., J Biol Chem, 276:14924-14932 (2001)). Thus, both TLR4 and TLR4 adaptor molecules, with their respective signals, are involved in the toxic shock syndrome and the associated cellular inflammatory infiltration at the organ levels.

Methimazole (MMI) has been largely used for the treatment of Graves' disease as well as in lupus eritematosus systemic (D. S. Singer, et al., J Immunol, 153:873-80 (1994); E. Mozes, et al., Isr J Med Sci, 32:19-21 (1996)), spontaneous autoimmune disease (E. Mozes, et al., J Clin Immunol, 18:106-13 (1998)) and periocular inflammation in mice with experimental systemic lupus erythematosus (C. C. Chan, et al., J Immunol, 154:4830-5 (1995)). The anti-inflammatory property of MMI has been attributed to anti-oxidant and immunomodulatory effects including effects on IFN-γ signaling (L. D. Kohn, et al., U.S. Pat. No. 6,365,616 (2002)). A more potent methimazole derivative in the family of tautomeric cyclic thiones, phenylmethimazole (C10 or pMMI) was developed based on its ability to suppress MHC gene expression (L. D. Kohn et al., U.S. Pat. No. 6,365,616 (2002)) but has now been shown to inhibit transcription of TNF-α-increased venular cell adhesion molecule-1 (VCAM-1) on human aortic endothelial cells (HAEC) and human umbilical venous endothelial cells (HUVEC)(N. M. Dagia, et al., J Immunol, 173:2041-9 (2004)). It was shown that C10 acts by inhibiting of TNF-α-induced overexpression of interferon regulatory factor 1 (IRF-1) gene not by inhibiting TNF-α activation of NF-κB promoter element on the VCAM-1 promoter (N. M. Dagia, et al., J Immunol, 173:2041-9 (2004)). IRF-1 binds to an element closer to the transcriptional start site on the VCAM-1 promoter than the NF-κB elements and is required for optimal TNF-α activation of the VCAM-1 promoter (N. M. Dagia, et al., J Immunol, 173:2041-9 (2004)).

Additionally, phenylmethimazole (C10) but not Methimazole (MMI) has been shown to suppress the inflammatory response and improve survival in DSS induced colitis by its down regulatory effects on TLR4 overexpression in intestinal epithelial cells and by its effects to decrease pathologically expressed TLR4 signals including TNF-α, IL-1, IL-6, interferon protein-10 (IP-10), and VCAM-1 gene transcription (L. D. Kohn, et al., Research Ohio, In press (2005)). In the following studies we focused on the ability of phenylmethimazole (C10 or pMMI) to reverse the pathologic signaling of the LPS-induced TLR4 mediated toxic shock syndrome in a rodent and a horse model of endotoxic shock.

In studies of C57BL/6J mice injected with 20 mg/kg LPS, the mice developed a toxic shock syndrome (hypotension, hypothermia, collapse) between 6 and 12 hours post injection and were dead by 12 to 36 hours (Table 5A). Phenylmethimazole (C10 or pMMI) protected the mice from death after LPS injection in 100% of animals examined (Table 5A) in this experiment and in 3 separate replicate experiments. This protection was due to CIO (PMMI) and not to the solvent used for C10, DMSO (Table 5A). When clinical symptoms were checked 12 hours after LPS injection, we observed that mice treated with pMMI or C10 showed mild symptoms, i.e. mild decreases of body temperature, but maintained normal feeding and drinking habits, as well as mobility (Table 5B). In stark contrast, all other mice developed profound hypothermia, hypotension, and shock (Table 5B). They were depressed, hypothermic, and stopped feeding and drinking (Table 5B). Moreover, all mice that developed severe shock died within 36 hours (Table 5A and 5B)).

Table 5. C10 dramatically increases viability and signs of shock in mice challenged with LPS. (A) C57BL/6J mice injected with 20 mg/kg LPS develop symptoms of shock within 12 hours and die within 36 hours. 100% of C57BL/6J mice injected intra-peritoneally (i/p) with C10 (1 mg/kg) 30 minutes before injection with LPS survive at 36 hours, whereas all mice treated with methimazole (MMI), which is less effective than CO (L. D. Kohn, et al., U.S. Pat. No. 6,365,616 (2002)), or prednisolone, and flunixin of meglumine, which are currently in use clinically to treat LPS shock in humans and animals, respectively, die. The mice treated with C10 survived for as long as they were observed (4 weeks). (B) Additionally, mice treated with C10 had only a slight decrease in body temperature 12 hrs after LPS and no signs of shock. (C) C10 administered in daily doses of 0.1 or 1 mg/kg 12 hours after challenge with LPS also results in 100% survival compared to 0% survival for control mice.

TABLE 5

C10 dramatically increases viability and signs of shock in mice challenged with LPS.

A. Number of surviving mice in each group of a representative experiment

| Treatment | 6 hrs | 12 hrs | 18 hrs | 36 hrs | 1 week |
|---|---|---|---|---|---|
| None | 8 | 8 | 8 | 8 | 8 |
| LPS | 8 | 8 | 4 | 0 | 0 |
| LPS + DMSO | 8 | 8 | 3 | 0 | 0 |
| LPS + C10 | 8 | 8 | *8* | *8* | *8* |
| LPS + MMI | 8 | 8 | 6 | 0 | 0 |
| LPS + prednisolone | 8 | 8 | 3 | 0 | 0 |
| LPS + flunixin of meglumine | 8 | 8 | 4 | 0 | 0 |

Bold Italicized Values reveal statistically significant improvement in survival, P < 0.01)
Experiment replicated three times.

B. Signs of shock measured at 12 hours in a representative experiment

| Treatment | 12 hrs | % of Animals |
|---|---|---|
| None | None | 100 |
| LPS | ++++ | 100 |
| LPS + DMSO | ++++ | 100 |
| LPS + C10 | + | 100 |
| LPS + MMI | +++ | 100 |
| LPS + prednisolone | ++++ | 100 |
| LPS + flunixin of meglumine | ++++ | 100 |

Bold Italicized Values reveal statistically significant improvement in parameters of shock, P < 0.01)
Experiment replicated three times. Shock was evaluated by such signs as immobility, prostration, hypothermia, dyspnea, etc. as noted below.

C. A. Number of surviving mice in each group of a representative experiment wherein mice were challenged with LPS first then treated with C10 after 12 hours at which time shock had appeared

| Treatment | 18 hrs | 36 hrs | 1 week |
|---|---|---|---|
| None | 8 | 8 | 8 |
| LPS | 4 | 0 | 0 |
| LPS + DMSO | 2 | 0 | 0 |
| LPS + C10 | *8* | *8* | *8* |
| LPS + MMI | 4 | 0 | 0 |
| LPS + prednisolone | 1 | 0 | 0 |
| LPS + flunixin of meglumine | 0 | 0 | 0 |

Bold Italicized Values reveal statistically significant improvemed survival, P < 0.01)

Even when we compared the effects of pMMI (C10) with Methimazole (MMI), Predsnisolone (PSL), and Flunixin of Meglumine (FM), we observed that only pMMI (C10) protected against shock (Table 5B). Today, prednisolone is commonly used as therapy in humans, Flunixin of Meglumine is used as treatment in animals. Mice injected with LPS and treated with drugs other than C10 (PMMI) showed signs of shock at 12 hours and were dead within 36 hours post LPS injection. (Table 5A and 5B), a novel result with important clinical implications.

In these experiments C10 was administered 30 min before LPS injection at 1 mg/kg. C10, 0.1 to 1 mg/kg administered 30 min to 12 hours after lethal LPS injection, also survived in 100% of cases (Table 5C). Some mild signs of shock such as hypothermia and slight hypotension did develop in these mice, depending on the treatment time post LPS injection and the C10 dose, 0.1 to 1 mg/kg. Nevertheless, taken together, these results show that C10 can both protect from endotoxic shock and death in LPS induced endotoxic shock in mice and can reverse the toxic shock syndrome post LPS treatment in a dose-dependent manner despite the onset of toxic shock symptoms and signs.

IRF-1, MCP-1, and IP-10 as well as downstream genes such as pro-inflammatory cytokine genes, COX genes, and INOS are altered by LPS-induced endotoxic shock in mice and reversed to normal levels by C10 (PMMI) in association with successful therapy.

Figure 7:
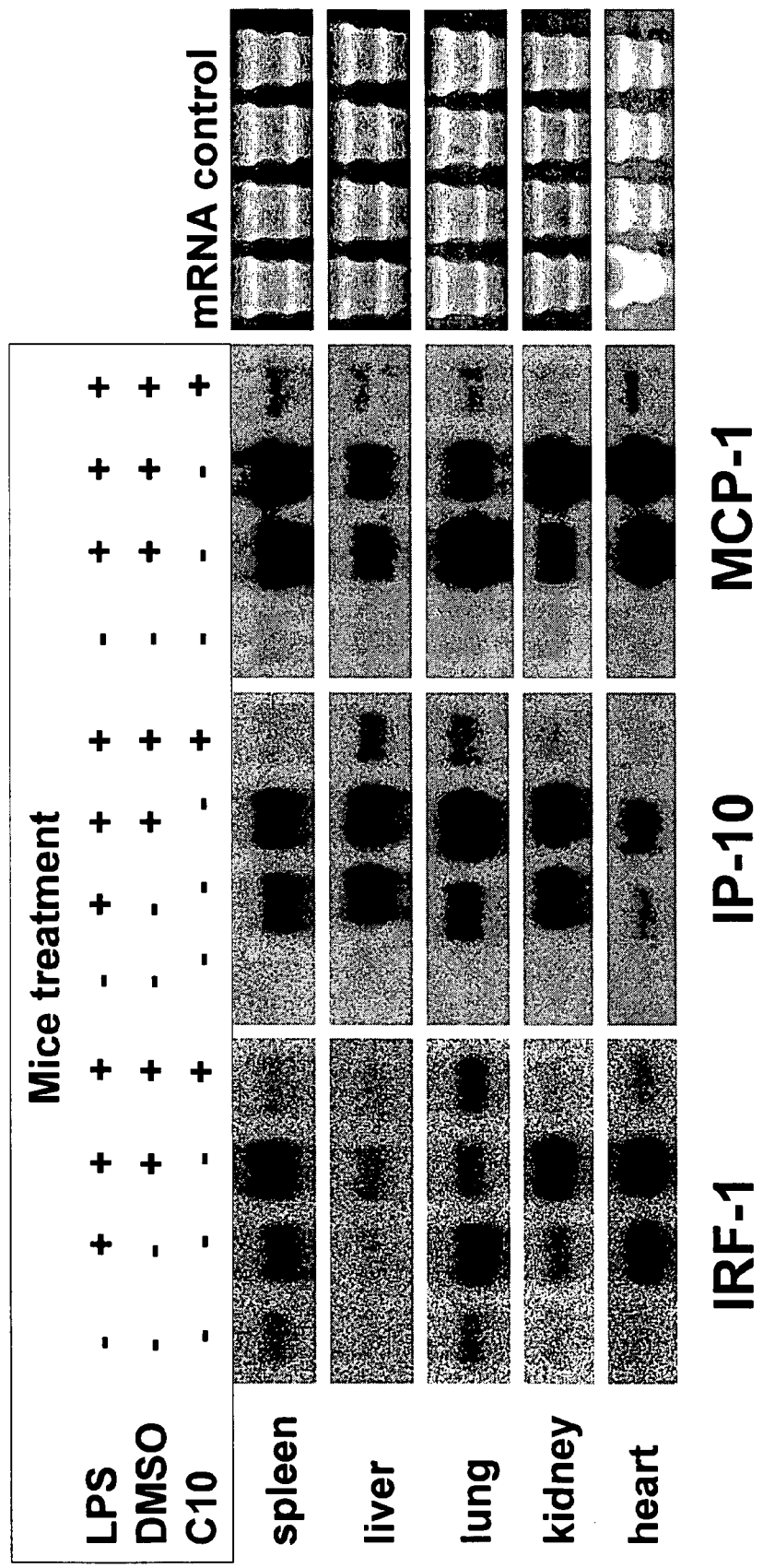
FIG. 7. C-10 inhibits LPS induced MCP-1, IRF-1, and IP-10 expression in different tissues, reputed products of both the TLR4 increased MyD88 dependent or MyD88 independent signaling pathways. Northern analysis (M. Saji, et al., J Clin Endocrinol Metab, 75:871-8 (1992); D. S. Singer, et al., U.S. Pat. No. 5,556,754 (1996); V. Montani, et al., Endocrinology, 139:290-302 (1998)) of RNA from various organs of control mice or mice treated with LPS, LPS+C10, LPS+DMSO (vehicle control), all from Table 5). Ribosomal bands are shown as control for loading and integrity of samples. The Northern blots demonstrate that LPS induced expression of products from both the NF-κB (MCP-1) and IRF-3/IFN-β (IP-10, IRF-1) signal pathways that are activated by TLR4 are significantly increased by LPS but attenuated by C10 treatment.

Whereas the interferon inducible genes, IRF-1 and IP-10, are the main reported inducible genes after LPS activation of the MyD88 independent, IRF-3/IFN-β pathway, MCP-1 is a gene activated primarily by the MyD88-dependent, NF-κB-linked pathway. Given the action of C10 to block the IRF-3, IFN-β, Stat1, ISRE, IRF-1 pathway, but not the NF-κB path (N. Harii, et al., Mol Endocrinol, 19:1231-50 (2005); (N. M. Dagia, et al., J Immunol, 173:2041-9 (2004)) and above, we anticipated C10 would only inhibit IRF-1 and IP-10 and not MCP-1 in vivo. As illustrated, however, the over-expression of all three of these genes was suppressed by C10 (PMMI) to normal levels in most organs (FIG. 7). Thus, LPS-treatment profoundly increased IRF-1 RNA levels in most organs, albeit less in liver, and C10 (PMMI) reverted mRNA levels to those in normal tissues under normal conditions. IP-10 gene expression followed the IRF-1 pattern in all organs, except in liver where IP-10 was expressed more than IRF-1. Similarly, the MCP-1 pattern with LPS and LPS plus C10 (pMMI) replicated the profound ability of this agent to decrease RNA increases induced by LPS activation of the NF-κB pathway. In short, C10 (pMMI) was an effective suppressor of LPS-increased mRNA levels of genes reported to be important in both MyD88-independent and dependent pathways. Thus, despite the in vitro evidence for primary pathway selectivity, pathologic expression of genes downstream of both the TLR4-mediated NF-κB as well as the IRF-3/IFN-β signal paths were suppressed. It is suggested in the literature that the NF-κB activation of the MCP-1 can be the result of a delayed signal secondary to IFN-β activity. Also, it is possible that there is pathway cross-over in vivo, in part because of mixed cell populations, i.e. the presence of vascular endothelial cells in every tissue. In sum, in vivo, these data thus suggested that C10 inhibited expression of genes in the IRF-3/IFN-β-inducible pathway and even possibly secondary IFN-β effects on the NF-κB pathway in vivo.

Figure 8:
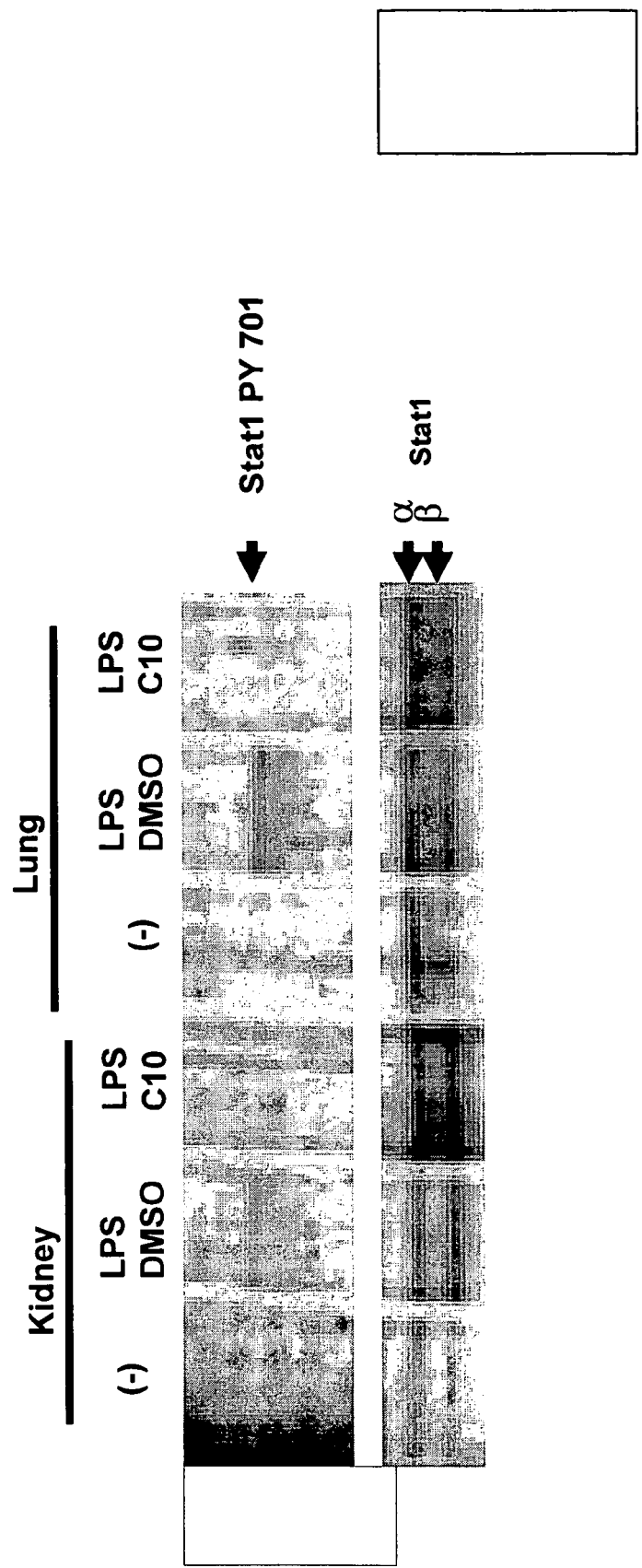
FIG. 8. Mice protected from Endotoxic shock by C10 have reduced tissue levels of activated Stat1. In order to determine if LPS-induced IFN-β signaling and LPS-induced increases in IRF-1 in vivo might be attenuated by an effect of C10 treatment on Stat1 activation, protein phosphorylation levels of Stat1 in whole tissue lysates was examined. Both kidney and lung tissues displayed detectable levels of activated Stat1 protein in mice treated with LPS plus control solvent (DMSO) and not protected from shock (lanes 2 and 5 respectively) by comparison to controls (Lanes 1 and 4). These levels were reduced to basal in mice that were protected from LPS induced shock by treatment with C10 (lanes 3 and 6 respectively). Similar results were evident using an antibody measuring phosphoserine activated Stat1, i.e., C10 inhibited both transcriptional activation and dimerization needed for full expression of IRF-1 as a representative gene. Control mice and mice treated with LPS, LPS+C10, or LPS+DMSO (solvent control) were all from Table 5).

In order to more definitively determine if LPS-induced IFN-β signaling and LPS-induced increases in IRF-1 and IP-10 in vivo might be attenuated by an effect of C10 treatment on Stat1 activation, protein phosphorylation levels of Stat1 in whole tissue lysates were examined in mice from Table 5. Both kidney and lung tissues displayed detectable levels of activated Stat1 protein measured using a specific antibody to phosphorylated phenylalanine 701 in mice treated with LPS plus control solvent (DMSO) and not protected from shock (FIG. 8, lanes 2 and 5 respectively) by comparison to controls who were never exposed to exogenous LPS injections (FIG. 8, Lanes 1 and 4). These levels were reduced to basal in mice, which were protected from LPS induced shock by treatment with C10 (FIG. 8, lanes 3 and 6, kidney and lung, respectively). In contrast neither LPS nor C10 had any effect on total Stat1 in these tissues (FIG. 8, bottom blots). These data establish that C10 inhibits Stat1 as well as IRF-1 gene expression in vivo in toxic shock. Based on literature studies described in immune cells and results we have described in nonimmune cells (FIGS. 4-6; Tables 2, 3), it is reasonable to state that C10 blocks Stat1/IRF-1 signals in vivo as well as in vitro, this is important in the therapy of toxic shock where these genes are not only involved but critical to disease expression. C10 therapy is thus important in reducing pathologic changes in multiple tissues whose organ failure is known to contribute to the signs and symptoms of toxic shock.

Figure 9:
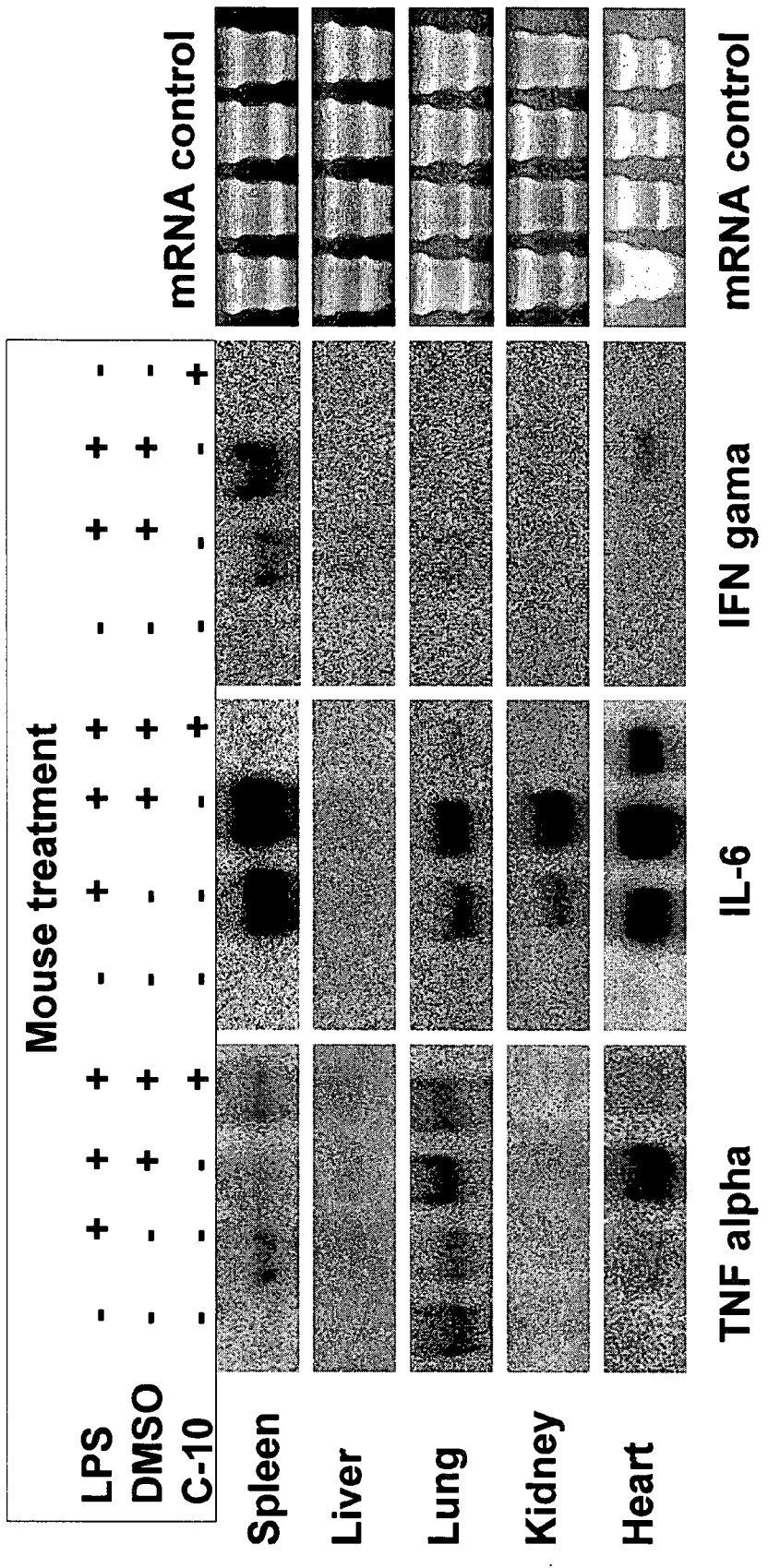
FIG. 9. Proinflammatory cytokines induced by endotoxic shock are suppressed by C10. The pro-inflammatory cytokines TNF α, IL-1β, IL-6, IL-12 and IFN γ are reported to be secreted by the activation of LPS-TLR-4-MyD88 dependent pathway but involve also the MyD88 independent signals. Expression of these pro-inflammatory cytokine genes in spleen, liver, lung, kidney and heart of LPS injected and mice at 24 hours, was strongly induced by endotoxic shock and suppressed by C10 as determined by Northern analyses. These results were confirmed by determination of cytokine concentrations in blood using an ELISA technique (Table 6). Most of the cytokine levels increased in mice LPS and LPS plus DMSO treated mice increased as much as 1000 fold compared to mice treated with C10. Phenylmethimazole (C-10) normalized these cytokines to levels approaching those in normal control mice. Blood was collected from the inner canthus of the eye under anesthesia and serum was taken and kept at −20 degree centigrade until use. ELISA kits from R&D System were used and the results were expressed in picograms per ml of serum.

The pro-inflammatory cytokines TNF-α, IL-1β, IL-6, IL-12 and IFN-γ are reported to be synthesized and secreted by the activation of the LPS-TLR-4-MyD88 dependent pathway through NF-κB gene activation. These pro-inflammatory cytokine genes, as determined by histochemistry in multiple tissues from the animals in Table 5, were strongly increased by inducing endotoxic shock with LPS at 24 hours. Induction was suppressed, however, by C10 (PMMI) treatment. This was evidenced for IL-6 and TNF-α in all tissues examined by Northern analyses (FIG. 9). In the case of IFN-γ, this phenomenon was true in most tissues examined (FIG. 9). These results were additionally confirmed by determination of the cytokine concentrations in blood (Table 6). Thus, using an ELISA technique, many of the cytokine levels that were increased in LPS and LPS plus DMSO treated mice were elevated more than 1000 fold by comparison to control or C10 (pMMI)-treated mice who received LPS (Table 6). Very clearly, phenylmethimazole C10 (PMMI) reduced these cytokine levels to levels in normal control mice in association with efficacious effects on disease expression in toxic shock.

TABLE 6

C10 decreases the serum level of cytokines increased by C10 in mice evaluated 1 hour after initiation of the experiment of Table 5.

| Cytokine | Cytokine Level (% of Control ± 12%) | | | |
|---|---|---|---|---|
| | Control | LPS | LPS + DMSO | LPS + C |
| IL-1β | 100 | 6000 | 5900 | *125* |
| IL-6 | 100 | 2800 | 2600 | *55* |
| TNF-α | 100 | 4000 | 4200 | *2000* |
| IFN-γ | 100 | 4500 | 1900 | *100* |
| IL-12p70p | 100 | 200 | 260 | *150* |

Bold values with LPS or LPS + DMSO Vehicle control are statistically increased (p < 0.001).
Bold and italicized values in mice treated with C10 were statistically lower than LPS or LPS plus vehicle control (P < 0.001).
Experiments were representative of three separate replicated groups.

In sum, C10 (PMMI) suppressed pro-inflammatory cytokine production induced by the LPS-TLR-4-MyD88 dependent and independent pathways in vivo consistent with its effects to prevent or reverse toxic shock (Table 5). The data are consistent with previous data in vitro, that C10 (PMMI) down regulates the IRF3/IFN-β/Stat1/ISRE/IRF-1 signal transduction pathway (N. Harii, et al., Mol Endocrinol, 19:1231-50 (2005); N. M. Dagia, et al., J Immunol, 173: 2041-9 (2004)). However, the data additionally suggest that in vivo, in nonimmune organs with cell heterogeneity, C10 (PMMI) also regulated genes linked to the NF-κB activation pathway, possibly by a secondary effect on IFN-β autocrine/paracrine effects on nonimmune cells, rather than a direct block of the MyD88-linked signal system.

The cyclooxygenase (COX) enzyme system catalyzes the synthesis of prostaglandins and regulates their tissue levels. Prostaglandins are well described as important in the induction of hypotension in endotoxic shock. COX-2 is over-expressed in toxic shock and in autoimmune-inflammatory diseases related to toxic shock, as well as in cancer progression. It is responsible for catalyzing the formation of PGE2 which is the prostaglandin responsible for blood pressure decreases and hypotension in septic shock. In contrast to COX-2, COX-1 is the "house-keeping" enzyme with a protective role. C10 selectively suppressed the expression of COX-2, which is increased in tissues by LPS-induced endotoxic shock and increased COX-1 gene expression, which is decreased in tissues by LPS-induced endotoxic shock, to the normal level. The ratio of COX-2/COX-1 is considered important both to disease expression and therapeutic efficacy.

Figure 10:
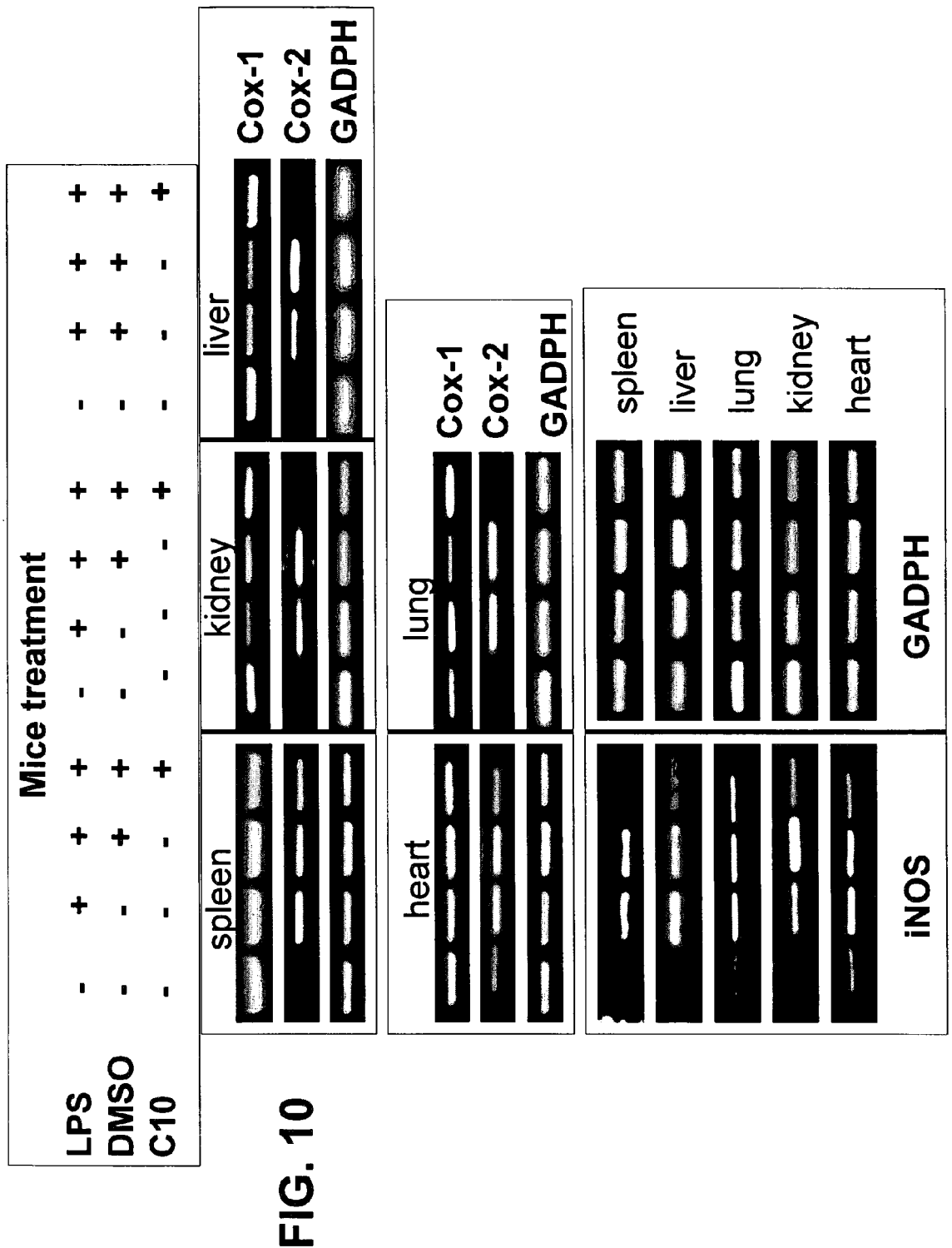
FIG. 10. C10 decreases LPS/toxic shock increased COX-2, and iNOs expression but decreases COX-1 expression in mice. LPS and C10 oppositely affect COX-1, COX-2 and iNOS expression as analyzed by PCR. LPS injection in mice from the Experiment in Table 5 decreased COX-1 expression at 24 hours compared to normal levels, in heart, kidney and liver. C10 treatment attenuated this LPS effect on COX-1 in these organs, causing expression to revert to normal levels. No variation on COX-1 expression due to LPS injection was observed in spleen. COX-2 and iNOS were over-expressed in all five organs after LPS injection; C10 treatment reversed the overexpression to normal levels.

Thus, when expression of COX-1 and COX-2 RNA levels were evaluated by RT-PCR in the organs of different groups of mice described in Table 5, the COX-1 RNA levels were down-regulated in most examined organs of LPS treated mice except spleen and heart, while the C10 returned RNA levels to the normal levels (FIG. 10). These data indicate that C10 protects cells from damage induced by LPS, since COX-1 is a protective enzyme in the inflammatory process. Moreover, the absence of an LPS effect on spleen, which is dominated by immune cells, but a significant effect of LPS and C10 in lung, kidney, and liver indicates that the dominant increase and significant action of C10 was on the nonimmune cells in these tissues, since they dominate those organs unlike the case in spleen.

In contrast to COX-1, the COX-2 RNA levels were up-regulated in kidney, liver, lung, spleen, and heart of mice suffering from endotoxic shock (FIG. 10) establishing that all organs suffer a strong inflammatory process. Further elevated COX-2 RNA levels were completely suppressed and returned to normal by C10 in kidney, liver and lung and also suppressed in spleen and heart, albeit less dramatically. These data establish that C10 is a selective COX-2 inhibitor compared to COX-1 and acts as a more physiologic regulator by reversing both the increased COX-2 and decreased COX-1 toward normal levels. The changes in spleen indicate that the COX-2 enzyme changes in immune cells are an important component of disease expression in immune as well as non-immune cells. Nevertheless, the absence of COX-1 changes in the spleen emphasize that the LPS-induced, and C10 decreased, COX-2 changes in nonimmune cells are also important in toxic shock and its effective therapy by C10.

INOS is only one of the several terminal mediators of shock and inflammation. The overproduction of nitric oxide (NO) in endotoxic shock has been well documented, as it has been in autoimmune-inflammatory diseases and atherosclerosis. Similarly, the tissue damage induced by peroxinitrites from multiple pathways is documented. The data (FIG. 10) show that iNOS mRNA gene expression is undetectable or poorly expressed as measured by RT-PCR in normal tissue (FIG. 10, non treated mice). This gene is clearly induced by LPS in the organs of mice (FIG. 10, iNOS in spleen, liver, lung, kidney, heart). C10 suppressed iNOS RNA levels increased by LPS, returning them toward normal. These data support the idea that C10 can ameliorate peroxinitrites formation and tissue damage induced in tissues by toxic shock and autoimmune inflammatory disorders.

IRF-1 regulates the expression of several genes involved in autoimmunity and inflammation. Genes regulated by IRF-1 include among others, the Type 1 IFN cytokines (IFN-$\alpha$ and IFN-$\beta$), the type 2 IFNS (IFN-$\gamma$), Interleukin-12 (IL-12) and IL-15 as well as nitric oxide, COX-2, MHC-1 and $\beta$-2 microglobulins. Thus, IRF-1 seems to be positioned at the intersection of multiple different downstream paths leading to a Th1 response and to host defense again microorganisms and environmental insults—moreover it is critically positioned to affect TLR3 and TLR4 signals.

It is reasonable to presume from the sum of the data in FIGS. 1-10 and Tables 3-6, plus our previous work (L. D. Kohn et al., U.S. Pat. No. 6,365,616, April:(2002)) that C10 is a lead compound representative of a group of agents which blocks autoimmune-inflammatory disease in vivo and that it acts by a critical effect on pathological increases in IRF-1 gene expression not evident in normal tissues. This has two important consequences. First, because of the absence of high IRF-1 gene expression in normal tissues, C10 (pMMI) will have no significant effect in normal tissues or normal individuals. Second, pathologic increases in IRF-1 gene expression can be mediated by pathologic expression of TLR3/TLR4 in nonimmune tissues, macrophages, monocytes, and dendritic cells. Thus, C10 is a lead compound that blocks pathologic expression of multiple genes important in pathologic autoimmune-inflammatory disorders by blocking the IRF-3/Type 1 IFN/STAT/ISRE/IRF1 signal path. Further, because of autocrine/paracrine actions of type 1 IFNs which secondarily can increase NF-$\kappa$B signaled genes, or perhaps because of the cell heterogeneity of an organ and the different effects of C10 on different cells as the signals progress (vascular vs nonvascular), as will be evident below, the C10 family of compounds can act in vivo to attenuate the NF-$\kappa$B signaled increases in downstream genes or gene products. The bottom line is that C10 and its family members block the pathological innate immune response in nonimmune tissues that are associated with TLR4 as well as TLR3-associated autoimmune-inflammatory disorders, as evidenced for TLR4 associated diseases in the colitis and toxic shock models and in TLR3 mediated disease, as evidenced for insulinitis and Type I diabetes model, but likely in its related disease, Hashimoto's thyroiditis.

Phenylmethimazole (pMMI or C10) ameliorates the microvasculature damage, decreases inflammatory cellular infiltration, and decreases adhesion molecule expression on the vascular endothelial cells of tissues affected by endotoxic shock.

Decreases in inflammatory infiltrates: The histo-pathological observation of sections stained with H.& E. from animals at 18 hours after LPS injection showed the inflammatory changes already described by other authors. These changes were evident on the microcirculation of the different tissues evaluated. In lung all these changes are usually most severe and both TLR3 and TLR4 related (L. Guillot, et al., *J Biol Chem*, 280:5571-80 and 279:2712-8 (2004)). We thus evaluated the effect of C10 (pMMI) on the inflammatory changes induced by LPS in lung sections. In LPS treated mice the lumen of microvasculature was full of blood cells and there was an increased number of acute inflammatory cells, due to the slowing of the blood flow seen at both 20× magnification, and 40× magnification (FIG. 11). Margination, i.e. moving to the edge of the dynamic flow or movement process, of granulocytes along the vascular endothelium and stacking on the vessel endothelia was more evident in the LPS group. In some animals, where the histopathological picture was more severe, microemboli in the lumina of small vessels was observed. The septa of alveoli are thicker than normal, due to the infiltration and migration of acute inflammatory cells, making them more dense in the pulmonary tissue of LPS-treated mice. Microcirculatory damage as well as inflammatory cellular infiltration was ameliorated by C10 (pMMI) (FIG. 11). In other organs where the inflammatory process induced by LPS was evident, e.g liver, heart, or kidney, the same results were found. Taken together, these data indicated that the systemic inflammation induced by endotoxic shock was suppressed by C10 (pMMI).

Adhesion molecules that are up-regulated in the vascular endothelium of organs suffering from endotoxic shock are suppressed by C10 (pMMI): Sections from different organs were study by immunohistochemistry in order to evaluate the effect of pMMI on ICAM-1 and VCAM-1 adhesion molecules in endotoxic shock. Both ICAM-1 and VCAM-1 are the ligands for systemic inflammatory cells to bind to the endothelium and infiltrate tissues in septic shock. Moreover, organ infiltration by inflammatory cells has been largely associated to the systemic organ failure. The data showed that ICAM-1 and VCAM-1 adhesion molecules were strongly up-regulated in mice treated with LPS and suffering from endotoxic shock. ICAM-1 is over-expressed in lung and liver. ICAM-1 specific staining on the endothelial cells of lung capillaries is decreased by C10 (pMMI) as well as in endothelial cells of vein and reticulooendothelial space of the liver. VCAM-1 is specifically up-regulated in the large veins and C10 (pMMI) suppress the VCAM-1 levels.

These results thus showed that in mice injected with LPS, ICAM-1 and VCAM-1 staining were clearly increased and stronger than in normal and C10 (pMMI) treated mice. The results were the same comparing results from C10 treated mice with results from LPS plus DMSO treated mice or those treated with LPS alone. These data showed that C10 (p-MMI) suppressed both ICAM-1 and VCAM-1 over-expression that is induced by LPS-TLR4 activation on endothelial cells.

Materials and Methods

Figure 18:
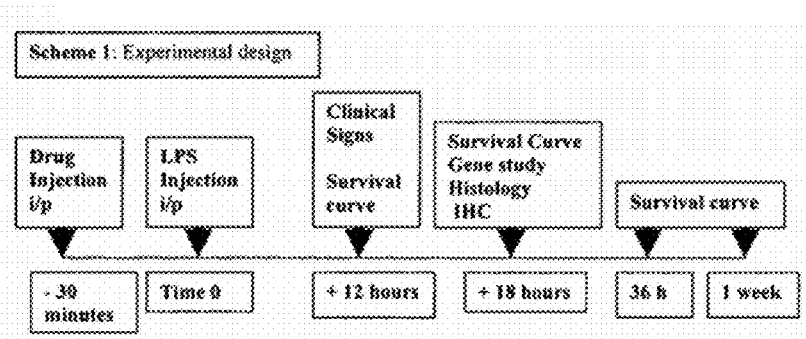
FIG. 18 shows an experimental scheme for certain experiments, as described hereinbelow.

Experimental design: In order to determine the survival curve of C57BL/6J mice, they were injected intra-peritoneally (Up) with different drugs and solvents (See Table 7 below) 30 minutes before LPS injection (See FIG. 18). Twenty (20) mg/Kg LPS from *E. coli* was then injected intra-peritoneally (i/p) into each mouse. The experiment was performed using at least 8 mice in each of 3 experiments. After LPS injection, the survival curve was determined at 6, 12, 18, 36 hours and 1 week. The result is expressed as a percentage of survival without LPS treatment.

TABLE 7

| Drugs and vehicles | | |
| --- | --- | --- |
| Treatment | Dose | Solvent |
| Methimazole (MMI) | 1 mg/kg | PBS |
| C10 (pMMI) | 1 mg/kg | 10% DMSO |
| Prednisolone | 5 mg/kg | PBS |
| Flunixin of Meglumine | 1 mg/kg | Commercial |
| DMSO | 10% (v/v) | PBS |
| PBS | Phosphate buffered Saline pH 7.2-7.4 | Water |

Mice were evaluated 18 hours after the induction of endotoxic shock by intraperitoneal LPS injection. Samples were collected for mRNA isolation, Histology and Immunohistochemistry (see Scheme 1). C10 (pMMI) effects on LPS-TLR4-increased TNF-α, IL-1β, IL-6, IL-12, IFN-γ, COX-2, iNOs, and MCP-1 gene expression were measured by Northern analysis and RT-PCR in spleen, lung, liver, heart and kidney. Results were confirmed by protein studies using ELISA and by immunohistochemistry. The LPS-TLR4-MyD88 independent, IFN-β-signaled genes including IRF-1, IP-10, COX-2 and iNOS were similarly studied. The results of the gene and protein expression were correlated with histological studies. Tissues obtained at 18 hrs were also used to measure the systemic inflammatory response at the organ level. The expression of adhesion molecules ICAM-1 and VCAM-1 was correlated with immunohistochemistry markers of inflammation and TLR4 signaled changes. Lung was used as a reference organ for inflammatory histological studies and lung and liver for adhesion molecule studies.

Histology: Tissue from liver, lung, kidney and heart from normal, LPS and LPS plus C-10 treated mice (experiment in Table 5), were fixed in 4%-PBS-formalin overnight. They then were dehydrated serially in alcohols 50%-70%-90%-100%, clarified in chloroform, and embedded in paraffin. Five (5) sections were obtained and mounted on Vectabond™ (Vector Laboratories, Inc. Burlingame, Calif.) pretreated slides. The sections were incubated twice (10 minutes each) in xylol and re-hydrated by serial alcohol treatments, 100%-90-70-50, followed by distilled water. Tissues were stained with Hematoxylin-Eosin using standard protocols, mounted, and observed by optical microscopy in a double blind manner.

Immunohistochemistry (IHC): C10 (pMMI) effects on the over-expression of adhesion molecules induced by LPS were studied in different organs. These results focus lung and liver. At 18 h after LPS injection, mice were sacrificed and the heart, lung, liver spleen and kidney were removed and fixed in 4% formalin in PBS. The tissue was then dehydrated in serial alcohols (50% v/v, twice; 70% v/v, twice; 80% v/v, twice; 95% v/v, twice; and 100% v/v, twice), cleared in pure chloroform, embedded in paraffin and sectioned (5 prm thickness) and mounted on Vectabond™ (Vector Laboratories, Inc. Burlingame, Calif.) pre-treated slides. The section were then cleared of paraffin by exposure to xylol twice (10 minutes each) and rehydrated using serial alcohol treatments, 100%-90-70-50. After endogenous peroxidase inhibition with 3% $H_2O_2$ in methanol and nonspecific protein blocking using 5% BSA (Sigma Aldrich), the tissue sections were incubated overnight at 4° C. with 5 ul/ml of anti-mouse VCAM-1 polyclonal goat IgG or 3 ul/ml of anti-mouse ICAM-1 extracellular domain specific goat IgG as primary antibodies (R&D System, Inc. Minneapolis, Minn.). The samples were extensively rinsed with PBS and subsequently incubated (1 hr) with biotinylated anti-goat IgG diluted 1/20 using the Goat Extravidin Staining Kit (Sigma-Aldrich St. Louis, Mo.). After extensive washing, the sections were incubated with streptavidin-peroxidase diluted 1/20 from the same kit. The sections were then washed three times and incubated (10 minutes) with DAB Chromogen reagent (Sigma-Aldrich). The slides were washed and were subsequently counterstained with methyl green (Vector Laboratories, Inc. Burlingame, Calif.), then dehydrated in ethanol followed by pure xylene. Slides were mounted and examined under a light microscope at 40× (Nikon Eclipse-E600).

Quantification of pro-inflammatory cytokines in blood: The cytokines TNF-α, IL-1β, IL-6, IFN-γ and IL-12 were quantified in serum using ELISA techniques. Blood was collected from the inner canthus of the eye under anesthesia and serum saved at −20° C. until use. The ELISA kits were from R&D System and the results were expressed in pg/ml serum.

RNA isolation and Northern Blot analysis of gene expression: RNA used to measure expression of TNF-α, IL-1β, IL-6, IFN-γ, IRF-1, IP-10 and MCP-1 genes was extracted using Trizol (Invitrogen, Carlsbad, Calif.) and subjected to Northern blot analysis in a similar manner to that described previously (V. Toshchakov, et al., J Endotoxin Res, 9:169-75 (2003)). The GAPDH cDNA was from Clontech (Palo Alto, Calif.). TNF-α cDNA was excised from pORF9-mTNF vectors (Invivogen, San Diego, Calif.). Other probe sequences were synthesized by RT-PCR (ibid) using the following cDNA specific primers: (SEQ ID NO: 13) mIP-10: 5'CCAT-CAGCACCATGAACCCAAGTCCTGCCG 3' and (SEQ ID NO: 14) 5'GGACGTCCTCCTCATCGTCGACTACACTGG 3' (469 bp); mIL-1β): (SEQ ID NO: 15) CTCATCTGG-GATCCTCTCCAGCCAAGCTTC 3' and (SEQ ID NO: 16) 5'CCATGGTTTCTTGTGACCCTGAGCGACCTG 3' (1006 bp).

RNA isolation and RT-PCR analysis of gene expression. Expression of COX-1, COX-2 and iNOs were studied in different organs. Tissues were isolated from different groups of mice and washed with sterile Phosphate Buffered saline (PBS), pH 7.2-7.4. After tissues were homogenized in 0.5 ml of Trizol (Invitrogen, Carlsbad, Calif.), the RNA was extracted by chloroform-isopropanol, washed in alcohol 70%, dried and redissolved in RNase free water. Total RNA was treated in order to remove any DNA contamination using the DNase Free Kit (Ambion cat#1906). cDNA was obtained using the Clontech RT for PCR kit (Clontech cat #K 1402-2). PCR was performed using the Takara kit for PCR (Takara BIO, Inc, by Fisher Scientific #R001A) after optimizing conditions for each set of primers. Primers were designed using standard procedure and obtained from BIO Synthesis Inc. After specific DNA amplification, the samples were run in a 2% agars gel in TAE buffer with 4% of Ethidium Bromide. The samples were analyzed by fluorescence intensity. Relative quantities of RNA for Cox-1, Cox-2, iNOs and the "housekeeping gene," GAPDH, were determined by coupled reverse transcription (RT)-PCR. The primers used in each case were as follows: Cox-1 sense primer 5' CCCAGAGT-CATGAGTCGAAGGAG-3' (SEQ ID NO:17), antisense 5'-CAGGCGCATGAGTACTTCTCGG-3' (SEQ ID NO:18); Cox-2 sense primer 5'-GCAAATCCTTGCTGTTCCAATC-3' (SEQ ID NO:19), antisense primer 5'-GCAGAAGGCT-TCCCAGCTTTTG-3' (SEQ ID NO:20); iNOS sense primer 5'-CCCTTCCGAAGTTTCTGGCGACAGCGGC-3' (SEQ ID NO:21), antisense primer 5'-GGCTGTCAGAGC-CTCGTGGCTTTGG-3' (SEQ ID NO:22).

Example 4

Phenylmethimazole (C10) decreases LPS induced TLR4 signaling in Macrophages.

Macrophages in animals treated with LPS display a rapid induction of many genes which are regulators of the inflammatory response (M. A. Dobrovolskaia, et al., *Microbes Infect*, 4:903-14 (2002)). Cultured murine macrophages themselves, when treated with LPS, also display a rapid induction of many genes which are regulators of the inflammatory response (M. A. Dobrovolskaia, et al., *Microbes Infect*, 4:903-14 (2002)). In order to obtain a more complete understanding of how C10 may be preventing endotoxic shock in our animal model we chose to examine the affect of C10 on LPS stimulated genes in cultured murine macrophages in particular the murine macrophage cell line RAW 264.7. RAW 264.7 cells are a transformed functional macrophage cell line (W. C. Raschke, et al., *Cell*, 15:261-7 (1978)). The RAW 264.7 cell line has been a common and well accepted tool in the scientific literature used to further understand the affects of LPS on macrophages (V. Toshchakov, et al., *J Endotoxin Res*, 9:169-75 (2003); T. Horng, et al., *Nat Immunol*, 2:835-41 (2001); D. Schilling, et al., *J Immunol*, 169:5874-80 (2002); B. W. Jones, et al., *Ann Rheum Dis*, 60 Suppl 3:iii6-12 (2001)).

We studied the expression profile of genes which were deemed relevant in the current body of literature. Thus, we examined the effect of C10 on a multi functional and complex array of factors which included proinflammatory cytokines (IFN-β, IL-1β, TNF-α, IL-6, and IL-12), a CXC chemokine (IP-10), an enzyme which catalyzes the production of nitric oxide (iNOS), and a transcription factor (IRF-1), each of which have been reported to play a role in endotoxic shock (M. A. Dobrovolskaia, et al., *Microbes Infect*, 4:903-14, (2002)). Although the proinflammatory cytokines, IL-1β, TNF-α, IL-6, and IL-12, can be directly or indirectly induced by LPS signaling through TLR4 (M. A. Dobrovolskaia, et al., *Microbes Infect*, 4:903-14, (2002)) and certainly play a role in endotoxic shock (N. C. Riedemann, et al., *J Clin Invest*, 112:460-7, (2003)), a recent report identified IFN-β as a critical secondary effector, which is induced upon LPS activation of TLR4 signaling and contributes to mortality in a murine septic shock model (M. Karaghiosoff, et al., *Nat Immunol*, 4:471-7, (2003)). Due to evidence that IFN-β plays a critical role in the mortality of animals in the murine model of endotoxic shock (M. Karaghiosoff, et al., *Nat Immunol*, 4:471-7 (2003)), we examined the effects of C10 on LPS stimulation of IFN-β dependent mechanisms in greater detail.

Results

LPS induced genes are down regulated in cultured mouse macrophages: LPS can activate monocytes and macrophages to produce cytokines such as IFN-β, IL-10, TNF-α, IL-6, and IL-1.2 (M. A. Dobrovolskaia, et al., *Microbes Infect*, 4:903-14, (2002)) which act on either the macrophages/monocytes themselves or other target cells to regulate the inflammatory process which occurs in septic shock. Upon stimulation with LPS, macrophages can also produce CXC chemokines such as IP-10 which serve to further attract immune cells to a site of inflammation (K. M. Kopydlowski, et al., *J Immunol*, 163:1537-44 (1999)). Macrophages stimulated with LPS can also produce nitric oxide (NO) as a result of expression of the inducible nitric oxide synthase enzyme (iNOS) (C. Bogdan, *Nat Immunol*, 2:907-16 (2001)).

Figure 12A:
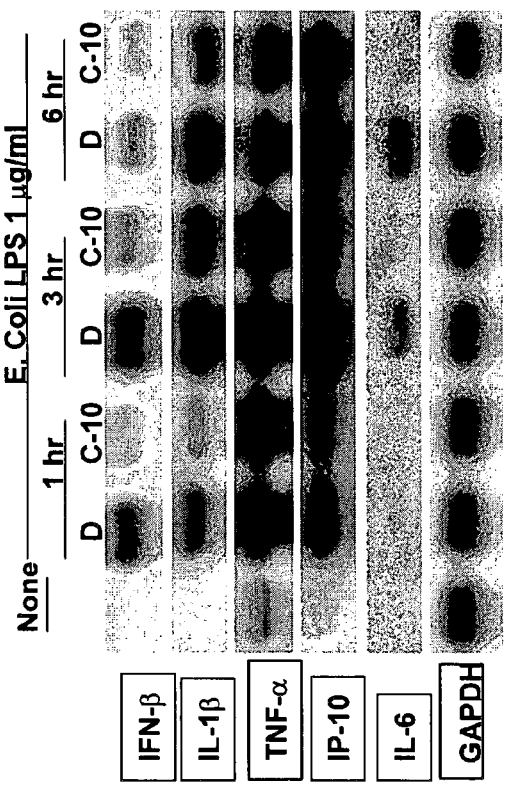
FIG. 12. C10 decreases LPS-increased IFN-β, IL-1β, TNF-α, IP-10, and IL-6 in RAW macrophages. RAW mouse macrophages were stimulated with LPS (1 μg/mL) for different times and RNA extracted for Northern analyses (A) or for real time quantitative polymerase chain reaction (PCR) (B). In (A), Northern analysis compared mRNA expression profiles in the presence of C10 or the vehicle control (DMSO). In the case of IFN-β, IL-1β, IP-10, and IL-6 there was a significant decrease evident in LPS-treated macrophages exposed to C10 by comparison to the DMSO control. This affect was less pronounced for TNF-α and may be attributed to a different TLR4 signaling mechanism of activation or insensitivity of the assay. In (B), using real-time PCR, mRNA levels were quantified by normalizing to an endogenous control (GAPDH) and comparing C10 treatment to the untreated (DMSO control). LPS-increased IFN-β gene expression was strongly decreased by C10 at the one hour time point (8 fold) and was subsequently maintained at a low level throughout the time course by C10. IL-6 was maximally decreased (16-fold) at the 3 hour time point; IL-1β was maximally decreased (11-fold) at 1 hr; and IL-12 p40 was not detectable until 4.5 hours but was strongly reduced at 6 hours (16 fold). TNF-α reduction was evident (4 fold) at 3 hours but showed no reduction at 1 or 6 hours. Taken together these data show that C10 effectively reduces the LPS dependent production of a broad range of proinflammatory cytokines in RAW macrophages and that the results in large measure duplicate those in the in vivo experiments depicted in FIG. 10 and Table 4.
Figure 13A:
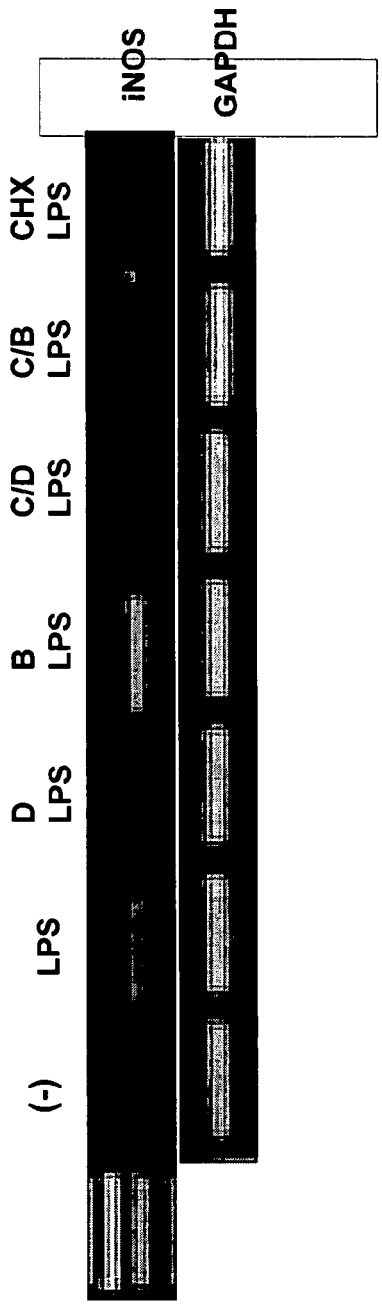
FIG. 13. C10 decreases LPS-increased iNOS mRNA and Stat1 activation in RAW macrophages. In (A), the RAW 264.7 cells were treated with LPS in the presence of C10 or control DMSO or another vehicle (Vehicle B) for 3 hours. In the LPS treatment with the DMSO control (lane 4) or with vehicle B only (lane 5), little or no iNOS reduction was detected when compared to LPS only (lane 3). In contrast, cells treated with C10 showed a strong reduction of LPS induced iNOS mRNA (lanes 6 and 7 vs. lanes 4 and 5). C10 had a strong inhibitory effect regardless of the vehicle used to dissolve the compound. Cyclohexamide treatment was performed to confirm that new protein synthesis is required for the LPS induction of iNOS mRNA and thus confirm that interferon signaling was responsible for the increase in iNOS not direct TLR4 signaling. This is consistent with the ability of C10 to reduce the LPS induced increase in IFN-β mRNA (FIG. 12). Phosphorylation of Stat1 is a key component for the transduction of the IFN-β signal to the nucleus to induce expression of iNOS and IP-10 in the mouse macrophage (Y. Ohmori, et al., *J Leukoc Biol*, 69:598-604 (2001)). In (B), C10 was able to reduce the level of LPS induced Stat1 phosphorylation in both cytoplasmic and nuclear fractions (lanes 5 and 9). No apparent affect was observed with DMSO control only (lanes 4 and 8). The cyclohexamide control (lane 10) indicates that LPS induced Stat 1 phosphorylation requires new protein synthesis, presumably IFN-β (V. Toshchakov, et al., *J Endotoxin Res*, 9:169-75 (2003)). Since C10 has a similar affect as does cyclohexamide (lanes 9 vs. 10), albeit by different mechanisms, C10 may be acting as an inhibitor of IFN-β synthesis as well. It would appear that C10 can reduce signal transduction through the IFN-β signal pathway by reducing LPS induced autocrine/paracrine increases of IFN-β available to initiate Stat1 activation.

Each of these factors that are considered to be important in the pathogenesis of septic shock are typically absent or found at extremely low levels in unstimulated RAW 264.7 macrophages as confirmed by northern analyses (FIG. 12A, lane 1) or by RT-PCR for iNOS (see FIG. 13A). Upon stimulation of mouse macrophages with LPS (1 ug/mL) for 1, 3, or 6 hours northern blot analysis revealed an mRNA expression profile in the presence of C10 or the vehicle control (DMSO) for IFN-β, IL-1β, TNF-α, IP-10, and IL-6 (FIG. 12A). In the case of each mRNA measured there was a difference between the DMSO lane and the C10 lane. This affect was less pronounced for TNF-α and may be attributed to the ability of LPS to increase TNF-α directly through the NF-κB signaling mechanism.

Figure 12B:
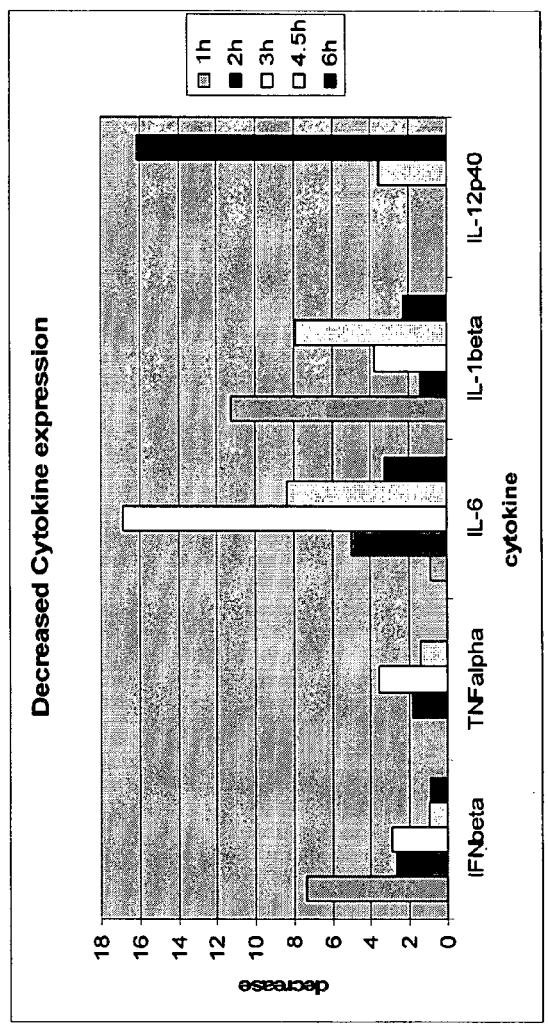

While northern blotting provides a reliable method for qualitative determination of gene expression levels, a more quantitative and sensitive method was required to accurately determine the affect of C10 on LPS induced cytokine gene expression in macrophages. Real time polymerase chain reaction (real-time PCR) was employed to obtain a quantitative profile of mRNA expression inhibition by C10. We measured IFN-β, TNF-α, IL-6, IL-1β, and IL12p40 gene expression after 1, 2, 3, 4.5, or 6 hour treatments with LPS (1 ug/mL) in the presence of DMSO control or C10 drug treatment (FIG. 12B). Gene expression levels were quantified by normalizing to an endogenous control (GAPDH) and normalizing to the untreated (DMSO control), which allowed the comparison of mRNA levels in C10 treated versus DMSO control treated, LPS stimulated macrophages (FIG. 12B).

The fold decrease in induced IFN-β gene expression was most strongly decreased at the one hour time point (8 fold) and was maintained at a low level throughout the time course (FIG. 12B). The reduction in the TNF-α increase induced by LPS was at a maximum at 3 hours (4 fold) (FIG. 12B) but showed no reduction at 1 or 6 hours when LPS-increased TNF-α levels were low. The LPS-induced increase in IL-6 was maximally reduced at the 3 hour time point at greater than a 16 fold reduction (FIG. 12B). LPS induced IL-1β was maximally decreased at 1 hour (11 fold) (FIG. 12B). IL-12 p40 was not detectable until 4 to 5 hours but was strongly reduced at 6 hours (16 fold) (FIG. 12B). Taken together these real time PCR data show that C10 effectively reduces the LPS dependant production of a broad range of proinflammatory cytokines in monocyte/macrophages classically used to study LPS action.

In macrophages NO production occurs as a result of LPS induction of iNOS (C. Bogdan, *Nat Immunol*, 2:907-16 (2001)) and is a process that depends on autocrine signaling by IFN-β. We used standard reverse transcriptase polymerase chain reaction to detect the inhibition of LPS induced iNOS transcription in the presence of C10 (FIG. 13A). The RAW 264.7 cells were treated with LPS in the presence of C10, its vehicle control, DMSO, or another excipient vehicle (compound B; see Table 8) for 3 hours. Table 8 establishes that C10 is effective in vivo in the mouse toxic shock model and in FRTL-5 cell assays in vitro when solubilized in water in the presence of the compound B excipient, i.e., water soluble forms of C10 are effective in both in vivo and in vitro just as C10 in DMSO. In the presence of DMSO control (FIG. 13A, lane 4) or vehicle B only (FIG. 13A, lane 5) little or no iNOS reduction was detected respectively when compared to LPS only (FIG. 13A lane 3). Cells treated with C10 showed a strong reduction of LPS induced iNOS mRNA (FIG. 13A lanes 6 and 7 vs. lanes 4 and 5). Because a modest affect was observed in the presence of DMSO control only (FIG. 13A lane 4) C10 was dissolved in another vehicle called Solution B, which had no affect alone (FIG. 13A lane 5). In sum, C10 had a strong inhibitory effect on iNOS RNA levels regardless of the vehicle used to dissolve the compound.

TABLE 8

C10 can improve toxic shock whether in DMSO or solubilized in excipient (Compound B) making it water soluble; excipient is also effective in
C-10 Use in DMSO or Excipient in Mouse Models and in vitro Assays

| Experiment | Animals | C10 Dosage | Route of Admin | # days | Survival % of Control |
|---|---|---|---|---|---|
| Colitis model | 10 | 0.1 mg/kg | Ip freshly diluted in DMSO | 14 | 100% |
| Colitis model | 10 | 0.1 mg/kg | Oral stored in excipient 1 week | 14 | 100% |
| Toxic Shock model | 10 | 1 mg/kg | Ip freshly diluted in DMSO | 1.5 | 100% |
| Toxic Shock model | 10 | 1 mg/kg | Oral stored in excipient 1 week | 1.5 | 100% |
| Toxic Shock model | 10 | 1 mg/kg | Oral diluted & stored in excipient 6 wks | 1.5 | 100% |
| Toxic Shock model | 10 | 1 mg/kg | Ip diluted & stored in DMSO 1 wk | 1.5 | 0% |

| Assay | Replicates | C10 Conc. | % TLR3 Inhibition vs Control |
|---|---|---|---|
| dsRNA increased TLR3 RNA | 3 | 0.1 mM in DMSO | 90% |
| IFN-β increased TLR3 RNA | 3 | 0.1 mM in Excip. | 90% |

Table 8 shows that C10 in excipient is as good as C10 in DMSO in vitro and in vivo. In the studies described in Table 5, C10 was formulated in DMSO and administered i.p. DMSO was used due to the low solubility of C10 in aqueous environments but can have well documented independent effects (M. S. Ivanovic, et al., *Toxicology Letters*, 147:153-159 (2004))]. In addition, C10 solubilized in DMSO and diluted to a working concentration is not stable for prolonged periods of time. To circumvent these issues, we used a proprietary cyclodextrin (CD) excipient that is approved by the FDA for use in humans to make an aqueous formulation of C10. C10 stored in the aqueous preparation for 6 weeks prior to use was equally effective in decreasing TLR3 and IFN-β-mRNA levels in thyrocytes by comparison to solutions with DMSO. In a test using LPS-induced toxic shock, oral excipient-solubilized C10, stored in diluted form at 4° C. for 8 weeks, was as effective in preventing death as was freshly made C10 i.p. in DMSO at the same 1 mg/kg dose. Solutions of C10 diluted in DMSO and stored in diluted form at either 4° C. or −70° C. were inactive in vitro or in vivo.

A cyclohexamide treatment was done (FIG. 13A, CHX) to confirm that new protein synthesis is required for the LPS induction of iNOS mRNA and support that Type 1 interferon signaling might be responsible for the increase in iNOS, rather than direct effects of TLR4 signaling. Effectively we considered whether C10 might be acting via a mechanism that required new protein synthesis, i.e. the synthesis of IFN-β. This is the case as shown by a loss of LPS increased iNOS equivalent to that of C10 in the presence of cyclohexamide (FIG. 13A, CHX) We have already seen that C10 can reduce the LPS induced transcription of IFN-β mRNA (FIGS. 12A and B). Previous reports have found that LPS induction of iNOS in mouse macrophages can occur via binding of autocrine IFN-β to its receptor and subsequent Stat1 activation (D. Schilling, et al., *J Immunol*, 169:5874-80, (2002)).

Figure 13B:
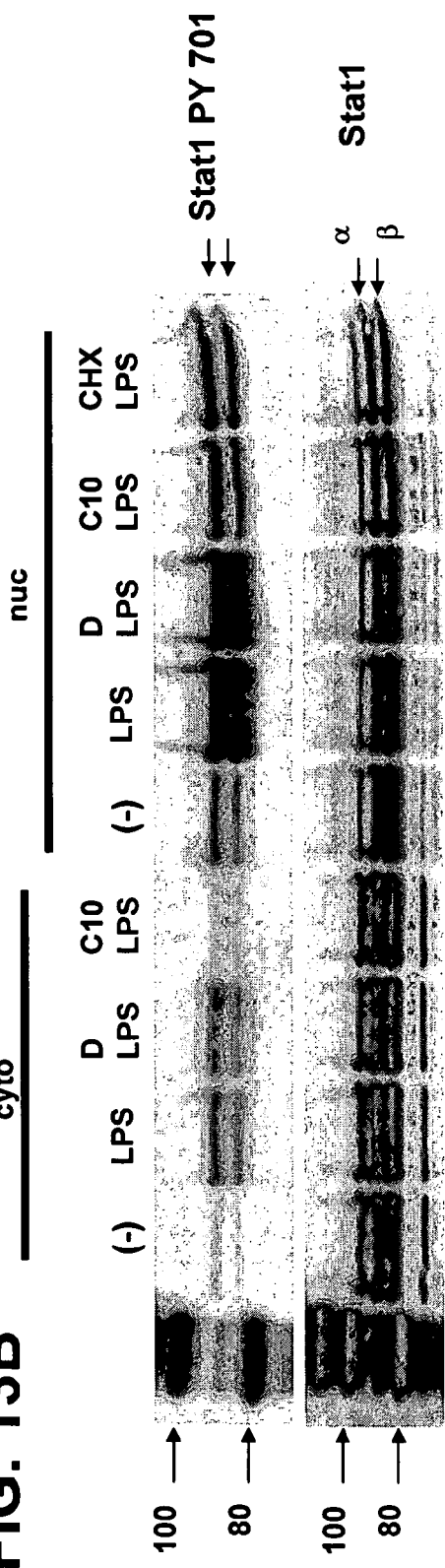

C10 inhibits the LPS induced activation of Stat1 in cultured macrophages: The important role of type i interferons in LPS induced septic shock was recently demonstrated in mouse models (M. Karaghiosoff, et al., *Nat Immunol*, 4:471-7 (2003)). We have already shown in FIGS. 12A and 12B that LPS induced increases of IFN-β (a type I interferon) mRNA levels are strongly inhibited by C10. It is has been shown that binding of IFN-β to the type I interferon receptor results in phosphorylation of Stat1 as a key component for the transduction of a signal to the nucleus to induce expression of iNOS and IP-10 in the mouse macrophage (Y. Ohmori, et al., *J Leukoc Biol*, 69:598-604 (2001)). C10 was able to reduce the level of LPS induced Stat1 phosphorylation in both cytoplasmic and nuclear fractions (FIG. 13B lanes 5 and 9). No apparent affect was observed with the DMSO control only (FIG. 13B lanes 4 and 8). The cyclohexamide control (FIG. 13B, lane 10) indicates that LPS induced Stat1 phosphorylation requires new protein synthesis, presumably IFN-β (V. Toshchakov, et al., *J Endotoxin Res*, 9:169-75, (2003)). C10 had a similar affect as cyclohexamide (FIG. 13B, lanes 9 vs. 10) indicating that C10 may be acting as an inhibitor of IFN-β synthesis as well. When the data in FIGS. 12A and 12B, showing reduced IFN-β mRNA and protein, are taken in combination with the data in FIG. 13B showing reduced Stat I phosphorylation the following hypothesis can be stated. C10 can reduce signal transduction through the IFN-β signal pathway by reducing the LPS induced autocrine/paracrine action of IFN-β, thereby decreasing Stat1 activation.

Figure 14A:
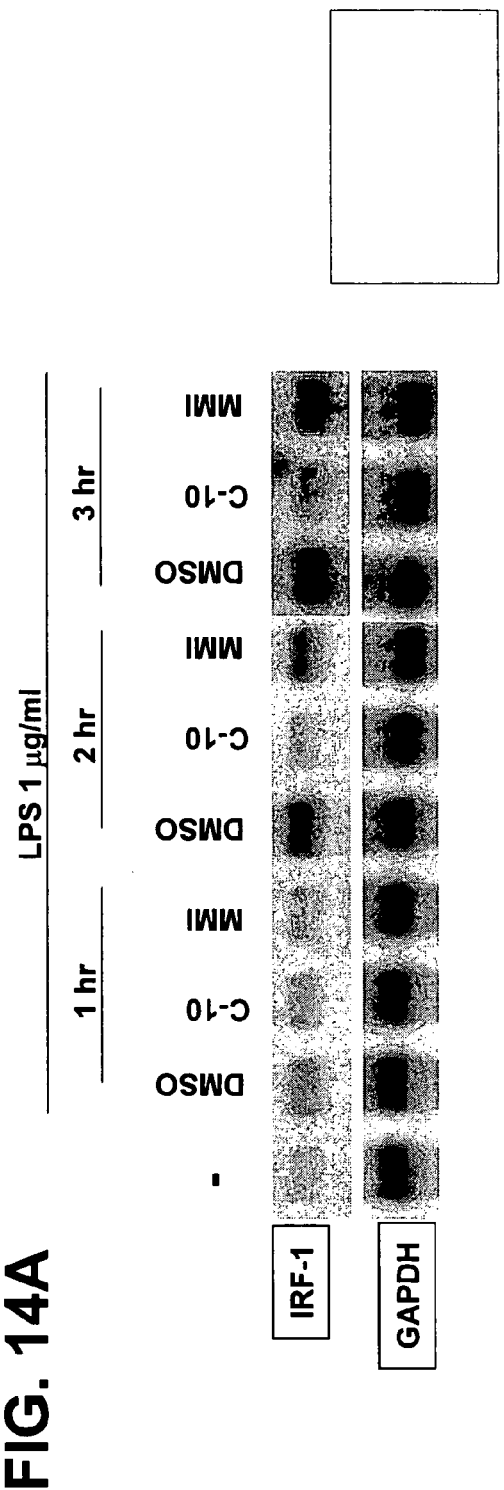
FIG. 14. C10 down regulates LPS-increased IRF-1 RNA levels and IRF-1 DNA binding to ISRE elements in RAW macrophages. (A) LPS increased IRF-1 mRNA levels, as measured by northern analysis when macrophages were treated with LPS (1 μg/mL) for periods of 1, 2, or 3 hour. C10 caused a strong reduction in IRF-1mRNA at 2 and 3 hour. Methimazole (MMI) has a significantly less impressive effect but also decreases IRF-1 mRNA levels. In order for IRF-1 to enhance gene transcription it must bind to cis-DNA elements located on the target gene. Using the Mx ISRE (IRF-1 binding site) and EMSA (B), the effect of C10 on LPS induced IRF-1 binding to the MxISRE element was measured. Two complexes were induced upon LPS stimulation (1 μg/mL) for 2 hours when compared to extracts from untreated cells (lane 2, 5, 8 vs. lane 1). A concentration dependent reduction was observed with both C10 (lanes 3 and 4) and methimazole (MMI) treatment (lanes 6 and 7). Specificity was observed upon incubation of extracts with unlabeled MxISRE probe (self, lane 9). Complexes were identified using super shift studies in which nuclear extract was incubated with antibody directed toward either IRF-1 (lane 11) or IRF-3 (lane 12). When incubated with IRF-1 antibody there was a supershift that identified the complex as an IRF-1 containing complex (lane 11). No supershift was observed using two different IRF-3 antibodies (lane 12 Ab.#1; data not shown for Ab. #2). Interestingly, when the extracts were preincubated with unlabeled probe against the human IFN-β IRF-1 binding site, IRF-1 binding to the MxISRE probe was also eliminated (lane 10), indicating that LPS induced IRF-1 in these extracts would also bind to the human IFN-β IRF-1/ISRE binding element.

C10 down regulates IRF-1 and IRF-1 DNA binding in LPS treated macrophages: IRF-1 is a transcription factor which is induced upon LPS stimulation of macrophages through a Stat1 dependent mechanism (Y. Ohmori, et al., *J Leukoc Biol*, 69:598-604 (2001)). Therefore IRF-1 provides another example of a response that may be affected by an inhibitor of LPS induced IFN-β signaling. Unlike other molecules studied thus far, IRF-1 acts as a transcription factor to directly bind to DNA to enhance transcription of other genes such as iNOS (R. Kamijo, et al., *Science*, 263:1612-5, (1994)). In macrophages treated with LPS, IRF-1 is required for the transcriptional control of the iNOS gene (R. Kamijo, et al., *Science*, 263:1612-5 (1994)). Macrophages were treated with LPS (1 ug/mL) for 1, 2, or 3 hours and longer in the presence of C10, a DMSO control, or a commercially available derivative of C10 (MMI) (FIG. 14A). Typical LPS induction for each time point is observed in each LPS plus DMSO lane (FIG. 14A, lanes 2, 5, 8). LPS increased IRF-1 RNA is small at 1 hr but becomes maximal by 3 in the presence of DMSO, the C10 solvent (FIG. 14A, lane 8). A strong reduction in LPS-increased IRF-1 mRNA is still observed upon treatment with C10 at 2 and 3 hours (FIG. 14A, lanes 6 and 9 vs 5 and 8, respectively). The decrease by C10 is much greater than by MMI (FIG. 14A, lanes 6 and 9 vs 7 and 10, respectively).

In order for IRF-1 to enhance gene transcription it must bind to cis-DNA elements located on the target gene. iNOS is an example of a target gene that contains an IRF-1 cis-binding element (R. Kamijo, et al., *Science*, 263:1612-5 (1994)). Several other IRF-1 target genes exist such as the interferon inducible MX gene which codes for the antiviral Mx protein (D. Damino, et al., *Curr Opin Cell Biol*, 13:454-60 (2001)). The MX promoter has been shown to contain strong IRF-1 binding elements (C. E. Grant, et al., *Nucleic Acids Res*, 28:4790-9 (2000)). We used the Mx ISRE (IRF-1 binding site) and EMSA to measure the effect of C10 on LPS induced IRF-1 binding to the MxISRE element.

Figure 14B:
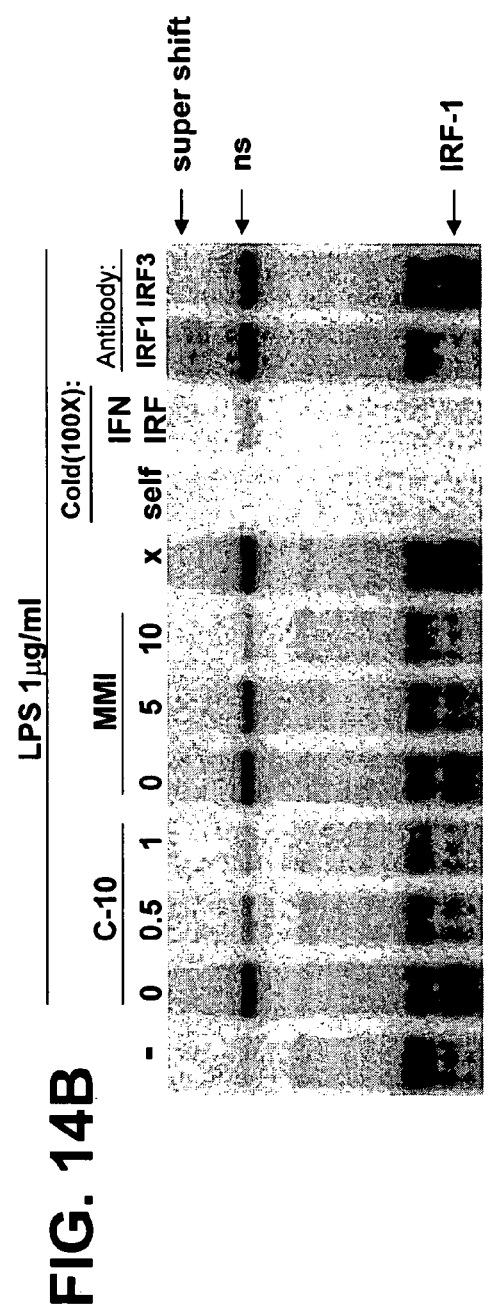
Figure 15B:
FIG. 15. C10 reduces vascular inflammation in ApoE−/− mice fed a high fat diet. C10 was given orally (1 mg/kg) every other day to mice for 8 weeks. Control mice received DMSO alone. Mice were sacrificed at 8 weeks and histopathology examined in different tissues as determined by hematoxylin and eosin staining. Sections of the base of the aorta in C10 treated (Panel A) and untreated mice (Panel B) are presented as well as sections of the coronary artery vasculature in C10 treated (Panel C) and untreated mice (Panel D). Significant improvement in both is evident by the decrease in the extent of lesion and vessel patency in Panel A vs. B at the base of the aorta and the patency vs. occlusion in coronary arteries in Panel C vs. D. In Panel B, the arrows show the severity of lesions in the base of the aorta is markedly greater in untreated mice by comparison to C10 treated mice (Panel A). Similarly in Panel D, the picture is representative of long sections of the coronary arteries which were nearly fully occluded with lesions containing foam cells in untreated mice whereas in C10 treated mice (shown in Panel C), coronary arteries were largely unobstructed. In short, C10 clearly reduced extent of disease in multiple sections as illustrated here. Even more dramatic effects were seen in vessels in the myocardium when they are compared in C10 treated and untreated mice. First, even where lesions were evident the lumens of vessels remained patent. Moreover, vessels within the myocardium were obstructed by lesions containing foam cells in the absence of C10 but patent and nearly free of lesions containing foam cells in the mice treated with C10. Sections of the coronary arteries from untreated mice were immunstained with anti-TLR4 anti-VCAM-1, anti-ICAM-1. VCAM-1 was overexpressed in the lesion but also in the endothelial layer opposite the lesion area. TLR4 was more expressed in the area opposite the lesion and, surprisingly, throughout the smooth muscle layer surrounding the vessel, particularly opposite the plaque. TLR4 was also expressed in the myocardial musculature. The expression suggests a widespread inflammatory response wherein TLR4 positive cells abound in the macrophages infiltrating the area or in other cells, i.e. interstitial cells around the myocardial sheaths. These data were similar in human disease illustrated below. C10 attenuated expression of both as noted in Table 15. Data are representative of multiple slides taken from multiple animals.
Figure 15D:
Figure 15A:
Figure 15C:

Two complexes were induced upon LPS stimulation (1 ug/mL) for 2 hours when compared to untreated (FIG. 14B, lanes 2, 5, and 8 vs 1). A dose dependent reduction was observed in samples from both C10 (FIG. 14B, lanes 3 and 4) and MMI (FIG. 14B, lanes 6 and 7) treated cells. Specificity was observed upon incubation of extracts with unlabeled MxISRE probe (FIG. 14B, lane 9). Complexes were identified using super shift studies in which nuclear extract was incubated with antibody directed toward either IRF-1 or IRF-3 (FIG. 14B, lanes 11 and 12, respectively). When incubated with IRF-1 antibody there was an observed supershift identifying that complex as an IRF-1 containing complex (FIG. 14B, lane 11) No supershift was observed using two different IRF-3 antibodies (FIG. 14B, lane 12 Ab#1; the Ab#2 data are not shown) indicating no IRF-3 in the complex. Interestingly when the extracts were preincubated with unlabeled probe against the human IFN-β IRF-1 binding element, which acts as a competitive inhibitor, the IRF-1 complex was also eliminated (FIG. 14, lane 10). These last data indicated that LPS induced IRF-1 in these extracts would also bind to the human IFN-β IRF-1 binding element.

Relevance to Endotoxic Shock in Example 3: Endotoxic Shock Protected Mice Have Reduced Tissue Levels of Activated Stat1

It was recently demonstrated that Stat1 null animals show an approximately 50% enhanced survival rate when challenged with a lethal dose of LPS (M. Karaghiosoff, et al., *Nat Immunol*, 4:471-7 (2003)). In the same study IFN-β null mice which were challenged with a lethal LPS dose showed a 100% enhancement of survival (M. Karaghiosoff, et al., *Nat Immunol*, 4:471-7 (2003)). Therefore blocking parts of the IFN-β signal pathway is not as effective as blocking the pathway completely, i.e., by preventing the ligand receptor interaction or blocking the initial signal induced by the ligand-receptor interaction. In order to determine if LPS induced IFN-β signaling in vivo might be attenuated by C10 treatment, we examined protein phosphorylation levels of Stat1 in whole tissue lysates from mice in the experiments of Table 5. Both kidney and lung tissues, as well as mouse macrophages, displayed detectable levels of activated Stat1 protein in mice which were not protected from shock (FIG. 8 lanes 2 and 5 respectively) these levels were reduced to basal in mice which were protected from LPS induced shock by treatment with C10 (FIG. 8, lanes 3 and 6 respectively).

In summary these data in RAW 264.7 indicate that C10 has a strong inhibitory effect on multiple factors that have been shown to be involved in endotoxic shock. These data are important to understand the mechanisms of C10 protection in the murine model of endotoxic shock. C10 appears to be suppressing the induction of very early genes such as IFN-β and IL-1β, whose induction is a direct result of LPS dependent TLR4 signaling. TNF-α is also rapidly induced by direct TLR4 signaling, however the effect of C10 on TNF-α is negligible at 1 hour, indicating that C10 does not affect all aspects of TLR 4 signaling equally. This is particularly interesting to contrast with the in vivo data of Example 3. Thus, in vivo, C10 did decrease TNF-αRNA levels and protein but it seemed possible this reflected a secondary action through IFN-β or the possibility that multiple interacting cell types were affected by the C10 primary action on nonimmune cells. It is nevertheless evident that LPS induced IFN-β is an attractive therapeutic target due to its multiple down stream affects which stem from the activation of Stat1 which is required in macrophages for the transcriptional upregulation of IRF-1, iNOS, and IP-10. The Stat1 reduction in the macrophages and in nonimmune cells in tissues can partially explain the reduction of the genes in the mouse tissues of Example 3.

Materials and Methods

Cell culture: The mouse macrophage cell line RAW 264.7 (TIB-71) was obtained from the American Type Culture Collection (Manassas, Va.). RAW 264.7 were cultured in DMEM supplemented with glutamine and 10% FBS.

RNA isolation and Northern blot analysis: Northern blot analysis was used to characterize the mRNA levels of key inflammatory mediators involved in endotoxic shock (M. A. Dobrovolskaia, et al., *Microbes Infect* 4:903-14, (2002)). RNA was extracted using Trizol® (Invitrogen, Carlsbad, Calif.) and subjected to Northern blot analysis in a manner similar to that described previously (K. Suzuki, et al., *Proc Natl Acad Sci USA*, 96:2285-90 (1999)). The G3PDH cDNA was from Clontech (Palo Alto, Calif.). The mTNF-α probe was excised from pORF9-mTNF-α (Invivogen, San Diego, Calif.). Other probe sequences were synthesized by RT-PCR (K. Suzuki, et al., *Proc Natl Acad Sci USA*, 96:2285-90 (1999)) using the following cDNA specific primers: mIP-10, 5'CCATCAGCACCATGAACCCAAGTCCTGCCG3' (SEQ ID NO:23) and 5'GGACGTCCTCCTCATCGTCGACTA- CACTGG3' (469 bp) (SEQ ID NO:24); mIL-1β5'CTCATCTGGGATCCTCTCCAGCCAAGCTTC3' (SEQ ID NO:25) and 5'CCATGGTTTCTTGTGACCCT- GAGCGACCTG 3' (1006 bp) (SEQ ID NO:26); mIL-6, 5' CCAGTTGCCTTCTTGGGACTGATGCTGGTG 3' (SEQ ID NO:27) and 5'GTCCTTAGCCACTCCTTCTGT- GACTCCAGC 3' (530 bp) (SEQ ID NO:28); mIFN-β, 5' AAGATCATTCTCACTGCAGCC 3' (SEQ ID NO:29) and 5' TGAAGACTTCTGCTCGGACC 3' (586 bp) (SEQ ID NO:30). The IRF-1 probe was prepared as described previously (K. Suzuki, et al., *Proc Natl Acad Sci USA*, 96:2285-90 (1999)).

Real time PCR: Total RNA was isolated using Trizol® (Invitrogen, Carlsbad, Calif.). In order to eliminate any carry over of genomic DNA, total RNA was treated with DNAse using the DNA-free™ kit (Ambion, Austin, Tex.). cDNA was synthesized from total RNA using the Advantage® RT for PCR (BD Biosciences, Palo Alto, Calif.). Briefly, 1 µg of total RNA was used in a 50 µl reaction mixture with the random hexamer primer. Real time primers and FRET probes for TNF-α IL-6, IL-12p40, and GAPDH, were purchased from (Biosource, Camarillo, Calif.) and were used according to the manufacturer's instructions. Briefly, 2.5 µl of cDNA template was used in a 25 µl real time PCR reaction with ABI Taqman® Universal Master Mix (Applied Biosystems, Branchburg, N.J.). The IFN-β reactions were done with Sybr® green dye using the Quantitect Sybr® Green kit according to the manufacturer's instructions using 1 µl of cDNA template in a 25 µl reaction volume. Primers used for IFN-β were as follows 5' ATGAGTGGTGGTTGCAGGC 3' (SEQ ID NO:31) and 5' TGACCTTTCAAATGCAGTAGATTCA 3' (SEQ ID NO:32). Thermal cycling conditions consisted of 10 min at 95° C. followed by 40 cycles of 15 at 95° C. and 1 min at 60° C. in a Bio-Rad iCycler iQ Real-Time PCR Detection System (Bio-Rad, Hercules, Calif.).

Threshold cycle (Ct) values were calculated with the iCycler iQ software (Bio-Rad, Hercules, Calif.). A standard curve for each gene was prepared from a 10-fold dilution series of the corresponding cDNA. The standard curves were plotted in terms of number of cDNA molecules (copy number) vs. threshold cycle (Ct). The software was then used to calculate copy number of starting cDNA in each sample based on the standard curve for the gene of interest. Copy number for each gene was then normalized against GAPDH. We determined the affect of C10 on LPS induced mRNA level, given as the n-fold decrease in transcription for the gene of interest by normalization to the RNA level determined from the standard curve for GAPDH and relative to expression levels before LPS stimulation (basal levels).

Standard reverse transcriptase PCR for INOS: RNA was isolated as described above and treated with DNAse a described above. One fig of DNA free RNA was then reverse transcribed with the Advantage® RT-for PCR kit (BD Biosciences, Palo Alto, Calif.) in a total volume of 20 µl. Five µl of cDNA was then amplified using ExTaq™ DNA polymerase (Takara, Madison, Wis.) in a reaction volume of 25 µl. Thermal cycling conditions consisted of 94° C. for 3 min followed by 35 cycles of 94° C. 10 s, 58° C. 30 s, and 72° C. for 45 s. Primer sequences were the same as in example 3. Twenty µl of each reaction was resolved on a 2% agarose gel and ethidium bromide stained.

Immunoblot analysis of RAW 264.7 and mouse tissues: Nuclear and cytoplasmic extracts for RAW cells were prepared using NE-PER® extraction reagents (Pierce, Rockford, Ill.) in the presence of a protease inhibitor mixture (PMSF, leupeptin, and pepstatin A). Mouse tissues were homogenized in 1xPBS, homogenate was pelleted by centrifugation and PBS removed prior to lysis in lysis buffer (150 mM NaCl, 1% IGE-PAL CA 630, and 50 mM Tris-HCl, pH 8.0) in the presence of a protease inhibitor mixture (PMSF, leupeptin, and pepstatin A). Twenty five µg of nuclear cytoplasmic, or whole tissue lysate were resolved on 3-8% Tris-Acetate PAGE gels under denaturing conditions using the NuPAGE Bis-Tris System (Invitrogen Life Technologies, Carlsbad, Calif.), then transferred to nitrocellulose membranes, which were probed with rabbit anti-human phospho-Stat1 (Tyr 701) Ab (9171; Cell Signaling Technology, Beverly, Mass.) for detection of activated Stat-1 then stripped and reprobed with rabbit anti-human Stat1 p84/p91 (E-23) X Ab (sc-346X; Santa Cruz Biotechnology, Inc., Santa Cruz, Calif.) for detection of unactivated Stat1 as a loading control. Binding of HRP-conjugated goat anti-rabbit Ab (sc-2054; Santa Cruz Biotechnology, Inc., Santa Cruz, Calif.) was detected using the ECLplus Western Blotting Detection System (Amersham Biosciences, Piscataway, N.J.).

EMSA in RAW 264.7 cells: Nuclear extracts were prepared using NE-PER® extraction reagents (Pierce Chemical Co.; Rockford, Ill.) in the presence of a protease inhibitor cocktail (PMSF, Leupeptin, Pepstatin-A). Oligonucleotide sense strand probe sequences were as follows MxISRE probe: 5' CGGAGAAACGAAACTAAGATC-3' (SEQ ID NO:33) and. the IFN-β-IRF site probe: 5'-GACATAGGAAAACT-GAAAGGGAGAAGTGAAAGTGGGAA-3' (SEQ ID NO:34). Oligonucleotides (sense and antisense strands) (Biosynthesis Inc.; Lewisville, Tex.) were annealed and the resultant double stranded oligonucleotides precipitated, then end-labeled with $^{32}$P-ATP using T4 polynucleotide kinase enzyme. Binding reactions (20 min., room temperature) included $^{32}$P-labeled probe (activity 100,000 cpm), 5 µg RAW nuclear extract, 1 µg poly (dI-dC), 1 mM DTT, 10% glycerol and 1x binding buffer. Binding buffer (10x) for EMSA was 100 mM Tris-HCL (pH 7.5), 500 mM NaCl, 50 mM MgCl$_2$, 10 mM EDTA (pH 8.0). In competition studies, nuclear extracts were incubated with 100 fold molar excess of unlabeled double stranded oligonucleotide. In supershift studies, nuclear extracts were incubated with 2 µg of appropriate antibodies to IRF-1 (H-205; Santa Cruz Biotechnology, Santa Cruz, Calif.) or IRF-3 (Active Motif, Carlsbad, Calif.). After the incubations, reaction mixtures were electrophoresed (160V, room temperature) on 5% non-denaturing polyacrylamide gels containing 5% glycerol in 1xTBE (50 mM Tris, 50 mM boric acid, and 1 mM EDTA). Gels were dried and autoradiographed.

Example 5

C10 protects horses from Endotoxic shock induced by LPS or peritonitis.

Studies in mice can be argued to be nonrelevant to humans. Often large animals with more close phylogenetic relationships to humans and with diseases similar to those in humans are desired as experimental models. Endotoxemia in horses is one such model of endotoxic shock in humans. Endotoxemia in horses is caused by the biological consequences of endotoxins in blood. Endotoxins are structural components of the walls of gram negative bacteria, the main representative molecule being lipopolysaccharide (LPS). LPS can be released from the gut to its surrounding environment, i.e. the peritoneal cavity and bloodstream. Once LPS reaches either, it can interact with mononuclear phagocytic cells. This interaction increases the sensitivity of those cells to endotoxins by 1000-fold and induces an excessive response of an inflammatory cascade including activation of arachidonic acid, activation of the TLR4 signal pathway, and activation of a coagulation cascade. The end result is the production of pro-inflammatory mediators with development of circulatory shock, e.g., TNF-α.

The TNF-α synthesis and release, mediated through the TLR4 signal, is associated with the synthesis of other inflammatory mediators, including Interleukins 1, (IL-1) Interleukin 6 (IL-6), prostaglandins and tissue factors such as acute phase protein (D. D. Morris, *J Vet Intern Med*, 5:167-81 (1991); D. L. Hawkins, et al., *Vet Immunol Immunopathol*, 66:1-10 (1998); H. Kato, et al., *Vet Immunol Immunopathol*, 48:221-31 (1995)). Serum concentration of IL-6 activity begins to increase approximately 1 hour after serum TNF-α and peaks between 3 to 6 hours after onset of endotoxemia. IL-6 and IL-1 mediate the endotoxin-induced febrile response and are responsible for the inflammatory cascade, which constitutes the acute phase response.

Superoxide radicals can react with endogenous nitric oxide (NO), resulting in the production of peroxynitrite anions, which are potent oxidizing agents (C. Gonzalez, et al., *Biochem Biophys Res Commun*, 186:150-6 (1992); B. Zingarelli, et al., *Br J Pharmacol*, 120:259-67 (1997); C. Gagnon, et al., *FEBS Lett*, 431:107-10, (1998)). Additionally, nitric oxide, is a well known mediator of endotoxic shock tissue injury in animal and human (A. Petros, et al., *Cardiovasc Res*, 28:34-9 (1994); P. Wang, et al., *Arch Surg*, 129:1137-43 (1994); J. A. Avontuur, et al., *Circ Res*, 76:418-25 (1995); C. Szabo, et al., *Proc Biol Sci*, 253:233-8 (1993); C. Szabo, *Ann N Y Acad Sci*, 851:422-5 (1998)). LPS is a potent inducer of inducible nitric oxide synthase (iNOS) (P. P. Wolkow, *Inflamm Res*, 47:152-66 (1998)) which catalyzes the synthesis of large amounts of NO and peroxynitrite, which, among other factors, are responsible for the late phase of hypotension, vasospasm, cellular suffocation, apoptosis, lactic acidosis and multi-organ failure in endotoxic shock in horses as well as another animals and humans (P. P. Wolkow, *Inflamm Res*, 47:152-66 (1998)). Indeed, experimental and clinical use of NOS inhibitors, which do not differentiate clearly between constitutive endothelial NOS (ceNOS) and iNOS, prevents LPS-induced hypotension (P. P. Wolkow, *Inflamm Res*, 47:152-66 (1998)).

The intestinal lumen of the horse usually contains large amount of endotoxins. It has been estimated that ceacum and ventral colon of a normal horse contains more than 2 grams of endotoxin, which is restricted to the intestinal lumen by an efficient mucosal barrier. Thus, any pathology that damages the mucosal barrier will allow the endotoxins to reach the peritoneal cavity and the blood (D. D. Morris, *J Vet Intern Med*, 5:167-81 (1991); J. N. Moore, et al., *Can J Comp Med*, 45:330-2 (1981); D. Chakravortty, et al., *Microbiol Immunol*, 43:527-33 (1999); J. Drabkova, *Cesk Epidemiol Mikrobiol Immunol* 42:102-5, (1992)). Consequently, horses with ischemic intestines experience the deleterious effects of endotoxins before surgery and several days after the ischemic intestine has been removed. The most common clinical findings in affected animals include: alteration in mucous membrane color with the presence of a "toxic line," prolongation of the capillary refill time, increased heart and respiratory rates, reduced borborygmi, fever, hemoconcentration, neutropenia, collapse and abdominal pain.

Using a mouse model of inflammatory bowel disease and colitis as well as endotoxic shock, C-10 exhibited suppressive action on interferon inducibles genes, IP-10, IRF-1, and MCP-1, a multiplicity of pro-inflammatory cytokine genes (TNF-α, IL-1, IL-6) as well as IRF-1 dependent genes (COX-2, iNOS).

C-10 inhibits IFN-β and IRF-1 gene expression and/or secretion in vitro in multiple cell systems (thyrocytes, macrophages, human aortic vascular endothelial cells) and in vivo in mouse models of colitis and toxic shock. Further, our results in mice showed (Table 5) that mice were 100% protected against LPS-induced toxic shock and death when C10 was administered as one single dose before LPS injection. In Example 3, C-10 was able to inhibit pro-inflammatory cytokines, adhesion molecules, chemoattractant proteins, IRF-1, IFN-β, iNOS and COX-2 in the target organs, as well as circulating inflammatory mediators in the LPS-treated animals associated with the signs and symptoms of endotoxic shock, i.e. the hypotension, multi-systemic failure and disseminated intravascular coagulation.

Based on the foregoing data and background, we examined the ability of C-10 to act as an effective therapeutic (i) on toxic shock in a LPS induced horse model of endotoxic-shock and (ii) in a horse model of peritonitis induced either by injecting foreign endotoxin-laden caecal material from the gut into the peritoneal cavity or by abdominal operative procedures to correct lesions causing peritonitis.

Results

Establishment of clinical parameters of endotoxemia in horses: We classified endotoxemia clinically, based on analyses of symptoms and signs in the LPS treated group. Further, we took into account symptoms at different stages: early symptoms, the collapse or shock stage, and the normalization stage. In the early stage of endotoxemia (0:15, 0:30 to 1:00 hr after LPS injection), we observed abundant sweating, excitation, weak muscular tone, abdominal pain, diarrhea with watery deposits. We also observed nasal discharge, significant respiratory distress (dyspnea), increased respiratory rate (tachypnea), and increased cardiac rate (tachycardia). The pulse was weak and undetectable and the capillary refill time increased. Thirty (30) minutes after endotoxin injection, all horses showed progressive decreases in blood pressure until the animal developed a systolic pressure under 100 mmHg and a diastolic pressure under 70 mmHg. At this time all horses became hypotensive and hypoxemic with strong cyanosis. The increase of capillary refill time reached a peak but was still significant during the time of circulatory shock, from 1 to 6 hours.

Oxygen saturation in blood (% $sPO_2$) was decreased coincident with the shock, causing the mucosal membranes to become strongly cyanotic; total collapse followed shortly. At the time of shock the digestive system was characterized by suppression of borborygmi, suppression of intestinal ileocecal activity, abdominal pain, colic, intestinal obstruction, strangulation and alteration of the mucosal barrier. Temperature increased at 6 hours and was normalized at 24 hours.

Laboratory studies detected hyperglycemia at 3 hours that was normalized at 24 hours. Leucopenia developed at 3 hours and normalized at 6 hours. Creatinine and urea in the blood were increased several fold at 24 hours and normalized at 1 week post LPS inoculation. These results showed that endotoxic shock induced transient acute renal failure. An increased red cell concentration was measured, likely due to the loss of water from blood and its presence as edema in some organs.

Finally, 24 hours after LPS injection, there was normalization of the blood pressure and normal $sPO_2$, although mucosal membranes remained hyperemic and cyanotic, suggesting that hypoxemia and tissue perfusion had not recovered.

These changes are illustrated in Tables 9-13 which show effects of LPS to cause increased respiratory distress, diarrhea, and collapse as well as the ability of C10 to prevent these very nearly in entirety.

As shown in Tables 9 and 10, C10 protects horses from Endotoxic shock induced by LPS. Horses were treated with a sub-lethal dose of LPS (10 μg/kg) after pretreatment with pure DMSO (10 ml) or C10 (2 mg/kg) dissolved in 10 ml pure DMSO injected intravenously (iv). Horses with LPS developed toxic shock over a 24 hour period with hypotension, hypothermia, tachypnea, rapid pulse, abnormal cardiograms, and, finally, collapse, whereas C10 treated animals had none of these changes. The results in Tables 9 and 10 are from a typical experiment with LPS or LPS+DMSO vs. LPS+C10 treated animals studied at early time points and up to 24 hrs, with 1 week follow up, wherein cardiovascular parameters of circulatory shock were measured: toxemia, congestion, and cyanosis.

TABLE 9

C10 protects horses from LPS-induced shock as measured by Toxemia and Vascular Congestion

| Time (hours) | LPS Group | LPS + DMSO Group | LPS + c10 Group |
|---|---|---|---|
| 0.00 | Normal | Normal | Normal |
| 0.15 | | | |
| 0.3 | Toxemic | Toxemic + | Weak Congestion |
| 1.0 | | Toxemic ++ | |
| 3 | Toxemic + | Toxemic ++++ | Weak Congestion |
| 6 | Toxemic ++ | Toxemic ++++ | |
| 24 | Toxemic | Toxemic ++ | Normal |
| 1 week | Normal | Normal | Normal |

TABLE 10

C10 protects horses from LPS-induced shock as measured by Toxemia, Vascular Congestion, Cyanosis

| Time (hours) | LPS Group | LPS + DMSO Group | LPS + c10 Group |
|---|---|---|---|
| 0.00 | Normal | Normal | Normal |
| 0.15 | Toxemic | Toxemic | Normal |
| 0.3 | Toxemic | Toxemic | Weak Congestion |
| 1.0 | Toxic Line | Toxic Line | |
| 3 | Cyanotic +++ | Cyanotic +++ Cyanotic +++ | Weak Congestion |
| 6 | Cyanotic +++ | | |
| 24 | Toxemic Toxic Line | Toxemic Toxic Line | Normal |
| 1 week | Normal | Normal | Normal |

The ability of C10 to protect horses from Endotoxic shock induced by LPS is also evidenced in Tables 11 and 12. Horses were treated with a sub-lethal dose of LPS (10 μg/kg) after pretreatment with pure DMSO (10 ml) or C10 (2 mg/kg) in 10 ml pure DMSO injected iv. Horses with LPS developed toxic shock over a 24 hour period with decreased blood pressure, hypothermia, rapid respiration, rapid pulse, abnormal cardiograms, and, ultimately, collapse, whereas C10 treated animals had none of these changes. Tables 11 and 12 depict a typical experiment comparing LPS or LPS+DMSO vs. LPS+C10 treated animals studied at early time points and up to 24 hrs, with 1 week follow up, wherein fluid in the lungs was measured by auscultation, as well as tachypnea, and dyspnea. They demonstrate that C10 suppresses the signs of pulmonary distress suffered during toxic shock.

TABLE 11

C10 protects horses from LPS-induced toxic shock as measured by Lung Auscultation.

| Time (hours) | LPS Group | LPS + DMSO Group | LPS + c10 Group |
|---|---|---|---|
| 0.00 | Normal | Normal | Normal |
| 0.15 | | | |
| 0.3 | Crackles | Crackles | Normal |
| 1.0 | | | |
| 3 | Crackles | Crackles | Normal |
| 6 | Wheezes | Wheezes | |
| 24 | Crackles Wheezes | Crackles Wheezes | Normal |
| 1 week | Normal | Normal | Normal |

TABLE 12

C10 protects horses from LPS-induced toxic shock as measured by Dyspnea and Tachypnea.

| Time (hours) | LPS Group | LPS + DMSO Group | LPS + c10 Group |
|---|---|---|---|
| 0.00 | Normal | Normal | Normal |
| 0.15 | Dyspnea Tachypnea | Dyspnea Tachypnea | Normal |
| 0.3 | Dyspnea | Dyspnea | Normal |
| 1.0 | Tachypnea | Tachypnea | |
| 3 | Dyspnea | Dyspnea | Normal |
| 6 | Tachypnea | Tachypnea | |
| 24 | Dyspnea | Dyspnea | Normal |
| 1 week | Normal | Dyspnea | Normal |

As seen in Table 13, C10 also protects horses from Endotoxic shock induced by LPS as measured by abdominal pain, diarrhea, increased number of stools, and collapse or prostration to a lying rather than standing state. Horses were treated with a sublethal dose of LPS (10 μg/kg) after pretreatment with 10 ml of pure DMSO or C10 (1 mg/kg) in 10 ml of pure DMSO injected iv. Horses with LPS developed toxic shock over a 24 hour period with decreased blood pressure, hypothermia, rapid respiration, rapid pulse, abnormal cardiograms, and total prostration or collapse, whereas C10 treated animals had none of these changes. Table 13 depicts typical LPS or LPS+DMSO vs. LPS+C10 treated animals studied at early time points and up to 24 hrs, with 1 week follow up, wherein abdominal pain, watery diarrhea, number of stools, and collapse to a lying state vs. normal gastrointestinal function and disposition were measured. The severe abdominal pain, diarrhea, and increased frequency of stools were evident in a typical LPS or LPS+DMSO treated animal by 3 hours as was the collapse and shock response of LPS treated animals. None of this occurred in animals treated with LPS plus C10. These data are representative of all animals in each group.

TABLE 13

C10 protects horses from Endotoxic shock induced by LPS as measured by abdominal pain, diarrhea, increased number of stools, and collapse or prostration to a lying rather than standing state

| Time (Hours) | LPS Group | LPS + DMSO | LPS + C10 |
|---|---|---|---|
| 0 | normal | normal | normal |
| 0.15-6 | Abdominal pain Diarrhea 10 ± 2 stools Collapsed and prostrate | Abdominal pain Diarrhea 10 ± 2 stools Collapsed and prostrate | Normal 1 stool |
| 24 | normal | Weak but upright | normal |
| 1 week | normal | normal | normal |

Phenylmethimazole (C10) protects horses form LPS-induced endotoxemia and endotoxic shock: In sum, C-10 clearly blocked symptoms of endotoxemia including hypotension and hypoxemia, as well as endotoxic shock collapse, cardiac anoxia, acute renal failure, and loses of water from blood in all respects (Tables 9-13). In contrast the DMSO vehicle had no protection from hypotension, hypoxemia, shock, collapse and organ failure after endotoxin (LPS) inoculation (Tables 9-13).

Phenylmethimazole (C10) protects horses form peritonitis—induced endotoxemia and endotoxic shock: C10 protected horses from endotoxic shock and death by septic peritonitis induced by intestinal fluid. After intestinal (caecal) fluid was inoculated intraperitoneally into normal horses, the animals rapidly exhibited clear symptoms of endotoxemia, presumably because the fluid had free endotoxin. C10 protected in the first stage of endotoxemia due to free lipopolysaccharide present in the intestinal lumen (Table 14). Clinical evaluation of the animal at 0:30, 1, 3, 6, showed clinical signs of endotoxemia in non C10 treated animal but not in the C10 treated animal that were clinically protected from endotoxemia.

At 12 hours, all animals began to develop clinical peritonitis with abdominal pain and fever (Table 14). At this time all animals started to be treated with antibiotics (penicillin-streptomycin) in order to avoid clinical progression of the bacterial infection and further release of LPS by bacterial death. At 12 hours, one group of two animals was inoculated with C10 (2 mg/kg) given intravenously in a bolus, whereas two other horses remained without treatment, i.e. only with antibiotics. At 24 hours the non C10 treated animals were dead (Table 14), whereas those animals treated with C10 survived with only a slight depression and mild signs of endotoxemia (Table 14). After the C-10 bolus, the animals immediately got better, ate and drank water. Signs of any collapse or depression disappeared within 15 minutes. The survivors showed no signs of organ failure at 24 hours or even 1 week after the end of the experiment (Table 14), showing that C-10 protected from organ failure (respiratory distress, acute renal failure, hypotension, cardiac anoxia, and hypoxemia).

TABLE 14

C10 protects horses from death after peritonitis induced by intraperitoneal injection of intestinal (Caecal) fluid.
Toxic Shock Symptoms
(% of horses and severity
% survival measured as +, ++, etc.)

| Time (Hours) | Antibiotic Therapy | C10 plus Antibiotics | Antibiotic Therapy | C10 plus Antibiotics |
|---|---|---|---|---|
| 0.0 | 100 | 100 | 0 | 0 |
| 0.15 | 100 | 100 | 0 | 0 |

TABLE 14-continued

C10 protects horses from death after peritonitis induced by
intraperitoneal injection of intestinal (Caecal) fluid.
Toxic Shock Symptoms
(% of horses and severity
% survival measured as +, ++, etc.)

| Time (Hours) | Antibiotic Therapy | C10 plus Antibiotics | Antibiotic Therapy | C10 plus Antibiotics |
|---|---|---|---|---|
| 0.3 | 100 | 100 | 0 | 0 |
| 1 | 100 | 100 | 0 | 0 |
| 3 | 100 | 100 | 0 | 0 |
| 6 | 100 | 100 | 50 (+) | *50(−)* |
| 12 | 100 | 100 | 50 (++) | *50(+)* |
| 24 | 100 | 100 | 100 (+++) | *50(±)* |
| 36 | 0 | *100* | ND | *50* |
| 1 week | 0 | *100* | ND | *50* |

Bold and Italicized Values are statistically significant from control group with antibiotics only. ND is not determined.
Toxic shock symptoms were measured as described above.

As shown in Table 14, C10 protects horses from death after peritonitis induced by intraperitoneal injection of intestinal (Caecal) fluid. Animals were injected intraperitoneally with 100 ml of caecal fluid containing bacteria and free endotoxin. One group received an intravenous dose of 2 mg/kg C10 in 10 ml of 100% DMSO 30 min. before caecal fluid injection; the other group got 10 ml of 100% DMSO alone 30 min. before caecal fluid injection. Between the time of caecal fluid injection and 12 hours post injection, C10 treated animals had minimal symptoms of endotoxemia by comparison to DMSO control animals. At 12 hours all animals began to exhibit signs of peritonitis. Horses treated with antibiotics only and who had progressive signs of peritonitis, developed toxic shock over a 24 hour period with decreased blood pressure, hypothermia, rapid respiration, rapid pulse, abnormal cardiograms, and collapse, whereas C10 treated animals had none of these changes. Animals pretreated with C10 received a second dose of 2 mg/kg C10 in 10 ml of 100% DMSO at 12 hours whereas the other group got 10 ml of 100% DMSO alone. Both groups were also given therapeutic doses of penicillin and streptomycin at 12 hours. Animal plus C10 were walking and eating, within 24 hours and had a full recovery in all cases, whereas the others developed toxic shock in all cases and died. This experiment combines several groups of two horses in each group. These results indicate C10 is effective to prevent toxic shock in horses subjected to peritonitis and endotoxic shock. The treatment was 100% effective in 10 animals so treated, and was effective even in repeat treatment of the same animals.

Effect of Phenylmethimazole (C10) on horses subjected to operative procedures to repair necrotic bowels: A group of animals were also subjected to an operative procedure that clamped vessels in a small portion of bowel. Within 2 days, bowel necrosis and peritonitis ensued. At that point animals were re-operated to remove the necrotic bowel and treated with 2 mg/kg C10 or DMSO alone pre-op and post-op for three days. Animals treated with C10 were walking and eating within 24 hours and had full recovery in all cases, whereas those without C10 developed toxic shock in most cases, were severely ill, and died. Both groups had the same antibiotic therapy as used above. These results indicate C10 is effective to prevent toxic shock in horses subjected to surgical procedures or endotoxin administration.

In sum, endotoxemia and endotoxic shock are the leading causes of death in horses, being intimately related to the pathogenesis of gastrointestinal disorders that cause colic and neonatal foal septicemia. Phenylmethimazole (C10) is a methimazole derivative and lead compound of a family of tautomeric cyclic thione drugs that block pathologic activation of TLR3/TLR4 signaling in nonimmune tissues, monocytes, macrophages, and dendritic cells. They suppress the expression type I interferon genes (e.g. INF-β), interferon inducible genes (IP-10, IRF-1), pro-inflammatory cytokines TNF-α, IL-1β, IL-6, chemokines such as MCP-1, COX-2 and iNOS. Endotoxemia and endotoxic shock in horses are associated by the up-regulation of several mediators, COX-2 dependent mediators such as prostaglandins, TNF-α, IL-1, IL-6 and iNOS. The Endotoxic shock survival rate is strongly dependent on type I interferon transcription genes in knock out rodent models. Using an endotoxemia horse model we carried out clinical studies showing that phenylmethimazole (C10) protects horses from clinical signs of endotoxemia and endotoxic shock induced by $E.\ coli$ lipopolysaccharide: hypotension, hypoxemia, tachypnea, tachycardia, hypoxemia, respiratory distress, abdominal pain and colic, watery diarrhea, intestinal hypomotility and anus relaxation, acute renal failure, hyperglycemia and circulatory shock or collapse. When we induced endotoxemia and shock due to septic peritonitis using intraperitoneal inoculation of intestinal flora, the C10 survival rate was 100% compared with 0% of survival in non-treated animal.

Material and Methods

Endotoxemia protection experiment: In order to determine the effect of C-10 on experimental endotoxemia induced by $E.\ coli$ LPS, we used 3 groups of horses. In Group 1 (LPS group), horses were injected with 10 μg/kg of $E.\ coli$ (055 LPS from Sigma, St. Louis) by intravenous bolus injection as recommended by others (J. N. Moore, et al., *Equine Vet J*, 13:95-8 (1981); G. E. Burrows, *Am J Vet Res*, 40:991-8 (1979)). Group 2 horses (LPS+DMSO) were injected with the same dose of vehicle (100% DMSO) and the effect of DMSO alone was analyzed. Group 3 (LPS+C-10) horses were injected with LPS plus 100% DMSO used as the vehicle. Horses from the different groups were studied clinically at different time points. In the groups LPS+C-10 and LPS+DMSO, C-10 and DMSO were injected 30 minutes before LPS.

Time 0 was defined as a normal horse before injection of LPS. After LPS injection, we evaluated the animals at 15 minutes, 30 minutes, 1 hour, 3 hours, 6 hours, 24 hours and 1 week. We evaluated changes in the following biological systems targeted by LPS: cardiovascular, circulatory, abdominal, and pulmonary. Time of capillary flow, integrity of the vessels and other vessel alterations were evaluated clinically. Maximum venous blood pressure (NIBP max.), minimum venous blood pressure (NIBP min.), electrocardiogram (ECG), and oxygen saturation in blood ($PsO_2$), expressed by %, were determined using a Cardell Monitor 9403. Study of normal abdominal intestinal activity, ileocecal sphincter activity, number of depositions (stools) and their characteristic (diarrhea), as well as anus muscular tone were also evaluated clinically. Respiratory rate, dyspnea, pulmonary auscultation, presence of fluid in the respiratory tract and pulmonary congestion were evaluated clinically. Glucose, GOT (glutamic oxalacetic transaminase enzyme), GPT (glutamic pyruvate transaminase enzyme), creatinine, urea, hemogram, hemoglobin (Hb), hematocrit (Ht), red cell number, PMN number (neutrophils, eosinophils, basophils), monocyte number and lymphocyte number were determined at different time points. Clinical observations were recorded by skilled veterinarians who were unaware of which animal received C10, i.e. results were evaluated in a blinded fashion.

Endotoxic shock survival experiments: The ceacum and ventral colon of normal horses contain more than 2 g of free endotoxin as well as gram-negative bacteria which are restricted to the intestinal lumen by an intact intestinal barrier. The pathologies that damage the mucosal barrier allow the endotoxins to reach the peritoneal cavity as well as the blood. To evaluate the protective effect of C-10 on horse endotoxic shock survival rate we injected 100 ml of ceacum fluid intraperitoneally to induce peritonitis and endotoxic shock. Ceacal fluid was extracted from horse under anesthesia. The group of horses that were inoculated intraperitoneally with intestinal fluid developed clinical peritonitis and symptoms of endotoxemia 12 hours after intraperitoneal fluid inoculation.

All animals were treated with therapeutic doses of penicillin and streptomycin. One group of horses was inoculated with same dose of ceacal fluid and also treated with antibiotic 12 hours after fluid inoculation, but received C-10, 2 mg/kg, 30 minutes before and 12 hours after the injection of caecal fluid. We evaluated survival at 0-15-30 minutes, 1, 3, 6, 12, 18 and 24 hours as well as 1 week later.

Example 6

Phenylmethimazole (C10) decreases TLR4-mediated inflammation associated with atherosclerosis.

Atherosclerosis is a systemic disease of the circulation involving abnormal TLR4 expression and signaling causing increases in genes downstream, such as VCAM-1. Increased VCAM-1 on vascular endothelial cells is important to attract leukocytes to the inflammatory region. Atherosclerosis is more advanced in patients with diabetes, hypertension, and hyperlipidemia. The epidemic of obesity is associated with the epidemic of cardiovascular complications broadly considered as atherosclerosis complications: myocardial infarcts, strokes, etc. A drug that might attenuate the inflammatory response has been suggested as potentially effective by TLR4 knockouts. This does not eliminate lesions, because the damaging insult, hyperlipidemia, remains. The oxidized lipids can be construed as environmental signature molecules that elicit inflammation when they penetrate the endothelial layer. An important point, however, to recall is that lesions can be selective—located primarily in one or another vascular bed. Further they may be influenced by the inflammatory response that causes swelling of the vessel wall and diminished size of the lumen. That decrease in lumen, plus leukocyte/platelet binding which further decreases the lumenal opening, results in occlusive disease.

A critical component of many physiological and pathological inflammatory processes is thus the adhesion of leukocytes to the endothelium in the fluid dynamic environment of the circulation. Leukocyte adhesion to the endothelium occurs through a cascade of adhesive events involving tethering (i.e. attachment) to the endothelium from the free stream, rolling on the apical surface of the endothelium, cessation of rolling termed "arrest", spreading to more pleomorphic shapes, and migration between adjacent endothelial cells to reach the extravascular space. This adhesion cascade is mediated, in part, by non-covalent bonds that form between molecules present on the surface of the leukocyte (ligands such as integrins) and cognate molecules present on the surface of the endothelium (receptors; e.g. E-selectin, ICAM-1, VCAM-1).

The endothelial receptors for the leukocyte ligands are commonly referred to as endothelial cell adhesion molecules (ECAMs). Certain ECAMs known to play a role in leukocyte recruitment are increased at sites of pathological inflammation. For example, VCAM-1 is present in a localized fashion on aortic endothelium that overlies early foam cell lesions in atherosclerosis. The increased expression of ECAMs mediates, in part, the selective recruitment of leukocytes to a site of inflammation (T. A. Springer, Cell, 76:301-314, (1994)). The up-regulated expression of ECAMs at sites of pathological inflammation contributes to aberrant leukocyte adhesion and infiltration of tissue that is a key component of inflammation and disease progression and/or tissue damage [e.g VCAM-1 is up-regulated at sites of developing and developed atherosclerotic lesions (M. I. Cybulsky, et al., Science, 251:788-791 (1991)) and participates in monocyte adhesion to the endothelium during atherogenesis (F. W. Luscinskas, et al., J. Cell Biol., 125:1417-27 (1994); C. L. Ramos, et al., Circ. Res., 84:1237-44 (1999)). Thus, a promising therapeutic approach for treating pathological inflammation is to reduce aberrant leukocyte adhesion to the endothelium via suppression of ECAMs (J. Panes, et al., Br. J. Pharmacol., 126:537-550 (1999)).

ECAM expression is regulated at the gene level by the activity of transcription factors. Pro-inflammatory cytokine (e.g. TNF-α) treatment of endothelial cells stimulates the activity of certain transcription factors (e.g. NF-κB) (M. J. May, et al., Immunol. Today, 19:80-88 (1998)) and also induces the expression of other transcription factors (e.g. IRF-1) (A. S, Neish, et al., Mol. Cell. Biol., 15:2558-2569 (1995)). The active/induced transcription factors ligate to their respective binding sites leading to ECAM gene transcription and ultimately protein expression. Several therapeutics for pathological inflammation work, at least in part, by modulating the activity of transcription factors (E. M. Conner, et al., J. Pharmacol. Exp. Ther., 282:1615-1622 (1997); J. W. Pierce, et al., J. Immunol., 156:3961-3969 (1996); C. Weber, et al., Circulation, 91:1914-1917 (1995); J. W. Pierce, et al., J. Biol. Chem., 272:21096-21103 (1997); M. Umetani, et al., Biochem. Biophys. Res. Commun., 272:370-4 (2000)). Indeed, compounds that block cytokine induced ECAM expression at the transcription level have been shown to inhibit leukocyte adhesion to the endothelium (J. W. Pierce, et al., J. Immunol., 156:3961-3969 (1996); N. M. Dagia, et al., Am. J. Phys., 285:C813-C822 (2003); C. Weber, et al., Circulation, 91:1914-1917 (1995); J. W. Pierce, et al., J. Biol. Chem., 272:21096-21103 (1997)) and to reduce inflammation in animal models (E. M. Conner, et al., J. Pharmacol. Exp. Ther., 282:1615-1622 (1997); J. W. Pierce, et al., J. Biol. Chem., 272:21096-21103 (1997)).

Phenyl methimazole (C10) could potentially serve this purpose (N. M. Dagia, et al., J Immunol, 173:2041-9 (2004)). C10 (i) inhibits monocytic cell adhesion to cytokine inflamed human aortic endothelial cells (HAEC) under in vitro flow conditions that mimic conditions present in vivo, (ii) strongly inhibits cytokine-induced HAEC expression of VCAM-1 via suppression of the transcription factor IRF-1, and not NF-κB, (iii) has a more modest effect on E-selectin expression and (iv) has very little effect on ICAM-1 expression. While several other transcription inhibitors are known, very few, if any, have been shown to selectively suppress VCAM-1, to act via IRF-1, and to inhibit monocytic cell adhesion to cytokine inflamed endothelium under fluid shear. Use of C10 in atherosclerosis is thus a reasonable consideration.

Previous work with the Apolipoprotein E-deficient (ApoE$^{-/-}$) mouse, a well-accepted model of human atherosclerosis, revealed that VCAM-1 is present on endothelium at lesion-prone sites (as early as 5 weeks) and developed lesions (Y. Nakashima, et al., Arterioscler. Thromb. Vasc. Biol., 18:842-51 (1998)). Elegant studies by Ley's group (C. L. Ramos, et al., Circ. Res., 84:1237-44 (1999)) demonstrated that monocytes exhibit greatly increased adhesion to carotid arteries isolated from ApoE$^{-/-}$ mice compared to carotid arteries isolated from wild-type mice. This increased adhesion is mediated, in part, by VCAM-1 (C. L. Ramos, et al., Circ. Res., 84:1237-44 (1999); M. Kobayashi, et al., *J Clin Invest,* 111:1297-308 (2003)). Michelsen et al. (K. S. Michelsen, et al., *Proc Natl Acad Sci USA,* 101:10679-84 (2004)) found that mice deficient in TLR4 had a significant reduction in aortic plaque development in atherosclerosis-prone apolipoprotein E-deficient (ApoE−/−) mice suggesting an important role for TLR4 in atherosclerosis.

Results

The well-accepted ApoE$^{-/-}$ murine model (Y. Nakashima, et al., *Arterioscler. Thromb. Vasc. Biol.,* 18:842-51 (1998)) was our animal model of atherosclerosis. In initial experiments, these mice were fed a high fat diet and received injections of C10 intraperitoneally every other day or orally every other day. Mice were sacrificed at 8 weeks and lesions characterized, including VCAM-1 and TLR4 expression in accord with literature based studies (Y. Nakashima, et al., *Arterioscler. Thromb. Vasc. Biol.,* 18:842-51 (1998)). The heart, aorta and carotid artery were removed for gross, microscopic and molecular analyses. This included determination of lesion size and sectioning of tissue with subsequent staining for presence and cell localization of ECAMs and TLR4 at the protein level as well as assessment of leukocyte/macrophage infiltration. Results from mice treated with C10 were compared to controls to determine if C10 has a statistical effect on lesions in the carotid arteries.

C10 reduced vascular inflammation in ApoE−/− mice fed a high fat diet: C10 was given i.p. (1 mg/kg) every other day to mice for 8 weeks. Control mice received DMSO alone. Mice were sacrificed at 8 weeks and histopathology examined in different tissues as determined by hematoxylin and eosin staining. In FIG. 15, sections from the base of the aorta in C10 treated (FIG. 15, Panel A) and untreated mice (FIG. 15, Panel B) are presented as well as sections of the coronary artery vasculature in C10 treated (FIG. 15, Panel C) and untreated mice (FIG. 15, Panel D). Vessels in the myocardium were also compared in C10 treated and untreated mice. In Panel B, the arrows show that the severity of the lesions in the base of the aorta is markedly greater in untreated mice by comparison to C10 treated mice (Panel A). Similarly in Panel D, the picture is representative of long sections of the coronary arteries that were nearly fully occluded with plaque in untreated mice whereas in C10 treated mice (Panel C), coronary arteries were largely unobstructed. Further, even where lesions were evident the lumens of vessels remained patent. Vessels within the myocardium were obstructed by plaque in the absence of C10 but patent and nearly free of plaque in the mice treated with C10. Data are representative of multiple slides taken from multiple animals.

When lesions were qualitatively evaluated, C10 reduced disease severity and progression (Table 15) in association with decreases in TLR4 mediated inflammatory markers (Table 15).

TABLE 15

Effect of C10 on Severity of Inflammation and TLR4/VCAM-1 Staining

| GROUP | CORONARY AND MYOCARDIAL VESSELS INFLAMMATION | AORTIC INFLAMMATION |
|---|---|---|
| C10 | +* | +* |
| No C10 | ++++ | +++ |

*Significant Decrease by C10 compared to No C10.

As shown in Table 15, atherosclerotic lesions are decreased in C10 treated mice. Sections of the coronary arteries and myocardium as well as the base of the aorta were compared in untreated mice vs. C10 treated mice both for extent of lesion, quality of lesion, overexpressed TLR4, overexpressed VCAM-1, and extent of inflammation and plaque. Lesions and observations were qualitatively evaluated using ++++ for severe to + for very mild. C10 treated animals were clearly improved. The results indicated that C10 decreased the widespread inflammatory response wherein TLR4 positive cells abound and there are macrophages infiltrating the area. Evaluation was double blinded.

Figure 16:
FIG. 16. Atherosclerotic lesions in human tissues are associated with overexpressed TLR4 and VCAM-1. Sections of the coronary arteries from surgically removed plaques were immunstained with anti-TLR4 (Bottom Right Panel), anti-VCAM-1 (Top Right Panel), anti-ICAM-1 (Bottom Left Panel) in sequential slices from the paraffin imbedded block. An H &E stain (Top Left Panel) shows the occluded vessel with a foam cell, lipid laden "plaque" surrounded by a muscle wall and myocardial tissue. VCAM-1 (dark color) is overexpressed in the lesion but also in the endothelial layer opposite the lesion area. TLR4 (dark color) is more expressed in the area opposite the lesion and, surprisingly, throughout the smooth muscle layer surrounding the vessel, particularly opposite the plaque. TLR4 is also expressed in the myocardial musculature. The expression suggests a widespread inflammatory response wherein TLR4 positive cells abound be they macrophages infiltrating the area or other cells. In all respects these data duplicate those in the ApoE−/− mice and thus should be, like the lesions in the ApoE−/− mice (Table 15), sensitive to C10 therapy.

The ApoE−/− model in mice is representative of changes in human atherosclerotic plaques. Atherosclerotic lesions in human tissues are associated with overexpressed TLR4 and VCAM-1. Sections of the coronary arteries from surgically removed plaques were immunstained with anti-TLR4 (FIG. 16, Bottom Right Panel), anti-VCAM-1 (FIG. 16, Top Right Panel), anti-ICAM-1 (FIG. 16, Bottom Left Panel) in sequential slices from the paraffin imbedded block. An H &E stain (FIG. 16, Top Left Panel) shows the occluded vessel with a foam cell, lipid laden "plaque" surrounded by a muscle wall and myocardial tissue. VCAM-1 (dark grey color) is overexpressed in the lesion but also in the endothelial layer opposite the lesion area. TLR4 (dark grey color) is more expressed in the area opposite the lesion and, surprisingly, throughout the smooth muscle layer surrounding the vessel, particularly opposite the plaque. TLR4 is also expressed in the myocardial musculature. The expression suggests a widespread inflammatory response wherein TLR4 positive cells abound be they macrophages infiltrating the area or other cells. In all respects these data duplicate those in the ApoE−/− mice and thus should be, like the lesions in the ApoE−/− mice (Table 15), sensitive to C10 therapy.

Figure 17A:
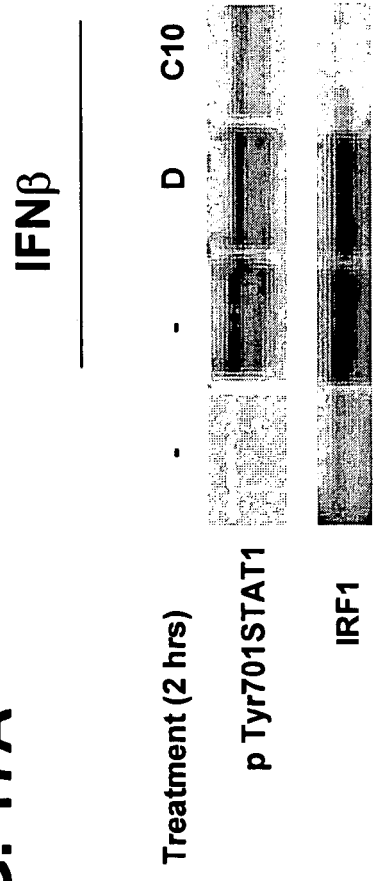
FIG. 17. C10 decreases IFN-β induction of phosphorylation of Stat1 and the activation of IRF-1 in human aortic endothelial cells (HAEC); C10 also decreases Stat1 serine phosphorylation in HAEC as well as rat thyrocytes and RAW cells. In (A), IFN-β induction of IRF-1 protein was strongly decreased by C10 but not the DMSO vehicle control (noted as D). The same blot, stripped and reprobed for an activated form of Stat1 (phosphorylated at Y701), showed a decrease of IFN-β induced Stat1 phosphorylation. Therefore the C10 ability to decrease TLR3/4 increased IFN-β dependent induction of IRF-1 gene expression may be due to a decrease in activated Stat1. HAEC were treated for 2 hours in the absence or presence of C10 (1 mM) or DMSO (D) carrier control. A non infected/non treated sample was included as a control (far left lane). Twenty five (25) mg of whole cell lysate were resolved by SDS-PAGE and then blotted onto nitrocellulose membranes. In (B), the affect of C10 was also observed on Stat1 serine phosphorylation at residue 727 in rat thyrocytes, HAEC cells, and RAW cells by western blot using a phosphoserine specific Stat1 antibody. Rat thyrocytes (FRTL-5) were (lane 2) or were not infected (lane 1) with Influenza A virus for 24 hours and then treated with either DMSO (1%) (lane 3) or 1 mM C10 (lane 4). Human aortic endothelial cells (HAEC) were incubated with 100 U/mL of hIFN-β for 2 hours in the presence of either DMSO (1%) (lane 5) or 1 mM C10 (lane 6). Mouse macrophages (RAW 264.7) were incubated for 3 hours with *E. coli* LPS at a concentration of 500 ng/ml either alone (lane 7), in the presence of DMSO (0.5%) (lane 8), or with 0.5 mM C10 (lane 9). As in Panel A, 25 µg of each whole cell lysate was resolved by SDS-PAGE, blotted onto a nitrocellulose membrane and then probed with the indicated antibodies. Loading was controlled by stripping and reprobing with an antibody directed against non phosphorylated Stat 1. C10 inhibits Stat1 serine phosphorylation independent of cell type [nonimmune cell (thyrocyte, HAEC cell) or macrophage] or stimulus (IFN-β, Influenza A, or LPS). Stat3 phosphorylation was similarly inhibited.

C10 decreases IFN-β induction of phosphorylation of Stat1 and the activation of IRF-1 in human aortic endothelial cells (HAEC): To evaluate vascular endothelial cells directly, we used human aortic endothelial cells in culture. Fundamental to C10 action in vivo appeared to be its ability to inhibit the IRF-3/IFN-β/Stat-1/IRF-1 signal pathway in vitro. Thus, IFN-β induction of IRF-1 protein was decreased by C10 (FIG. 17A, bottom, lanes 4 vs lane 2) and was not mimicked by the vehicle alone (DMSO or D in FIG. 17A lane 3). In the same blot, stripped and reprobed for an activated form of Stat1 (phosphorylated at Y701), there was also a decrease of IFN-β induced Stat1 phosphorylation (FIG. 17A, top, lanes 4 vs lane 2) and was not mimicked by the vehicle alone (DMSO or D in FIG. 17A lane 3).

Figure 17B:
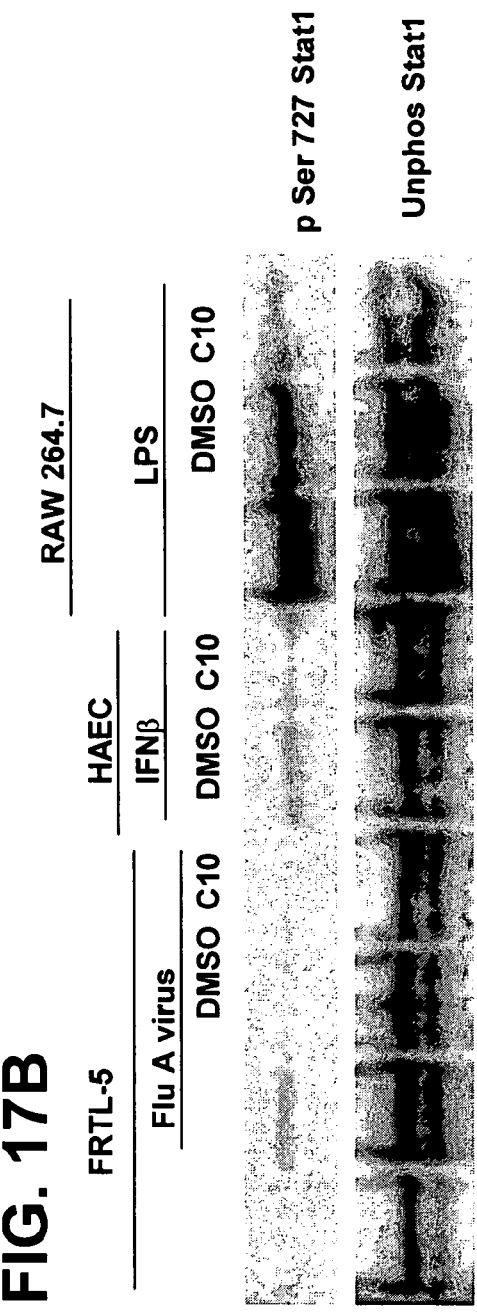

Tyrosine phosphorylation of Stat1 is one requirement for its activation of downstream genes; tyrosine phosphorylation is important in the dimerization process necessary for Stat binding to promoter elements on sensitive genes. Another requirement is serine phosphorylation, which contributes to full Stat1 transcriptional activation. To evaluate effects on serine phosphorylation of Stat1 the following experiments were performed: (i) Rat thyrocytes (FRTL-5) were infected (FIG. 17B, lane 2) or not (FIG. 17B, lane 1) with Influenza A virus for 24 hours and then treated with either DMSO (1%) (FIG. 17B, lane 3) or 1 mM C10 (FIG. 17B, lane 4); (ii) Human aortic endothelial cells (HAEC) were incubated with 100 U/mL of hIFN-β (Biosource, Camarillo, Calif.) for 2 hours in the presence of either DMSO (1%) (FIG. 17B, lane 5) or 1 mM C10 (FIG. 17B, lane 6); and (iii) mouse macrophages (RAW 264.7) were incubated for 3 hours with *E. coli* LPS serotype 0111:B4 (Sigma, Milwaukee, Wis.) at a concentration of 500 ng/mL either alone (FIG. 17B, lane 7) or in the presence of DMSO (0.5%) (FIG. 17B, lane 8) or 0.5 mM C10 (FIG. 17B, lane 9). As can be seen in FIG. 17B, IFN-β given with vehicle control DMSO also increases serine phosphorylation in HAEC (FIG. 17B lane 5) and this is decreased by C10 (FIG. 17B, lane 6). The effect of C10 to reduce pathologically induced serine phosphorylation of Stat1 is not limited to HAEC but is also seen in FRTL-5 cells (FIG. 17B, lane 4 vs lanes 2 and 3) and RAW cells (FIG. 17B, lane 9 vs lanes 7 and 8). Additionally, it is not limited to pathologic induction by IFN-β (FIG. 17B, lane 6 vs 5), but also is effective in pathologic induction mimicked with FluA infection (FIG. 17B lane 4 vs lanes 2 and 3) and by pathologic induction mimicked by treatment of cells with LPS (FIG. 17B, lane 9 vs lanes 7 and 8). In sum, C10 is a inhibitor of IRF-3/IFN-β/Stat/IRF-1/ISRE activation pathways and blocks pathologically increased effects on Stat1 tyrosine and serine phosphorylation induced by TLR3/TLR4 pathologic signals in nonimmune cells, monocytes, macrophages, and dendritic cells.

Compound 10 is an effective agent in a mouse model of atherosclerosis even given every other day and evaluated 8 weeks after insult onset (high fat feeding). However, it is also effective at earlier time points. Thus, when we compared the effect of C10 on mice at 4 weeks, given both orally and ip, there were significant effects on weight. This strain of mice is the same as used in obese animal studies related to the rapid onset of Type 2 diabetes (M. Fujimoto, et al., *Diabetes*, 54:1340-8, (2005)). In this regard, chronic inflammation has been postulated to play an important role in the pathogenesis of insulin resistance and linked to overexpression of iNOS (M. Fujimoto, et al., *Diabetes*, 54:1340-8 (2005)). C10 decreased weight gain evident before the 4 week time period and also reduced the inflammatory TLR4 mediated response.

Materials and Methods

Experimental animals: Twenty female Apo E−/− mice (Jackson Laboratory), 5 weeks old and weighing 14.5 g (average weight), were divided in 4 groups: (1) animals treated with 10% DMSO; (2) animals treated orally with C-10 in DMSO (1 mg/kg body weight); (3) animals treated I/P with C-10 in DMSO (same dose); and (4) control animals without treatment.

The treatment was done every other day (8 week expt) or every day. The animals were fed on a Western-type diet (TD 88137 from Harlan, Teklan). The experiment was terminated after 4 or 8 weeks.

Tissue preparation: At the end of the experiment, the animals were anesthetized by IP injection of Avertin 0.1 ml/5 g of body weight. In situ perfusion-fixation was performed with PBS for 10 min followed by PBS/4% formaldehyde at 37° C. Heart and aorta were removed; the arch, thoracic and abdominal portions of the aorta were dissected; and the surrounding tissues were carefully removed. The tissues were post fixed by immersion in PBS/4% formaldehyde over night at 4° C. Tissue samples were then washed 10 minutes with PBS; after dehydration they were embedded in paraffin and sectioned (7 μm thick). Sections were stained with Hematoxylin-eosin and examined under a light microscope.

Immunoblot analysis in HAEC: To determine if C10 blocks IFN-β mediated activation of tyrosine phosphorylation of Stat1 in HAEC we treated confluent HAEC with 1000/ml IFN-β in the absence or presence of C10 (1.0 mM), 0.25% DMSO (carrier control for C10) for 2 hours. Whole cell lysates were prepared in lysis buffer (150 mM NaCl, 1% IGE-PAL CA 630, and 50 mM Tris-HCl, pH 8.0) in the presence of a protease inhibitor mixture (PMSF, leupeptin, and pepstatin A). Twenty five μg of lysate was resolved on 3-8% Tri-Acetate PAGE gels under denaturing conditions using the NuPAGE Bis-Tris System (Invitrogen Life Technologies, Carlsbad, Calif.), then transferred to nitrocellulose membranes, which were probed first with rabbit anti-human IRF-1 (H-205) Ab (sc-13041; Santa Cruz Biotechnology, Inc., Santa Cruz, Calif.), membranes were then stripped and reprobed with rabbit anti-human phospho-Stat-1 (Tyr 701) Ab (9171; Cell Signaling Technology, Beverly, Mass.) for detection of activated Stat1. Binding of secondary HRP-conjugated goat anti-rabbit Ab (sc-2054; Santa Cruz Biotechnology, Inc., Santa Cruz, Calif.) was detected using the ECLplus Western Blotting Detection System (Amersham Biosciences, Piscataway, N.J.).

The affect of C10 on Stat1 serine phosphorylation at residue 727 was observed by Western blot using a phosphoserine specific Stat1 antibody (Biosource, Camarillo, Calif.). Three different cell types were stimulated as follows: (i) Rat thyrocytes (FRTL-5) were infected with Influenza A virus for 24 hours and then treated with either DMSO (1%) or 1 mM C10. (ii) Human aortic endothelial cells (HAEC) were incubated with 100 U/mL of hIFN-β (Biosource, Camarillo, Calif.) for 2 hours in the presence of either DMSO (1%) or 1 mM C10; (iii) Mouse macrophages (RAW 264.7) were incubated for 3 hours with *E. coli* LPS serotype 0111:B4 (Sigma, Milwaukee, Wis.) at a concentration of 500 ng/mL either alone or in the presence of DMSO (0.5%) or 0.5 mM C10. Twenty-five μg of each whole cell lysate was resolved by SDS-PAGE, blotted on nitrocellulose membranes, then probed with the indicated antibodies. Loading was controlled by stripping and re-probing with an antibody directed against non phosphorylated Stat1 (Santa Cruz Biotechnology Inc., Santa Cruz, Calif.).

Discussion

We have demonstrated that phenylmethimazole (C10), a lead compound of the methimazole, methimazole derivative, tautomeric cyclic thione family is effective to reduce pathologic TLR3/TLR4 overexpression and/or signaling in nonimmune cells, monocytes, macrophages, and dendritic cells. We have demonstrated this both in vitro and in vivo and shown this action has efficacy in diseases representative of each: Type 1 diabetes (TLR3) and Endotoxic shock, colitis, and atherosclerosis (TLR4). We have demonstrated efficacy not only in mice but also in horses afflicted with a disease mimicking a human disease state. By analogy, this drug should be effective in any disease with pathologic TLR expression and signaling causing autoimmune-inflammatory diseases.

We demonstrate that nonimmune cells as well as macrophages in continuous culture express basal levels of TLR3 or TLR4, that the TLR3 or TLR4 are functional, and that their activation causes increases or decreases in genes and gene products of two signal paths which have been linked to TLR3 or TLR4 signaling via its MyD88 and/or its TRIF adaptor protein: (i) the NF-κB and ERK1/2 MAPK path reputed to emanate from TRAF6 interactions and (ii) the IRF-3 and IFN-β signal path. These observations are relevant not only to mouse or rat cells (FRTL-5 thyrocytes, RAW macrophages) but human as well (HAEC, NPA thyrocytes, HUVEC). The C10 effect is shown to be applicable to multiple pathologic stimuli from infectious agents to dsRNA and to noxious environmental insults such as hyperlipidemias linked to overeating high lipid containing diets.

We have demonstrated that TLR3/4 overexpression and signaling, with its downstream cytokine-mediated inflammatory response, can be blocked by C10 and this family of compounds in vitro and in vivo. We show that disease caused by transfection by dsRNA mimics infection by a virus (Influenza A), which is a single strand RNA virus whose replication and activity after infection is likely to be mimicked by the dsRNA transfection. Reports in pancreatic cell systems associated with insulinitis and diabetes as well as lung epithelial cells associated with pulmonary autoimmune inflammatory disorders also link virus infection, dsRNA transfection, and TLR3 overexpression, indicating this phenomenon and the action of C10 is applicable to nonimmune cells in multiple tissues.

We show that TLR3 and IFN-β protein are expressed in situ in thyrocytes from patients with Hashimoto's thyroiditis which are surrounded by immune cells but not in thyrocytes from normal individuals or Graves' autoimmune hyperthyroidism, a novel finding never previously demonstrated. The results from human thyrocytes in culture indicate that TLR3 activation and increases can occur in a human as well as rat thyrocyte in culture and this can occur in the absence of lymphocytes or a lymphocyte-produced IFN, since lymphocytes primarily produce type II interferon (63). The results thus raise the possibility that thyrocytes are affected by a primary insult that activates the TLR3 system to produce an innate immune response mimicking that of a dendritic cell. The resultant cytokine and co-stimulatory molecule changes in the thyrocyte may then contribute to attracting lymphocytes to the gland, since unlike dendritic cells, the thyrocytes cannot migrate to the lymphoid organ.

The results in thyrocytes are startlingly similar to studies of another disease with TLR3 involvement and overexpression, a role for pathogen induction and dsRNA, involvement of a Type 1 IFN as an apparent autocrine/paracrine factor, immune cell infiltrates, and cell specific destruction causing hypofunction: insulinitis and type 1 diabetes (D. Devendra, et al., *Clin Immunol*, 111:225-33 (2004); L. Wen, et al., *J Immunol*, 172:3173-80 (2004)). Wen, et al. (L. Wen, et al., *J Immunol*, 172:3173-80 (2004)) show that dsRNA could induce insulinitis and type I diabetes in animals, consistent with the known animal model wherein Coxsackie virus induces Type 1 diabetes in NOD mice. Devendra and Eisenbarth (D. Devendra, et al., *Clin Immunol*, 111:225-33 (2004)) emphasize human relevance and note that enteroviruses have been the focus of many research studies as a potential agent in the pathogenesis of type 1 diabetes. They note that the mechanism of viral infection leading to β cell destruction involves IFN-α [a Type I IFN like IFN-β]. They hypothesize that activation of TLR by double stranded RNA or Poly-IC (a viral mimic), through induction of IFN-α, may activate or accelerate immune-mediated β cell destruction. They note that numerous clinical case reports have associated IFN-α therapy with autoimmune diseases [thyroiditis, in particular (see below)] and that elevated serum IFN-α levels have been associated with Type 1 diabetes as well as thyroid autoimmune/inflammatory disease (M. F. Prummel, et al., *Thyroid*, 13:547-51 (2003)). Taken together with data in the present report, the possibility is raised of an important mechanistic association relevant to disease pathogenesis. Hashimoto's and Type 1 diabetes may have immune cell infiltrates and destructive thyrocyte or β-cell changes because of a primary insult to the specific tissue cell that activates TLR3 and an innate immune response in the tissue cells; this may be an early event in the pathogenic mechanism (D. Devendra, et al., Clin Immunol, 111:225-33 (2004); L. Wen, et al., *J Immunol*, 172:3173-80 (2004); B. Beutler, *Nature*, 430:257-63 (2004); K. S. Michelsen, et al., *J Immunol*, 173:5901-7 (2004)).

Devendra and Eisenbarth suggest (D. Devendra, et al., *Clin Immunol*, 111:225-33 (2004)) that therapeutic agents targeting IFN-α [over production or activity] may potentially be beneficial in the prevention of type 1 diabetes and autoimmunity. We show a better effect would be suppression of the TLR-signaling event increasing the type 1 IFN, rather than a partial action on type 1 IFN only. Thus, we had asked whether TLR3 overexpression/signaling might be sensitive to the immunomodulatory actions of methimazole (MMI) or its more potent derivative, phenylmethimazole (C10) (M. Saji, et al., *J Clin Endocrinol Metab*, 75:871-8 (1992); V. Montani, et al., *Endocrinology*, 139:290-302 (1998); L. D. Kohn et al., U.S. Pat. No. 6,365,616 (2002); E. Mozes, et al., *Science*, 261:91-3 (19.93); D. S. Singer, et al., *J Immunol*, 153:873-80 (1994)) and show that C10, to a significantly greater extent than MMI, blocks overexpression of TLR/TLR signaling by inhibition of the TLR3 regulated IRF-3/IFN-β/ISRE/STAT signal path not the TLR-MyD88-coupled NF-6B signal path. It acts more broadly than just inhibition of IRF-3 transactivation and, therefore, may inhibit activation of a broad range of ISRE sequences on other genes. In this respect, it is notable that, in addition to an NF-6B site, IRF-1 has a GAS, which binds Stat1. It is reasonable to suggest that the ability of C10 to block IRF-1 gene expression, both herein and in our studies of C10 inhibition of TNF-.A.-inverted.-induced VCAM-1 and leukocyte adhesion, is related to its action on components of the TLR3 regulated IRF-3/IFN-β/ISRE/STAT signal path. In short, C10 may be an example of an agent that meets the new therapeutic paradigm requested by Davendra and Eisenbath in their review (D. Devendra, et al., *Clin Immunol*, 111:225-33 (2004)) not by its effect solely on Type 1 IFN, but by blocking the entire TLR3/4 mediated signal path involving IRF-3/IRF-3/IFN-β/ISRE/STAT signal signaling. We show C10 is particularly effective since it can block tyrosine and serine phosphorylation important both in Stat1 dimerization and full transcriptional activation, respectively. It is recognized that these different phosphorylation events can effect gene activation differently, emphasizing the selectivity of C10 along with its inability to directly inhibit NF-κB signaling. The activation of NF-κB signaled genes is a normal process controlling many genes in the absence of a disease state. Super activation of the IRF-3/IFN-β/ISRE/STAT signal for example by VAK kinases is a pathologic event induced, for example, by viral infection. It is this that C10 inhibits. IRF-1 is normally not expressed, is increased only in pathologic states, and is effectively blocked by C10 therapy.

TLR signaling remains complex with many unknowns. The role of PI3 kinase and Akt involvement in phosphorylation of IRF-3 has recently emerged (S. N. Sarkar, et al., *Nat Struct Mol Biol*, 11:1060-7 (2004)); full phosphorylation of IRF-3 requires TBK-1 and Akt. Reactive oxygen species involvement in virus-induced activation of STATs is recognized (T. Liu, et al., *J Biol Chem*, 279:2461-9 (2004)). The P38alphaMap kinase pathway is important in downstream effectors that participate in Type I IFN-dependent gene transcription and involvement (Y. Li, et al., J Biol Chem, 279: 970-9 (2004)). Transcriptional activation of the IFN-β gene requires assembly of an enhanceosome containing transcription factors ATF-2/c-Jun, IRF-3/IRF-7, NF-κB, and HMGI (Y) (D. Panne, et al., Embo J, 23:4384-93 (2004)) and thus indicates the two signal paths are intertwined both at the earliest level of IRF-3/IFN-β activation as well as at downstream molecules such as VCAM-1 gene expression. Nevertheless, our data are important mechanistic steps and demonstrate at the very least C10 is a novel agent both to help dissect the complexity of the TLR3/4 signal pathway but more importantly to treat autoimmune-inflammatory diseases induced by pathologic TLR3/TLR4 expression and signaling in nonimmune cells, macrophages, monocytes, and dendritic cells.

Our previous description of C10 efficacy in inhibiting TNF-α-induced VCAM-1 gene expression and leukocyte adhesion is highly relevant to atherosclerosis and colitis, two other diseases where TLR4 overexpression or signaling in nonimmune cells is linked to autoimmune/inflammatory disease (K. S. Michelsen, et al., *Proc Natl Acad Sci USA*, 101: 10679-84 (2004); G. Pasterkamp, et al., *Eur J Clin Invest*, 34:328-34 (2004); G. Andonegui, et al., *J Clin Invest,* 111: 1011-1020 (2003); B. Beutler, *Nature,* 430:257-63 (2004); K. S. Michelsen, et al., *J Immunol,* 173:5901-7 (2004); N. M. Dagia, et al., *J Immunol,* 173:2041-9 (2004); C. Fiocchi, *Am J Physiol,* 273:G769-75, (1997); N. Harii, et al., *Mol Endocrinol,* 19:1231-50 (2005)).

It is reasonable to conclude that Hashimoto's may, therefore, not only be grouped with insulinitis and Type 1 diabetes, but also with colitis and atherosclerosis as autoimmune/inflammatory diseases associated with TLR3/4 overexpression and signaling in nonimmune cells, whose overexpression involves induction by molecular signatures of environmental pathogens (K. S. Michelsen, et al., *Proc Natl Acad Sci USA,* 101:10679-84 (2004); G. Pasterkamp, et al., *Eur J Clin Invest,* 34:328-34 (2004); D. Devendra, et al., *Clin Immunol,* 111: 225-33 (2004); L. Wen, et al., *J Immunol,* 172:3173-80 (2004); G. Andonegui, et al., *J Clin Invest,* 111: 1011-1020 (2003); B. Beutler, *Nature,* 430:257-63 (2004); K. S. Michelsen, et al., *J Immunol,* 173:5901-7 (2004); C. Fiocchi, *Am J Physiol,* 273:G769-75 (1997); N. Harii, et al., *Mol Endocrinol,* 19:1231-50 (2005)).

The DSS model is used to study ulcerative colitis and Crohn's disease. Recent work indicates that TLR4 is strongly up-regulated in both (E. Cario, et al., *Infect Immun,* 68:7010-7 (2000)) and that enterocolitis in another mouse enterocolitis model is significantly improved in TLR4-deficient mice. These data indicate the importance of innate immunity and TLR4 in Th1-dependent enterocolitis (M. Kobayashi, et al., *J Clin Invest,* 111:1297-308 (2003)) and thus the importance of C10 in blocking TLR4 overexpression in vitro and in vivo in colonic epithelial cells in the DSS model.

Without wishing to be bound be theory in any way herein, it is reasonable to speculate that Hashimoto's and Type 1 diabetes may be prototypes of each other and that studies in FRTL-5 thyrocytes are a relevant model for studies in pancreatic p islet cells and diabetes. High glucose levels can transcriptionally increase MHC I expression and amplify interferon-(action in FRTL-5 thyroid cells (G. Napolitano, et al., *Endocrinology,* 143:1008-17 (2002)). In retrospect, this is applicable to the islet cell changes induced by high glucose levels.

We (N. Harii, et al., *Mol Endocrinol,* 19:1231-50 (2005)), as well as others (K. S. Michelsen, et al., *Proc Natl Acad Sci USA,* 101:10679-84, (2004); G. Pasterkamp, et al., *Eur J Clin Invest,* 34:328-34, (2004); D. Devendra, et al., *Clin Immunol,* 111:225-33, (2004); L. Wen, et al., *J Immunol,* 172:3173-80, (2004); G. Andonegui, et al., *J Clin Invest,* 111:1011-1020 (2003); B. Beutler, Nature, 430:257-63 (2004); K. S. Michelsen, et al., *J Immunol,* 173:5901-7 (2004); C. Fiocchi, *Am J Physiol,* 273:G769-75 (1997); L. Guillot, et al., *J Biol Chem,* 279:2712-8 (2004)), show that Type I IFN (IFN-α or β) is an important factor in the innate viral immune response. We suggest, an increase in Type I IFN gene expression in nonimmune cells can result in an autocrine/paracrine manner to further upregulate TLR3 by activation of IRFs. Type I IFNs act as potent extracellular mediators of host defense and homeostasis and lead to the synthesis of proteins that mediate antiviral, growth inhibitory, and immunomodulatory responses. The secreted Type I IFN can sensitize the same or adjacent cells to dsRNA or dsDNA by increasing expression of dsRNA recognition molecules such as TLR3 and PKR or dsDNA recognition by PKR. A similar model invoking TLR3 and Type I IFN in the innate immune response of nonimmune cells has been invoked in Influenza A infected lung tissue (L. Guillot, et al., *J Biol Chem,* 279:2712-8 (2004)).

Because it is a protective cytokine, Type I IFNs have been used in the clinical setting to treat hepatitis C and B, chronic myelogenous leukemias, melanoma, and renal cancer (C. E. Samuel, *Clin Microbiol Rev,* 14:778-809 (2001)). One side effect of Type I IFN therapy is, however, a higher incidence of autoimmune disease. The risk of Hashimoto's thyroiditis is increased with type I IFN treatment in HCV hepatitis patients. Thyroid auto antibodies are found in up to 20% of patients who receive treatment with type I IFNs and approximately 5% of these patients develop clinical hypothyroidism (P. Burman, et al., *J Clin Endocrinol Metab,* 63:1086-90 (1986); H. Gisslinger, et al., *Clin Exp Immunol,* 90:363-7 (1992); A. Imagawa, et al., *J Clin Endocrinol Metab,* 80:922-6 (1995)). Consistent with the possible autoimmune-inducing activity of type I IFNs, upregulation of Type I IFNs was observed in some patients with psoriasis, systemic lupus erythematosus and insulin dependent diabetes mellitus (P. Schmid, et al., *J Interferon Res,* 14:229-34 (1994); X. Huang, et al., *Diabetes,* 44:658-64 (1995); A. A. Bengtsson, et al., *Lupus,* 9:664-71 (2000); L. Farkas, et al., *Am J Pathol,* 159:237-43 (2001)). Thus, C10 therapy supplants that of Type I Interferon since the latter is only a partial therapy that can cause as well as cure disease, whereas C10, methimazole, methimazole derivatives, and tautomeric cyclic thiones offer a means to block total pathologic expression of the autoimmune-inflammatory response.

Several last points are worth noting. The dsRNA transfection was used to activate PKR-dependent NF-κB activation or a separate kinase system leading to IFN-β gene expression through IRF-3 activation. The upstream mechanism resulting in IRF-3 activation following dsRNA transfection or viral infection in vitro has been clarified. Pharmacological and molecular studies suggested that a novel viral-activated serine/threonine kinase (VAK), instead of PKR, might activate IRF-3 in response to cytosolic dsRNA (M. J. Servant, et al., *J Biol Chem,* 276:355-63 (2001); M. J. Servant, et al., *J Interferon Cytokine Res,* 22:49-58 (2002); M. J. Servant, et al., *J Biol Chem,* 278:9441-7 (2003)). We now know this is a complex phenomenon involving P13 kinase/Akt and 16B-related kinases (IKK)-IKKepsilon/TANK binding kinase 1 (TBK1) (M. J. Servant, et al., *J Biol Chem,* 276:355-63 (2001); M. J. Servant, et al., *J Interferon Cytokine Res,* 22:49-58 (2002); M. J. Servant, et al., *J Biol Chem,* 278:9441-7 (2003)). Consistent with these observations, PKR−/− mice are physically normal and the induction of type I IFNs by Poly (I:C) and virus is unimpaired, despite the evidence that PKR is a major intracellular RNA-recognition molecule, leading to an anti-viral cellular response.

Second, the sum of data suggests that the presence of TLR3/TLR4 upregulation and signaling by dsRNA transfection or LPS can account for the data in our previous study (K. Suzuki, et al., *Proc Natl Acad Sci USA,* 96:2285-90 (1999)) which showed that viral infection, plasmid transfection, transfection of dsDNA, or transfection of dsRNA into the cytoplasm of the cell could increase expression of MHC class I, cause aberrant expression of MHC class II, and cause the expression of other genes necessary for antigen presentation (APC generation). The action of the dsRNA or dsDNA transfection appeared to involve NF-κB activation but only the dsRNA transfection, increased IFN-β RNA levels (K. Suzuki, et al., *Proc Natl Acad Sci USA,* 96:2285-90 (1999)). These phenomena were evidenced in other cells including monocytes and macrophages and were associated with an immune-inflammatory response in animals (K. J. Ishii, et al., *J Immunol,* 167:2602-7 (2001)). C10 by blocking the TLR signal events, blocks these downstream epiphenomena.

Last, the C10 family is effective on nonimmune cells, macrophages, monocytes and dendritic cells but has been shown to be minimally active on other immune cells. Further, the C10 family is restrictive in its action on the IRF-3/Type 1 IFN/STAT/ISRE/IRF-1 signal; its effect on direct activities of the NF-κB signal system is minimal. If IRF-1 is not expressed in the normal cell, but only induced after pathologic induction, i.e. by virus infection, LPS, dsRNA transfection, or noxious environmental insult, this family of compounds is clearly selective in affecting only pathologic overexpression leading to disease and not normal host immune defenses. They appear to be selective agents.

In sum, these last four points emphasize the novelty and usefulness of the present invention. They defy current thoughts regarding therapy directed at immune cells by instead attacking nonimmune cell events. They defy current concepts of attacking genes causing disease susceptibility as the sole true therapeutic approach, but rather attacks the common set of inciting environmental events even in genetically susceptible animals. They can thus prevent by blocking recurrent environmental events both as causative agents (Type 1 diabetes, Hashimoto's, toxic shock) and also remediate complications in chronic recurrent diseases such as colitis and atherosclerosis.

What is claimed is:

1. A method of treatment or prevention of septic shock, sepsis or toxic shock syndrome in horses, comprising the step of administering an effective amount of

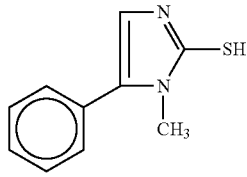

or a pharmaceutically acceptable salt thereof; and a pharmaceutically acceptable carrier.

2. The method of claim 1, wherein said method is a method of treating septic shock, sepsis or toxic shock syndrome in horses.

3. The method of claim 1, wherein said method is a method of preventing septic shock, sepsis or toxic shock syndrome in horses.

4. The method of claim 1, wherein said treatment comprises amelioration of septic shock, sepsis or toxic shock syndrome in horses.

5. The method of claim 1, wherein said treatment comprises amelioration of toxic shock syndrome in horses.

6. The method of claim 1, wherein said treatment comprises amelioration of septic shock in horses.

7. The method of claim 1, wherein said treatment comprises amelioration of sepsis in horses.

8. The method of claim 1, wherein said method is a method of preventing toxic shock syndrome in horses.

9. The method of claim 1, wherein said method is a method of preventing septic shock in horses.

10. The method of claim 1, wherein said method is a method of preventing sepsis in horses.

11. The method of claim 1, wherein the effective amount of

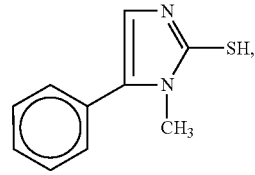

or pharmaceutical salt thereof, is administered systemically.

12. The method of claim 1, wherein the effective amount of

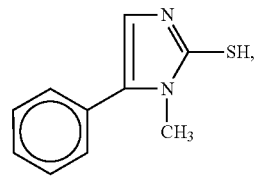

or pharmaceutical salt thereof, is provided as a pharmaceutical composition comprising from about 0.01% to about 25% of the

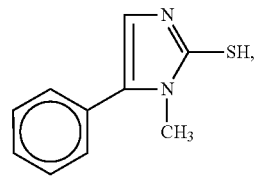

or pharmaceutical salt thereof, and from about 75% to about 99.99% of a pharmaceutically-acceptable carrier.

13. The method of claim 1, wherein the effective amount of

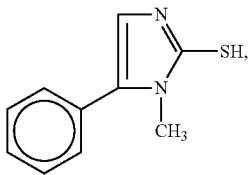

or pharmaceutical salt thereof, is administered in conjunction with at least one additional active agent, for the prophylaxis or treatment of septic shock, sepsis or toxic shock syndrome.

14. The method of claim 1, wherein the effective amount of

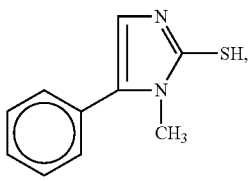

or pharmaceutical salt thereof, is administered in conjunction with one or more drugs, agents or therapeutics selected from 5-lipoxygenase inhibitors, PDE4 inhibitors, PDE inhibitors, dopamine agonists, anti-IL-8 antibodies, and anti-IL-5 antibodies.

15. The method of claim 1, wherein the effective amount of

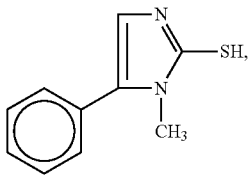

or pharmaceutical salt thereof, is administered in conjunction with one or more drugs, agents or therapeutics selected from beta-2 adrenoceptor agonists, muscarinic M1 and M3 antagonists, muscarinic M2 agonists, NK3 antagonists, LTB4 antagonists, cysteinyl leukotriene antagonists, bronchodilators, MMP inhibitors, phospholipase A2 inhibitors, phospholipase D inhibitors, histamine H1 antagonists, histamine H3 antagonists, adenosine A2 agonists, NK1 and NK2 antagonists, GABA-B agonists, nociceptin agonists, expectorants, mucolytic agents, decongestants, antioxidants, anti-IgE antibodies, anti-TNF antibodies, IL-10, adhesion molecule inhibitors, and growth hormones.

16. The method of claim 1, wherein the effective amount of

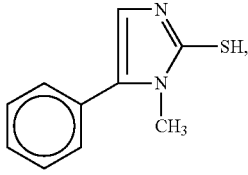

or pharmaceutical salt thereof, is administered in conjunction with one or more therapeutic steroids.

17. The method of claim 1, wherein the effective amount of

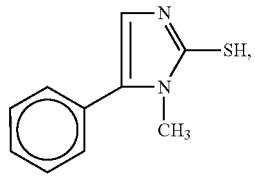

or pharmaceutical salt thereof, is administered in conjunction with one or more therapeutic steroids selected from corticoids, glucocorticoids, dexamethasone, prednisone, prednisolone, and betamethasone.

18. The method of claim 1, wherein the effective amount of

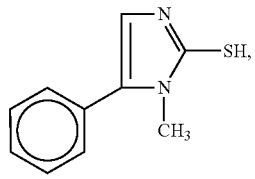

or pharmaceutical salt thereof, is administered in conjunction with one or more additional agents selected from sulfonylureas, meglitinides, biguanides, alpha-glucosidase inhibitors, peroxisome proliferators-activated receptor-gamma agonists, insulin, insulin analogues, HMG-CoA reductase inhibitors, cholesterol-lowering drugs, anti-platelet agents, angiotensin-converting enzyme inhibitors, angiotensin II receptor antagonists, adiponectin, a lipid modifying compound or agent, and a statin.

19. The method of claim 18, wherein the statin is selected from lovastatin, simvastatin, dihydroxy open-acid simvastatin, pravastatin, fluvastatin, atorvastatin, cerivastatin, and pitavastatin.

20. The method of claim 1, wherein the effective amount of

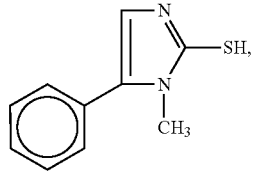

or pharmaceutical salt thereof, is administered in conjunction with one or more additional agents selected from HMG-CoA synthase inhibitors, squalene epoxidase inhibitors, squalene synthetase inhibitors, acyl-coenzyme A:cholesterol acyltransferase inhibitors, microsomal triglyceride transfer protein inhibitors, probucol, niacin, bile acid sequestrants, LDL receptor inducers, platelet aggregation inhibitors, human peroxisome proliferator activated receptor gamma agonists, PPAR agonists, PPAR alpha/gamma dual agonists, vitamin B6 and the pharmaceutically acceptable salts thereof, vitamin B12, folic acid or a pharmaceutically acceptable salt or ester thereof, anti-oxidant vitamins, beta-blockers, angiotensin II antagonists, angiotensin converting enzyme inhibitors, calcium channel blockers, endothelian antagonists, agents that enhance ABCA1 gene expression, FXR ligands, bisphosphonate compounds, and cyclooxygenase-2 inhibitors.

21. The method of claim 1, wherein the effective amount of

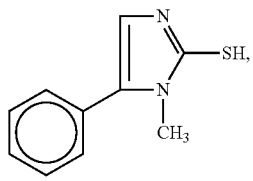

or pharmaceutical salt thereof, is administered in conjunction with one or more additional agents selected from hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, CETP inhibitors, LDL receptor inducers, ACAT inhibitors, antioxidants, squalene synthetase inhibitors, insulins, sulfonylureas, biguanides, meglitinides, thiazolidinediones, alpha-glucosidase inhibitors, cannabinoid 1 receptor antagonists, CCK agonists, serotonin reuptake inhibitors, bombesin agonists, galanin antagonists, leptin agonists, and lipase inhibitors.

22. The method of claim 1, wherein the effective amount of

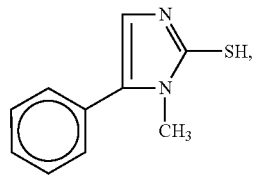

or pharmaceutical salt thereof, is administered in conjunction with one or more additional agents selected from bile acid absorption inhibitors, polymeric bile acid adsorbents, lipoprotein lipase inhibitors, ATP-citrate lyase inhibitors, lipoprotein(a) antagonists, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, beta-3 agonists, MSH agonists, mixed sertoninergic and noradrenergic compounds, 5HT agonists, growth hormones, growth hormone-releasing compounds, TRH agonists, uncoupling protein 2 or 3 modulators, amylase inhibitors, PPAR modulators, RXR modulators, TR-beta agonists, and amphetamines.

* * * * *